(12) United States Patent
Liao et al.

(10) Patent No.: US 10,815,473 B2
(45) Date of Patent: *Oct. 27, 2020

(54) ACETYL-COA CARBOXYLASES

(71) Applicant: CARGILL, INCORPORATED, Wayzata, MN (US)

(72) Inventors: Hans Liao, Plymouth, MN (US); Christopher Patrick Mercogliano, Minneapolis, MN (US); Travis Robert Wolter, Plymouth, MN (US); Michael Tai Man Louie, Maple Grove, MN (US); Wendy Kathleen Ribble, Arvada, CO (US); Tanya Lipscomb, Boulder, CO (US); Eileen Colie Spindler, Lafayette, CO (US); Michael D. Lynch, Durham, NC (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/216,588

(22) Filed: Dec. 11, 2018

(65) Prior Publication Data
US 2019/0127725 A1    May 2, 2019

Related U.S. Application Data

(63) Continuation of application No. 15/269,382, filed on Sep. 19, 2016, now Pat. No. 10,155,937, which is a
(Continued)

(51) Int. Cl.
*C12N 9/00* (2006.01)
*C12N 15/62* (2006.01)
(Continued)

(52) U.S. Cl.
CPC ............... *C12N 9/93* (2013.01); *C07C 59/01* (2013.01); *C12N 9/0006* (2013.01);
(Continued)

(58) Field of Classification Search
None
See application file for complete search history.

(56) References Cited

U.S. PATENT DOCUMENTS 2,408,889 A    10/1946   Short et al.
2,464,768 A    3/1949    Griffin et al.
(Continued)

FOREIGN PATENT DOCUMENTS

CA    2520795 A1   10/2004
CA    2591599 A1   7/2006
(Continued)

OTHER PUBLICATIONS

Rathnasingh et al., "Production of 3-hydroxypropionic acid via malonyl-CoA pathway using recombinant *Escherichia coli* strains", J. Biotechnology, 2012 (availabe on-line Jun. 23, 2011), vol. 157, pp. 633-640. doi:10.1016/j.jbiotec.2011.06.008.*
(Continued)

*Primary Examiner* — Suzanne M Noakes

(57) ABSTRACT

The present invention provides various combinations of genetic modifications to a transformed host cell that provide increase conversion of carbon to a chemical product. The present invention also provides methods of fermentation and methods of making various chemical products.

14 Claims, 9 Drawing Sheets

Specification includes a Sequence Listing.

Related U.S. Application Data continuation of application No. 14/215,379, filed on Mar. 17, 2014, now Pat. No. 9,447,438.

(60) Provisional application No. 61/852,387, filed on Mar. 15, 2013.

(51) Int. Cl.
  *C12N 15/52*   (2006.01)
  *C12P 7/42*    (2006.01)
  *C12N 15/70*   (2006.01)
  *C07C 59/01*   (2006.01)
  *C12P 7/52*    (2006.01)
  *C12N 9/04*    (2006.01)
  *C12N 9/02*    (2006.01)
  *C12N 9/06*    (2006.01)

(52) U.S. Cl.
  CPC ......... *C12N 9/0008* (2013.01); *C12N 9/0016* (2013.01); *C12N 15/52* (2013.01); *C12N 15/62* (2013.01); *C12N 15/70* (2013.01); *C12P 7/42* (2013.01); *C12P 7/52* (2013.01); *C12Y 604/01002* (2013.01); *Y02P 20/52* (2015.11)

(56) References Cited

U.S. PATENT DOCUMENTS

| | | |
|---|---|---|
| 2,469,701 A | 5/1949 | Redmon et al. |
| 2,798,053 A | 7/1957 | Brown et al. |
| 3,687,885 A | 8/1972 | Murray et al. |
| 3,872,037 A | 3/1975 | MacLeod |
| 3,875,101 A | 4/1975 | MacLeod |
| 3,891,591 A | 6/1975 | Chang et al. |
| 3,904,685 A | 9/1975 | Shahidi |
| 3,915,921 A | 10/1975 | Schlatzer |
| 4,029,577 A | 6/1977 | Godlewski et al. |
| 4,268,641 A | 5/1981 | Koenig et al. |
| 4,301,266 A | 11/1981 | Muenster et al. |
| 4,431,547 A | 2/1984 | Dubin et al. |
| 4,666,983 A | 5/1987 | Tsubakimoto et al. |
| 4,685,915 A | 8/1987 | Hasse et al. |
| 4,708,997 A | 11/1987 | Stanley et al. |
| 4,734,478 A | 3/1988 | Tsubakimoto et al. |
| 4,857,610 A | 8/1989 | Pauen et al. |
| 4,952,505 A | 8/1990 | Cho |
| 4,985,518 A | 1/1991 | Alexander et al. |
| 5,009,653 A | 4/1991 | Osborn |
| 5,093,472 A | 3/1992 | Bresciani et al. |
| 5,135,677 A | 8/1992 | Yamaguchi et al. |
| 5,145,906 A | 9/1992 | Chambers et al. |
| 5,180,798 A | 1/1993 | Nakamura et al. |
| 5,252,474 A | 10/1993 | MacNeil; et al. |
| 5,274,073 A | 12/1993 | Gruber et al. |
| 5,331,059 A | 7/1994 | Engelhardt et al. |
| 5,342,899 A | 8/1994 | Graham et al. |
| 5,350,799 A | 9/1994 | Woodrum et al. |
| 5,426,199 A | 6/1995 | Lundquist |
| 5,470,928 A | 11/1995 | Harwood et al. |
| 5,487,989 A | 1/1996 | Fowler et al. |
| 5,510,307 A | 4/1996 | Narayanan et al. |
| 5,510,526 A | 4/1996 | Baniel et al. |
| 5,558,656 A | 9/1996 | Bergman |
| 5,616,496 A | 4/1997 | Draths et al. |
| 5,723,639 A | 3/1998 | Datta et al. |
| 5,817,870 A | 10/1998 | Haas et al. |
| 5,827,255 A | 10/1998 | Crainic |
| 5,876,983 A | 3/1999 | Suzuki et al. |
| 6,004,773 A | 12/1999 | Yoshihara et al. |
| 6,013,494 A | 1/2000 | Picataggio et al. |
| 6,087,140 A | 7/2000 | Cameron et al. |
| 6,117,658 A | 9/2000 | Dennis et al. |
| 6,143,538 A | 11/2000 | Somerville et al. |
| 6,284,495 B1 | 9/2001 | Sato et al. |
| 6,297,319 B1 | 10/2001 | Nagasuna et al. |
| 6,306,636 B1 | 10/2001 | Haselkorn et al. |
| 6,355,412 B1 | 3/2002 | Stewart et al. |
| 6,472,188 B1 | 10/2002 | Lee et al. |
| 6,489,508 B1 | 12/2002 | Van Gansbeghe et al. |
| 6,509,156 B1 | 1/2003 | Stewart et al. |
| 6,534,679 B2 | 3/2003 | Eyal et al. |
| 6,586,229 B1 | 7/2003 | Ben-Bassat et al. |
| 6,593,116 B1 | 7/2003 | Huisman et al. |
| 6,623,944 B2 | 9/2003 | Rieping |
| 6,709,919 B2 | 3/2004 | Tu et al. |
| 6,723,799 B2 | 4/2004 | Higley et al. |
| 6,852,517 B1 | 2/2005 | Suthers et al. |
| 6,960,455 B2 | 11/2005 | Akhverdian et al. |
| 7,090,998 B2 | 8/2006 | Ishikawa et al. |
| 7,118,896 B2 | 10/2006 | Kalscheuer et al. |
| 7,141,154 B2 | 11/2006 | Lin et al. |
| 7,153,663 B2 | 12/2006 | Payne et al. |
| 7,166,743 B2 | 1/2007 | Whitehouse et al. |
| 7,186,541 B2 | 3/2007 | Buckel et al. |
| 7,186,856 B2 | 3/2007 | Meng et al. |
| 7,223,567 B2 | 5/2007 | Sanchez et al. |
| 7,279,598 B2 | 10/2007 | Meng et al. |
| 7,285,406 B2 | 10/2007 | Payne et al. |
| 7,309,597 B2 | 12/2007 | Gokarn et al. |
| 7,326,557 B2 | 2/2008 | San et al. |
| 7,358,071 B2 | 4/2008 | Payne et al. |
| 7,393,676 B2 | 7/2008 | Buckel et al. |
| 7,524,660 B2 | 4/2009 | Caimi et al. |
| 7,538,247 B2 | 5/2009 | Craciun et al. |
| 7,638,316 B2 | 12/2009 | Buckel et al. |
| 7,678,869 B2 | 3/2010 | Matyjaszewski et al. |
| 7,687,661 B2 | 3/2010 | Lilga et al. |
| 7,803,620 B2 | 9/2010 | Zirkle et al. |
| 7,826,975 B2 | 11/2010 | Maranas et al. |
| 7,833,761 B2 | 11/2010 | Terashita et al. |
| 7,846,688 B2 | 12/2010 | Gill et al. |
| 7,943,362 B2 | 5/2011 | Frost et al. |
| 7,987,056 B2 | 7/2011 | Gill et al. |
| 8,048,624 B1 | 11/2011 | Lynch et al. |
| 8,076,111 B2 | 12/2011 | Fukui et al. |
| 8,097,439 B2 | 1/2012 | Alibhai et al. |
| 8,110,093 B2 | 2/2012 | Friedman et al. |
| 8,110,670 B2 | 2/2012 | Valle et al. |
| 8,183,028 B2 | 5/2012 | Schirmer et al. |
| 8,268,599 B2 | 9/2012 | Schirmer et al. |
| 8,283,143 B2 | 10/2012 | Valle et al. |
| 8,313,934 B2 | 11/2012 | Bhatia et al. |
| 8,323,924 B2 | 12/2012 | Schirmer et al. |
| 8,372,610 B2 | 2/2013 | Haliburton et al. |
| 8,377,666 B2 | 2/2013 | Niu et al. |
| 8,467,975 B2 | 6/2013 | Ryan et al. |
| 8,530,221 B2 | 9/2013 | Hu et al. |
| 8,535,916 B2 | 9/2013 | Del et al. |
| 8,597,922 B2 | 12/2013 | Rude et al. |
| 8,652,816 B2 | 2/2014 | Lynch et al. |
| 8,658,404 B2 | 2/2014 | Rude et al. |
| 8,753,840 B2 | 6/2014 | Vermaas et al. |
| 8,809,027 B1 | 8/2014 | Mercogliano et al. |
| 8,835,137 B2 | 9/2014 | Cross et al. |
| 8,859,259 B2 | 10/2014 | Rude |
| 8,883,464 B2 | 11/2014 | Gill et al. |
| 9,388,419 B2 | 7/2016 | Gill et al. |
| 9,428,778 B2 | 8/2016 | Gill et al. |
| 9,447,438 B2 | 9/2016 | Louie et al. |
| 9,587,231 B2 | 3/2017 | Trinh et al. |
| 2002/0081684 A1 | 6/2002 | Grobler et al. |
| 2002/0164729 A1 | 11/2002 | Skraly et al. |
| 2003/0004375 A1 | 1/2003 | Mizrahi et al. |
| 2003/0087381 A1 | 5/2003 | Gokarn et al. |
| 2003/0101486 A1 | 5/2003 | Facciotti et al. |
| 2003/0158441 A1 | 8/2003 | Zhong et al. |
| 2003/0159175 A1 | 8/2003 | Ghulam et al. |
| 2003/0191146 A1 | 10/2003 | Kabbash et al. |
| 2003/0211131 A1 | 11/2003 | Martin et al. |
| 2003/0233675 A1 | 12/2003 | Cao et al. |
| 2003/0235892 A1 | 12/2003 | Katz et al. |
| 2004/0009466 A1 | 1/2004 | Maranas et al. |
| 2004/0076982 A1 | 4/2004 | Gokarn et al. |
| 2004/0077090 A1 | 4/2004 | Short |

(56) References Cited

U.S. PATENT DOCUMENTS

| | | |
|---|---|---|
| 2004/0152159 A1 | 8/2004 | Causey et al. |
| 2004/0152174 A1 | 8/2004 | Cervin et al. |
| 2004/0209337 A1 | 10/2004 | Frost et al. |
| 2004/0210087 A1 | 10/2004 | Meng et al. |
| 2004/0214294 A1 | 10/2004 | Rieping et al. |
| 2005/0003481 A1 | 1/2005 | Gabriel et al. |
| 2005/0054060 A1 | 3/2005 | Chateau et al. |
| 2005/0196758 A1 | 9/2005 | Rock et al. |
| 2005/0221457 A1 | 10/2005 | Tsobanakis et al. |
| 2005/0221466 A1 | 10/2005 | Liao et al. |
| 2005/0222458 A1 | 10/2005 | Craciun et al. |
| 2005/0233031 A1 | 10/2005 | Hughes et al. |
| 2005/0239179 A1 | 10/2005 | Skraly et al. |
| 2005/0272135 A1 | 12/2005 | Datta et al. |
| 2005/0283029 A1 | 12/2005 | Meng et al. |
| 2006/0014977 A1 | 1/2006 | Miller et al. |
| 2006/0084098 A1 | 4/2006 | Gill et al. |
| 2006/0166342 A1 | 7/2006 | Taoka et al. |
| 2007/0010708 A1 | 1/2007 | Ness et al. |
| 2007/0027342 A1 | 2/2007 | Meng et al. |
| 2007/0031918 A1 | 2/2007 | Dunson et al. |
| 2007/0087403 A1 | 4/2007 | Bestel-Corre et al. |
| 2007/0092957 A1 | 4/2007 | Donaldson et al. |
| 2007/0107080 A1 | 5/2007 | Liao et al. |
| 2007/0141574 A1 | 6/2007 | Keasling et al. |
| 2007/0148749 A1 | 6/2007 | Yasuda et al. |
| 2007/0184524 A1 | 8/2007 | Gokarn et al. |
| 2007/0219390 A1 | 9/2007 | Zacher et al. |
| 2007/0245431 A1 | 10/2007 | Metz et al. |
| 2007/0270494 A1 | 11/2007 | Metz et al. |
| 2007/0281343 A9 | 12/2007 | Arslanian |
| 2008/0076167 A1 | 3/2008 | Gokarn et al. |
| 2008/0124785 A1 | 5/2008 | Liao et al. |
| 2008/0182308 A1 | 7/2008 | Donaldson et al. |
| 2008/0193989 A1 | 8/2008 | Verser et al. |
| 2008/0199926 A1 | 8/2008 | Burgard et al. |
| 2008/0274523 A1 | 11/2008 | Renninger et al. |
| 2009/0017514 A1 | 1/2009 | Datta et al. |
| 2009/0023006 A1 | 1/2009 | Bub et al. |
| 2009/0031453 A1 | 1/2009 | Jessen et al. |
| 2009/0053783 A1 | 2/2009 | Gokarn et al. |
| 2009/0076297 A1 | 3/2009 | Bogan et al. |
| 2009/0082286 A1 | 3/2009 | Huang et al. |
| 2009/0111151 A1 | 4/2009 | Julien et al. |
| 2009/0148914 A1 | 6/2009 | Causey et al. |
| 2009/0203097 A1 | 8/2009 | Flint et al. |
| 2009/0234146 A1 | 9/2009 | Cooney et al. |
| 2009/0246141 A1 | 10/2009 | Hirai et al. |
| 2009/0291480 A1 | 11/2009 | Jessen et al. |
| 2009/0298144 A1 | 12/2009 | Tsobanakis et al. |
| 2009/0305369 A1 | 12/2009 | Donaldson et al. |
| 2009/0325248 A1 | 12/2009 | Marx et al. |
| 2010/0021978 A1 | 1/2010 | Burk et al. |
| 2010/0028962 A1 | 2/2010 | Hu et al. |
| 2010/0037329 A1 | 2/2010 | Frommer et al. |
| 2010/0064381 A1 | 3/2010 | Zou et al. |
| 2010/0068773 A1 | 3/2010 | Eggeling et al. |
| 2010/0099910 A1 | 4/2010 | Meng et al. |
| 2010/0113822 A1 | 5/2010 | Craciun et al. |
| 2010/0151536 A1 | 6/2010 | Baynes et al. |
| 2010/0170148 A1 | 7/2010 | Steen et al. |
| 2010/0186117 A1 | 7/2010 | Fabijanski et al. |
| 2010/0210017 A1 | 8/2010 | Gill et al. |
| 2010/0257777 A1 | 10/2010 | Sanchez-Riera et al. |
| 2010/0257778 A1 | 10/2010 | Gaertner et al. |
| 2010/0261239 A1 | 10/2010 | Soucaille et al. |
| 2010/0274033 A1 | 10/2010 | Sanchez-Riera et al. |
| 2010/0285549 A1 | 11/2010 | Muramatsu et al. |
| 2010/0291644 A1 | 11/2010 | Marx et al. |
| 2011/0020883 A1 | 1/2011 | Roessler et al. |
| 2011/0038364 A1 | 2/2011 | Monsieux et al. |
| 2011/0072714 A1 | 3/2011 | Gaertner et al. |
| 2011/0089016 A1 | 4/2011 | Winkelaar et al. |
| 2011/0124063 A1 | 5/2011 | Lynch et al. |
| 2011/0125118 A1 | 5/2011 | Lynch et al. |
| 2011/0144377 A1 | 6/2011 | Eliot et al. |
| 2011/0159558 A1 | 6/2011 | Grady et al. |
| 2011/0162259 A1 | 7/2011 | Gaertner et al. |
| 2011/0171702 A1 | 7/2011 | Reinecke et al. |
| 2011/0183382 A1 | 7/2011 | Schmalisch et al. |
| 2011/0183388 A1 | 7/2011 | Sabirova et al. |
| 2011/0183391 A1 | 7/2011 | Frost et al. |
| 2011/0190513 A1 | 8/2011 | Lynch et al. |
| 2011/0214979 A1 | 9/2011 | Chen et al. |
| 2011/0244575 A1 | 10/2011 | Lipscomb et al. |
| 2011/0275851 A1 | 11/2011 | Orjuela et al. |
| 2011/0281314 A1 | 11/2011 | Lynch et al. |
| 2012/0058530 A1 | 3/2012 | Zhang et al. |
| 2012/0129231 A1 | 5/2012 | Wang et al. |
| 2012/0135481 A1 | 5/2012 | Jessen et al. |
| 2012/0240289 A1 | 9/2012 | Feussner et al. |
| 2012/0244586 A1 | 9/2012 | Gokarn et al. |
| 2012/0244588 A1 | 9/2012 | Park et al. |
| 2012/0264902 A1 | 10/2012 | Lipscomb et al. |
| 2012/0329110 A1 | 12/2012 | Kim et al. |
| 2013/0071893 A1 | 3/2013 | Lynch et al. |
| 2013/0078684 A1 | 3/2013 | Holtzapple et al. |
| 2013/0078686 A1 | 3/2013 | Holtzapple et al. |
| 2013/0122541 A1 | 5/2013 | Lynch et al. |
| 2013/0122562 A1 | 5/2013 | Aldor et al. |
| 2013/0189787 A1 | 7/2013 | Lynch et al. |
| 2013/0316413 A1 | 11/2013 | Gonzalez et al. |
| 2013/0345470 A1 | 12/2013 | Tengler et al. |
| 2014/0051136 A1 | 2/2014 | Liao et al. |
| 2014/0121118 A1 | 5/2014 | Warner |
| 2014/0135526 A1 | 5/2014 | Lynch et al. |
| 2014/0215904 A1 | 8/2014 | Pandey et al. |
| 2014/0242648 A1 | 8/2014 | Ochiai et al. |
| 2014/0309451 A1 | 10/2014 | Tengler et al. |
| 2014/0330032 A1 | 11/2014 | Trahan et al. |
| 2015/0044746 A1 | 2/2015 | Meerman et al. |
| 2015/0056651 A1 | 2/2015 | Gill et al. |
| 2015/0056684 A1 | 2/2015 | Gill et al. |
| 2015/0057455 A1 | 2/2015 | Harkrader et al. |
| 2015/0064754 A1 | 3/2015 | Louie et al. |
| 2015/0072384 A1 | 3/2015 | Mercogliano et al. |
| 2015/0072399 A1 | 3/2015 | Lipscomb et al. |
| 2015/0119601 A1 | 4/2015 | Louie et al. |
| 2015/0299679 A1 | 10/2015 | Da et al. |
| 2016/0060663 A1 | 3/2016 | Grammann et al. |
| 2016/0090576 A1 | 3/2016 | Garg et al. |
| 2016/0257975 A1 | 9/2016 | Lynch et al. |
| 2016/0340700 A1 | 11/2016 | Liao et al. |
| 2016/0362710 A9 | 12/2016 | Lee et al. |

FOREIGN PATENT DOCUMENTS

| | | |
|---|---|---|
| CA | 2654133 A1 | 12/2007 |
| CN | 101573451 A | 11/2009 |
| CN | 101679924 A | 3/2010 |
| DE | 102008002309 A1 | 12/2009 |
| EP | 1124789 B1 | 9/2004 |
| EP | 1036190 B1 | 5/2005 |
| EP | 1305439 B1 | 6/2006 |
| EP | 1124979 B1 | 8/2006 |
| EP | 1731604 A1 | 12/2006 |
| EP | 1105514 B1 | 2/2008 |
| EP | 1778840 B1 | 6/2008 |
| EP | 1975236 A2 | 10/2008 |
| EP | 1654212 B1 | 7/2009 |
| EP | 2133420 A1 | 12/2009 |
| EP | 1706457 B1 | 2/2012 |
| EP | 3103867 A1 | 12/2016 |
| GB | 2473755 B | 9/2011 |
| JP | 09505463 A | 6/1997 |
| JP | 2009529890 A | 8/2009 |
| KR | 2007096348 | 10/2007 |
| KR | 20120108538 A | 10/2012 |
| WO | 9821339 A1 | 5/1998 |
| WO | 9855442 A1 | 12/1998 |
| WO | 9914343 A1 | 3/1999 |
| WO | 0039287 A2 | 7/2000 |
| WO | 0056693 A1 | 9/2000 |
| WO | 0061740 A1 | 10/2000 |

(56) References Cited

FOREIGN PATENT DOCUMENTS

| | | |
|---|---|---|
| WO | 0116346 A1 | 3/2001 |
| WO | 0138284 A1 | 5/2001 |
| WO | 0208428 A2 | 1/2002 |
| WO | 0234784 A2 | 5/2002 |
| WO | 0242418 A2 | 5/2002 |
| WO | 02090312 A1 | 11/2002 |
| WO | 03040690 A2 | 5/2003 |
| WO | 03062173 A2 | 7/2003 |
| WO | 03082795 A2 | 10/2003 |
| WO | 2004018621 A2 | 3/2004 |
| WO | 2004033646 A2 | 4/2004 |
| WO | 2005003074 A1 | 1/2005 |
| WO | 2005047498 A1 | 5/2005 |
| WO | 2005105770 A2 | 11/2005 |
| WO | 2005118719 A2 | 12/2005 |
| WO | 2006034156 A2 | 3/2006 |
| WO | 2006052871 A2 | 5/2006 |
| WO | 2006052914 A2 | 5/2006 |
| WO | 2006121755 A2 | 11/2006 |
| WO | 2007012078 A1 | 1/2007 |
| WO | 2007030830 A2 | 3/2007 |
| WO | 2007042494 A1 | 4/2007 |
| WO | 2007047680 A2 | 4/2007 |
| WO | 2007093848 A2 | 8/2007 |
| WO | 2007106903 A2 | 9/2007 |
| WO | 2007130745 A1 | 11/2007 |
| WO | 2007136762 A2 | 11/2007 |
| WO | 2008021765 A2 | 2/2008 |
| WO | 2008023039 A1 | 2/2008 |
| WO | 2008027742 A1 | 3/2008 |
| WO | 2008028002 A1 | 3/2008 |
| WO | 2008072920 A1 | 6/2008 |
| WO | 2008089102 A2 | 7/2008 |
| WO | 2008091627 A2 | 7/2008 |
| WO | 2008145737 A1 | 12/2008 |
| WO | 2008149951 A1 | 12/2008 |
| WO | 2009006430 A1 | 1/2009 |
| WO | 2009031737 A1 | 3/2009 |
| WO | 2009036095 A1 | 3/2009 |
| WO | 2009062190 A2 | 5/2009 |
| WO | 2009089457 A1 | 7/2009 |
| WO | 2009094485 A1 | 7/2009 |
| WO | 2009111513 A1 | 9/2009 |
| WO | 2009111672 A1 | 9/2009 |
| WO | 2009121066 A1 | 10/2009 |
| WO | 2009143401 A2 | 11/2009 |
| WO | 2009151342 A1 | 12/2009 |
| WO | 2010006076 A2 | 1/2010 |
| WO | 2010011874 A2 | 1/2010 |
| WO | 2010017230 A2 | 2/2010 |
| WO | 2010031083 A2 | 3/2010 |
| WO | 2010105095 A1 | 9/2010 |
| WO | 2011002892 A2 | 1/2011 |
| WO | 2011008565 A1 | 1/2011 |
| WO | 2011038364 A1 | 3/2011 |
| WO | 2011063304 A1 | 5/2011 |
| WO | 2011063363 A2 | 5/2011 |
| WO | 2011094457 A1 | 8/2011 |
| WO | 2012017083 A1 | 2/2012 |
| WO | 2012019175 A2 | 2/2012 |
| WO | 2012050931 A2 | 4/2012 |
| WO | 2012054400 A1 | 4/2012 |
| WO | 2012129450 A1 | 9/2012 |
| WO | 2012135760 A1 | 10/2012 |
| WO | 2012177726 A1 | 12/2012 |
| WO | 2013003608 A1 | 1/2013 |
| WO | 2013039563 A1 | 3/2013 |
| WO | 2013126855 A1 | 8/2013 |
| WO | 2013152051 A2 | 10/2013 |
| WO | 2013152052 A2 | 10/2013 |
| WO | 2013192450 A1 | 12/2013 |
| WO | 2013192461 A1 | 12/2013 |
| WO | 2013192463 A1 | 12/2013 |
| WO | 2014026162 A1 | 2/2014 |
| WO | 2014042693 A1 | 3/2014 |
| WO | 2014145096 A1 | 9/2014 |
| WO | 2014145297 A1 | 9/2014 |
| WO | 2014145332 A1 | 9/2014 |
| WO | 2014145334 A1 | 9/2014 |
| WO | 2014145343 A1 | 9/2014 |
| WO | 2014145344 A2 | 9/2014 |
| WO | 2014146026 A1 | 9/2014 |
| WO | 2014146047 A1 | 9/2014 |
| WO | 2014198831 A1 | 12/2014 |
| WO | 2015010103 A2 | 1/2015 |
| WO | 2015042626 A1 | 4/2015 |

OTHER PUBLICATIONS

Vedantam, et al., "Characterization of mutations contributing to sulfathiazole resistance in *Escherichia coli*", Antimicrob Agents Chemother. 42(1), Jan. 1998, 88-93.

Vilcheze, et al., "Inactivation of the inhA-Encoded Fatty Acid Synthase II (FASII) Enoyl-Acyl Carrier Protein Reductase Induces Accumulation of the FASI End Products and Cell Lysis of Mycobacterium smegmatis", doi: 10.1128/JB.182.14.4059-4067. 2000 J. Bacteriol. vol. 182 No. 14, Jul. 2000, 4059-4067.

Wankat, Phillip C., "Separation Process Engineering, Equilibrium Staged Separations", P.C. Wankat. Prentice Hall, Englewood Cliffs, NJ. USA., 1988.

Warnecke, et al., "A genomics approach to improve the analysis and design of strain selections", Metab Eng. 10(3-4), May-Jul. 2008, 154-65.

Warnecke, et al., "Engineering of Organic Acid Tolerance Genes in *E. coli* for Biorefinery Applications", 2006 AIChE Annual meeting in San Francisco, California, Nov. 12-17, 2006, https://aiche.confex.comlaiche/2006/techprogram/P67122.HTM.

Warnecke, et al., "Identification of a 21 amino acid peptide conferring 3¬hydroxypropionic acid stress-tolerance to *Escherichia coli*", Biotechnol Bioeng.109(5). doi: 10.1002/bit.24398., May 2012, 1347-52.

Warnecke, et al., "Organic acid toxicity, tolerance, and production in *Escherichia coli* biorefining applications.", Microbial Cell Factories. 4(25), 2005; 1-8.

Warnecke, et al., "Rapid dissection of a complex phenotype through genomic-scale mapping of fitness altering genes", Metab Eng. 12(3), May 2010, 241-50.

Wasewar, et al., "Fermentation of Glucose to Lactic Acid Coupled with Reactive Extraction: A Review.", Ind. Eng. Chem. Res. 43, 2004, 5969-5982.

Waterson, et al., "Enoyl coenzyme A hydratase (crotonase). Catalytic properties of crotonase and its possible regulatory role in fatty acid oxidation", J Biol Chem. 247(16), Aug. 25, 1972, 5258-65.

Welch, et al., "Extensive mosaic structure revealed by the complete genome sequence of uropathogenic *Escherichia coli*.", Proc Natl Acad Sci U S A. 99(26), Dec. 24, 2002, 17020-4.

Werpy, et al., "Top Value Added Chemicals From Biomass, vol. 1—Results of Screening for Potential candidates From Sugars and Synthesis Gas", Pacific Northwest National Laboratory. U.S. Department of Energy, Aug. 2004.

Whisstock, et al., "Prediction of protein function from protein sequence and structure", Q Rev Biophys. 36(3), Aug. 2003, 307-40.

White, et al., "The overexpression, purification and complete amino acid sequence of chorismate synthase from *Escherichia coli* K12 and its comparison with the enzyme from Neurospora crassa", Biochem J. 251(2), Apr. 15, 1988, 313-22.

Wishart, et al., "A single mutation converts a novel phosphotyrosine binding domain into a dual-specificity phosphatase", J Biol Chem. 270(45), Nov. 10, 1995, 26782-5.

Witkowski, et al., "Conversion of a beta-ketoacyl synthase to a malonyl decarboxylase by replacement of the active-site cysteine with glutamine.", Biochemistry. 38(36), Sep. 7, 1999, 11643-50.

Wyckoff, et al., "Characterization and sequence analysis of a stable cryptic plasmid from Enterococcus faecium 226 and development of a stable cloning vector", Appl Environ Microbial. Apr. 1996; 62(4): 1481-1486.

Xie, Dongming, et al., "Microbial Synthesis of Triacetic Acid Lactone", Biotechnol Bioeng. 93(4), Mar. 5, 2006, 727-36.

(56) References Cited

OTHER PUBLICATIONS

Xu, Xiaowei, "Fatty acid synthase inhibitors: research advances", Journal of international pharmaceutical research. vol. 36 (2). (English abstract), 2009, 105-108, 120.
Yee, et al., "On the role of helix 0 of the tryptophan synthetase alpha chain of Escherichia coli.", J Biol Chem. 271(25), Jun. 21, 1996, 14754-63.
Yiming Ren, et al., "Molecular Iodine in Ionic Liquid: A Green Catalytic System for Esterification and Transesterification", Synthetic Communications. 40(11), 2010, 1670-1676.
Yoshida, et al., "Identification of PhoB binding sites of the yibD and ytfK promoter regions in Escherichia coli.", J Microbial. 49(2), Apr. 2011, 285-289.
Zha, Wenjuan, et al., "Improving cellular malonyl-CoA level in Escherichia coli via metabolic engineering", Metab Eng, 11(3), May 2009, 192-8.
Zhang, et al., "Inhibiting bacterial fatty acid synthesis", J. Biol. Chem. 281(26), Jun. 30, 2006, 17541-17544.
Zhao, "Binding of two flaviolin substrate molecules, oxidative coupling, and crystal structure of Streptomyces coelicolor A3(2) cytochrome P450 158A2.", J Biol Chem. 280(12), Mar. 25, 2005, 11599-607.
Zhou, et al., "Interdomain communication between the thiolation and thioesterase domains of EntF explored by combinatorial mutagenesis and selection", Chem Biol. 13(8), Aug. 2006, 869-79.
"GenBank Accession No. NP 415816.1; available 1997".
Branden, Carl, et al., "Introduction to Protein Structure", Garland Publishing Inc., New York, 1991, 247.
Chang, et al., "Probable polyketide synthase/thioesterase. NCBI Direct Submission, Accession No. GI50082961", Jun. 14, 2004.
Cheng, et al., "Mammalian wax biosynthesis: I. Identification of two fatty acyl-Coenzyme A reductases with different substrate specificities and tissue distributions", Journal of Biological Chemistry, Sep. 3, 2004, vol. 279, No. 36, pp. 37789-37797.
Doroshenko, Vera G., et al., "Pho regulon promoter-mediated transcription of the key pathway gene aroGFbr improves the performance of an L-phenylalanine-producing Escherichia coli strain", Applied Microbiology and Biotechnology 88, 2010, 1287-1295.
Erb, et al., "Carboxylation mechanism and stereochemistry of crotonyl-CoA carboxylase/reductase, a carboxylating enoylthioester reductase", Proc Natl Acad Sci U S A, Jun. 2, 2009; 106(22): 8871-8876, Published online May 20, 2009, doi: 10.1073/pnas.0903939106, 8871-8876.
Gu, et al., "Polyketide Decarboxylative Chain Termination Preceded by O-Sulfonation in Curacin A Biosynthesis", J Am Chem Soc. Nov. 11, 2009: 131(44): 16033-16035: doi: 10.1021/ja9071578.
Helge, Jans, et al., "Fatty acid synthesis in Escherichia coil and its applications towards the production of fatty acid based biofuels", Biotechnology for Biofuels, vol. 7, No. 1, XP-021173667, Jan. 9, 2014.
Jenkins, et al., "Genetic and molecular characterization of the genes involved in short-chain fatty acid degradation in Escherichia coli: the ato system", J Bacteriol. Jan. 1987; 169(1): 42-52.
Jung, et al., "Jung et al., Wax-deficient antherl is involved in cuticle and wax production in rice anther walls and is required for pollen development", and is required for pollen development, Plant Cell, Nov. 2006, vol. 18, No. 11, pp. 3015-3032.
Knothe, Gerhard, et al., "Biodiesel and renewable diesel: A comparison", Progress in Energy and Combustion Science, vol. 36, No. 3 XP026919218, Jun. 1, 2010, 364-373.
Masayuki, et al., "Expression of Clostridium acetobutylicum butanol synthetic genes in Escherichia coli", Applied Microbiology and Biotechnology, Jan. 2008, vol. 77, Issue 6, pp. 1305-1316.
Park, et al., "Production of alternatives to fuel oil from organic waste by the alkane-producing", Vibrio furnissii MI. Journal of Applied Microbiology, 2005, vol. 98, No. 2, pp. 324-331.
Sadowski, M. I., et al., "The sequence-structure relationship and protein function prediction", Current Opinion in Structural Biology 19, 2009, 357-362.

Smirnova, N., et al., "Engineered Fatty Acid Biosynthesis in Streptomyces by Altered Catalytic Function of B-Ketoacyl-Acyl Carrier Protein Synthase III", Journal of Bacteriology, vol. 183, No. 7., Apr. 2001, 2335-2342 & 2335, 2336.
Stephens, et al., "Mitochondrial fatty acid in Trypanosoma brucei", Journal of Biologic Chemistry, vol. 282, No. 7, Feb. 16, 2007, 4427-36.
Valentin H E, et al., "Production of poly(3-hydroxybutyrate-co-4-hydroxybutyrate) in recombinant Escherichia coli grown on glucose", Journal of Biotechnology, Elsevier Science Publishers, Amsterdam, NL, Elsevier Science Publishers, Amsterdam, NL, vol. 58, No. 1, doi:10.1016/S0168-1656(97)00127-2, ISSN 0168-1656, XP004126101, Oct. 2, 1997, 33-38.
Weilbacher, et al., "A novel sRNA component of the carbon storage regulatory system of Escherichia coli.", Molecular Microbiology, vol. 48, No. 3, [online] [Retrieved on Jul. 11, 2007], [Retrieved from the internet: http://www.blackwell-synergy.com/links/doi/10.1046/1.1365-2958.2003.03459.x/full/], May 2003, 657-670.
Winkler, Christoph K., et al., "Asymmetric bioreduction of activated alkenes to industrially relevant optically active compounds", J Biotechnol. 162(4), Dec. 31, 2012, 381-9.
Xu, et al., "English Translation: Principles and Experiments of Biotechnology", China Minzu University Press, (English Translation), Jul. 2006, 229-231.
Popp, J., "Sequence and overexpression of the menD gene from Escherichia coli", J Bacteriol. 171(8), Aug. 1989, 4349-54.
Prather, Kristala L, et al., "De novo biosynthetic pathways: rational design of microbial chemical factories", Curr Opin Biotechnol 19(5), Oct. 19, 2008, 468-74.
Price-Carter, et al., "Polyphosphate kinase protects Salmonella enterica from weak organic acid stress", Journal of Bacteriology. 187, 2005, 3088-3099.
Ramalinga, et al., "A mild and efficient method for esterification and transesterification catalyzed by iodine", Tetrahedron Letters. 43(5), 2002, 879-882.
Ramey, et al., "Poster—Translation of genomics data into useful metabolic engineering strategies: construction of a 3-hydroxypropionic acid tolerant E. coli", 2010.
Ramilo, et al., "Overexpression, purification, and characterization of tyrosine-sensitive 3-deoxy-D-arabino-heptulosonic acid 7-phosphate synthase from Escherichia coli", Protein Expr Purif. 9(2), Mar. 1997, 253-61.
Rathnasingh, et al., "Development and evaluation of efficient recombinant Escherichia coli strains for the production of 3-hydroxypropionic acid from glycerol", Biotechnol Bioeng. 104(4). doi: 10.1002/bit.22429., Nov. 1, 2009, 729-39.
Rathnasingh, Chelladurai, et al., "Production of 3-hydroxypropionic acid via malonyl-COA pathway using recombinant Escherichia coli strains", J Biotechnol. 157(4), Feb. 20, 2012, 633-40.
Ray, et al., "Mutational analysis of the catalytic and feedback sites of the tryptophan-sensitive 3-deoxy-D-arabino-heptulosonate-7-phosphate synthase of Escherichia coli". J Bacteriol. 170(12), Dec. 1988 5500-6.
Renault, et al., "Plasmid vectors for Gram-positive bacteria switching from high to low copy number", Gene. vol. 183, Issues 1-2, 1996, pp. 175-182.
Rodriguez, et al., "Structure-cytoprotective activity relationship of simple molecules containing an alpha,beta-unsaturated carbonyl system", J Med Chem. 40(12), Jun. 6, 1997, 1827-34.
Roe, et al., "Inhibition of Escherichia coli growth by acetic acid: a problem with methionine biosynthesis and homocysteine toxicity", Microbiology. 148(Pt 7), Jul. 2002, 2215-2222.
Saerens, S. M. G., et al., "Parameters Affecting Ethyl Ester Production by Saccharomyces cerevisiae during Fermentation", Appl Environ Microbiol, 74(2), Jan. 2008, 454-61.
Saier, et al., "The catabolite repressor/activator (Cra) protein of enteric bacteria", J Bacteriol. 178(12), Jun. 1996, 3411-7.
Salis, Howard M., et al., "Automated Design of Synthetic Ribosome Binding Sites to Precisely Control Protein Expression", Nat Biotechnol 27(10), Oct. 2009, 946-50.
Sambrook and Russell, "Molecular Cloning: A Laboratory Manual", Third Edition (vols. 1-3), Cold Spring Harbor Laboratory Press, Cold Spring Harbor, N.Y., 2001.

(56) References Cited

OTHER PUBLICATIONS

Sauna, et al., "Silent polymorphisms speak: how they affect pharmacogenomics and the treatment of cancer", Cancer Research. 67(20), Oct. 15, 2007, 9609-12.
Schmid, Katherine M., et al., "Lipid Metabolism in Plants", Biochemistry of Lipids, Lipoproteins and memebranes. Ch 4, 2002, 93-126.
Schmidt-Dannert, et al., "Molecular breeding of carotenoid biosynthetic pathways", Nat Biotechnol. 18(7), Jul. 2000 750-3.
Seffernick, Jennifer L., et al., "Melamine Deaminase and Atrazine Chlorohydrolase: 98 Percent Identical but Functionally Different", J Bacteriol. 183(8), Apr. 2001, 2405-10.
Sen, S., et al., "Developments in Directed Evolution for Improving Enzyme Functions", Appl Biochem Biotechnol. 143(3), Dec. 2007, 212-23.
Service, "Sugary Recipe Boosts Grow-Your-Own Plastics", Science. 312(5782), Jun. 30, 2006, 1861.
Shelden, Megan C., et al., "Membrane topology of the cyanobacteria( bicarbonate transporter, BicA, a member of the SulP (SLC26A) family", Molecular Membrane Biology vol. 27(1), 2010, 12-22.
Singh, et al., "Genes restoring redox balance in fermentation-deficient *E. coli* NZN111", Metabolic Engineering. vol. 11, Issue 6, Nov. 2009, 347-354.
Singh, Raushan Kumar, et al., "Protein Engineering Approaches in the Post-Genomic Era", Curr Protein Pept Sci. 18, 2017, 1-11.
Skerra, Arne, "Use of the tetracycline promoter for the tightly regulated production of a murine antibody fragment in *Escherichia coli*", Gene. 151(1-2), Dec. 30, 1994, 131-5.
Sousa, Silvino, et al., "The ARO4 gene of Candida albicans encodes a tyrosine-sensitive DAHP synthase: evolution, functional conservation and phenotype of Aro3p-, Aro4p-deficient mutants", Microbiology 148(Pt5), 2002, 1291-1303.
Stephanie C. Weatherly, "Expression and characterization of recombinant fungal acetyl-CoA carboxylase and isolation of a soraphen-binding domain", Biochemical Journal, GB, (May 15, 2004), vol. 380, No. 1, doi:10.1042/bj20031960, ISSN 0264-6021, pp. 105-110, XP055302533, May 15, 2004.
Stephanopoulos, et al., "Challenges in engineering microbes for biofuels production", Science. 315(5813), Feb. 9, 2007, 801-4.
Stephanopoulos, et al., "Network Rigidity and Metabolic Engineering in Metabolite Overproduction", Science. 252(5013), Jun. 21, 1991, 1675-81.
Stim, et al., "Nucleotide sequence of the adi gene, which encodes the biodegradative acid-induced arginine decarboxylase of *Escherichia coli*", J Bacteriol. 175(5), Mar. 1993, 1221-34.
Stone, Scot J., et al., "Lipids and Lipoproteins: Lipopenia and Skin Barrier Abnormalities in DGAT2-deficient Mice", J Biol Chem. 279(12), Mar. 19, 2004, 11767-76.
Straathoff, et al., "Feasibility of acrylic acid production by fermentation", Appl Microbiol Biotechnol.67(6), Jun. 2005, 727-34.
Strauss, et al., "Enzymes of a novel autotrophic CO2 fixation pathway in the phototrophic bacterium Chloroflexus aurantiacus, the 3-hydroxypropionate cycle", Eur J Biochem. 215(3), Aug. 1, 1993, 633-43.
Stryer, "Biochemistry", 4th Ed. Freeman and Co., New York., 1995, 463-650.
Studier, William F., et al., "Use of Bacteriophage T7 RNA Polymerase to Direct Selective High-level Expression of Cloned Genes", J Mol Biol. 189(1), May 5, 1900, 113-30.
Subrahmanyam, Satyanarayana, et al., "Overproduction of a Functional Fatty Acid Biosynthetic Enzyme Blocks Fatty Acid Synthesis in *Escherichia coli*", J Bacteriol. 180(17), Sep. 1998, 4596-602.
Suh, Ml Chung, et al., "Cuticular Lipid Composition, Surface Structure, and Gene Expression in *Arabidopsis* Stem Epidermis", Plant Physiol. 139(4), Dec. 13, 2005, 1649-65.
Sulter, G. J., et al., "Proliferation and metabolic significance of peroxisomes in Candida boidinii during growth on D-alanine or oleic acid as the sole carbon source", Arch Microbiol. 153(5), 1990, 485-9.
Sun, et al., "ZrOC12 x 8H20: an efficient, cheap and reusable catalyst for the esterification of acrylic acid and other carboxylic acids with equimolar amounts of alcohols", Molecules. 11(4):, Apr. 10, 2006, 263-71.
Taghavi, et al., "Electroporation of Alcaligenes eutrophus with (mega) plasmids and genomic DNA fragments", Appl Environ Microbiol. Oct. 1994: 60(10): 3585-3591.
Takamizawa, et al., "Beta-Hydroxypropionic Acid Production by *Byssochlamys* Sp. Grown on Acrylic Acid", Appl Microbiol Biotechnol. 40, 1993, 196-200.
Takamura, et al., "Changes in the intracellular concentration of acetyl-CoA and malonyl-CoA in relation to the carbon and energy metabolism of *Escherichia coli* K12", J Gen Microbiol. 134(8), Aug. 1988, 2249-53.
Tanimoto, et al., "Analysis of the Conjugal Transfer System of the Pheromone-Independent Highly Transferable Enterococcus Plasmid pMG1: Identification of a tra Gene (traA) Up-Regulated during Conjugation", doi: 10.1128/JB.184.20.5800-5804.2002 J. Bacteriol. Oct. 2002 vol. 184 No. 20 5800-5804.
Tian, et al., "Mycobacterium tuberculosis appears to lack an alpha-ketoglutarate dehydrogenase and encodes pyruvate dehydrogenase in widely separated genes", Mol Microbiol. 57(3), Aug. 2005, 859-68.
Tian, et al., "Variant tricarboxylic acid cycle in Mycobacterium tuberculosis: Identification of alpha-ketoglutarate decarboxylase", Proc Natl Acad Sci U S A. 102(30), Jul. 26, 2005, 10670-5.
Tomar, A., "Master Thesis. Production of Pyruvate by *Escherichia coli* Using Metabolic Engineering", the University of Georgia, May 2002, 1-171.
Tunnicliff, et al., "The inhibition by substrate analogues of gamma-aminobutyrate aminotransferase from mitochondria of different subcellular fractions of rat brain", Can J Biochem. 55(4), Apr. 1977, 479-84.
Turlin, et al., "3-phenylpropionate catabolism and the *Escherichia coli* oxidative stress response", Res Microbiol. 156(3), Apr. 2005, 312-21.
Van Kranenburg, et al., "Functional Analysis of Three Plasmids from Lactobacillus plantarum", doi: 10.1128/AEM.71.3.1223-1230. 2005 Appl. Environ. Microbiol. Mar. 2005, vol. 71 No. 3 1223-1230.
Kurcok, et al., "Reactions of l3-lactones with potassium alkoxides and their complexes with 18-crown-6 in aprotic solvents", Journal of Organic Chemistry. 58(16), 1993, 4219-4220.
Kwon, et al., "A physiology study of *Escherichia coli* overexpressing phosphoenolpyruvate carboxykinase", Biosci. Biotechnol. Biochem., 72 (4), 2008, 1138-1141.
Kwon, et al., "Influence of gluconeogenic phosphoenolpyruvate carboxykinase (PCK) expression on succinic acid fermentation in *Escherichia coli* under high bicarbonate condition", Journal of Microbiology and Biotechnology 16(9)., Sep. 2006, 1448-1452.
Lambert, et al., "Cre-lox-Based System for Multiple Gene Deletions and Selectable-Marker Removal in Lactobacillus plantarum", AEM, vol. 73, No. 4, Jan. 1, 1900, 1126-1135.
Langlois, et al., "A new preparation of trifluoromethanesulfinate salts", Journal of Fluorine Chemistry. 128(7), 2007, 851-856.
Lassner, Michael W., et al., "Lysophosphatidic Acid Acyltransferase from Meadowfoam Mediates Insertion of Erucic Acid at the sn-2 Position of Triacylglycerol in Transgenic Rapeseed Oil", Plant Physiol. 109(4), Dec. 1995, 1389-94.
Lee, Soo Hee, et al., "Fatty Acid Synthesis by Elongases in Trypanosomes", Cell. 126(4), Aug. 25, 2006, 691-9.
Leeper, Stephen A., "Membrane Separations in the Recovery of Biofuels and Biochemicals: An Update Review", Separation and Purification Technology, Norman N. Li and Joseph M. Cabo, Eds., Marcel Dekker, 1992, 99-194.
Lennen, et al., "A process for microbial hydrocarbon synthesis: Overproduction of fatty acids in *Escherichia coli* and catalytic conversion to alkanes", Biotechnol Bioeng. vol. 106, Issue 2, Jun. 1, 2010, 193-202.
Leonard, Effendi, et al., "Engineering Central Metabolic Pathways for High-Level Flavonoid Production in *Escherichia coli*", Appl Environ Microbiol. 73(12), Jun. 2007, 3877-86.

(56) References Cited

OTHER PUBLICATIONS

Li, Wang, et al., "Characterization of two temperature-inducible promoters newly isolated from B. subtilis", Biochem Biophys Res Commun. 358(4), Jul. 13, 2007, 1148-53.
Li, Jianguo, et al., "Chronic intermittent hypoxia upregulates genes of lipid biosynthesis in obese mice", J Appl Physiol. 99(5), Nov. 2005, 1643-8.
Li, et al., "Effect of poxB gene knockout on metabolism in *Escherichia coli* based on growth characteristics and enzyme activities", World Journal of Microbiology and Biotechnology. vol. 23, Issue 4, Apr. 2007, 573-580.
Liang, et al., "Fe2(SO4)3.4H20/concentrated H2SO4: an efficient catalyst for esterification", Journal of Chemical Research, Synopses. 3, 2004, 226-227.
Lilly, Mariska, et al., "The effect of increased yeast alcohol acetyltransferase and esterase activity on the flavour profiles of wine and distillates", Yeast. 23(9), Jul. 15, 2006, 641-59.
Lioa, et al., "Metabolic engineering for a malonyl-CoA-dependent pathway for fatty acid production in *Escherichia coli* (abstract)", SIMB Annual Meeting & Exhibition. Aug. 12-16, 2012. Washington Hilton, Washington, DC. Available at http://sim.confex.com/sim/2012/webprogram/Paper23197.html, Aug. 2012.
Lipscomb, et al., "Poster—Understanding production of 3-Hydroxypropionic Acid (3¬HP) in a genomic context." OPX Biotechnologies. Metabolic Engineering, Sep. 17, 2008.
Lu, Xuefeng, et al., "Overproduction of free fatty acids in *E. coli*: Implications for biodiesel production", Metab Eng. 10(6), Nov. 2008, 333-9.
Lutke-Eversloh, et al., "Feedback inhibition of chorismate mutase/prephenate dehydrogenase (TyrA) of *Escherichia coli*: generation and characterization of tyrosine-insensitive mutants". Appl Environ Microbiol. vol. 71 No. 11, 2005 Nov, 7224-8.
Lynch, "Rapid optimization of microorganisms for the cost superior production of chemicals & fuels", OPX Biotechnologies, Sep. 15, 2008.
Lynch, M., et al., "SCALEs: multiscale analysis of library enrichment. Nat Methods", Nat Methods. 4(1)., Jan. 2007, 87-93.
Magnuson, Kelly, et al., "Regulation of fatty acid biosynthesis in *Escherichia coli*", Microbiological Reviews, vol. 57, No. 3, 1993, 522-542.
Mandaokar, Ajin, et al., "Transcriptional regulators of stamen development in *Arabidopsis* identified by transcriptional profiling", Plant J. 46(6), Jun. 2006, 984-1008.
Martin, et al., "Engineering a mevalonate pathway in *Escherichia coli* for production of terpenoids", Nat Biotechnol. 21(7)., Jul. 2003, 796-802.
McCabe, Warren L., et al., "Unit Operations of Chemical Engineering", 5th Ed., W.L. McGraw Hill, New York, 1993.
Meades, Glen, et al., "A tale of two functions: enzymatic activity and translational repression by carboxyltransferase", Nucleic Acids Res. 38(4), Mar. 2010, 1217-27.
Mehta, et al., "Aminotransferases: demonstration of homology and division into evolutionary subgroups", Eur J Biochem. 214(2). Jun. 1, 1993, 549-61.
Meng, Xin, et al., "Increasing fatty acid production in *E. coli* by simulating the lipid accumulation of oleaginous microorganisms", Journal of Industrial Microbiology and Biotechnology. 38(8), 2011, 919-925.
Meng, et al., "Nucleotide sequence of the *Escherichia coli* cad operon: a system for neutralization of low extracellular pH.", J. Bacteriol. vol. 174 No. 8, Apr. 1992, 2659-2669.
Milton, et al., "In vitro mutagenesis and overexpression of the *Escherichia coli* trpA gene and the partial characterization of the resultant tryptophan synthase mutant alpha-subunits", Biol Chem. 261(35), Dec. 15, 1986, 16604-15.
Mohan Raj, et al., "Effect of process parameters on 3-hydroxypropionic acid production from glycerol using a recombinant *Escherichia coli*", Appl Microbiol Biotechnol. 84(4), Sep. 2009, 649-57.
Moreau, et al., "Diversion of the metabolic flux from pyruvate dehydrogenase to pyruvate oxidase decreases oxidative stress during glucose metabolism in nongrowing *Escherichia coli* cells incubated under aerobic, phosphate starvation conditions", J Bacteriol. 186(21), Nov. 2004, 7364-8.
Muday, et al., "The tyrosine repressor negatively regulates aroH expression in *Escherichia coli*", 173(12), Jun. 1991, 3930-2.
Nackley, et al., "Human Catechol-O-Methyltransferase Haplotypes Modulate Protein Expression by Altering mRNA Secondary Structure", Science. 314(5807)., Dec. 22, 2006, 1930-3.
Nelson, David L., et al., "Principles of Biochemistry 3rd Ed.", Worth Publishers New York, 2000, 527-658.
Nichols, "Cloning and sequencing of *Escherichia coli* ubiC and purification of chorismate lyase", J Bacteriol. 174(16), Aug. 1992, 5309-16.
Nicholson, Donald, "Lipid Metabolism Graphic Design", 2002, 1 page.
Nugent, Patricia, "Development of Improved Chemicals and Plastics from Oilseeds. Final technical report", the Dow Chemical Company. DE-FC36-01IDI4213, Jul. 31, 2006.
Ohmiya, et al., "Structure of Cellulases and Their Applications", Biotechnol. Genet. Eng. Rev., vol. 14, 1997, 365-414.
Ohnishi, et al., "A novel methodology employing Corynebacterium glutamicum genome information to generate a new L-lysine-producing mutant", Appl Microbiol Biotechnol. 58(2), Feb. 2002, 217-23.
Okamura, Eiji, et al., "Unprecedented acetoacetyl-coenzyme a synthesizing enzyme of the thiolase superfamily involved in the mevalonate pathway", Proc. Natl. Acad. Sci. USA. 107., 2010, 11265-70.
Oliveira, et al., "Cloning and Overexpression in Soluble Form of Functional Shikimate Kinase and 5-Enolpyruvylshikimate 3-Phosphate Synthase Enzymes from Mycobacterium tuberculosis", Protein Expr Purif. 22(3)., Aug. 2001, 430-5.
Orjuela, et al., "Presentation: Recovery of succinic acid from fermentative broth through esterification with ethanol", Department of Chemical Engineering and Materials Science. Michigan State University. East Lansing, Michigan 48824, Jun. 29, 2010.
O'Sullivan, et al., "High- and low-copy-number Lactococcus shuttle cloning vectors with features for clone screening", Gene. vol. 137, Issue 2, Dec. 31, 1993, pp. 227-231.
Ozcelik, et al., "Metabolic engineering of aromatic group amino acid pathway in Bacillus subtilis for L-phenylalanine production", Chemical Engineering Science. 59(22-23):, 2004, 5019-5026.
Papanikolaou, Seraphim, et al., "Lipid production by Yarrowia lipolytica growing on industrial glycerol in a single-stage continuous culture", Bioresour Technol. 82(1), Mar. 2002, 43-9.
Parikh, et al., "Directed evolution of RuBisCO hypermorphs through genetic selection in engineered *E.coli*", Protein Eng Des Sel. 19(3), Mar. 2006, 113-9.
Patnaik, et al., "Genome shuffling of Lactobacillus for improved acid tolerance", Nat Biotechnol. 20(7), Jul. 2002, 707-12.
Pohl, et al., "A new perspective on thiamine catalysis", Curr Opin Biotechnol. 15(4), Aug. 2004, 335-42.
Ponce, et al., "Ioning of the Two Pyruvate Kinase Isoenzyme StructuralGenes from *Escherichia coli*: the Relative Roles of These Enzymes in Pyruvate Biosynthesis.", J Bacteriol. 177(19), Oct. 1995, 5719-22.
"Agriculture Project Fact Sheet", U.S. Department of Energy, Office of Industrial Technologies. Jul. 2001.
"GenBank Accession No. AAC74497.1; Apr. 24, 2007. 2 pgs."
"GenBank Accession No. NP 415933.1; available 1997".
"GenBank Accession No. NP 418045.4; available 1997".
"GenBank Accession No. X81461", AF473544, Sep. 7, 1994.
"GenBank Accession No. AAS20429.1", Jan. 19, 2004.
"NCBI Reference Sequence: NP_414657.1", Jan. 16, 1997.
"NCBI Reference Sequence: NP_415792.1", Jan. 16, 1997.
"NCBI Reference Sequence: NP_416366.1", Jan. 16, 1997.
"NCBI Reference Sequence: NP_2418812.1", Jan. 16, 1997.
"NCBI Reference Sequence: WP_011957906.1", Jun. 6, 2007.
"NCBI Reference Sequence: WP_012121415.1", Sep. 4, 2007.
"NCBI Reference Sequence: WP_012616528.1", Dec. 29, 2008.
"NCBI Reference Sequence: YP_001636209.1", Dec. 21, 2007.
"NCBI Reference Sequence: ZP_01039179.1", Jan. 16, 2006.
"NCBI Reference Sequence: ZP_01626393.1", Dec. 15, 2006.

(56) References Cited

OTHER PUBLICATIONS

"NCBI Reference Sequence: ZP_04957196.1", Sep. 15, 2008.
"NCBI Reference Sequence: ZP_05125944.1". Sep. 15, 2008.
"Nexant, Inc. Chemsystems Perp Program, Acrylic Acid, 08/09-3", Jul. 2010.
Abdel-Hamid, Ahmed M., et al., "Coordinate Expression of the Acetyl Coenzyme A Carboxylase Genes, accB and accC, is Necessary for Normal Regulation of Biotin Synthesis in *Escherichia coli*", J Bacteriol. 189(2), Jan. 2007, 369-76.
Alber, et al., "Malonyl-coenzyme A reductase in the modified 3-hydroxypropionate cycle for autotrophic carbon fixation in archaeal Metallosphaera and *Sulfolobus* spp.", spp. J Bacteriol. Dec. 2006;188(24):8551-9.
Alberts, Bruce, et al., "Molecular Biology of the Cell", 3rd Ed. Garland Publishing, New York, 1994, 42-45 66-74.
Anagnostopoulos, C., et al., "Requirements for Transformation in Bacillus Subtilis", J Bacteriol. 81(5), May 1961, 741-6.
Anton, et al., "Sequencing and Overexpression of the *Escherichia coli* Aroe Gene Encoding Shikimate Dehydrogenase", Biochem J. Jan. 15, 1988;249(2):319-26.
Armstrong, S. M., et al., "Abiotic conversion of dihydrophloroglucinol to resorcinol", Canadian Journal of Microbiology. 39(9), 1993, 899-902.
Arthur, et al., "Contribution of VanY D,D-carboxypeptidase to glycopeptide resistance in Enterococcus faecalis by hydrolysis of peptidoglycan precursors", Antimicrob Agents Chemother. 38(9), Sep. 1994, 1899-1903.
Asano, et al., "A new enzymatic method of acrylamide production", Agricultural and Biological Chemistry. 46(5), 1982, 1183-1189.
Baek, Jong Hwan, et al., "Novel gene members in the Pho regulon of *Escherichia coli*", FEMS Microbiol Lett. 264(1), Nov. 2006, 104-9.
Bailey, James E., et al., "Biochemical Engineering Fundamentals", 2nd Ed. McGraw Hill, New York, entire book for purposes indicated and Chapter 9, 1986, 533-657.
Bailey, et al., "Inverse metabolic engineering: A strategy for directed genetic engineering of useful phenotypes", BBiotechnol Bioeng. 79(5), Sep. 5, 2002, 568-79.
Bailey, et al "Toward a science of metabolic engineering", Science;252(5013):, Jun. 21, 1991, 1668-75.
Barbin, et al., "Induction of specific base-pair substitutions in *E. coli* trpA mutants by chloroethylene oxide, a carcinogenic vinyl chloride metabolite", Mutat Res. Nov.-Dec. 1985;152(2-3):147-56.
Bastian, et al., "Engineered ketol-acid reductoisomerase and alcohol dehydrogenase enable anaerobic 2-methylpropan-l-ol production at theoretical yield in *Escherichia coli*", Metab Eng. May 2011;13(3):345-52.
Beguin, et al., "The biological degradation of cellulose", FEMS Microbiol Rev. Jan. 1994;13(1):25-58.
Beisson, Frederic, et al., "*Arabidopsis* Genes Involved in Acyl Lipid Metabolism. A 2003 Census of the Candidates, a Study of the Distribution of Expressed Sequence Tags in Organs, and a Web-Based Database", Plant Physiol. 132(2), Jun. 2003, 681-97.
Bellion, Edward, et al., "Methylamine Utilization in Yeast and Bacteria: Studies Using in vivo NMR", Micro b. Growth C1 Compd. (Int. Symp.) 7th Editors: Murrell, J. Collin: Kelly, Don P. Publisher: Intercept, Andover, UK, 1993, 415-32.
Ben-Aroya, Shay, et al., "Toward a Comprehensive Temperature-Sensitive Mutant Repository of the Essential Genes of *Saccharomyces cerevisiae*", Molecular Cell. 30, 2008, 248-258.
Bergler, et al., "Sequences of the envM gene and of two mutated alleles in *Escherichia coli*", J Gen Microbiol. Oct. 1992;38(10):2093-100.
Bergler, et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", Eur J Biochem. 242(3), Dec. 15, 1996, 689-94.
Bloch, et al., "Control mechanisms in the synthesis of saturated fatty acids", Annu Rev Biochem. 46, 1977, 263-98.

Bonner, et al., "A core catalytic domain of the TyrA protein family: arogenate dehydrogenase from Synechocystis", Biochem J. 382(Pt 1), Aug. 15, 2004, 279-91.
Bonner, William M., et al., "Purification and Properties of Fatty Acyl Thioesterase I from *Escherichia coli*", J Biol Chem. 247(10), Mar. 25, 1972, 3123-33.
Borgaro, Janine G., et al., "Substrate Recognition by B-Ketoacyl-ACP Synthases", Biochemistry. 50(49), Dec. 13, 2011, 10678-86.
Bowie, James U., et al., "Deciphering the Message in Protein Sequences: Tolerance to Amino Acid Substitutions", Science 247(4948), Mar. 16, 1990, 1306-10.
Bressler, et al., "Studies on the mechanism of fatty acid synthesis. XI. The product of the reaction and the role of sulfhydryl groups in the synthesis of fatty acids", J. Biol Chem. vol. 237, May 1962, 1441-1448.
Brock, Thomas D., "Biotechnology: A Textbook of Industrial Microbiology", Second Edition Sinauer Associates, Inc. Sunderland, Mass., 1989.
Brock, et al., "Naturally occurring adenines within mRNA coding sequences affect ribosome binding and expression in *Escherichia coli*", J Bacteriol. Jan. 2007;189(2):501-10. Epub Nov. 3, 2006.
Brosius, Jurgen, et al., "Spacing of the -10 and -35 Regions in the tac Promoter. Effect on its in vivo activity", J Biol Chem. 260(6), Mar. 25, 1985, 3539-41.
Broun, Pierre, et al., "Catalytic Plasticity of Fatty Acid Modification Enzymes Underlying Chemical Diversity of Plant Lipids", Science. 282(5392), Nov. 13, 1998, 1315-7.
Brown, et al., "Synthesis of labeled acrylamide and N-methylolacrylamide (NMA): 15N-acrylamide, 13C-NMA, 15N-NMA, and 13C,15N-NMA", Journal of labelled compounds & radiopharmaceuticals. 48(14):1031-1039., Nov. 14, 2005.
Brutlag, Douglas L., et al., "Improved sensitivity of biological sequence database searches", Comput Appl Biosei. 6(3), Mar. 25, 1990, 237-45.
Bunch, et al., "The IdhA gene encoding the fermentative lactate dehydrogenase of *Escherichia coli*", Microbiology. Jan. 1997;143 ( Pt 1):187-95.
Canada, et al., "Directed evolution of toluene ortho-monooxygenase for enhanced 1¬naphthol synthesis and chlorinated ethene degradation", J Bacteriol. Jan. 2002;184(2):344-9.
Chang, et al., "Acetate metabolism in a pta mutant of *Escherichia coli* W3110: importance of maintaining acetyl coenzyme A flux for growth and survival", J Bacteriol. Nov. 1999;181(21):6656-63.
Chao, et al., "Selective production of L-aspartic acid and L-phenylalanine by coupling reactions of aspartase and aminotransferase in *Escherichia coli*", Enzyme Microb Technol. 27(1-2), Jul. 1, 2000, 19-25.
Chica, Roberto A., et al., "Semi-rational approaches to engineering enzyme activity: combining the benefits of directed evolution and rational design", Curr Opin Biotechnol. 16(4), Aug. 2005, 378-84.
Cho, et al., "Simultaneous synthesis of enantiomerically pure (S)-amino acids and (R)¬amines using coupled transaminase reactions", Biotechnol Bioeng. Mar. 30, 2003;81(7):783-9.
Choi-Rhee, Eunjoo, et al., "The Biotin Carboxylase-Biotin Carboxyl Carrier Protein Complex of *Escherichia coli* Acetyl-CoA Carboxylase", J Biol Chem. 278(33), Aug. 15, 2003, 30806-12.
Chotani, et al., "The commercial production of chemicals using pathway engineering", Biochim Biophys Acta. Dec. 29, 2000;1543(2):434-455.
Cleusix, et al., "Inhibitory activity spectrum of reuterin produced by Lactobacillus reuteri against intestinal bacteria", BMC Microbiology, 7: 101, Nov. 12, 2007, 9 Pages.
Coleman, Rosalind A., et al., "Enzymes of triacylglycerol synthesis and their regulation", Prog Lipid Res. 43(2), Mar. 2004, 134-76.
Cowan, Peter J., et al., "Characterization of the Major Promoter for the Plasmid-Encoded Sucrose Genes scrY, scrA, and scrB", J Bacteriol. 173(23), Dec. 1991, 7464-70.
Crameri, et al., "DNA shuffling of a family of genes from diverse species accelerates directed evolution", Nature, Jan. 15, 1998;391(6664):288-91.
Cronan, et al., "Genetic and biochemical analyses of pantothenate biosynthesis in *Escherichia coli* and *Salmonella typhimurium*.", J Bacteriol. Mar. 1982;149(3):916-22.

(56) References Cited

OTHER PUBLICATIONS

Cronan, J.E , "Beta-Alanine Synthesis in *Escherichia coli*", J Bacteriol. Mar. 1980;141(3):1291-7.

Cronk , et al., "Cloning, crystallization and preliminary characterization of a beta-carbonic anhydrase from *Escherichia coli*", Acta Crystallogr D Biol Crystallogr. Sep. 2000;56(Pt 9):1176-9.

Daley, Daniel O., et al., "Global Topology Analysis of the *Escherichia coli* Inner Membrane Proteome", Science. 308(5726), May 27, 2005, 1321-3.

Daniel, Jaiyanth , et al., "Induction of a Novel Class of Diacylglycerol Acyltransferases and Triacylglycerol Accumulation in Mycobacterium tuberculosis as it Goes into a Dormancy-Like State in Culture", J Bacteriol. 186(15), Aug. 2004, 5017-30.

Daruwala , et al., "Menaquinone (vitamin K2) biosynthesis: overexpression, purification, and characterization of a new isochorismate synthase from *Escherichia coli*", J. Bacteriol. 179(10), May 1997, 3133-8.

Datsenko, Kirill A., et al., "One-step inactivation of chromosomal genes in *Escherichia coli* K-12 using PCR products", Proc Natl Acad Sci USA. 97(12), Jun. 6, 2000, 6640-5.

Datta, Simanti , et al., "A set of recombineering plasmids for gram-negative bacteria", Gene. 379, Sep. 1, 2006, 109-15.

Davis, Mark S., et al., "Overproduction of Acetyl-CoA Carboxylase Activity Increases the Rate of Fatty Acid Biosynthesis in *Escherichia coli*\*", the Journal of Biological Chemistry (2000), vol. 275, pp. 28593-28598, 2000, 28593-28598.

De Boer, Herman A., et al., "The tac promoter: A functional hybrid derived from the trp and lac promoters", Proc Natl Acad Sci USA. 80(1), Jan. 1983, 21-5.

De Mendoza , et al., "Thermal regulation of membrane lipid fluidity in bacteria", Trends Biochem. Sci. 1983; 8:49-52.

Dell'Aquila , et al., "Acid-base balance in peritoneal dialysis", J Nephrol. Mar.-Apr. 2006;19 Suppl 9:S104-7.

Dellomonaco , et al., "Engineered reversal of the β-oxidation cycle for the synthesis of fuels and chemicals", Nature Aug. 18, 2011, 476 (7360): 355-9.

Demmer, Ulrike , et al., "Structural Basis for a Bispecific NADP and CoA Binding Site in an Archaeal Malonyl-Coenzyme A Reductase", J Biol Chem. 288(9), Mar. 1, 1990, 6363-70.

Den , et al., "Enzymatic Conversion of l3-Hydroxypropionate to Malonic Semialdehyde\*", J Biol Chem Jul. 1959;234(7):1666-1671.

Denic , et al., "A Molecular Caliper Mechanism for Determining Very Long-Chain Fatty Acid Length", vol. 130, Issue 4, Aug. 24, 2007, Aug. 24, 2007, 663-377.

Deshpande, Mukund V., "Ethanol Production from Cellulose by Coupled Saccharification/Fermentation using *Saccharomyces cerevisiae* and Cellulase Complex from Sclerotium rolfsii UV-8 Mutant", Appl Biochem Biotechnol. 36(3), 1992, 227-34.

Devos, Damien , et al., "Practical Limits of Function Prediction", Proteins. 41(1), Oct. 1, 2000, 98-107.

Dewick, P. , "Chapter 4. The Shikimate Pathway: Aromatic Amino Acids and Phenylpropanoids", Medicinal Natural Products: A Biosynthetic Approach, Second Edition (2002): 121-166.

Diaz , et al., "Characterization of the hca cluster encoding the dioxygenolytic pathway for initial catabolism of 3-phenylpropionic acid in *Escherichia coli* K-12", J Bacteriol. Jun. 1998;180(11):2915-23.

Dittrich, Franziska , et al., "Fatty acid elongation in yeast. Biochemical characteristics of the enzyme system and isolation of elongation-defective mutants". Eur J Biochem. 252(3), Mar. 15, 1998, 477-85.

Dohr, Olaf , et al., "Engineering of a functional human NADH-dependent cytochrome P450 system", Proc Nati Acad Sci USA. 98(1), Jan. 2, 2001, 81-6.

Drake , et al., "Structure of the EntB Multidomain Nonribosomal Peptide Synthetase and Functional Analysis of Its Interaction with the EntE Adenylation Domain", Chem Biol. Apr. 2006;13(4):409-19.

Duncan , et al., "Lactate-utilizing bacteria, isolated from human feces, that produce butyrate as a major fermentation product", Appl Environ Microbiol. Oct. 2004;70(10):5810-7.

Duncan , et al., "The overexpression and complete amino acid sequence of *Escherichia coli* 3-dehydroquinase", Biochem J. Sep. 1, 1986;238(2):475-83.

Elvin, Christopher M., et al., "Modified bacteriophage lambda promoter vectors for overproduction of proteins in *Escherichia coli*", Gene. 87(1), Mar. 1, 1990, 123-6.

Eppink, Michel H. M., et al., "Switch of Coenzyme Specificity of p-Hydroxybenzoate Hydroxylase", J Mol Biol. 292(1), Sep. 10, 1999, 87-96.

Epstein , et al., "Oil: A Life Cycle Analysis of its Health and Environmental Impacts", The Center for Health and the Global Environment, Harvard Medical School. Mar. 2002. www.med.harvard.edu/chge/oil.html.

Farmer , et al., "Improving lycopene production in *Escherichia coli* by engineering metabolic control", Nat Biotechnol. May 2000;18(5):533-7.

Felce, Jeremy , et al., "Carbonic Anhydrases Fused to Anion Transporters of the SulP Family Evidence for a Novel Type of Bicarbonate Transporter", J Mol Microbiol Biotechnol. 8(3), 2004, 169-76.

Fernando , et al., "Biorefineries: current status, challenges and future direction", Energ. Fuel. May 2006; 20:1727-1737.

Figge , "Methionine biosynthesis is *Escherichia coli* and Corynebacterium glutamicum", Microbiol Monogro. 2007; 5:163-193.

Fleming , et al., "Extracellular enzyme synthesis in a sporulation-deficient strain of Bacillus licheniformis", Appl Environ Microbiol, Nov. 1995, 61 (11):3775-3780.

Fodor , et al., "Light-Directed, Spatially Addressable Parallel Chemical Synthesis", Science. Feb. 15, 1991;251(4995):767-73.

Fowler, Zachary L., et al., "Increased Malonyl Coenzyme A Biosynthesis by Tuning the *Escherichia coli* Metabolic Network and Its Application to Flavanone Production", Appl Environ Microbiol. 75(18), Sep. 2009, 5831-9.

Freshney , "Culture of animal cells : a manual of basic technique", Journal of Chemical Technology and Biotechnology, 2nd Edition, 1987.

Fujimoto , et al., "pAM401-Based Shuttle Vectors That Enable Overexpression of Promoterless Genes and One-Step Purification of Tag Fusion Proteins Directly from Enterococcus faecalis", doi: 10.1128/AEM.67.3.1262-1267.2001 Appl. Environ. Microbiol. Mar. 2001 vol. 67 No. 3 1262-1267.

Funa , et al., "A novel quinone-forming monooxygenase family involved in modification of aromatic polyketides", J Biol Chem. Apr. 15, 2005;280(15):14514-23. Epub Feb. 8, 2005.

Gietz, R. Daniel , et al., "Transformation of Yeast by Lithium Acetate/Single-Stranded Carrier DNA/Polyethylene Glycol Method", Methods Enzymol, 350, 2002, 87-96.

Giladi , et al., "FoIM, a new chromosomally encoded dihydrofolate reductase in *Escherichia coli*.", J Bacteriol. 185(23), Dec. 2003, 7015-8.

Gilbert, Walter , et al., "Useful Proteins from Recombinant Bacteria", Sci Am. 242(4), Apr. 1980, 74-94.

Gill , et al., "Genome-wide screening for trait conferring genes using DNA microarrays", Proc Natl Acad Sci U S A. May 14, 2002;99(10):7033-8, Epub May 7, 2002.

Ginkel , et al., "Identification and cloning of the *Mycobacterium avium* folA gene, required for dihydrofolate reductase activity", FEMS Microbiology Letters. vol. 156, Issue 1, Nov. 1, 1997, 69-78.

Gokarn , et al., "Metabolic analysis of *Escherichia coli* in the presence and absence of the carboxylating enzymes phosphoenolpyruvate carboxylase and pyruvate carboxylase", Appl Environ Microbiol. May 2000;66(5):1844-50.

Goodwin , et al., "Purification and characterization of methylmalonate-semialdehyde dehydrogenase from rat liver. Identity to malonate-semialdehyde dehydrogenase", J Biol Chem. Sep. 5, 1989;264(25):14965-71.

Gray , et al., "Monofunctional chorismate mutase from Bacillus subtilis: purification of the protein, molecular cloning of the gene,

(56) References Cited

OTHER PUBLICATIONS and overexpression of the gene product in *Escherichia coli*", Biochemistry. Jan. 16, 1990;29(2):376-83.

Gronenborn, Bruno, "Overproduction of Phage Lambda Repressor under Control of the lac Promotor of *Escherichia coli*", Mol Gen Genet. 148(3), Nov. 17, 1976, 243-50.

Gulmezian, et al., "Genetic Evidence for an Interaction of the UbiG O-Methyltransferase with UbiX in *Escherichia coli* Coenzyme Q Biosynthesis", J Bacteriol. Sep. 2006;188(17):6435-9.

Guzman, L. M., et al., "Tight regulation, modulation, and high-level expression by vectors containing the arabinose PBAD promoter", J Bacteriol. 177(14), Jul. 1995, 4121-30.

Haldimann, Andreas, et al., "Use of New Methods for Construction of Tightly Regulated Arabinose and Rhamnose Promoter Fusions in Studies of the *Escherichia coli* Phosphate Regulon", J Bacteriol. 180(5), Mar. 1998, 1277-86.

Hall, Neil, et al., "Structure-function analysis of NADPH: nitrate reductase from Aspergillus nidulans: analysis of altered pyridine nucleotide specificity in vivo", Microbiology. 146 (Pt.6), Jun. 2000, 1399-406.

Hatzimanikatis, et al., "Exploring the diversity of complex metabolic networks", Bioinformatics. Apr. 15, 2005;21(8):1603-9. Epub Dec. 21, 2004.

He, et al., "A T42M Substitution in Bacterial 5-Enolpyruvylshikimate-3-phosphate Synthase (EPSPS) Generates Enzymes with Increased Resistance to Glyphosate", Biosci Biotechnol Biochem. vol. 67, 2003—Issue 6, 1405-1409.

Heath. Richard J., et al., "Enoyl-Acyl Carrier Protein Reductase (fabI) Plays a Determinant Role in Completing Cycles of Fatty Acid Elongation in *Escherichia coli*", J Biol Chem. 270(44), Nov. 3, 1995, 26538-42.

Henry, et al., "Discovery of novel routes for the biosynthesis of industrial chemicals: 3¬Hydroxypropanoate. Slides", AICHE Annual Meeting. Nov. 8, 2007. Salt Lake City, UT.

Herter, "Autotrophic CO2 Fixation by Chloroflexus aurantiacus: Study of Glyoxylate Formation and Assimilation via the 3-Hydroxypropionate Cycle", J Bacteriol Jul. 2001;183(14):4305-4316.

Hondorp, et al., "Oxidation of cysteine 645 of cobalamin-independent methionine synthase causes a methionine limitation in *Escherichia coli*", J Bacteriol. May 2009;191(10):3407-10. Epub Mar. 13, 2009.

Hugler, et al., "Malonyl-Coenzyme A Reductase from Chloroflexus aurantiacus, a Key Enzyme of the 3-Hydroxypropionate Cycle for Autotrophic CO2 Fixation", J Bacteriol May 2002;184(9):2404-2410.

Ikuo Miyahisa, et al., "Efficient production of (2S)-flavanones by *Escherichia coli* containing an artificial biosynthetic gene cluster", Applied Microbiology and Biotechnology, Springer, Berlin, DE, (Sep. 1, 2005), vol. 68, No. 4, doi:10.1007/S00253-005-1916-3, ISSN 1432-0614, pp. 498-504, XP019331939.

Ivanova, et al., "Genome sequence of Bacillus cereus and comparative analysis with Bacillus anthracis", Nature. May 1, 2003;423(6935):87-91.

James, Ethan S., et al., "Expression of two *Escherichia coli* acetyl-CoA carboxylase subunits is autoregulated", J Biol Chem. 279(4), Jan. 23, 2004, 2520-7.

Jan Podkowinski, et al., "Opinions Acetyl-coenzyme A carboxylase—an attractive enzyme for biotechnology", Biotechnologia, PL, (Jan. 1, 2011), vol. 4, doi:10.5114/bta.2011.46549, ISSN 0860-7796, pp. 321-335, XP055303418.

Jiang, et al., "Biosynthetic pathways for 3-hydroxypropionic acid production", Appl Microbio( Biotechnol. Apr. 2009;82(6):995-1003.

Jiang, et al., "Cloning and Expression of aroG Gene of *E. coli* and Its Co-expression with pheA and tyrB Genes. Sheng Wu Hua Xue Yu Sheng Wu Wu Li Xue Bao (Shanghai)", 1998;30(6):593-596. (in Chinese with English abstract).

Jing, et al., "Phylogenetic and experimental characterization of an acyl-ACP thioesterase family reveals significant diversity in enzymatic specificity and activity", BMC BiochemistryDec. 2011:44. https://doi.org/10.1186/1471-2091-12-44.

Joike, et al., "Amino acid substitutions affecting catalytic activity and subunit interactions of aminodeoxychorismate synthase in *E. coli*", Abstracts of the General Meeting of the American Society for Microbiology. 2002; 102:275-276, and 102nd General Meeting of the American Society for Microbiology; Salt Lake, UT, USA; May 19-23, 2002.

Juliano Alves, et al., "Cloning, expression, and enzymatic activity ofandacetyl-coenzyme A carboxylases", Analytical Biochemistry, Academic Press Inc, New York, vol. 417, No. 1, doi:10.1016/J.AB. 2011.05.041, ISSN 0003-2697, (May 25, 2011), pp. 103-111, (Jun. 1, 2011), XP028245778.

Kapol, et al., "Purification and characterization of 2-oxoglutarate decarboxylase of Leuconostoc oenos", Journal of General Microbiology 136 (1990), 1497-1499.

Katavic, Vesna, et al., "Alteration of Seed Fatty Acid Composition by an Ethyl Methanesulfonate-Induced Mutation in *Arabidopsis thaliana* Affecting Diacylglycerol Acyltransferase Activity", Plant Physiol. 108(1), May 1995, 399-409.

Katsuyama, Yohei, et al., "Production of curcuminoids by *Escherichia coli* carrying an artificial biosynthesis pathway", Microbiology. 154(Pt 9), Sep. 2008, 2620-8.

Kern, et al., "Engineering primary metabolic pathways of industrial micro-organisms", J Biotechnol. Mar. 30, 2007;129(1):6-29. Epub Dec. 2, 2006.

Kiatpapan, Pornpimon, et al., "Molecular Characterization of Lactobacillus plantarum Genes for B-Ketoacyl-Acyl Carrier Protein Synthase III (fabH) and Acetyl Coenzyme A Carboxylase (accBCDA), Which are Essential for Fatty Acid Biosynthesis", Appl Environ Microbiol. 67(1), Jan. 2001, 426-33.

Kim, Youngnyun, et al., "Construction of an *Escherichia coli* K-12 Mutant for Homoethanologenic Fermentation of Glucose or Xylose without Foreign Genes", Appl Environ Microbiol. 73(6), Mar. 2007, 1766-71.

Kim, Youngnyun, et al., "Dihydrolipoamide Dehydrogenase Mutation Alters the NADH Sensitivity of Pyruvate Dehydrogenase Complex of *Escherichia coli* K-12", J Bacteriol. 190(11), Jun. 2008, 3851-8.

Kim, et al., "Effect of Overexpression of Actinobacillus succinogenes Phosphoenolpyruvate Carboxykinase on Succinate Production in *Escherichia coli*", Appl. Environ. Microbiol. vol. 70 No. 2, Feb. 2004, 1238-1241.

Kim, Joong Kyun, et al., "Extractive Recovery of Products from Fermentation Broths", Biotechnol. Bioprocess Eng, 4, 1999, 1-11.

Kim, Kwang-Seo, et al., "The Rut Pathway for Pyrimidine Degradation: Novel Chemistry and Toxicity Problems", J Bacteriol. 192(16), Aug. 2010, 4089-102.

Kimchi-Sarfaty, et al., "A "Silent" Polymorphism in the MDR1 Gene Changes Substrate Specificity", Science. Science 315(5811):, Jan. 26, 2007, 525-8.

Kinney, Anthony J., "Manipulating flux through plant metabolic pathways", Curr Opin Plant Biol. 1(2), Apr. 1998, 173-8.

Kisselev, "Polypeptide Release Factors in Prokaryotes and Eukaryotes: Same Function, Different Structure", Structure. 10(1), Jan. 2002, 8-9.

Kizer, Lance, et al., "Application of Functional Genomics to Pathway Optimization for Increased Isoprenoid Production", Appl Environ Microbiol. 74(10), May 2008, 3229-41.

Kleerebezem, et al., "Controlled gene expression systems for lactic acid bacteria: transferable nisin-inducible expression cassettes for Lactococcus, Leuconostoc, and *Lactobacillus* spp", Appl Environ Microbiol. Nov. 1997;63(11):4581-4584.

Kleerebezem, et al., "The qmeA (ts) mutation of *Escherichia coli* is localized in the fabI gene, which encodes enoyl-ACP reductase.", Res Microbiol, 147(8), Oct. 1996, 609-13.

Kozliak, et al., "Expression of proteins encoded by the *Escherichia coli* cyn operon: carbon dioxide-enhanced degradation of carbonic anhydrase", J Bacteriol. 176(18), Sep. 1994, 5711-7.

Kozliak, et al., "Role of bicarbonate/CO2 in the inhibition of *Escherichia coli* growth by cyanate", J. Bacteriol. vol. 177 No. 11, Jun. 1995, 3213-3219.

(56) References Cited

OTHER PUBLICATIONS

Kroeger, Jasmin K., et al., "A spectrophotometric assay for measuring acetyl-coenzyme A carboxylase", Anal Biochem. 411(1), Apr. 1, 2011, 100-5.
Kunin, et al., "A comparative analysis of the inventive step standard in the European and Japanese patent office from an US perspective", IP Litigator, Jan./Feb. 2008, 15-23.
Machado, et al., "A selection platform for carbon chain elongation using the CoA-dependent pathway to produce linear higher alchols", Metabolic Eng. 2012, 14, 504-11.
Okamura, et al., "Unprecedented acetoacetyl-coenzyme A synthesizing enzyme of thiolase superfamily involved in the mevalonate pathway", Proc. Natl. Acad. Sci. USA, 2010, 107, 11265-70.

\* cited by examiner

Plasmids:

Origin (copy number at 30C)
pBBR1 (15-20)
pBWT4, pBWM4
pSC101 (5)
pSC101
pSC101ts (RepA-A56V) (pKD46, pRed/pJ08)
P15 (15-20)
pACYC, pJZ4,
pMB1* (2C-2C, >200 at 37°C)
pUC, pCR4Blunt, pJ240
pMB1Co E1 (15-20)
pET, pITC, pFR322
ClonEF1 (20-40, ~50 at 37°C)
pCDF-Duet
RSF1030 (>100)
pRSF-Duet

Plasmid Selection:

Antibiotic
Amp/Carb
Kan
Cam
Tet
Strp
Bsd
Zeo

Non-antibiotic
ccdAB
gatA
CbSyr

Other Modules
Recombination Sites
FRT
oxP

Promoters:

Regulated
Phosphate
PgstH
PyibD
ProDpac
ProCpax

IPTO
PT7
PTrc
Plac

Temperature
Lambda repressor

Constitutive
PT5-a3
PT5-p11
PT5-max
Ptha
Ppia
Pspnc (PproA-0)
Pkan
PgapA
Library Designs

RBS
Many

Transcriptional terminators
rrnBTT2
tonE
sorR
BioBrick TT

FIG. 8

SEQUENCE LISTING

<160> NUMBER OF SEQ ID NOS: 120

<210> SEQ ID NO 1
<211> LENGTH: 317
<212> TYPE: PRT
<213> ORGANISM: Halomonas elongata

<400> SEQUENCE: 1

Met Asn Pro Asn Tyr Leu Asp Phe Glu Gln Pro Ile Ala Glu Leu Gln
1               5                   10                  15

Ala Lys Ile Glu Glu Leu Arg Met Val Gly Asn Asp Ser Gln Val Asn
            20                  25                  30

Leu Ser Asp Glu Ile Gly Arg Leu Glu Glu Lys Ser Arg Lys Leu Thr
        35                  40                  45

Glu Ser Ile Phe Lys Asp Leu Ser Ala Trp Gln Val Ser Gln Leu Ser
50                  55                  60

Arg His Pro Gln Arg Pro Tyr Thr Leu Asp Tyr Leu Glu His Val Phe
65                  70                  75                  80

Thr Asp Phe Asp Glu Leu His Gly Asp Arg Arg Phe Ala Asp Asp Ala
                85                  90                  95

Ala Ile Val Gly Gly Val Ala Arg Leu Asp Asp Lys Pro Val Met Val
            100                 105                 110

Ile Gly His Gln Lys Gly Arg Asp Val His Glu Lys Val Arg Arg Asn
        115                 120                 125

Phe Gly Met Pro Arg Pro Glu Gly Tyr Arg Lys Ala Cys Arg Leu Met
130                 135                 140

Glu Met Ala Glu Arg Phe His Met Pro Val Leu Thr Phe Ile Asp Thr
145                 150                 155                 160

Pro Gly Ala Tyr Pro Gly Ile Asp Ala Glu Glu Arg Gly Gln Ser Glu
                165                 170                 175

Ala Ile Ala Tyr Asn Leu Gly Val Met Ser Arg Leu Lys Thr Pro Ile
            180                 185                 190

Ile Ser Thr Val Val Gly Glu Gly Gly Ser Gly Gly Ala Leu Ala Ile
        195                 200                 205

Gly Val Cys Asp Glu Leu Ala Met Leu Gln Tyr Ser Thr Tyr Ser Val
210                 215                 220

Ile Ser Pro Glu Gly Cys Ala Ser Ile Leu Trp Lys Ser Ala Asp Lys
225                 230                 235                 240

Ala Ser Glu Ala Ala Gln Ala Met Gly Ile Thr Ala Glu Arg Leu Lys
                245                 250                 255

Glu Leu Gly Phe Val Asp Thr Leu Ile Pro Glu Pro Leu Gly Gly Ala
            260                 265                 270

His Arg Gln Pro Ser Ala Thr Ala Glu Arg Ile Lys Thr Ala Leu Leu
        275                 280                 285

Glu Ser Leu Asp Arg Leu Glu Thr Met Glu Thr Asp Ala Leu Leu Glu
290                 295                 300

Arg Arg Tyr Glu Arg Leu Met Ser Tyr Gly Ala Pro Val
305                 310                 315

<210> SEQ ID NO 2
<211> LENGTH: 954
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgaatccga actatctgga ctttgaacaa ccgatcgctg aactgcaagc caaaatcgaa     60
gaactgcgta tggtgggcaa cgactcacag gtgaacctgt ctgatgaaat tggccgtctg    120
gaagaaaaaa gtcgcaaact gaccgaatcc atctttaaag acctgtcagc gtggcaagtt    180
agccaactgt ctcgtcatcc gcaacgcccg tataccctgg attacctgga acatgtcttt    240

```
acggatttcg acgaactgca cggtgaccgt cgctttgcag atgacgcggc cattgttggc      300
ggtgtcgctc gtctggatga caaaccggtc atggtgatcg ccatcagaa  aggtcgtgat      360 gtgcacgaaa aagttcgtcg caacttcggc atgccgcgcc cggaaggtta tcgtaaagcg      420
tgccgcctga tggaaatggc cgaacgcttt cacatgccgg tgctgacctt cattgatacg      480
ccgggcgcat atccgggtat cgacgctgaa gaacgtggcc aaagcgaagc gattgcctac      540
aatctgggtg ttatgtcgcg cctgaaaacc ccgattatca gcacggtggt ggcgaaggc       600 ggttctggcg gtgcactggc tatcggtgtc tgcgatgaac tggcgatgct gcaatatagt      660
acctactccg tgatttcacc ggaaggctgt gcctcgatcc tgtggaaaag cgcagataaa      720
gcttctgaag cagctcaagc gatgggcatt accgccgaac gtctgaaaga actgggtttc      780
gttgacacgc tgatcccgga accgctgggc ggtgcacatc gtcagccgag tgcgaccgcc      840
gaacgcatta aaacggccct gctggaaagc ctggatcgcc tggaaacgat ggaaacggat      900
gccctgctgg aacgccgcta tgaacgcctg atgtcttacg gtgccccggt ctga            954

<210> SEQ ID NO 3
<211> LENGTH: 155
<212> TYPE: PRT
<213> ORGANISM: Halomonas elongata

<400> SEQUENCE: 3

Met Asp Ile Arg Lys Val Lys Lys Leu Ile Glu Leu Leu Glu Glu Ser
1               5                   10                  15

Asn Ile Ser Glu Ile Glu Ile Gln Glu Gly Glu Glu Ser Val Arg Ile
            20                  25                  30

Ser Arg His Pro Asn Gly Thr Glu His Pro Gln Pro Ala Ala Pro Ala
        35                  40                  45

Trp Pro Ala Thr Ala Ala Ala Pro Ala Pro Gln Pro Ala Ala Ala Pro
    50                  55                  60

Val Glu Ser Pro Ala Glu Val Asp Glu Gly Pro Ala Tyr Gln Gly Gln
65                  70                  75                  80

Pro Ile Val Ser Pro Met Val Gly Thr Phe Tyr Arg Ala Pro Ala Pro
                85                  90                  95

Gly Ala Lys Ala Phe Val Glu Leu Gly Gln Ser Val Lys Lys Gly Glu
            100                 105                 110

Thr Val Cys Ile Val Glu Ala Met Lys Met Met Asn Gln Ile Glu Ala
        115                 120                 125

Asp Arg Asp Gly Val Val Glu Ala Ile Leu Val Glu Asp Gly Glu Pro
    130                 135                 140

Val Glu Phe Glu Gln Pro Met Val Val Ile Ser
145                 150                 155

<210> SEQ ID NO 4
<211> LENGTH: 468
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atggacatcc gcaaagtgaa aaaactgatc gaactgctgg aagaaagtaa catctctgaa       60
attgaaatcc aagaaggcga agaaagcgtg cgtattagtc gccatccgaa cggcaccgaa      120
cacccgcagc cggcggcacc ggcatggccg gccacggcag ctgcgccggc gccgcaaccg      180
```

```
gccgcagctc cggtggaaag cccggcagaa gttgatgaag ccccggctta tcagggtcaa    240
ccgatcgttt ctccgatggt cggcaccttt taccgtgcgc cggcaccggg tgcaaaagct    300
ttcgtcgaac tgggccagag cgttaaaaaa ggtgaaacgg tctgcattgt ggaagccatg    360
aaaatgatga atcaaatcga agccgatcgc gacggtgtgg ttgaagcaat cctggtggaa    420
gatggtgaac cggtggaatt tgaacagccg atggtggtga ttagttaa                468
```

<210> SEQ ID NO 5
<211> LENGTH: 446
<212> TYPE: PRT
<213> ORGANISM: Halomonas elongata
<400> SEQUENCE: 5

```
Met Leu Asp Lys Val Leu Ile Ala Asn Arg Gly Glu Ile Ala Leu Arg
1               5                   10                  15

Ile Leu Arg Ala Cys Lys Glu Leu Gly Ile Arg Thr Val Ala Val His
            20                  25                  30

Ser Lys Ala Asp Arg Glu Leu Met His Val Arg Leu Ala Asp Glu Ala
        35                  40                  45

Val Cys Ile Gly Pro Ala Ser Ser Ala Gln Ser Tyr Leu Asn Ile Pro
    50                  55                  60

Ala Leu Ile Ser Ala Ala Glu Val Thr Asp Thr Ser Ala Ile His Pro
65                  70                  75                  80

Gly Tyr Gly Phe Leu Ser Glu Asn Ala Asp Phe Ala Glu Gln Val Glu
                85                  90                  95

Arg Ser Gly Phe Thr Phe Ile Gly Pro Ser Ala Glu Thr Ile Arg Leu
            100                 105                 110

Met Gly Asp Lys Val Ser Ala Ile Asn Ala Met Lys Glu Ala Gly Val
        115                 120                 125

Pro Thr Val Pro Gly Ser Asn Gly Pro Leu Gly Asp Asp Glu Gly Glu
    130                 135                 140

Ile Leu Ala Thr Ala Arg Arg Ile Gly Tyr Pro Val Ile Ile Lys Ala
145                 150                 155                 160

Ala Ala Gly Gly Gly Gly Arg Gly Met Arg Val Val His Ala Glu Gly
                165                 170                 175

His Leu Leu Ser Ala Val Asn Val Thr Arg Thr Glu Ala His Ser Ser
            180                 185                 190

Phe Gly Asp Gly Thr Val Tyr Met Glu Lys Phe Leu Glu Asn Pro Arg
        195                 200                 205

His Val Glu Val Gln Val Leu Ala Asp Gly Gln Gly Asn Ala Ile His
    210                 215                 220

Leu Tyr Asp Arg Asp Cys Ser Leu Gln Arg Arg His Gln Lys Val Leu
225                 230                 235                 240

Glu Glu Ala Pro Ala Pro Gly Leu Asp Gln Gln Ala Arg Glu Gln Val
                245                 250                 255

Phe Lys Ala Cys Arg Asp Ala Cys Val Lys Ile Gly Tyr Arg Gly Ala
            260                 265                 270

Gly Thr Phe Glu Phe Leu Tyr Glu Asn Gly Glu Phe Phe Phe Ile Glu
        275                 280                 285

Met Asn Thr Arg Val Gln Val Glu His Pro Val Thr Glu Met Val Thr
    290                 295                 300

Gly Val Asp Ile Val Arg Glu Gln Leu Arg Ile Ala Ser Gly Leu Pro
305                 310                 315                 320
```

```
Leu Ser Ile Arg Gln Glu Asp Val Glu Leu Ser Gly His Ala Phe Glu
            325                 330                 335

Cys Arg Ile Asn Ala Glu Asp Ser Arg Thr Phe Met Pro Ser Pro Gly
            340                 345                 350

Arg Val Thr Leu Tyr His Pro Pro Gly Gly Leu Gly Val Arg Met Asp
            355                 360                 365

Ser His Val Tyr Thr Gly Tyr Thr Val Pro Pro His Tyr Asp Ser Leu
            370                 375                 380

Ile Gly Lys Leu Ile Thr Trp Gly Asp Asp Arg Glu Thr Ala Leu Ile
385                 390                 395                 400

Arg Met Arg Asn Ala Leu Asp Glu Leu Val Glu Gly Ile Lys Thr
            405                 410                 415

Asn Thr Asp Leu His Lys Asp Leu Val Arg Asp Gly Tyr Phe Gln Gln
            420                 425                 430

Gly Gly Val Asn Ile His Tyr Leu Glu Lys Lys Leu Gly Leu
            435                 440                 445

<210> SEQ ID NO 6
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgctggaca aagtgctgat tgcgaatcgt ggcgaaattg cgctgcgtat cctgcgtgcg      60
tgtaaagaac tgggtatccg taccgtcgct gttcattcaa aagcggaccg tgaactgatg     120
cacgtccgcc tggccgatga agcagtgtgc attggtccgg ctagctctgc gcagtcgtat     180
ctgaacattc cggcactgat cagtgcggcc gaagtgaccg acacgtccgc gatccatccg     240
ggctacggtt tcctgagcga aaatgccgat tttgcagaac aagtcgaacg ttcaggtttc     300
acctttattg gcccgtcggc cgaaacgatc cgcctgatgg gtgataaagt tagtgctatt     360
aacgcgatga agaagcagg cgtgccgacc gttccgggtt ccaatggtcc gctgggtgat     420
gacgaaggtg aaattctggc caccgcacgt cgcatcggct atccggttat tatcaaagca     480
gctgcgggcg gtggcggtcg tggtatgcgt gtggttcatg ctgaaggcca cctgctgagc     540
gcggtcaacg tgacccgtac ggaagcgcat agttccttcg cgatggcac cgtttatatg     600 gaaaaatttc tggaaaaccc gcgtcacgtt gaagtccagg tgctggccga tggccagggt     660
aatgcaattc atctgtacga tcgcgactgc tctctgcaac gtcgccacca aaaagtgctg     720
gaagaagctc cggcaccggg tctggaccag caagcacgtg aacaggtttt taaagcctgc     780
cgcgatgcat gtgtcaaaat tggttatcgt ggcgcgggca ccttcgaatt ctgtacgaa     840 aacggcgaat ttttcttat cgaaatgaat acgcgcgttc aggtcgaaca tccggtgacc     900
gaaatggtca cgggtgtgga tattgttcgt gaacagctgc gtatcgcatc aggtctgccg     960
ctgtcgattc gccaagaaga cgttgaactg agcggtcatg ccttcgaatg tcgtatcaat    1020
gcagaagata ccgccacctt tatgccgtct ccgggtcgtg tcacgctgta tcacccgccg    1080
ggcggtctgg gtgtccgtat ggacagccat gtgtataccg gctacacggt tccgccgcac    1140
tacgattctc tgattggtaa actgatcacc tggggcgatg accgtgaaac ggctctgatt    1200
cgtatgcgca acgccctgga tgaactgctg gttgaaggca tcaaaaccaa tacggatctg    1260
cacaaagacc tggttcgcga tggctacttt cagcaaggcg gtgtcaacat tcactacctg    1320
```
gaaaaaaaac tgggtctgta a                                                          1341

<210> SEQ ID NO 7
<211> LENGTH: 346
<212> TYPE: PRT
<213> ORGANISM: Halomonas elongata

<400> SEQUENCE: 7

Met Ser Trp Leu Asp Lys Ile Val Pro Ser Gly Arg Ile Gln Arg
1               5                   10                  15

Lys Glu Arg Arg Thr Ser Val Pro Asp Gly Leu Trp Arg Lys Cys Pro
                20                  25                  30

Lys Cys Glu Ser Val Leu Tyr Leu Pro Glu Leu Glu Lys His His Asn
            35                  40                  45

Val Cys Pro Lys Cys Asp His His Leu Arg Leu Thr Ala Arg Lys Arg
        50                  55                  60

Leu Asp Trp Phe Leu Asp Lys Glu Gly Arg Glu Ile Ala Ala Asp
65                  70                  75                  80

Leu Glu Pro Val Asp Arg Leu Lys Phe Arg Asp Ser Lys Tyr Lys
                85                  90                  95

Asp Arg Leu Ser Ala Ala Gln Lys Ala Thr Gly Glu Lys Asp Gly Leu
            100                 105                 110

Val Ala Met Arg Gly Thr Leu Glu Gly Leu Pro Val Val Ala Val Ala
        115                 120                 125

Phe Glu Phe Thr Phe Met Gly Gly Ser Met Gly Ala Val Val Gly Glu
130                 135                 140

Lys Phe Val Arg Ala Ala Thr Gln Ala Leu Asp Glu Gly Val Pro Leu
145                 150                 155                 160

Val Cys Phe Ser Ala Ser Gly Gly Ala Arg Met Gln Glu Ala Leu Phe
                165                 170                 175

Ser Leu Met Gln Met Ala Lys Thr Ser Ala Ala Leu Glu Lys Leu Lys
            180                 185                 190

Gln Ala Gly Val Pro Tyr Ile Ser Val Leu Thr Asp Pro Val Phe Gly
        195                 200                 205

Gly Val Ser Ala Ser Leu Ala Met Leu Gly Asp Leu Asn Ile Ala Glu
    210                 215                 220

Pro Asn Ala Leu Ile Gly Phe Ala Gly Pro Arg Val Ile Glu Gln Thr
225                 230                 235                 240

Val Arg Glu Gln Leu Pro Glu Gly Phe Gln Arg Ser Glu Phe Leu Leu
                245                 250                 255

Glu His Gly Ala Val Asp Met Ile Val His Arg Gln Ile Arg Glu
            260                 265                 270

Arg Leu Gly Gly Val Leu Arg Lys Leu Thr His Gln Pro Ala Ser Gly
        275                 280                 285

Pro Ala Val Val Glu Asn Asp Glu Pro Asp Leu Val Asp Ala Ala Glu
    290                 295                 300

Gln Ala Glu Pro Gln Pro Glu Ala Pro Glu Ala Val Glu Thr Ser Glu
305                 310                 315                 320

Ser Glu Ala Pro Thr Glu Lys Gly Val Glu Ala Asp Ser Glu Glu Thr
                325                 330                 335

Asp Glu Ser Pro Arg Ser Gly Asp Asn Arg
            340                 345

<210> SEQ ID NO 8
<211> LENGTH: 1041

<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 8

```
atgtcttggt tagataaaat cgtcccgtca gtgggtcgca ttcaacgcaa agaacgtcgc    60
acctcggtcc cggatggtct gtggcgtaaa tgcccgaaat gtgaatcagt tctgtatctg   120
ccggaactgg aaaaacatca aacgtctgc ccgaaatgtg atcatccct gcgtctgacc    180
gcgcgtaaac gcctggactg gttcctggat aaagaaggcc gcgaagaaat tgcggccgac   240
ctggaaccgg tggatcgtct gaaatttcgc gacagcaaaa aatacaaaga tcgtctgagc   300
gcggcgcaga agcaaccggt gaaaaagac ggtctggtgg ccatgcgtgg cacgctggaa    360
ggtctgccgg tggttgcagt tgctttgaa tttacctta tgggcggtag catgggcgca    420
gtcgtgggtg aaaaattcgt tcgtgcggcc acgcaggctc tggatgaagg tgtgccgctg   480
gtttgcttca gcgcatctgg cggtgcccgc atgcaggaag cactgtttag tctgatgcaa   540
atggctaaaa cctccgcagc tctggaaaaa ctgaacagg cgggcgtgcc gtatatttct    600
gttctgacgg acccggtctt cggcggtgtg agtgcgtccc tggccatgct gggtgatctg   660
aacattgcag aaccgaatgc tctgatcggc tttgcgggtc gcgtgtcat cgaacagacc    720
gtgcgcgaac aactgccgga aggcttccag cgttcagaat ttctgctgga acatggtgcc   780
gttgatatga ttgtccaccg tcagcaaatc cgtgaacgcc tgggcggtgt gctgcgcaaa   840
ctgacgcatc aaccggcatc gggtccggcc gttgtcgaaa atgatgaacc ggacctggtc   900
gatgcggccg aacaggcaga accgcaaccg gaagcaccgg aagctgttga acctcagaa    960
tcggaagcac cgacggaaaa aggcgtggaa gcagactcgg aagaaacgga tgaatcaccg  1020
cgctcaggcg acaaccgcta a                                             1041
```

<210> SEQ ID NO 9
<211> LENGTH: 604
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 9

```
Met Leu Asp Lys Ile Val Ile Ala Asn Arg Gly Glu Ile Ala Leu Arg
1               5                   10                  15

Ile Leu Arg Ala Cys Lys Glu Leu Gly Ile Lys Thr Val Ala Val His
            20                  25                  30

Ser Ser Ala Asp Arg Asp Leu Lys His Val Leu Leu Ala Asp Glu Thr
        35                  40                  45

Val Cys Ile Gly Pro Ala Pro Ser Val Lys Ser Tyr Leu Asn Ile Pro
    50                  55                  60

Ala Ile Ile Ser Ala Ala Glu Ile Thr Gly Ala Val Ala Ile His Pro
65                  70                  75                  80

Gly Tyr Gly Phe Leu Ser Glu Asn Ala Asn Phe Ala Glu Gln Val Glu
                85                  90                  95

Arg Ser Gly Phe Ile Phe Ile Gly Pro Lys Ala Glu Thr Ile Arg Leu
            100                 105                 110

Met Gly Asp Lys Val Ser Ala Ile Ala Ala Met Lys Lys Ala Gly Val
        115                 120                 125
```

```
Pro Cys Val Pro Gly Ser Asp Gly Pro Leu Gly Asp Met Asp Lys
    130                 135             140

Asn Arg Ala Ile Ala Lys Arg Ile Gly Tyr Pro Val Ile Ile Lys Ala
145                 150                 155                 160

Ser Gly Gly Gly Gly Arg Gly Met Arg Val Val Arg Gly Asp Ala
                165                 170                 175

Glu Leu Ala Gln Ser Ile Ser Met Thr Arg Ala Glu Ala Lys Ala Ala
                180                 185                 190

Phe Ser Asn Asp Met Val Tyr Met Glu Lys Tyr Leu Glu Asn Pro Arg
            195                 200                 205

His Val Glu Ile Gln Val Leu Ala Asp Gly Gln Gly Asn Ala Ile Tyr
    210                 215                 220

Leu Ala Glu Arg Asp Cys Ser Met Gln Arg Arg His Gln Lys Val Val
225                 230                 235                 240

Glu Glu Ala Pro Ala Pro Gly Ile Thr Pro Glu Leu Arg Arg Tyr Ile
                245                 250                 255

Gly Glu Arg Cys Ala Lys Ala Cys Val Asp Ile Gly Tyr Arg Gly Ala
                260                 265                 270

Gly Thr Phe Glu Phe Leu Phe Glu Asn Gly Glu Phe Tyr Phe Ile Glu
            275                 280                 285

Met Asn Thr Arg Ile Gln Val Glu His Pro Val Thr Glu Met Ile Thr
    290                 295                 300

Gly Val Asp Leu Ile Lys Glu Gln Leu Arg Ile Ala Ala Gly Gln Pro
305                 310                 315                 320

Leu Ser Ile Lys Gln Glu Glu Val His Val Arg Gly His Ala Val Glu
                325                 330                 335

Cys Arg Ile Asn Ala Glu Asp Pro Asn Thr Phe Leu Pro Ser Pro Gly
                340                 345                 350

Lys Ile Thr Arg Phe His Ala Pro Gly Gly Phe Gly Val Arg Trp Glu
            355                 360                 365

Ser His Ile Tyr Ala Gly Tyr Thr Val Pro Pro Tyr Tyr Asp Ser Met
    370                 375                 380

Ile Gly Lys Leu Ile Cys Tyr Gly Glu Asn Arg Asp Val Ala Ile Ala
385                 390                 395                 400

Arg Met Lys Asn Ala Leu Gln Glu Leu Ile Ile Asp Gly Ile Lys Thr
                405                 410                 415

Asn Val Asp Leu Gln Ile Arg Ile Met Asn Asp Glu Asn Phe Gln His
                420                 425                 430

Gly Gly Thr Asn Ile His Tyr Leu Glu Lys Lys Leu Gly Leu Gln Glu
            435                 440                 445

Lys Asp Ile Arg Lys Ile Lys Lys Leu Ile Glu Leu Val Glu Glu Ser
    450                 455                 460

Gly Ile Ser Glu Leu Glu Ile Ser Glu Gly Glu Ser Val Arg Ile
465                 470                 475                 480

Ser Arg Ala Ala Pro Ala Ala Ser Phe Pro Val Met Gln Gln Ala Tyr
                485                 490                 495

Ala Ala Pro Met Met Gln Gln Pro Ala Gln Ser Asn Ala Ala Ala Pro
            500                 505                 510

Ala Thr Val Pro Ser Met Glu Ala Pro Ala Ala Glu Ile Ser Gly
            515                 520                 525

His Ile Val Arg Ser Pro Met Val Gly Thr Phe Tyr Arg Thr Pro Ser
    530                 535                 540

Pro Asp Ala Lys Ala Phe Ile Glu Val Gly Gln Lys Val Asn Val Gly
```

Asp Thr Leu Cys Ile Val Glu Ala Met Lys Met Met Asn Gln Ile Glu
545                 550                 555                 560

Ala Asp Lys Ser Gly Thr Val Lys Ala Ile Leu Val Glu Ser Gly Gln
                565                 570                 575

Pro Val Glu Phe Asp Glu Pro Leu Val Val Ile Glu
        580                 585                 590

<210> SEQ ID NO 10
<211> LENGTH: 1815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | |
|---|---|
| atgctggaca agatcgtcat cgccaaccgc ggcgaaatcg ccctgcgcat cttgcgcgcg | 60 |
| tgtaaagagc tgggcattaa gactgttgcc gtgcattcca gcgcagaccg cgacctgaag | 120 |
| catgttctgc tggccgacga acggtttgc atcggtccgg caccgagcgt gaaaagctat | 180 |
| ctgaacatcc cggccatcat ctctgcggca gagatcaccg gtgcagtggc gattcatccg | 240 |
| ggctacggtt tcctgagcga gaacgctaac tttgctgaac aagtggagcg tagcggtttc | 300 |
| atcttcattg gccctaaggc ggagacgatt cgcctgatgg cgacaaagt gagcgccatt | 360 |
| gcagcgatga aaaaggccgg tgtgccgtgt gttccgggca gcgatggtcc gctgggtgac | 420 |
| gatatggaca gaaccgtgc catcgctaaa cgtattggct acccggtcat tatcaaagcc | 480 |
| tctggtggtg gcggtggccg tggtatgcgt gtcgtccgtg gtgatgcgga actggcgcaa | 540 |
| agcatcagca tgacccgtgc ggaagccaaa gcggcgttct ctaacgatat ggtgtatatg | 600 |
| gagaagtatc tggagaatcc gcgccacgtt gaaatccaag ttctggcgga tggtcagggc | 660 |
| aatgcgatct acttggcaga acgtgattgc tccatgcaac gccgtcatca gaaggtggtg | 720 |
| gaagaggcac cggctccggg tattacgccg gaactgcgtc gctacatcgg tgagcgctgt | 780 |
| gcgaaagcgt gtgtggacat tggttaccgt ggtgcgggta cgtttgagtt cctgttcgaa | 840 |
| aatggtgagt tttacttcat gaaatgaat accgcatcc aggttgagca cccggtgacc | 900 |
| gagatgatta ctggcgttga tctgatcaaa gagcaactgc gcattgcggc tggtcagccg | 960 |
| ctgtcgatca gcaagaaga ggtgcacgtt cgtggtcacg cggtcgagtg ccgtatcaat | 1020 |
| gcggaggacc cgaatacctt tctgccgagc cctggtaaga tcactcgttt tcacgcgcca | 1080 |
| ggtggttttg gcgttcgttg ggagtctcac atctacgccg gttacaccgt gccgccgtac | 1140 |
| tatgacagca tgattggtaa actgatctgc tatggcgaaa tcgtgatgt cgcgatcgcc | 1200 |
| cgcatgaaaa acgcgctgca agagctgatc attgatggca ttaagaccaa tgtggatttg | 1260 |
| cagatccgca ttatgaacga cgagaatttc cagcacggcg gtacgaacat tcactacctg | 1320 |
| gaaaagaaac tgggcctgca agagaaagac atccgcaaga tcaagaagct gatcgaactg | 1380 |
| gtggaagagt ctggcatcag cgagctggag atcagcgaag gtgaagagag cgtccgtatt | 1440 |
| tcccgtgcgg caccggcagc gagctttccg gttatgcagc aagcatacgc cgctccgatg | 1500 |
| atgcaacagc cggcacagag caacgccgct gcaccggcga ccgttccaag catggaggca | 1560 |
| ccggcagcgg ccgagatttc gggtcatatc gtgcgtagcc cgatggtggg caccttctat | 1620 |
| cgcacgccgt cgccggacgc aaaagccttc atcgaagtcg ccagaaggt caatgtcggc | 1680 |
| gacacgctgt gtatcgttga ggcaatgaaa atgatgaacc agattgaagc ggataagagc | 1740 |

```
ggtactgtta aagcgatcct ggtggaatcc ggccagcctg ttgagttcga tgaaccgctg    1800
gttgtgatcg agtaa                                                    1815
```

<210> SEQ ID NO 11
<211> LENGTH: 647
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Ser Trp Ile Glu Arg Ile Lys Ser Asn Ile Thr Pro Thr Arg Lys
1               5                   10                  15

Ala Ser Ile Pro Glu Gly Val Trp Thr Lys Cys Asp Ser Cys Gly Gln
            20                  25                  30

Val Leu Tyr Arg Ala Glu Leu Glu Arg Asn Leu Glu Val Cys Pro Lys
        35                  40                  45

Cys Asp His His Met Arg Met Thr Ala Arg Asn Arg Leu His Ser Leu
    50                  55                  60

Leu Asp Glu Gly Ser Leu Val Glu Leu Gly Ser Glu Leu Glu Pro Lys
65                  70                  75                  80

Asp Val Leu Lys Phe Arg Asp Ser Lys Lys Tyr Lys Asp Arg Leu Ala
                85                  90                  95

Ser Ala Gln Lys Glu Thr Gly Glu Lys Asp Ala Leu Val Val Met Lys
            100                 105                 110

Gly Thr Leu Tyr Gly Met Pro Val Val Ala Ala Ala Phe Glu Phe Ala
        115                 120                 125

Phe Met Gly Gly Ser Met Gly Ser Val Val Gly Ala Arg Phe Val Arg
    130                 135                 140

Ala Val Glu Gln Ala Leu Glu Asp Asn Cys Pro Leu Ile Cys Phe Ser
145                 150                 155                 160

Ala Ser Gly Gly Ala Arg Met Gln Glu Ala Leu Met Ser Leu Met Gln
                165                 170                 175

Met Ala Lys Thr Ser Ala Ala Leu Ala Lys Met Gln Glu Arg Gly Leu
            180                 185                 190

Pro Tyr Ile Ser Val Leu Thr Asp Pro Thr Met Gly Gly Val Ser Ala
        195                 200                 205

Ser Phe Ala Met Leu Gly Asp Leu Asn Ile Ala Glu Pro Lys Ala Leu
    210                 215                 220

Ile Gly Phe Ala Gly Pro Arg Val Ile Glu Gln Thr Val Arg Glu Lys
225                 230                 235                 240

Leu Pro Pro Gly Phe Gln Arg Ser Glu Phe Leu Ile Glu Lys Gly Ala
                245                 250                 255

Ile Asp Met Ile Val Arg Arg Pro Glu Met Arg Leu Lys Leu Ala Ser
            260                 265                 270

Ile Leu Ala Lys Leu Met Asn Leu Pro Ala Pro Asn Pro Glu Ala Pro
        275                 280                 285

Arg Glu Gly Val Val Val Pro Pro Val Pro Asp Gln Glu Pro Glu Ala
    290                 295                 300

Leu Ser Gly Gly Gly Gly Ser Gly Gly Gly Ser Gly Gly Gly Gly
305                 310                 315                 320

Ser Gly Gly Gly Gly Ser Ala Ala Ala Ser Leu Asn Phe Leu Asp Phe
                325                 330                 335
```

```
Glu Gln Pro Ile Ala Glu Leu Glu Ala Lys Ile Asp Ser Leu Thr Ala
                340                 345                 350

Val Ser Arg Gln Asp Glu Lys Leu Asp Ile Asn Ile Asp Glu Val
            355                 360                 365

His Arg Leu Arg Glu Lys Ser Val Glu Leu Thr Arg Lys Ile Phe Ala
        370                 375                 380

Asp Leu Gly Ala Trp Gln Ile Ala Gln Leu Ala Arg His Pro Gln Arg
385                 390                 395                 400

Pro Tyr Thr Leu Asp Tyr Val Arg Leu Ala Phe Asp Glu Phe Asp Glu
                405                 410                 415

Leu Ala Gly Asp Arg Ala Tyr Ala Asp Asp Lys Ala Ile Val Gly Gly
            420                 425                 430

Ile Ala Arg Leu Asp Gly Arg Pro Val Met Ile Ile Gly His Gln Lys
        435                 440                 445

Gly Arg Glu Thr Lys Glu Lys Ile Arg Arg Asn Phe Gly Met Pro Ala
    450                 455                 460

Pro Glu Gly Tyr Arg Lys Ala Leu Arg Leu Met Gln Met Ala Glu Arg
465                 470                 475                 480

Phe Lys Met Pro Ile Ile Thr Phe Ile Asp Thr Pro Gly Ala Tyr Pro
                485                 490                 495

Gly Val Gly Ala Glu Glu Arg Gly Gln Ser Glu Ala Ile Ala Arg Asn
            500                 505                 510

Leu Arg Glu Met Ser Arg Leu Gly Val Pro Val Val Cys Thr Val Ile
        515                 520                 525

Gly Glu Gly Gly Ser Gly Gly Ala Leu Ala Ile Gly Val Gly Asp Lys
    530                 535                 540

Val Asn Met Leu Gln Tyr Ser Thr Tyr Ser Val Ile Ser Pro Glu Gly
545                 550                 555                 560

Cys Ala Ser Ile Leu Trp Lys Ser Ala Asp Lys Ala Pro Leu Ala Ala
                565                 570                 575

Glu Ala Met Gly Ile Ile Ala Pro Arg Leu Lys Glu Leu Lys Leu Ile
            580                 585                 590

Asp Ser Ile Ile Pro Glu Pro Leu Gly Gly Ala His Arg Asn Pro Glu
        595                 600                 605

Ala Met Ala Ala Ser Leu Lys Ala Gln Leu Leu Ala Asp Leu Ala Asp
    610                 615                 620

Leu Asp Val Leu Ser Thr Glu Asp Leu Lys Asn Arg Arg Tyr Gln Arg
625                 630                 635                 640

Leu Met Ser Tyr Gly Tyr Ala
                645

<210> SEQ ID NO 12
<211> LENGTH: 1944
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgagctgga tcgagcgcat caagagcaac atcaccccga cccgcaaggc gagcatccct      60
gaaggcgtct ggaccaaatg cgatagctgc ggtcaggttt tgtatcgtgc ggagctggag     120
cgtaacctgg aagtgtgccc gaaatgcgac catcacatgc gtatgaccgc tcgtaatcgt     180
ctgcatagcc tgctggatga gggcagcctg gtcgagctgg gtagcgaact ggaaccgaaa     240
```

```
gatgttctga aattccgtga ttccaagaag tataaggatc gtttggcatc tgcacaaaaa      300
gaaaccggtg agaaggacgc actggttgtt atgaaaggca ccctgtatgg tatgccggtt      360
gttgctgcgg cgttcgagtt tgcgtttatg ggtggcagca tgggttccgt ggtgggcgca      420
cgctttgtgc gtgccgtgga gcaggcgctg aggataact gtcctctgat ttgtttcagc       480
gcgagcggtg gtgcgcgtat gcaagaggcc ctgatgagcc tgatgcagat ggcaaaaacc      540
tcggcagccc tggcgaagat gcaagaacgc ggcctgccgt acatttccgt cctgaccgac      600
cctacgatgg gcggtgtcag cgccagcttt gcgatgctgg gtgatttgaa catcgcagag      660
ccgaaggctc tgattggttt tgctggtccg cgtgttattg aacagacggt tcgcgaaaag      720
ttgccgcctg gtttccagcg cagcgagttc ctgattgaga aggtgccat cgacatgatc       780
gttcgccgtc cagaaatgcg tctgaaactg cgagcattc tggcgaaatt gatgaatctg       840
ccggctccga atcctgaagc accgcgtgag ggtgtcgtgg ttccgccggt cccggaccaa      900
gagccggagg ctctgagcgg cggaggtggc tctggtggag gcggttcagg aggcggtggc      960
agtggtggcg gcggatctgc ggcagcttct ctgaacttcc tggacttcga gcagccgatc     1020
gccgaactgg aggcgaagat tgacagcctg accgcggtta ccgtcaaga tgagaaactg      1080
gacattaaca tcgacgaaga ggtccaccgt ttgcgtgaga agtctgttga actgactcgc     1140
aaaatctttg ctgatttggg cgcatggcag attgcccagt tggctcgcca cccacaacgc     1200
ccatataccc tggactacgt gcgcctggcg tttgacgagt tcgacgaact ggcaggcgac     1260
cgcgcctatg cggacgataa agcaattgtc ggcggtattg ctcgtttgga tggccgtccg     1320
gtgatgatta tcggccatca aaaaggccgc gagacaaagg aaaagattcg tcgtaatttc     1380
ggaatgccgg caccggaggg ctaccgcaag gccctgcgtc tgatgcaaat ggccgaacgc     1440
tttaagatgc cgattatcac gttcattgat acgcctggtg cgtacccagg cgttggtgcg     1500
gaagagcgtg gtcagagcga ggccatcgca cgtaacctgc gtgagatgtc tcgtctgggt     1560
gtgccggtcg tttgcaccgt gattggcgag ggcggtagcg gtggtgcgtt ggcgatcggt     1620
gtcggtgata aggtcaacat gctgcaatac agcacgtaca gcgtcattag cccggaaggt     1680
tgcgcttcca ttctgtggaa gagcgcggat aaagcaccat ggcagcgga agcgatgggt      1740
atcatcgcac gcgtctgaa agaactgaag ttgattgatt ctatcatccc ggaaccgctg      1800
ggcggtgctc accgtaatcc ggaggcgatg gcagccagcc tgaaggccca gctgctggcg     1860
gacctggcgg atctggacgt gctgagcacg gaggatctga aaaccgtcg ctatcagcgc      1920
ttgatgagct atggctacgc ttaa                                            1944
```

<210> SEQ ID NO 13
<211> LENGTH: 566
<212> TYPE: PRT
<213> ORGANISM: Synechococcus sp.

<400> SEQUENCE: 13

Met Gln Ile Thr Asn Lys Ile His Phe Arg Asn Ile Arg Gly Asp Ile
1               5                   10                  15

Phe Gly Gly Leu Thr Ala Ala Val Ile Ala Leu Pro Met Ala Leu Ala
            20                  25                  30

Phe Gly Val Ala Ser Gly Ala Gly Ala Glu Ala Gly Leu Trp Gly Ala
        35                  40                  45

Val Leu Val Gly Phe Phe Ala Ala Leu Phe Gly Gly Thr Pro Thr Leu
    50                  55                  60

Ile Ser Glu Pro Thr Gly Pro Met Thr Val Val Met Thr Ala Val Ile

```
                65                  70                  75                  80
Ala His Phe Thr Ala Ser Ala Ala Thr Pro Glu Glu Gly Leu Ala Ile
                        85                  90                  95

Ala Phe Thr Val Val Met Met Ala Gly Val Phe Gln Ile Ile Phe Gly
                100                 105                 110

Ser Leu Lys Leu Gly Lys Tyr Val Thr Met Met Pro Tyr Thr Val Ile
                115                 120                 125

Ser Gly Phe Met Ser Gly Ile Gly Ile Ile Leu Val Ile Leu Gln Leu
                130                 135                 140

Ala Pro Phe Leu Gly Gln Ala Ser Pro Gly Gly Val Ile Gly Thr
145                 150                 155                 160

Leu Gln Asn Leu Pro Thr Leu Leu Ser Asn Ile Gln Pro Gly Glu Thr
                165                 170                 175

Ala Leu Ala Leu Gly Thr Val Ala Ile Ile Trp Phe Met Pro Glu Lys
                180                 185                 190

Phe Lys Lys Val Ile Pro Pro Gln Leu Val Ala Leu Val Leu Gly Thr
                195                 200                 205

Val Ile Ala Phe Phe Val Phe Pro Pro Glu Val Ser Asp Leu Arg Arg
210                 215                 220

Ile Gly Glu Ile Arg Ala Gly Phe Pro Glu Leu Val Arg Pro Ser Phe
225                 230                 235                 240

Ser Pro Val Glu Phe Gln Arg Met Ile Leu Asp Ala Ala Val Leu Gly
                245                 250                 255

Met Leu Gly Cys Ile Asp Ala Leu Leu Thr Ser Val Val Ala Asp Ser
                260                 265                 270

Leu Thr Arg Thr Glu His Asn Ser Asn Lys Glu Leu Ile Gly Gln Gly
                275                 280                 285

Leu Gly Asn Leu Phe Ser Gly Leu Phe Gly Gly Ile Ala Gly Ala Gly
                290                 295                 300

Ala Thr Met Gly Thr Val Val Asn Ile Gln Ser Gly Gly Arg Thr Ala
305                 310                 315                 320

Leu Ser Gly Leu Val Arg Ala Phe Val Leu Leu Val Ile Leu Gly
                325                 330                 335

Ala Ala Ser Leu Thr Ala Thr Ile Pro Leu Ala Val Leu Ala Gly Ile
                340                 345                 350

Ala Phe Lys Val Gly Val Asp Ile Ile Asp Trp Ser Phe Leu Lys Arg
                355                 360                 365

Ala His Glu Ile Ser Pro Lys Gly Ala Leu Ile Met Tyr Gly Val Ile
                370                 375                 380

Leu Leu Thr Val Leu Val Asp Leu Ile Val Ala Val Gly Val Gly Val
385                 390                 395                 400

Phe Val Ala Asn Val Leu Thr Ile Glu Arg Met Ser Asn Leu Gln Ser
                405                 410                 415

Glu Lys Val Gln Thr Val Ser Asp Ala Asp Asn Ile Arg Leu Thr
                420                 425                 430

Thr Thr Glu Lys Arg Trp Leu Asp Glu Gly Gln Gly Arg Val Leu Leu
                435                 440                 445

Phe Gln Leu Ser Gly Pro Met Ile Phe Gly Val Ala Lys Ala Ile Ala
                450                 455                 460

Arg Glu His Asn Ala Met Gly Asp Cys Asp Ala Leu Val Phe Asp Ile
465                 470                 475                 480

Gly Glu Val Pro His Met Gly Val Thr Ala Ser Leu Ala Leu Glu Asn
                485                 490                 495
```

Ala Ile Glu Glu Ala Leu Asp Lys Glu Arg Gln Val Tyr Ile Val Gly
                500                 505                 510

Ala Ala Gly Gln Thr Arg Arg Leu Glu Lys Leu Lys Leu Phe Lys
            515                 520                 525

Arg Val Pro Pro Asp Lys Cys Leu Met Ser Arg Glu Glu Ala Leu Lys
        530                 535                 540

Asn Ala Val Leu Gly Ile Tyr Pro His Leu Ala Asp Gly Val Thr Ala
545                 550                 555                 560

Pro Ser Ser Glu Met Gly
                565

<210> SEQ ID NO 14
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgcagatta ccaacaagat ccatttccgt aacattcgtg cgacatttt tggtggcctg      60 accgctgctg tgattgcgct gccgatggca ctggcttttg tgtggcaag tggtgcaggt    120 gcagaagcag gtctgtgggg tgcagttctg gtgggctttt cgcagcact gttcggtggt    180 acgccgaccc tgatttcaga accgacgggc ccgatgaccg tggttatgac ggccgtgatc    240
gcacatttta ccgcatcggc agctacgccg gaagaaggcc tggctattgc gttcaccgtc    300
gtgatgatgg ccggtgtttt tcagattatc ttcggcagcc tgaaactggg caagtatgtt    360
accatgatgc cgtacacggt catcagtggt tttatgtccg gtattggcat tatcctggtg    420
atcctgcagc tggcaccgtt cctgggtcaa gccagtccgg gcggtggcgt tattggcacc    480
ctgcagaacc tgccgacgct gctgtccaat atccaaccgg gtgaaaccgc cctggcactg    540
ggtacggtcg cgattatctg gttcatgccg gaaaagttca agaaggttat cccgccgcag    600
ctggttgcgc tggttctggg caccgtcatc gcgtttttcg tgtttccgcc ggaagttagc    660
gatctgcgtc gcattggcga aatccgtgca ggtttcccgg aactggtgcg tccgagcttt    720
tctccggttg aatttcagcg catgattctg gatgcggccg tgctgggcat gctgggttgc    780
atcgatgcgc tgctgaccag cgttgtcgcc gactctctga cgcgtaccga acataacagc    840
aataaagaac tgattggtca gggcctgggt aacctgtttt ctggcctgtt cggtggtatt    900
gctggtgcag gtgcaacgat gggcaccgtg gttaatatcc aaagtggtgg ccgtaccgca    960
ctgtccggtc tggtgcgtgc ttttgttctg ctggtcgtga ttctgggtgc agcttctctg   1020
acggcaacca ttccgctggc tgtgctggca ggcatcgcct ttaaagtggg tgttgatatt   1080
atcgactggt cattcctgaa acgcgcccac gaaatctcgc gaagggcgc actgattatg   1140 tatggtgtga tcctgctgac cgtcctggtg atctgattg ttgcggtcgg cgtgggtgtt   1200
tttgtcgcca acgttctgac catcgaacgt atgtcaaatc tgcagtcgga aaaagtccaa   1260
accgtgagcg atgcggatga caacattcgc ctgaccacga ccgaaaagcg ttggctggac   1320
gagggtcagg gtcgtgtgct gctgtttcaa ctgtctggcc cgatgatttt cggtgttgca   1380
aaagctatcg cgcgtgaaca taacgcaatg ggtgattgcg acgctctggt gtttgatatt   1440
ggcgaagtcc cgcacatggg tgtgaccgca agtctggctc tggaaaatgc gattgaagaa   1500
gccctggaca agaacgcca ggtttacatc gtcggtgcag caggtcaaac ccgtcgccgt   1560

```
ctggaaaaac tgaagctgtt taaacgcgtg ccgccggata agtgtctgat gtcccgtgaa    1620
gaagcactga agaatgctgt tctgggtatc tatccgcatc tggctgacgg tgttacggct    1680
ccgagttccg aaatgggcta a                                              1701
```

<210> SEQ ID NO 15
<211> LENGTH: 1071
<212> TYPE: DNA
<213> ORGANISM: Sulfolobus tokodaii

<400> SEQUENCE: 15

```
atgtctcgtc gcaccctgaa agcggctatc ctgggcgcca ccggcctggt tggtatcgaa      60
tatgtccgta tgctgtcaaa tcatccgtat atcaaaccgg cgtatctggc cggcaaaggt     120
tcagttggca aaccgtacgg tgaagtggtt cgttggcaga ccgttggcca agtcccgaaa     180
gaaatcgccg atatggaaat taaaccgacg gacccgaaac tgatggatga cgtggatatt     240
atcttttcgc cgctgccgca gggtgcggcc ggtccggttg aagaacaatt tgcaaaagaa     300
ggcttcccgg tcatcagcaa ctctccggat catcgtttcg atccggacgt cccgctgctg     360
gtgccggaac tgaatccgca caccattagt ctgatcgatg aacagcgcaa acgtcgcgaa     420
tggaaaggtt ttattgttac cacgccgctg tgcacggcac aaggtgcagc tatcccgctg     480
ggtgctatct tcaaagatta caaaatggac ggcgcgttca ttaccacgat ccagagtctg     540
tccggtgcag gttacccggg tatcccgtct ctggatgtcg tggacaacat tctgccgctg     600
ggcgatggtt atgacgcgaa aaccattaaa gaaatcttcc gtattctgtc agaagttaaa     660
cgcaatgtcg atgaaccgaa actggaagac gtttcgctgg cggccaccac gcatcgtatc     720
gccaccattc atggccacta tgaagtgctg tacgttagtt ttaaagaaga aaccgcagct     780
gaaaaagtga agaaacgctg gaaaaacttc cgcggtgaac cgcaggatct gaaactgccg     840
accgcaccgt ccaaaccgat tatcgtcatg aatgaagata cgcgtccgca agtgtacttt     900
gatcgctggg ctggcgacat tccgggtatg agcgttgtcg tgggccgtct gaaacaggtg     960
aacaaacgta tgatccgcct ggtgtctctg attcacaata ccgttcgcgg tgcggcgggc    1020
ggtggcatcc tggctgctga actgctggtt gaaaaaggtt acattgaaaa a             1071
```

<210> SEQ ID NO 16
<211> LENGTH: 357
<212> TYPE: PRT
<213> ORGANISM: Sulfolobus tokodaii

<400> SEQUENCE: 16

```
Met Ser Arg Arg Thr Leu Lys Ala Ala Ile Leu Gly Ala Thr Gly Leu
1               5                   10                  15

Val Gly Ile Glu Tyr Val Arg Met Leu Ser Asn His Pro Tyr Ile Lys
            20                  25                  30

Pro Ala Tyr Leu Ala Gly Lys Gly Ser Val Gly Lys Pro Tyr Gly Glu
        35                  40                  45

Val Val Arg Trp Gln Thr Val Gly Gln Val Pro Lys Glu Ile Ala Asp
    50                  55                  60

Met Glu Ile Lys Pro Thr Asp Pro Lys Leu Met Asp Asp Val Asp Ile
65                  70                  75                  80

Ile Phe Ser Pro Leu Pro Gln Gly Ala Ala Gly Pro Val Glu Glu Gln
                85                  90                  95

Phe Ala Lys Glu Gly Phe Pro Val Ile Ser Asn Ser Pro Asp His Arg
            100                 105                 110
```

```
Phe Asp Pro Asp Val Pro Leu Leu Val Pro Glu Leu Asn Pro His Thr
            115                 120                 125

Ile Ser Leu Ile Asp Glu Gln Arg Lys Arg Arg Glu Trp Lys Gly Phe
        130                 135                 140

Ile Val Thr Thr Pro Leu Cys Thr Ala Gln Gly Ala Ala Ile Pro Leu
145                 150                 155                 160

Gly Ala Ile Phe Lys Asp Tyr Lys Met Asp Gly Ala Phe Ile Thr Thr
                165                 170                 175

Ile Gln Ser Leu Ser Gly Ala Gly Tyr Pro Gly Ile Pro Ser Leu Asp
            180                 185                 190

Val Val Asp Asn Ile Leu Pro Leu Gly Asp Gly Tyr Asp Ala Lys Thr
        195                 200                 205

Ile Lys Glu Ile Phe Arg Ile Leu Ser Glu Val Lys Arg Asn Val Asp
210                 215                 220

Glu Pro Lys Leu Glu Asp Val Ser Leu Ala Ala Thr Thr His Arg Ile
225                 230                 235                 240

Ala Thr Ile His Gly His Tyr Glu Val Leu Tyr Val Ser Phe Lys Glu
                245                 250                 255

Glu Thr Ala Ala Glu Lys Val Lys Glu Thr Leu Glu Asn Phe Arg Gly
            260                 265                 270

Glu Pro Gln Asp Leu Lys Leu Pro Thr Ala Pro Ser Lys Pro Ile Ile
        275                 280                 285

Val Met Asn Glu Asp Thr Arg Pro Gln Val Tyr Phe Asp Arg Trp Ala
290                 295                 300

Gly Asp Ile Pro Gly Met Ser Val Val Gly Arg Leu Lys Gln Val
305                 310                 315                 320

Asn Lys Arg Met Ile Arg Leu Val Ser Leu Ile His Asn Thr Val Arg
                325                 330                 335

Gly Ala Ala Gly Gly Gly Ile Leu Ala Ala Glu Leu Leu Val Glu Lys
            340                 345                 350

Gly Tyr Ile Glu Lys
        355

<210> SEQ ID NO 17
<211> LENGTH: 1098
<212> TYPE: DNA
<213> ORGANISM: Escherichia coli

<400> SEQUENCE: 17
atgtcatctg aaaaactgta ttccccactg aaagtgggcg cgatcacggc ggcaaaccgt        60 attttatgg caccgctgac gcgtctgcgc agtattgaac cgggtgacat tcctacccccg       120 ttgatggcgg aatactatcg ccaacgtgcc agtgccggtt tgattattag tgaagccacg       180
caaatttctg cccaggcaaa aggatatgca ggtgcgcctg gcatccatag tccggagcaa       240
attgccgcat ggaaaaaaat caccgctggc gttcatgctg aaaatggtca tatggccgtg       300
cagctgtggc acaccggacg catttctcac gccagcctgc aacctggcgg tcaggcaccg       360
gtagcgcctt cagcacttag cgcgggaaca cgtacttctc tgcgcgatga aaatggtcag       420
gcgatccgtg ttgaaacatc catgccgcgt gcgcttgaac tggaagagat tccaggtatc       480
gtcaatgatt tccgtcaggc cattgctaac gcgcgtgaag ccggttttga tctggtagag       540
ctccactctg ctcacggtta tttgctgcat cagttccttt ctccttcttc aaaccatcgt       600
accgatcagt acggcggcag cgtggaaaat cgcgcacgtt ggtactgga agtggtcgat       660 gccgggattg aagaatgggg tgccgatcgc attggcattc gcgtttcacc aatcggtact       720
```

```
ttccagaaca cagataacgg cccgaatgaa gaagccgatg cactgtatct gattgaacaa    780
ctgggtaaac gcggcattgc ttatctgcat atgtcagaac cagattgggc gggggggtgaa   840 ccgtatactg atgcgttccg cgaaaaagta cgcgcccgtt tccacggtcc gattatcggc    900
gcaggtgcat acacagtaga aaagctgaaa acgctgatcg caaagggtt aattgatgcg     960 gtggcatttg tcgtgactg gattgcgaac ccggatctgg tcgcccgctt gcagcgcaaa     1020
gctgagctta acccacagcg tgccgaaagt ttctacggtg cggcgcgga aggctatacc     1080 gattacccga cgttgtaa                                                  1098
```

```
<210> SEQ ID NO 18
<211> LENGTH: 365
<212> TYPE: PRT
<213> ORGANISM: Escherichia coli

<400> SEQUENCE: 18

Met Ser Ser Glu Lys Leu Tyr Ser Pro Leu Lys Val Gly Ala Ile Thr
1               5                   10                  15

Ala Ala Asn Arg Ile Phe Met Ala Pro Leu Thr Arg Leu Arg Ser Ile
                20                  25                  30

Glu Pro Gly Asp Ile Pro Thr Pro Leu Met Ala Glu Tyr Tyr Arg Gln
            35                  40                  45

Arg Ala Ser Ala Gly Leu Ile Ile Ser Glu Ala Thr Gln Ile Ser Ala
    50                  55                  60

Gln Ala Lys Gly Tyr Ala Gly Ala Pro Gly Ile His Ser Pro Glu Gln
65                  70                  75                  80

Ile Ala Ala Trp Lys Lys Ile Thr Ala Gly Val His Ala Glu Asn Gly
                85                  90                  95

His Met Ala Val Gln Leu Trp His Thr Gly Arg Ile Ser His Ala Ser
            100                 105                 110

Leu Gln Pro Gly Gly Gln Ala Pro Val Ala Pro Ser Ala Leu Ser Ala
        115                 120                 125

Gly Thr Arg Thr Ser Leu Arg Asp Glu Asn Gly Gln Ala Ile Arg Val
    130                 135                 140

Glu Thr Ser Met Pro Arg Ala Leu Glu Leu Glu Ile Pro Gly Ile
145                 150                 155                 160

Val Asn Asp Phe Arg Gln Ala Ile Ala Asn Ala Arg Glu Ala Gly Phe
                165                 170                 175

Asp Leu Val Glu Leu His Ser Ala His Gly Tyr Leu Leu His Gln Phe
            180                 185                 190

Leu Ser Pro Ser Ser Asn His Arg Thr Asp Gln Tyr Gly Gly Ser Val
        195                 200                 205

Glu Asn Arg Ala Arg Leu Val Leu Glu Val Val Asp Ala Gly Ile Glu
    210                 215                 220

Glu Trp Gly Ala Asp Arg Ile Gly Ile Arg Val Ser Pro Ile Gly Thr
225                 230                 235                 240

Phe Gln Asn Thr Asp Asn Gly Pro Asn Glu Glu Ala Asp Ala Leu Tyr
                245                 250                 255

Leu Ile Glu Gln Leu Gly Lys Arg Gly Ile Ala Tyr Leu His Met Ser
            260                 265                 270

Glu Pro Asp Trp Ala Gly Gly Glu Pro Tyr Thr Asp Ala Phe Arg Glu
        275                 280                 285

Lys Val Arg Ala Arg Phe His Gly Pro Ile Ile Gly Ala Gly Ala Tyr
    290                 295                 300
```

```
Thr Val Glu Lys Ala Glu Thr Leu Ile Gly Lys Gly Leu Ile Asp Ala
305                 310                 315                 320

Val Ala Phe Gly Arg Asp Trp Ile Ala Asn Pro Asp Leu Val Ala Arg
            325                 330                 335

Leu Gln Arg Lys Ala Glu Leu Asn Pro Gln Arg Ala Glu Ser Phe Tyr
        340                 345                 350

Gly Gly Gly Ala Glu Gly Tyr Thr Asp Tyr Pro Thr Leu
        355                 360                 365

<210> SEQ ID NO 19
<211> LENGTH: 591
<212> TYPE: DNA
<213> ORGANISM: Escherichia coli

<400> SEQUENCE: 19
atgaacgaag ccgttagccc aggtgcgctt agcaccctgt tcaccgatgc ccgcactcac      60
aacggctggc gggagacacc cgtcagcgat gagacgttac gggagattta tgccctgatg     120 aaatggggc cgacatcagc taactgttct ccggcacgga tcgtgtttac ccgcacggca     180
gaaggaaaag aacgtctgcg cccggcactt tccagcggca atctgcaaaa aaccctgacc     240
gcgcccgtca ccgctatcgt cgcctgggac agtgaatttt atgaacggtt accactactg     300
tttccccacg gtgatgcccg cagttggttt acctccagcc acaacttgc cgaagaaaca     360 gcgtttcgca acagttccat gcaggcggcc tatctgatcg tcgcctgccg ggcgctggga     420
ctggataccg gcccgatgtc gggctttgac cgtcaacacg tggacgacgc ctttttttacg     480 ggcagcacgc tgaagagcaa tctgctgatt aatatcggct atggcgatag cagcaagctt     540
tatgcgcgcc tgccacgtct gtcctttgaa gaagcctgcg ggctgttgta a             591

<210> SEQ ID NO 20
<211> LENGTH: 196
<212> TYPE: PRT
<213> ORGANISM: Escherichia coli

<400> SEQUENCE: 20

Met Asn Glu Ala Val Ser Pro Gly Ala Leu Ser Thr Leu Phe Thr Asp
1               5                   10                  15

Ala Arg Thr His Asn Gly Trp Arg Glu Thr Pro Val Ser Asp Glu Thr
            20                  25                  30

Leu Arg Glu Ile Tyr Ala Leu Met Lys Trp Gly Pro Thr Ser Ala Asn
        35                  40                  45

Cys Ser Pro Ala Arg Ile Val Phe Thr Arg Thr Ala Glu Gly Lys Glu
    50                  55                  60

Arg Leu Arg Pro Ala Leu Ser Ser Gly Asn Leu Gln Lys Thr Leu Thr
65                  70                  75                  80

Ala Pro Val Thr Ala Ile Val Ala Trp Asp Ser Glu Phe Tyr Glu Arg
                85                  90                  95

Leu Pro Leu Leu Phe Pro His Gly Asp Ala Arg Ser Trp Phe Thr Ser
            100                 105                 110

Ser Pro Gln Leu Ala Glu Glu Thr Ala Phe Arg Asn Ser Ser Met Gln
        115                 120                 125

Ala Ala Tyr Leu Ile Val Ala Cys Arg Ala Leu Gly Leu Asp Thr Gly
    130                 135                 140

Pro Met Ser Gly Phe Asp Arg Gln His Val Asp Asp Ala Phe Phe Thr
145                 150                 155                 160
```

Gly Ser Thr Leu Lys Ser Asn Leu Leu Ile Asn Ile Gly Tyr Gly Asp
              165                 170                 175

Ser Ser Lys Leu Tyr Ala Arg Leu Pro Arg Leu Ser Phe Glu Glu Ala
          180                 185                 190

Cys Gly Leu Leu
          195

<210> SEQ ID NO 21
<211> LENGTH: 747
<212> TYPE: DNA
<213> ORGANISM: Escherichia coli

<400> SEQUENCE: 21

```
atggtcgttt tagtaactgg agcaacggca ggttttggtg aatgcattac tcgtcgtttt      60
attcaacaag ggcataaagt tatcgccact ggccgtcgcc aggaacggtt gcaggagtta     120
aaagacgaac tgggagataa tctgtatatc gcccaactgg acgttcgcaa ccgcgccgct     180
attgaagaga tgctggcatc gcttcctgcc gagtggtgca atattgatat cctggtaaat     240
aatgccggcc tggcgttggg catggagcct gcgcataaag ccagcgttga agactgggaa     300
acgatgattg ataccaacaa caaaggcctg gtatatatga cgcgcgccgt cttaccgggt     360
atggttgaac gtaatcatgg tcatattatt aacattggct caacggcagg tagctggccg     420
tatgccggtg gtaacgttta cggtgcgacg aaagcgtttg ttcgtcagtt tagcctgaat     480
ctgcgtacgg atctgcatgg tacggcggtg cgcgtcaccg acatcgaacc gggtctggtg     540
ggtggtaccg agttttccaa tgtccgcttt aaaggcgatg acggtaaagc agaaaaaacc     600
tatcaaaata ccgttgcatt gacgccagaa gatgtcagcg aagccgtctg gtgggtgtca     660
acgctgcctg ctcacgtcaa tatcaatacc ctggaaatga tgccggttac ccaaagctat     720
gccggactga atgtccaccg tcagtaa                                          747
```

<210> SEQ ID NO 22
<211> LENGTH: 248
<212> TYPE: PRT
<213> ORGANISM: Escherichia coli

<400> SEQUENCE: 22

Met Val Val Leu Val Thr Gly Ala Thr Ala Gly Phe Gly Glu Cys Ile
1               5                  10                  15

Thr Arg Arg Phe Ile Gln Gln Gly His Lys Val Ile Ala Thr Gly Arg
              20                  25                  30

Arg Gln Glu Arg Leu Gln Glu Leu Lys Asp Glu Leu Gly Asp Asn Leu
          35                  40                  45

Tyr Ile Ala Gln Leu Asp Val Arg Asn Arg Ala Ala Ile Glu Glu Met
      50                  55                  60

Leu Ala Ser Leu Pro Ala Glu Trp Cys Asn Ile Asp Ile Leu Val Asn
65                  70                  75                  80

Asn Ala Gly Leu Ala Leu Gly Met Glu Pro Ala His Lys Ala Ser Val
                  85                  90                  95

Glu Asp Trp Glu Thr Met Ile Asp Thr Asn Asn Lys Gly Leu Val Tyr
              100                 105                 110

Met Thr Arg Ala Val Leu Pro Gly Met Val Glu Arg Asn His Gly His
          115                 120                 125

Ile Ile Asn Ile Gly Ser Thr Ala Gly Ser Trp Pro Tyr Ala Gly Gly
      130                 135                 140

Asn Val Tyr Gly Ala Thr Lys Ala Phe Val Arg Gln Phe Ser Leu Asn

```
145                 150                 155                 160
Leu Arg Thr Asp Leu His Gly Thr Ala Val Arg Val Thr Asp Ile Glu
                165                 170                 175

Pro Gly Leu Val Gly Gly Thr Glu Phe Ser Asn Val Arg Phe Lys Gly
            180                 185                 190

Asp Asp Gly Lys Ala Glu Lys Thr Tyr Gln Asn Thr Val Ala Leu Thr
                195                 200                 205

Pro Glu Asp Val Ser Glu Ala Val Trp Trp Val Ser Thr Leu Pro Ala
            210                 215                 220

His Val Asn Ile Asn Thr Leu Glu Met Met Pro Val Thr Gln Ser Tyr
225                 230                 235                 240

Ala Gly Leu Asn Val His Arg Gln
                245

<210> SEQ ID NO 23
<211> LENGTH: 897
<212> TYPE: DNA
<213> ORGANISM: Pseudomonas aeruginosa

<400> SEQUENCE: 23
atggccgaca ttgcgtttct gggtctgggc aatatgggcg gtccgatggc cgcgaacctg      60
ctgaaagccg gccaccgtgt gaatgtgttc gacctgcaac aaaagcggt cctgggcttg     120 gttgagcaag gcgcgcaggg cgcagactct gctctgcaat gttgtgaggg tgcggaggtc     180
gtgatttcta tgctgccagc aggccagcat gtggaaagcc tgtacctggg cgatgatggt     240
ctgctggcac gcgtggcggg caagcctttg ctgattgact gtagcaccat cgcaccggaa     300
acggcgcgta aggtggcgga ggcagccgca gcaaagggcc tgacgctgct ggatgccccg     360
gtttcgggcg gtgtcggtgg tgcccgtgca ggtacgctgt cgtttatcgt gggtggtccg     420
gcggagggtt ttgcgcgtgc gcgtccggtt ctggagaata tgggtcgcaa cattttccac     480
gcgggtgatc acggcgctgg tcaggtggcg aaaatctgta caacatgct gctgggtatc     540 ttgatggcgg gcaccgccga agccttggcg ctgggcgtca aaaacggtct ggacccggca     600
gtgctgtccg aagtgatgaa acagagcagc ggtggtaact gggcgctgaa tctgtacaat     660
ccgtggccgg gtgtgatgcc gcaggcccca gcctctaatg ctacgcagg cggcttccaa     720 gtgcgcctga tgaacaaaga cctgggcctg cgctggcga tgcgcaagc ggtccaagcg     780 agcaccccgc tgggcgcact ggcccgtaac ctgtttagcc tgcacgctca gccgacgcc     840 gagcacgaag gtctggactt cagctctatt caaaaactgt atcgcggtaa ggattag      897

<210> SEQ ID NO 24
<211> LENGTH: 298
<212> TYPE: PRT
<213> ORGANISM: Pseudomonas aeruginosa

<400> SEQUENCE: 24

Met Ala Asp Ile Ala Phe Leu Gly Leu Gly Asn Met Gly Gly Pro Met
1               5                   10                  15

Ala Ala Asn Leu Leu Lys Ala Gly His Arg Val Asn Val Phe Asp Leu
            20                  25                  30

Gln Pro Lys Ala Val Leu Gly Leu Val Glu Gln Gly Ala Gln Gly Ala
        35                  40                  45

Asp Ser Ala Leu Gln Cys Cys Glu Gly Ala Glu Val Val Ile Ser Met
    50                  55                  60

Leu Pro Ala Gly Gln His Val Glu Ser Leu Tyr Leu Gly Asp Asp Gly
```

```
             65                  70                  75                  80
Leu Leu Ala Arg Val Ala Gly Lys Pro Leu Leu Ile Asp Cys Ser Thr
                85                  90                  95

Ile Ala Pro Glu Thr Ala Arg Lys Val Ala Glu Ala Ala Ala Ala Lys
            100                 105                 110

Gly Leu Thr Leu Leu Asp Ala Pro Val Ser Gly Val Gly Gly Ala
            115                 120                 125

Arg Ala Gly Thr Leu Ser Phe Ile Val Gly Pro Ala Glu Gly Phe
            130                 135                 140

Ala Arg Ala Arg Pro Val Leu Glu Asn Met Gly Arg Asn Ile Phe His
145                 150                 155                 160

Ala Gly Asp His Gly Ala Gly Gln Val Ala Lys Ile Cys Asn Asn Met
                165                 170                 175

Leu Leu Gly Ile Leu Met Ala Gly Thr Ala Glu Ala Leu Ala Leu Gly
            180                 185                 190

Val Lys Asn Gly Leu Asp Pro Ala Val Leu Ser Glu Val Met Lys Gln
            195                 200                 205

Ser Ser Gly Gly Asn Trp Ala Leu Asn Leu Tyr Asn Pro Trp Pro Gly
210                 215                 220

Val Met Pro Gln Ala Pro Ala Ser Asn Gly Tyr Ala Gly Gly Phe Gln
225                 230                 235                 240

Val Arg Leu Met Asn Lys Asp Leu Gly Leu Ala Leu Ala Asn Ala Gln
                245                 250                 255

Ala Val Gln Ala Ser Thr Pro Leu Gly Ala Leu Ala Arg Asn Leu Phe
            260                 265                 270

Ser Leu His Ala Gln Ala Asp Ala Glu His Glu Gly Leu Asp Phe Ser
            275                 280                 285

Ser Ile Gln Lys Leu Tyr Arg Gly Lys Asp
            290                 295

<210> SEQ ID NO 25
<211> LENGTH: 900
<212> TYPE: DNA
<213> ORGANISM: Pseudomonas aeruginosa

<400> SEQUENCE: 25
atgggcaaac agatcgcctt catcggcctg ggccatatgg cgcaccctat ggccaccaac      60
ctgctgaagg ccggctacct gctgaatgtg ttcgacctgg tgcagagcgc cgtggatggt     120
ttagtggccg caggtgcaag tgcagcacgc agtgcacgcg atgccgttca gggtgccgac     180
gtggtgatca gcatgctgcc tgccagccaa cacgtggagg gtctgtacct ggacgacgat     240
ggtctgctgg cccacattgc ccctggcacc ttagtgctgg agtgcagcac aatcgccccg     300
accagtgcac gcaagattca tgcagcagcc cgcgagcgtg gtctggcaat gctggacgca     360
ccggttagcg gtggtacagc aggtgccgca gcaggcaccc tgaccttcat ggtgggcggt     420
gacgccgaag ccctggaaaa agcacgcccg ctgtttgagg caatgggccg taacatcttc     480
catgccggcc tgatggcgc aggtcaggtg gccaaagtgt gcaataacca gctgctggca     540
gtgctgatga tcgtaccgc cgaggcaatg gcactgggcg tggcaaacgg cttagaggcc     600
aaggtgctgg cagaaatcat gcgccgtagt agcggcggta actgggccct ggaggtgtac     660
aacccgtggc ctggcgtgat ggagaatgca ccggccagtc gtgactacag cggcggtttc     720
atggcacagc tgatggccaa ggacctgggc ttagcccaag aggcagccca agccagcgcc     780
agtagtaccc cgatgggcag cttagccctg agtctgtacc gcttactgct gaagcagggc     840
```
tacgccgaac gcgacttcag cgtggtgcag aagctgttcg acccgaccca aggccagtaa    900

```
<210> SEQ ID NO 26
<211> LENGTH: 299
<212> TYPE: PRT
<213> ORGANISM: Pseudomonas aeruginosa

<400> SEQUENCE: 26
```

| | | | | | | | | | | | | | | |
|---|---|---|---|---|---|---|---|---|---|---|---|---|---|---|
| Met | Gly | Lys | Gln | Ile | Ala | Phe | Ile | Gly | Leu | Gly | His | Met | Gly | Ala | Pro |
| 1 | | | | 5 | | | | | 10 | | | | | 15 | |
| Met | Ala | Thr | Asn | Leu | Leu | Lys | Ala | Gly | Tyr | Leu | Leu | Asn | Val | Phe | Asp |
| | | | 20 | | | | | 25 | | | | | 30 | | |
| Leu | Val | Gln | Ser | Ala | Val | Asp | Gly | Leu | Val | Ala | Ala | Gly | Ala | Ser | Ala |
| | | | 35 | | | | 40 | | | | | 45 | | | |
| Ala | Arg | Ser | Ala | Arg | Asp | Ala | Val | Gln | Gly | Ala | Asp | Val | Val | Ile | Ser |
| | 50 | | | | | 55 | | | | | 60 | | | | |
| Met | Leu | Pro | Ala | Ser | Gln | His | Val | Glu | Gly | Leu | Tyr | Leu | Asp | Asp | Asp |
| 65 | | | | | 70 | | | | | 75 | | | | | 80 |
| Gly | Leu | Leu | Ala | His | Ile | Ala | Pro | Gly | Thr | Leu | Val | Leu | Glu | Cys | Ser |
| | | | | 85 | | | | | 90 | | | | | 95 | |
| Thr | Ile | Ala | Pro | Thr | Ser | Ala | Arg | Lys | Ile | His | Ala | Ala | Ala | Arg | Glu |
| | | | 100 | | | | | 105 | | | | | 110 | | |
| Arg | Gly | Leu | Ala | Met | Leu | Asp | Ala | Pro | Val | Ser | Gly | Gly | Thr | Ala | Gly |
| | | | 115 | | | | | 120 | | | | | 125 | | |
| Ala | Ala | Ala | Gly | Thr | Leu | Thr | Phe | Met | Val | Gly | Gly | Asp | Ala | Glu | Ala |
| | 130 | | | | | 135 | | | | | 140 | | | | |
| Leu | Glu | Lys | Ala | Arg | Pro | Leu | Phe | Glu | Ala | Met | Gly | Arg | Asn | Ile | Phe |
| 145 | | | | | 150 | | | | | 155 | | | | | 160 |
| His | Ala | Gly | Pro | Asp | Gly | Ala | Gly | Gln | Val | Ala | Lys | Val | Cys | Asn | Asn |
| | | | | 165 | | | | | 170 | | | | | 175 | |
| Gln | Leu | Leu | Ala | Val | Leu | Met | Ile | Gly | Thr | Ala | Glu | Ala | Met | Ala | Leu |
| | | | 180 | | | | | 185 | | | | | 190 | | |
| Gly | Val | Ala | Asn | Gly | Leu | Glu | Ala | Lys | Val | Leu | Ala | Glu | Ile | Met | Arg |
| | | | 195 | | | | | 200 | | | | | 205 | | |
| Arg | Ser | Ser | Gly | Gly | Asn | Trp | Ala | Leu | Glu | Val | Tyr | Asn | Pro | Trp | Pro |
| | 210 | | | | | 215 | | | | | 220 | | | | |
| Gly | Val | Met | Glu | Asn | Ala | Pro | Ala | Ser | Arg | Asp | Tyr | Ser | Gly | Gly | Phe |
| 225 | | | | | 230 | | | | | 235 | | | | | 240 |
| Met | Ala | Gln | Leu | Met | Ala | Lys | Asp | Leu | Gly | Leu | Ala | Gln | Glu | Ala | Ala |
| | | | | 245 | | | | | 250 | | | | | 255 | |
| Gln | Ala | Ser | Ala | Ser | Ser | Thr | Pro | Met | Gly | Ser | Leu | Ala | Leu | Ser | Leu |
| | | | 260 | | | | | 265 | | | | | 270 | | |
| Tyr | Arg | Leu | Leu | Leu | Lys | Gln | Gly | Tyr | Ala | Glu | Arg | Asp | Phe | Ser | Val |
| | | | 275 | | | | | 280 | | | | | 285 | | |
| Val | Gln | Lys | Leu | Phe | Asp | Pro | Thr | Gln | Gly | Gln | | | | | |
| | 290 | | | | | 295 | | | | | | | | | |

```
<210> SEQ ID NO 27
<211> LENGTH: 262
<212> TYPE: PRT
<213> ORGANISM: Escherichia coli

<400> SEQUENCE: 27
```

| | | | | | | | | | | | | | | |
|---|---|---|---|---|---|---|---|---|---|---|---|---|---|---|
| Met | Gly | Phe | Leu | Ser | Gly | Lys | Arg | Ile | Leu | Val | Thr | Gly | Val | Ala | Ser |
| 1 | | | | 5 | | | | | 10 | | | | | 15 | |

-continued

Lys Leu Ser Ile Ala Tyr Gly Ile Ala Gln Ala Met His Arg Glu Gly
            20                  25                  30

Ala Glu Leu Ala Phe Thr Tyr Gln Asn Asp Lys Leu Lys Gly Arg Val
        35                  40                  45

Glu Glu Phe Ala Ala Gln Leu Gly Ser Asp Ile Val Leu Gln Cys Asp
50                  55                  60

Val Ala Glu Asp Ala Ser Ile Asp Thr Met Phe Ala Glu Leu Gly Lys
65                  70                  75                  80

Val Trp Pro Lys Phe Asp Gly Phe Val His Ser Ile Gly Phe Ala Pro
                85                  90                  95

Gly Asp Gln Leu Asp Gly Asp Tyr Val Asn Ala Val Thr Arg Glu Gly
            100                 105                 110

Phe Lys Ile Ala His Asp Ile Ser Ser Tyr Ser Phe Val Ala Met Ala
        115                 120                 125

Lys Ala Cys Arg Ser Met Leu Asn Pro Gly Ser Ala Leu Leu Thr Leu
130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
                165                 170                 175

Met Gly Pro Glu Gly Val Arg Val Asn Ala Ile Ser Ala Gly Pro Ile
            180                 185                 190

Arg Thr Leu Ala Ala Ser Gly Ile Lys Asp Phe Arg Lys Met Leu Ala
        195                 200                 205

His Cys Glu Ala Val Thr Pro Ile Arg Arg Thr Val Thr Ile Glu Asp
210                 215                 220

Val Gly Asn Ser Ala Ala Phe Leu Cys Ser Asp Leu Ser Ala Gly Ile
225                 230                 235                 240

Phe Gly Glu Val Val His Val Asp Gly Gly Phe Ser Ile Ala Ala Met
                245                 250                 255

Asn Glu Leu Glu Leu Lys
            260

<210> SEQ ID NO 28
<211> LENGTH: 406
<212> TYPE: PRT
<213> ORGANISM: Escherichia coli

<400> SEQUENCE: 28

Met Lys Arg Ala Val Ile Thr Gly Leu Gly Ile Val Ser Ser Ile Gly
1               5                   10                  15

Asn Asn Gln Gln Glu Val Leu Ala Ser Leu Arg Glu Gly Arg Ser Gly
            20                  25                  30

Ile Thr Phe Ser Gln Glu Leu Lys Asp Ser Gly Met Arg Ser His Val
        35                  40                  45

Trp Gly Asn Val Lys Leu Asp Thr Thr Gly Leu Ile Asp Arg Lys Val
        50                  55                  60

Val Arg Phe Met Ser Asp Ala Ser Ile Tyr Ala Phe Leu Ser Met Glu
65                  70                  75                  80

Gln Ala Ile Ala Asp Ala Gly Leu Ser Pro Glu Ala Tyr Gln Asn Asn
                85                  90                  95

Pro Arg Val Gly Leu Ile Ala Gly Ser Gly Gly Gly Ser Pro Arg Phe
            100                 105                 110

Gln Val Phe Gly Ala Asp Ala Met Arg Gly Pro Arg Gly Leu Lys Ala
        115                 120                 125

```
Val Gly Pro Tyr Val Val Thr Lys Ala Met Ala Ser Gly Val Ser Ala
    130                 135                 140

Cys Leu Ala Thr Pro Phe Lys Ile His Gly Val Asn Tyr Ser Ile Ser
145                 150                 155                 160

Ser Ala Cys Ala Thr Ser Ala His Cys Ile Gly Asn Ala Val Glu Gln
                165                 170                 175

Ile Gln Leu Gly Lys Gln Asp Ile Val Phe Ala Gly Gly Glu Glu
            180                 185                 190

Leu Cys Trp Glu Met Ala Cys Glu Phe Asp Ala Met Gly Ala Leu Ser
        195                 200                 205

Thr Lys Tyr Asn Asp Thr Pro Glu Lys Ala Ser Arg Thr Tyr Asp Ala
    210                 215                 220

His Arg Asp Gly Phe Val Ile Ala Gly Gly Gly Met Val Val
225                 230                 235                 240

Glu Glu Leu Glu His Ala Leu Ala Arg Gly Ala His Ile Tyr Ala Glu
                245                 250                 255

Ile Val Gly Tyr Gly Ala Thr Ser Asp Gly Ala Asp Met Val Ala Pro
                260                 265                 270

Ser Gly Glu Gly Ala Val Arg Cys Met Lys Met Ala Met His Gly Val
        275                 280                 285

Asp Thr Pro Ile Asp Tyr Leu Asn Ser His Gly Thr Ser Thr Pro Val
    290                 295                 300

Gly Asp Val Lys Glu Leu Ala Ala Ile Arg Glu Val Phe Gly Asp Lys
305                 310                 315                 320

Ser Pro Ala Ile Ser Ala Thr Lys Val Met Thr Gly His Ser Leu Gly
                325                 330                 335

Ala Ala Gly Val Gln Glu Ala Ile Tyr Ser Leu Leu Met Leu Glu His
            340                 345                 350

Gly Phe Ile Ala Pro Ser Ile Asn Ile Glu Glu Leu Asp Glu Gln Ala
        355                 360                 365

Ala Gly Leu Asn Ile Val Thr Glu Thr Thr Asp Arg Glu Leu Thr Thr
    370                 375                 380

Val Met Ser Asn Ser Phe Gly Phe Gly Gly Thr Asn Ala Thr Leu Val
385                 390                 395                 400

Met Arg Lys Leu Lys Asp
                405

<210> SEQ ID NO 29
<211> LENGTH: 309
<212> TYPE: PRT
<213> ORGANISM: Escherichia coli

<400> SEQUENCE: 29

Met Thr Gln Phe Ala Phe Val Phe Pro Gly Gln Gly Ser Gln Thr Val
1               5                   10                  15

Gly Met Leu Ala Asp Met Ala Ala Ser Tyr Pro Ile Val Glu Glu Thr
            20                  25                  30

Phe Ala Glu Ala Ser Ala Ala Leu Gly Tyr Asp Leu Trp Ala Leu Thr
        35                  40                  45

Gln Gln Gly Pro Ala Glu Glu Leu Asn Lys Thr Trp Gln Thr Gln Pro
    50                  55                  60

Ala Leu Leu Thr Ala Ser Val Ala Leu Tyr Arg Val Trp Gln Gln Gln
65                  70                  75                  80

Gly Gly Lys Ala Pro Ala Met Met Ala Gly His Ser Leu Gly Glu Tyr
```

```
                    85                  90                  95
Ser Ala Leu Val Cys Ala Gly Val Ile Asp Phe Ala Asp Ala Val Arg
                100                 105                 110

Leu Val Glu Met Arg Gly Lys Phe Met Gln Glu Ala Val Pro Glu Gly
            115                 120                 125

Thr Gly Ala Met Ala Ala Ile Ile Gly Leu Asp Asp Ala Ser Ile Ala
        130                 135                 140

Lys Ala Cys Glu Glu Ala Ala Glu Gly Gln Val Val Ser Pro Val Asn
145                 150                 155                 160

Phe Asn Ser Pro Gly Gln Val Val Ile Ala Gly His Lys Glu Ala Val
                165                 170                 175

Glu Arg Ala Gly Ala Ala Cys Lys Ala Ala Gly Ala Lys Arg Ala Leu
            180                 185                 190

Pro Leu Pro Val Ser Val Pro Ser His Cys Ala Leu Met Lys Pro Ala
        195                 200                 205

Ala Asp Lys Leu Ala Val Glu Leu Ala Lys Ile Thr Phe Asn Ala Pro
210                 215                 220

Thr Val Pro Val Val Asn Asn Val Asp Val Lys Cys Glu Thr Asn Gly
225                 230                 235                 240

Asp Ala Ile Arg Asp Ala Leu Val Arg Gln Leu Tyr Asn Pro Val Gln
                245                 250                 255

Gln Thr Lys Ser Val Glu Tyr Met Ala Ala Gln Gly Val Glu His Leu
            260                 265                 270

Tyr Glu Val Gly Pro Gly Lys Val Leu Thr Gly Leu Thr Lys Arg Ile
        275                 280                 285

Val Asp Thr Leu Thr Ala Ser Ala Leu Asn Glu Pro Ser Ala Met Ala
290                 295                 300

Ala Ala Leu Glu Leu
305

<210> SEQ ID NO 30
<211> LENGTH: 888
<212> TYPE: DNA
<213> ORGANISM: Escherichia coli

<400> SEQUENCE: 30
atgagcggtt cattacgtaa aatgccggtc tggttaccaa tagtcatatt gctcgttgcc      60
atggcgtcta ttcagggtgg agcctcgtta gctaagtcac ttttttcctct ggtgggcgca    120 ccgggtgtca ctgcgctgcg tctggcatta ggaacgctga tcctcatcgc gttctttaag    180
ccatggcgac tgcgctttgc caaagagcaa cggttaccgc tgttgtttta cggcgtttcg    240
ctgggtggga tgaattatct ttttttatctt tctattcaga cagtaccgct gggtattgcg    300
gtggcgctgg agttcaccgg accactggcg gtggcgctgt tctcttctcg tcgcccggta    360
gatttcgtct gggttgtgct ggcggttctt ggtctgtggt cctgctacc gctggggcaa    420 gacgtttccc atgtcgattt aaccggctgt gcgctggcac tggggccgg ggcttgttgg    480 gctatttaca tttttaagtgg gcaacgcgca ggagcggaac atggccctgc gacggtggca    540 attggtcgt tgattgcagc gttaattttc gtgccaattg agcgcttca ggctggtgaa      600 gcactctggc actggtcggt tattccattg ggtctggctg tcgctattct ctcgaccgct    660
ctgccttatt cgctggaaat gattgccctc accgtttgc caacacggac atttggtacg    720
ctgatgagca tggaaccggc gctggctgcc gtttccggga tgattttcct cggagaaaca    780
ctgacaccca tacagctact ggcgctcggc gctatcatcg ccgcttcaat ggggtctacg    840
```
ctgacagtac gcaaagagag caaaataaaa gaattagaca ttaattaa 888

<210> SEQ ID NO 31
<211> LENGTH: 295
<212> TYPE: PRT
<213> ORGANISM: Escherichia coli

<400> SEQUENCE: 31

| Met | Ser | Gly | Ser | Leu | Arg | Lys | Met | Pro | Val | Trp | Leu | Pro | Ile | Val | Ile |
|---|---|---|---|---|---|---|---|---|---|---|---|---|---|---|---|
| 1 | | | | 5 | | | | | 10 | | | | | 15 | |

| Leu | Leu | Val | Ala | Met | Ala | Ser | Ile | Gln | Gly | Gly | Ala | Ser | Leu | Ala | Lys |
|---|---|---|---|---|---|---|---|---|---|---|---|---|---|---|---|
| | | | 20 | | | | | 25 | | | | | 30 | | |

| Ser | Leu | Phe | Pro | Leu | Val | Gly | Ala | Pro | Gly | Val | Thr | Ala | Leu | Arg | Leu |
|---|---|---|---|---|---|---|---|---|---|---|---|---|---|---|---|
| | | 35 | | | | | 40 | | | | | 45 | | | |

| Ala | Leu | Gly | Thr | Leu | Ile | Leu | Ile | Ala | Phe | Phe | Lys | Pro | Trp | Arg | Leu |
|---|---|---|---|---|---|---|---|---|---|---|---|---|---|---|---|
| | 50 | | | | | 55 | | | | | 60 | | | | |

| Arg | Phe | Ala | Lys | Glu | Gln | Arg | Leu | Pro | Leu | Leu | Phe | Tyr | Gly | Val | Ser |
|---|---|---|---|---|---|---|---|---|---|---|---|---|---|---|---|
| 65 | | | | | 70 | | | | | 75 | | | | | 80 |

| Leu | Gly | Gly | Met | Asn | Tyr | Leu | Phe | Tyr | Leu | Ser | Ile | Gln | Thr | Val | Pro |
|---|---|---|---|---|---|---|---|---|---|---|---|---|---|---|---|
| | | | | 85 | | | | | 90 | | | | | 95 | |

| Leu | Gly | Ile | Ala | Val | Ala | Leu | Glu | Phe | Thr | Gly | Pro | Leu | Ala | Val | Ala |
|---|---|---|---|---|---|---|---|---|---|---|---|---|---|---|---|
| | | | 100 | | | | | 105 | | | | | 110 | | |

| Leu | Phe | Ser | Ser | Arg | Arg | Pro | Val | Asp | Phe | Val | Trp | Val | Val | Leu | Ala |
|---|---|---|---|---|---|---|---|---|---|---|---|---|---|---|---|
| | | 115 | | | | | 120 | | | | | 125 | | | |

| Val | Leu | Gly | Leu | Trp | Phe | Leu | Leu | Pro | Leu | Gly | Gln | Asp | Val | Ser | His |
|---|---|---|---|---|---|---|---|---|---|---|---|---|---|---|---|
| | 130 | | | | | 135 | | | | | 140 | | | | |

| Val | Asp | Leu | Thr | Gly | Cys | Ala | Leu | Ala | Leu | Gly | Ala | Gly | Ala | Cys | Trp |
|---|---|---|---|---|---|---|---|---|---|---|---|---|---|---|---|
| 145 | | | | | 150 | | | | | 155 | | | | | 160 |

| Ala | Ile | Tyr | Ile | Leu | Ser | Gly | Gln | Arg | Ala | Gly | Ala | Glu | His | Gly | Pro |
|---|---|---|---|---|---|---|---|---|---|---|---|---|---|---|---|
| | | | | 165 | | | | | 170 | | | | | 175 | |

| Ala | Thr | Val | Ala | Ile | Gly | Ser | Leu | Ile | Ala | Ala | Leu | Ile | Phe | Val | Pro |
|---|---|---|---|---|---|---|---|---|---|---|---|---|---|---|---|
| | | | 180 | | | | | 185 | | | | | 190 | | |

| Ile | Gly | Ala | Leu | Gln | Ala | Gly | Glu | Ala | Leu | Trp | His | Trp | Ser | Val | Ile |
|---|---|---|---|---|---|---|---|---|---|---|---|---|---|---|---|
| | | 195 | | | | | 200 | | | | | 205 | | | |

| Pro | Leu | Gly | Leu | Ala | Val | Ala | Ile | Leu | Ser | Thr | Ala | Leu | Pro | Tyr | Ser |
|---|---|---|---|---|---|---|---|---|---|---|---|---|---|---|---|
| | 210 | | | | | 215 | | | | | 220 | | | | |

| Leu | Glu | Met | Ile | Ala | Leu | Thr | Arg | Leu | Pro | Thr | Arg | Thr | Phe | Gly | Thr |
|---|---|---|---|---|---|---|---|---|---|---|---|---|---|---|---|
| 225 | | | | | 230 | | | | | 235 | | | | | 240 |

| Leu | Met | Ser | Met | Glu | Pro | Ala | Leu | Ala | Ala | Val | Ser | Gly | Met | Ile | Phe |
|---|---|---|---|---|---|---|---|---|---|---|---|---|---|---|---|
| | | | | 245 | | | | | 250 | | | | | 255 | |

| Leu | Gly | Glu | Thr | Leu | Thr | Pro | Ile | Gln | Leu | Leu | Ala | Leu | Gly | Ala | Ile |
|---|---|---|---|---|---|---|---|---|---|---|---|---|---|---|---|
| | | | 260 | | | | | 265 | | | | | 270 | | |

| Ile | Ala | Ala | Ser | Met | Gly | Ser | Thr | Leu | Thr | Val | Arg | Lys | Glu | Ser | Lys |
|---|---|---|---|---|---|---|---|---|---|---|---|---|---|---|---|
| | | 275 | | | | | 280 | | | | | 285 | | | |

| Ile | Lys | Glu | Leu | Asp | Ile | Asn |
|---|---|---|---|---|---|---|
| | 290 | | | | 295 | |

<210> SEQ ID NO 32
<211> LENGTH: 1269
<212> TYPE: DNA
<213> ORGANISM: Escherichia coli

<400> SEQUENCE: 32
atgcgactcc tccggcaaaa cggaagttta tcacttgtgc gttataacgg acaaatgcta      60
cggtgcctgt acgctataac gcacgaggtg actatgcgtc tgttttctat tcctccaccc     120

```
acgctactgg cggggtttct ggcggtatta attggctacg ccagttcagc ggcaataatc    180
tggcaagcag cgattgtcgc cggagccacc actgcacaaa tctctggctg gatgacggcg    240
ctggggctgg caatgggcgt cagtacgctg actctgacat tatggtatcg cgtacctgtt    300
ctcaccgcat ggtcaacgcc tggcgcggct ttgttggtca ccggattgca gggactaaca    360
cttaacgaag ccatcggcgt ttttattgtc accaacgcgc taatagtcct ctgcggcata    420
acgggactct tgctcgtct gatgcgcatt attccgcact cgcttgcggc ggcaatgctt    480
gccgggattt tattacgctt tggtttacag gcgtttgcca gtctggacgg tcaatttacg    540
ttgtgtggaa gtatgttgct ggtatggctg caaccaagg ccgttgcgcc gcgctatgcg    600
gtaattgccg cgatgattat tgggatcgtg atcgtcatcg cgcaaggtga cgttgtcaca    660
actgatgttg tctttaaacc cgttctcccc acttatatta cccctgattt ttcgtttgct    720
cacagcctga gcgttgcact ccccctttt ctggtgacga tggcatcgca aaacgcaccg    780
ggtatcgcag caatgaaagc agctggatat tcggctcctg tttcgccatt aattgtattt    840
actggattgc tggcactggt tttttcccct ttcggcgttt attccgtcgg tattgcggca    900
atcaccgcgg ctatttgcca aagcccggaa gcgcatccgg ataaagatca acgttggctg    960
gccgctgccg ttgcaggcat tttctatttg ctcgcaggtc tgtttggtag tgccattacc   1020
gggatgatgg ctgccctgcc cgtaagttgg atccagatgc tggcaggtct ggcgctgtta   1080
agtaccatcg gcggcagttt gtatcaggcg ctgcataatg agcgtgagcg agacgcggcg   1140
gtggtggcat ttctggtaac ggcaagtgga ttgacgctgg tcgggattgg ttctgcgttt   1200
tggggattaa ttgccggagg cgtttgttac gtggtgttga atttaatcgc tgacagaaac   1260
cgatattga                                                            1269
```

<210> SEQ ID NO 33
<211> LENGTH: 422
<212> TYPE: PRT
<213> ORGANISM: Escherichia coli

<400> SEQUENCE: 33

```
Met Arg Leu Leu Arg Gln Asn Gly Ser Leu Ser Leu Val Arg Tyr Asn
1               5                   10                  15

Gly Gln Met Leu Arg Cys Leu Tyr Ala Ile Thr His Glu Val Thr Met
            20                  25                  30

Arg Leu Phe Ser Ile Pro Pro Thr Leu Leu Ala Gly Phe Leu Ala
        35                  40                  45

Val Leu Ile Gly Tyr Ala Ser Ser Ala Ala Ile Ile Trp Gln Ala Ala
    50                  55                  60

Ile Val Ala Gly Ala Thr Thr Ala Gln Ile Ser Gly Trp Met Thr Ala
65                  70                  75                  80

Leu Gly Leu Ala Met Gly Val Ser Thr Leu Thr Leu Thr Leu Trp Tyr
                85                  90                  95

Arg Val Pro Val Leu Thr Ala Trp Ser Thr Pro Gly Ala Ala Leu Leu
            100                 105                 110

Val Thr Gly Leu Gln Gly Leu Thr Leu Asn Glu Ala Ile Gly Val Phe
        115                 120                 125

Ile Val Thr Asn Ala Leu Ile Val Leu Cys Gly Ile Thr Gly Leu Phe
    130                 135                 140

Ala Arg Leu Met Arg Ile Ile Pro His Ser Leu Ala Ala Ala Met Leu
145                 150                 155                 160
```

Ala Gly Ile Leu Leu Arg Phe Gly Leu Gln Ala Phe Ala Ser Leu Asp
            165                 170                 175

Gly Gln Phe Thr Leu Cys Gly Ser Met Leu Leu Val Trp Leu Ala Thr
        180                 185                 190

Lys Ala Val Ala Pro Arg Tyr Ala Val Ile Ala Met Ile Ile Gly
        195                 200                 205

Ile Val Ile Val Ile Ala Gln Gly Asp Val Thr Thr Asp Val Val
    210                 215                 220

Phe Lys Pro Val Leu Pro Thr Tyr Ile Thr Pro Asp Phe Ser Phe Ala
225                 230                 235                 240

His Ser Leu Ser Val Ala Leu Pro Leu Phe Leu Val Thr Met Ala Ser
                245                 250                 255

Gln Asn Ala Pro Gly Ile Ala Ala Met Lys Ala Ala Gly Tyr Ser Ala
                260                 265                 270

Pro Val Ser Pro Leu Ile Val Phe Thr Gly Leu Leu Ala Leu Val Phe
            275                 280                 285

Ser Pro Phe Gly Val Tyr Ser Val Gly Ile Ala Ala Ile Thr Ala Ala
        290                 295                 300

Ile Cys Gln Ser Pro Glu Ala His Pro Asp Lys Asp Gln Arg Trp Leu
305                 310                 315                 320

Ala Ala Ala Val Ala Gly Ile Phe Tyr Leu Leu Ala Gly Leu Phe Gly
                325                 330                 335

Ser Ala Ile Thr Gly Met Met Ala Ala Leu Pro Val Ser Trp Ile Gln
                340                 345                 350

Met Leu Ala Gly Leu Ala Leu Leu Ser Thr Ile Gly Gly Ser Leu Tyr
            355                 360                 365

Gln Ala Leu His Asn Glu Arg Glu Arg Asp Ala Ala Val Val Ala Phe
        370                 375                 380

Leu Val Thr Ala Ser Gly Leu Thr Leu Val Gly Ile Gly Ser Ala Phe
385                 390                 395                 400

Trp Gly Leu Ile Ala Gly Gly Val Cys Tyr Val Val Leu Asn Leu Ile
                405                 410                 415

Ala Asp Arg Asn Arg Tyr
            420

<210> SEQ ID NO 34
<211> LENGTH: 1037
<212> TYPE: PRT
<213> ORGANISM: Escherichia coli

<400> SEQUENCE: 34

Met Ala Asn Phe Phe Ile Asp Arg Pro Ile Phe Ala Trp Val Leu Ala
1               5                   10                  15

Ile Leu Leu Cys Leu Thr Gly Thr Leu Ala Ile Phe Ser Leu Pro Val
                20                  25                  30

Glu Gln Tyr Pro Asp Leu Ala Pro Pro Asn Val Arg Val Thr Ala Asn
            35                  40                  45

Tyr Pro Gly Ala Ser Ala Gln Thr Leu Glu Asn Thr Val Thr Gln Val
        50                  55                  60

Ile Glu Gln Asn Met Thr Gly Leu Asp Asn Leu Met Tyr Met Ser Ser
65                  70                  75                  80

Gln Ser Ser Gly Thr Gly Gln Ala Ser Val Thr Leu Ser Phe Lys Ala
                85                  90                  95

Gly Thr Asp Pro Asp Glu Ala Val Gln Gln Val Gln Asn Gln Leu Gln
            100                 105                 110

```
Ser Ala Met Arg Lys Leu Pro Gln Ala Val Gln Asn Gln Gly Val Thr
        115                 120                 125
Val Arg Lys Thr Gly Asp Thr Asn Ile Leu Thr Ile Ala Phe Val Ser
130                 135                 140
Thr Asp Gly Ser Met Asp Lys Gln Asp Ile Ala Asp Tyr Val Ala Ser
145                 150                 155                 160
Asn Ile Gln Asp Pro Leu Ser Arg Val Asn Gly Val Gly Asp Ile Asp
                165                 170                 175
Ala Tyr Gly Ser Gln Tyr Ser Met Arg Ile Trp Leu Asp Pro Ala Lys
                180                 185                 190
Leu Asn Ser Phe Gln Met Thr Ala Lys Asp Val Thr Asp Ala Ile Glu
            195                 200                 205
Ser Gln Asn Ala Gln Ile Ala Val Gly Gln Leu Gly Gly Thr Pro Ser
        210                 215                 220
Val Asp Lys Gln Ala Leu Asn Ala Thr Ile Asn Ala Gln Ser Leu Leu
225                 230                 235                 240
Gln Thr Pro Glu Gln Phe Arg Asp Ile Thr Leu Arg Val Asn Gln Asp
                245                 250                 255
Gly Ser Glu Val Arg Leu Gly Asp Val Ala Thr Val Glu Met Gly Ala
                260                 265                 270
Glu Lys Tyr Asp Tyr Leu Ser Arg Phe Asn Gly Lys Pro Ala Ser Gly
            275                 280                 285
Leu Gly Val Lys Leu Ala Ser Gly Ala Asn Glu Met Ala Thr Ala Glu
        290                 295                 300
Leu Val Leu Asn Arg Leu Asp Glu Leu Ala Gln Tyr Phe Pro His Gly
305                 310                 315                 320
Leu Glu Tyr Lys Val Ala Tyr Glu Thr Thr Ser Phe Val Lys Ala Ser
                325                 330                 335
Ile Glu Asp Val Val Lys Thr Leu Leu Glu Ala Ile Ala Leu Val Phe
                340                 345                 350
Leu Val Met Tyr Leu Phe Leu Gln Asn Phe Arg Ala Thr Leu Ile Pro
            355                 360                 365
Thr Ile Ala Val Pro Val Val Leu Met Gly Thr Phe Ser Val Leu Tyr
        370                 375                 380
Ala Phe Gly Tyr Ser Val Asn Thr Leu Thr Met Phe Ala Met Val Leu
385                 390                 395                 400
Ala Ile Gly Leu Leu Val Asp Asp Ala Ile Val Val Val Glu Asn Val
                405                 410                 415
Glu Arg Ile Met Ser Glu Glu Gly Leu Thr Pro Arg Glu Ala Thr Arg
                420                 425                 430
Lys Ser Met Gly Gln Ile Gln Gly Ala Leu Val Gly Ile Ala Met Val
            435                 440                 445
Leu Ser Ala Val Phe Val Pro Met Ala Phe Phe Gly Gly Thr Thr Gly
        450                 455                 460
Ala Ile Tyr Arg Gln Phe Ser Ile Thr Ile Val Ala Ala Met Val Leu
465                 470                 475                 480
Ser Val Leu Val Ala Met Ile Leu Thr Pro Ala Leu Cys Ala Thr Leu
                485                 490                 495
Leu Lys Pro Leu Lys Lys Gly Glu His His Gly Gln Lys Gly Phe Phe
                500                 505                 510
Ala Trp Phe Asn Gln Met Phe Asn Arg Asn Ala Glu Arg Tyr Glu Lys
            515                 520                 525
```

```
Gly Val Ala Lys Ile Leu His Arg Ser Leu Arg Trp Ile Val Ile Tyr
            530                 535                 540

Val Leu Leu Leu Gly Gly Met Val Phe Leu Phe Leu Arg Leu Pro Thr
545                 550                 555                 560

Ser Phe Leu Pro Leu Glu Asp Arg Gly Met Phe Thr Thr Ser Val Gln
                    565                 570                 575

Leu Pro Ser Gly Ser Thr Gln Gln Thr Leu Lys Val Val Glu Gln
                580                 585                 590

Ile Glu Lys Tyr Tyr Phe Thr His Glu Lys Asp Asn Ile Met Ser Val
            595                 600                 605

Phe Ala Thr Val Gly Ser Gly Pro Gly Gly Asn Gly Gln Asn Val Ala
610                 615                 620

Arg Met Phe Ile Arg Leu Lys Asp Trp Ser Glu Arg Asp Ser Lys Thr
625                 630                 635                 640

Gly Thr Ser Phe Ala Ile Ile Glu Arg Ala Thr Lys Ala Phe Asn Gln
                645                 650                 655

Ile Lys Glu Ala Arg Val Ile Ala Ser Ser Pro Pro Ala Ile Ser Gly
            660                 665                 670

Leu Gly Ser Ser Ala Gly Phe Asp Met Glu Leu Gln Asp His Ala Gly
                675                 680                 685

Ala Gly His Asp Ala Leu Met Ala Ala Arg Asn Gln Leu Leu Ala Leu
690                 695                 700

Ala Ala Glu Asn Pro Glu Leu Thr Arg Val Arg His Asn Gly Leu Asp
705                 710                 715                 720

Asp Ser Pro Gln Leu Gln Ile Asp Ile Asp Gln Arg Lys Ala Gln Ala
                725                 730                 735

Leu Gly Val Ala Ile Asp Asp Ile Asn Asp Thr Leu Gln Thr Ala Trp
                740                 745                 750

Gly Ser Ser Tyr Val Asn Asp Phe Met Asp Arg Gly Arg Val Lys Lys
            755                 760                 765

Val Tyr Val Gln Ala Ala Pro Tyr Arg Met Leu Pro Asp Asp Ile
770                 775                 780

Asn Leu Trp Tyr Val Arg Asn Lys Asp Gly Gly Met Val Pro Phe Ser
785                 790                 795                 800

Ala Phe Ala Thr Ser Arg Trp Glu Thr Gly Ser Pro Arg Leu Glu Arg
                805                 810                 815

Tyr Asn Gly Tyr Ser Ala Val Glu Ile Val Gly Glu Ala Ala Pro Gly
            820                 825                 830

Val Ser Thr Gly Thr Ala Met Asp Ile Met Glu Ser Leu Val Lys Gln
                835                 840                 845

Leu Pro Asn Gly Phe Gly Leu Glu Trp Thr Ala Met Ser Tyr Gln Glu
850                 855                 860

Arg Leu Ser Gly Ala Gln Ala Pro Ala Leu Tyr Ala Ile Ser Leu Leu
865                 870                 875                 880

Val Val Phe Leu Cys Leu Ala Ala Leu Tyr Glu Ser Trp Ser Val Pro
                885                 890                 895

Phe Ser Val Met Leu Val Val Pro Leu Gly Val Ile Gly Ala Leu Leu
                900                 905                 910

Ala Thr Trp Met Arg Gly Leu Glu Asn Asp Val Tyr Phe Gln Val Gly
                915                 920                 925

Leu Leu Thr Val Ile Gly Leu Ser Ala Lys Asn Ala Ile Leu Ile Val
                930                 935                 940

Glu Phe Ala Asn Glu Met Asn Gln Lys Gly His Asp Leu Phe Glu Ala
```

-continued

```
                945           950           955           960

Thr Leu His Ala Cys Arg Gln Arg Leu Arg Pro Ile Leu Met Thr Ser
                965                   970                   975

Leu Ala Phe Ile Phe Gly Val Leu Pro Met Ala Thr Ser Thr Gly Ala
            980                   985                   990

Gly Ser Gly Gly Gln His Ala Val Gly Thr Gly Val Met Gly Gly Met
            995                  1000                  1005

Ile Ser Ala Thr Ile Leu Ala Ile Tyr Phe Val Pro Leu Phe Phe
       1010                  1015                  1020

Val Leu Val Arg Arg Arg Phe Pro Leu Lys Pro Arg Pro Glu
       1025                  1030                  1035
```

<210> SEQ ID NO 35
<211> LENGTH: 591
<212> TYPE: PRT
<213> ORGANISM: Escherichia coli

<400> SEQUENCE: 35

```
Met Ala His Pro Pro Leu Leu His Leu Gln Asp Ile Thr Leu Ser Leu
1               5                   10                  15

Gly Gly Asn Pro Leu Leu Asp Gly Ala Gly Phe Ala Val Gly Arg Gly
            20                  25                  30

Glu Arg Leu Cys Leu Val Gly Arg Asn Gly Ser Gly Lys Ser Thr Leu
        35                  40                  45

Leu Lys Ile Ala Ala Gly Val Ile Gln Pro Asp Ser Gly Ser Val Phe
    50                  55                  60

Val Gln Pro Gly Ala Ser Leu Arg Tyr Leu Pro Gln Glu Pro Asp Leu
65                  70                  75                  80

Ser Ala Tyr Ala Thr Thr Ala Asp Tyr Val Val Gly Gln Ile Gly Asp
                85                  90                  95

Pro Asp Met Ala Trp Arg Ala Thr Pro Leu Leu Asp Ala Leu Gly Leu
            100                 105                 110

Thr Gly Arg Glu Ser Thr Gln Asn Leu Ser Gly Gly Glu Gly Arg Arg
        115                 120                 125

Cys Ala Ile Ala Gly Val Leu Ala Ala Pro Asp Val Leu Leu Leu
    130                 135                 140

Asp Glu Pro Thr Asn His Leu Asp Met Pro Thr Ile Glu Trp Leu Glu
145                 150                 155                 160

Arg Glu Leu Leu Ser Leu Gly Ala Met Val Ile Ser His Asp Arg
                165                 170                 175

Arg Leu Leu Ser Thr Leu Ser Arg Ser Val Val Trp Leu Asp Arg Gly
            180                 185                 190

Val Thr Arg Arg Leu Asp Glu Gly Phe Gly Arg Phe Glu Ala Trp Arg
        195                 200                 205

Glu Glu Val Leu Glu Gln Glu Arg Asp Ala His Lys Leu Asp Arg
    210                 215                 220

Lys Ile Ala Arg Glu Glu Asp Trp Met Arg Tyr Gly Val Thr Ala Arg
225                 230                 235                 240

Arg Lys Arg Asn Val Arg Arg Val Arg Glu Leu Ala Asp Leu Arg Thr
                245                 250                 255

Ala Arg Lys Glu Ala Ile Arg Ala Pro Gly Thr Leu Thr Leu Asn Thr
            260                 265                 270

Gln Leu Arg Pro His Arg Lys Leu Val Ala Val Ala Glu Asp Ile Ser
        275                 280                 285
```

```
Lys Ala Trp Gly Glu Lys Gln Val Arg His Leu Asp Leu Arg Ile
    290                 295                 300

Leu Arg Gly Asp Arg Leu Gly Ile Val Gly Ala Asn Gly Ala Gly Lys
305                 310                 315                 320

Thr Thr Leu Leu Arg Met Leu Thr Gly Leu Asp Gln Pro Asp Ser Gly
                    325                 330                 335

Thr Ile Ser Leu Gly Pro Ser Leu Asn Met Val Thr Leu Asp Gln Gln
                340                 345                 350

Arg Arg Thr Leu Asn Pro Glu Arg Thr Leu Ala Asp Thr Leu Thr Glu
                355                 360                 365

Gly Gly Gly Asp Met Val Gln Val Gly Thr Glu Lys Arg His Val Val
370                 375                 380

Gly Tyr Met Lys Asp Phe Leu Phe Arg Pro Glu Gln Ala Arg Thr Pro
385                 390                 395                 400

Val Ser Ala Leu Ser Gly Gly Glu Arg Gly Arg Leu Met Leu Ala Cys
                405                 410                 415

Ala Leu Ala Lys Pro Ser Asn Leu Leu Val Leu Asp Glu Pro Thr Asn
                420                 425                 430

Asp Leu Asp Leu Glu Thr Leu Asp Ile Leu Gln Asp Met Leu Ala Ser
                435                 440                 445

Cys Glu Gly Thr Val Leu Leu Val Ser His Asp Arg Asp Phe Leu Asp
450                 455                 460

Arg Val Ala Thr Ser Val Leu Ala Thr Glu Gly Asp Gly Asn Trp Ile
465                 470                 475                 480

Glu Tyr Ala Gly Gly Tyr Ser Asp Met Leu Ala Gln Arg His Gln Lys
                485                 490                 495

Pro Leu Thr Thr Ala Ser Val Val Glu Asn Glu Pro Thr Lys Pro Lys
                500                 505                 510

Glu Thr Thr Ala Ala Arg Gly Pro Thr Lys Lys Leu Ser Tyr Lys Asp
                515                 520                 525

Gln Phe Ala Leu Asp Asn Leu Pro Lys Glu Met Glu Lys Leu Glu Ala
                530                 535                 540

Gln Ala Ala Asn Cys Val Lys Asn Trp Gln Ile Gln Ile Tyr Met Glu
545                 550                 555                 560

Lys Thr Pro Arg Ser Leu Arg Asn Phe Arg Leu Ile Tyr Arg Ser Ser
                565                 570                 575

Lys Gln Ser Trp Gln Asn Leu Lys Asn Ala Gly Trp Asn Trp Lys
                580                 585                 590

<210> SEQ ID NO 36
<211> LENGTH: 396
<212> TYPE: PRT
<213> ORGANISM: Escherichia coli

<400> SEQUENCE: 36

Met Thr Thr Arg Gln His Ser Ser Phe Ala Ile Val Phe Ile Leu Gly
1               5                   10                  15

Leu Leu Ala Met Leu Met Pro Leu Ser Ile Asp Met Tyr Leu Pro Ala
                20                  25                  30

Leu Pro Val Ile Ser Ala Gln Phe Gly Val Pro Ala Gly Ser Thr Gln
                35                  40                  45

Met Thr Leu Ser Thr Tyr Ile Leu Gly Phe Ala Leu Gly Gln Leu Ile
                50                  55                  60

Tyr Gly Pro Met Ala Asp Ser Phe Gly Arg Lys Pro Val Val Leu Gly
65                  70                  75                  80
```

```
Gly Thr Leu Val Phe Ala Ala Ala Val Ala Cys Ala Leu Ala Asn
                85                  90                  95

Thr Ile Asp Gln Leu Ile Val Met Arg Phe His Gly Leu Ala Ala
            100                 105                 110

Ala Ala Ala Ser Val Val Ile Asn Ala Leu Met Arg Asp Ile Tyr Pro
        115                 120                 125

Lys Glu Glu Phe Ser Arg Met Met Ser Phe Val Met Leu Val Thr Thr
    130                 135                 140

Ile Ala Pro Leu Met Ala Pro Ile Val Gly Gly Trp Val Leu Val Trp
145                 150                 155                 160

Leu Ser Trp His Tyr Ile Phe Trp Ile Leu Ala Leu Ala Ala Ile Leu
                165                 170                 175

Ala Ser Ala Met Ile Phe Phe Leu Ile Lys Glu Thr Leu Pro Pro Glu
            180                 185                 190

Arg Arg Gln Pro Phe His Ile Arg Thr Thr Ile Gly Asn Phe Ala Ala
        195                 200                 205

Leu Phe Arg His Lys Arg Val Leu Ser Tyr Met Leu Ala Ser Gly Phe
    210                 215                 220

Ser Phe Ala Gly Met Phe Ser Phe Leu Ser Ala Gly Pro Phe Val Tyr
225                 230                 235                 240

Ile Glu Ile Asn His Val Ala Pro Glu Asn Phe Gly Tyr Tyr Phe Ala
                245                 250                 255

Leu Asn Ile Val Phe Leu Phe Val Met Thr Ile Phe Asn Ser Arg Phe
            260                 265                 270

Val Arg Arg Ile Gly Ala Leu Asn Met Phe Arg Ser Gly Leu Trp Ile
        275                 280                 285

Gln Phe Ile Met Ala Ala Trp Met Val Ile Ser Ala Leu Leu Gly Leu
    290                 295                 300

Gly Phe Trp Ser Leu Val Val Gly Val Ala Phe Val Gly Cys Val
305                 310                 315                 320

Ser Met Val Ser Ser Asn Ala Met Ala Val Ile Leu Asp Glu Phe Pro
                325                 330                 335

His Met Ala Gly Thr Ala Ser Ser Leu Ala Gly Thr Phe Arg Phe Gly
            340                 345                 350

Ile Gly Ala Ile Val Gly Ala Leu Leu Ser Leu Ala Thr Phe Asn Ser
        355                 360                 365

Ala Trp Pro Met Ile Trp Ser Ile Ala Phe Cys Ala Thr Ser Ser Ile
    370                 375                 380

Leu Phe Cys Leu Tyr Ala Ser Arg Pro Lys Lys Arg
385                 390                 395

<210> SEQ ID NO 37
<211> LENGTH: 1047
<212> TYPE: PRT
<213> ORGANISM: Escherichia coli

<400> SEQUENCE: 37

Met Ile Glu Trp Ile Arg Arg Ser Val Ala Asn Arg Phe Leu Val
1               5                   10                  15

Leu Met Gly Ala Leu Phe Leu Ser Ile Trp Gly Thr Trp Thr Ile Ile
            20                  25                  30

Asn Thr Pro Val Asp Ala Leu Pro Asp Leu Ser Asp Val Gln Val Ile
        35                  40                  45

Ile Lys Thr Ser Tyr Pro Gly Gln Ala Pro Gln Ile Val Glu Asn Gln
```

```
                50                  55                  60
Val Thr Tyr Pro Leu Thr Thr Met Leu Ser Val Pro Gly Ala Lys
 65                  70                  75                  80

Thr Val Arg Gly Phe Ser Gln Phe Gly Asp Ser Tyr Val Tyr Val Ile
                     85                  90                  95

Phe Glu Asp Gly Thr Asp Pro Tyr Trp Ala Arg Ser Arg Val Leu Glu
                100                 105                 110

Tyr Leu Asn Gln Val Gln Gly Lys Leu Pro Ala Gly Val Ser Ala Glu
                115                 120                 125

Leu Gly Pro Asp Ala Thr Gly Val Gly Trp Ile Tyr Glu Tyr Ala Leu
                130                 135                 140

Val Asp Arg Ser Gly Lys His Asp Leu Ala Asp Leu Arg Ser Leu Gln
145                 150                 155                 160

Asp Trp Phe Leu Lys Tyr Glu Leu Lys Thr Ile Pro Asp Val Ala Glu
                    165                 170                 175

Val Ala Ser Val Gly Val Val Lys Glu Tyr Gln Val Val Ile Asp
                180                 185                 190

Pro Gln Arg Leu Ala Gln Tyr Gly Ile Ser Leu Ala Glu Val Lys Ser
                    195                 200                 205

Ala Leu Asp Ala Ser Asn Gln Glu Ala Gly Gly Ser Ser Ile Glu Leu
                    210                 215                 220

Ala Glu Ala Glu Tyr Met Val Arg Ala Ser Gly Tyr Leu Gln Thr Leu
225                 230                 235                 240

Asp Asp Phe Asn His Ile Val Leu Lys Ala Ser Glu Asn Gly Val Pro
                    245                 250                 255

Val Tyr Leu Arg Asp Val Ala Lys Val Gln Ile Gly Pro Glu Met Arg
                    260                 265                 270

Arg Gly Ile Ala Glu Leu Asn Gly Glu Gly Val Ala Gly Val
                    275                 280                 285

Val Ile Leu Arg Ser Gly Lys Asn Ala Arg Glu Val Ile Ala Ala Val
                    290                 295                 300

Lys Asp Lys Leu Glu Thr Leu Lys Ser Ser Leu Pro Glu Gly Val Glu
305                 310                 315                 320

Ile Val Thr Thr Tyr Asp Arg Ser Gln Leu Ile Asp Arg Ala Ile Asp
                    325                 330                 335

Asn Leu Ser Gly Lys Leu Leu Glu Glu Phe Ile Val Val Ala Val Val
                    340                 345                 350

Cys Ala Leu Phe Leu Trp His Val Arg Ser Ala Leu Val Ala Ile Ile
                    355                 360                 365

Ser Leu Pro Leu Gly Leu Cys Ile Ala Phe Ile Val Met His Phe Gln
                    370                 375                 380

Gly Leu Asn Ala Asn Ile Met Ser Leu Gly Gly Ile Ala Ile Ala Val
385                 390                 395                 400

Gly Ala Met Val Asp Ala Ala Ile Val Met Ile Glu Asn Ala His Lys
                    405                 410                 415

Arg Leu Glu Glu Trp Gln His Gln His Pro Asp Ala Thr Leu Asp Asn
                    420                 425                 430

Lys Thr Arg Trp Gln Val Ile Thr Asp Ala Ser Val Glu Val Gly Pro
                    435                 440                 445

Ala Leu Phe Ile Ser Leu Leu Ile Ile Thr Leu Ser Phe Ile Pro Ile
                    450                 455                 460

Phe Thr Leu Glu Gly Gln Glu Gly Arg Leu Phe Gly Pro Leu Ala Phe
465                 470                 475                 480
```

```
Thr Lys Thr Tyr Ala Met Ala Gly Ala Ala Leu Leu Ala Ile Val Val
                485             490                 495
Ile Pro Ile Leu Met Gly Tyr Trp Ile Arg Gly Lys Ile Pro Pro Glu
                500             505                 510
Ser Ser Asn Pro Leu Asn Arg Phe Leu Ile Arg Val Tyr His Pro Leu
                515             520                 525
Leu Leu Lys Val Leu His Trp Pro Lys Thr Thr Leu Leu Val Ala Ala
                530             535                 540
Leu Ser Val Leu Thr Val Leu Trp Pro Leu Asn Lys Val Gly Gly Glu
545                 550             555                 560
Phe Leu Pro Gln Ile Asn Glu Gly Asp Leu Leu Tyr Met Pro Ser Thr
                565             570                 575
Leu Pro Gly Ile Ser Ala Ala Glu Ala Ala Ser Met Leu Gln Lys Thr
                580             585                 590
Asp Lys Leu Ile Met Ser Val Pro Glu Val Ala Arg Val Phe Gly Lys
                595             600                 605
Thr Gly Lys Ala Glu Thr Ala Thr Asp Ser Ala Pro Leu Glu Met Val
                610             615                 620
Glu Thr Thr Ile Gln Leu Lys Pro Gln Glu Gln Trp Arg Pro Gly Met
625                 630             635                 640
Thr Met Asp Lys Ile Ile Glu Glu Leu Asp Asn Thr Val Arg Leu Pro
                645             650                 655
Gly Leu Ala Asn Leu Trp Val Pro Pro Ile Arg Asn Arg Ile Asp Met
                660             665                 670
Leu Ser Thr Gly Ile Lys Ser Pro Ile Gly Ile Lys Val Ser Gly Thr
                675             680                 685
Val Leu Ala Asp Ile Asp Ala Met Ala Glu Gln Ile Glu Glu Val Ala
                690             695                 700
Arg Thr Val Pro Gly Val Ala Ser Ala Leu Ala Glu Arg Leu Glu Gly
705                 710             715                 720
Gly Arg Tyr Ile Asn Val Glu Ile Asn Arg Glu Lys Ala Ala Arg Tyr
                725             730                 735
Gly Met Thr Val Ala Asp Val Gln Leu Phe Val Thr Ser Ala Val Gly
                740             745                 750
Gly Ala Met Val Gly Glu Thr Val Glu Gly Ile Ala Arg Tyr Pro Ile
                755             760                 765
Asn Leu Arg Tyr Pro Gln Ser Trp Arg Asp Ser Pro Gln Ala Leu Arg
                770             775                 780
Gln Leu Pro Ile Leu Thr Pro Met Lys Gln Gln Ile Thr Leu Ala Asp
785                 790             795                 800
Val Ala Asp Ile Lys Val Ser Thr Gly Pro Ser Met Leu Lys Thr Glu
                805             810                 815
Asn Ala Arg Pro Thr Ser Trp Ile Tyr Ile Asp Ala Arg Asp Arg Asp
                820             825                 830
Met Val Ser Val Val His Asp Leu Gln Lys Ala Ile Ala Glu Lys Val
                835             840                 845
Gln Leu Lys Pro Gly Thr Ser Val Ala Phe Ser Gly Gln Phe Glu Leu
                850             855                 860
Leu Glu Arg Ala Asn His Lys Leu Lys Leu Met Val Pro Met Thr Leu
865                 870             875                 880
Met Ile Ile Phe Val Leu Leu Tyr Leu Ala Phe Arg Arg Val Gly Glu
                885             890                 895
```

```
Ala Leu Leu Ile Ile Ser Ser Val Pro Phe Ala Leu Val Gly Gly Ile
            900                 905                 910

Trp Leu Leu Trp Trp Met Gly Phe His Leu Ser Val Ala Thr Gly Thr
        915                 920                 925

Gly Phe Ile Ala Leu Ala Gly Val Ala Ala Glu Phe Gly Val Val Met
        930                 935                 940

Leu Met Tyr Leu Arg His Ala Ile Glu Ala Val Pro Ser Leu Asn Asn
945                 950                 955                 960

Pro Gln Thr Phe Ser Glu Gln Lys Leu Asp Glu Ala Leu Tyr His Gly
                965                 970                 975

Ala Val Leu Arg Val Arg Pro Lys Ala Met Thr Val Ala Val Ile Ile
            980                 985                 990

Ala Gly Leu Leu Pro Ile Leu Trp Gly Thr Gly Ala Gly Ser Glu Val
        995                 1000                1005

Met Ser Arg Ile Ala Ala Pro Met Ile Gly Gly Met Ile Thr Ala
    1010                1015                1020

Pro Leu Leu Ser Leu Phe Ile Ile Pro Ala Ala Tyr Lys Leu Met
    1025                1030                1035

Trp Leu His Arg His Arg Val Arg Lys
    1040                1045
```

<210> SEQ ID NO 38
<211> LENGTH: 384
<212> TYPE: PRT
<213> ORGANISM: Escherichia coli

<400> SEQUENCE: 38

```
Met Leu Leu Val Leu Val Leu Ile Gly Leu Asn Met Arg Pro Leu Leu
1               5                   10                  15

Thr Ser Val Gly Pro Leu Leu Pro Gln Leu Arg Gln Ala Ser Gly Met
            20                  25                  30

Ser Phe Ser Val Ala Ala Leu Leu Thr Ala Leu Pro Val Val Thr Met
        35                  40                  45

Gly Gly Leu Ala Leu Ala Gly Ser Trp Leu His Gln His Val Ser Glu
    50                  55                  60

Arg Arg Ser Val Ala Ile Ser Leu Leu Leu Ile Ala Val Gly Ala Leu
65                  70                  75                  80

Met Arg Glu Leu Tyr Pro Gln Ser Ala Leu Leu Leu Ser Ser Ala Leu
                85                  90                  95

Leu Gly Gly Val Gly Ile Gly Ile Ile Gln Ala Val Met Pro Ser Val
            100                 105                 110

Ile Lys Arg Arg Phe Gln Gln Arg Thr Pro Leu Val Met Gly Leu Trp
        115                 120                 125

Ser Ala Ala Leu Met Gly Gly Gly Gly Leu Gly Ala Ala Ile Thr Pro
    130                 135                 140

Trp Leu Val Gln His Ser Glu Thr Trp Tyr Gln Thr Leu Ala Trp Trp
145                 150                 155                 160

Ala Leu Pro Ala Val Val Ala Leu Phe Ala Trp Trp Gln Ser Ala
                165                 170                 175

Arg Glu Val Ala Ser Ser His Lys Thr Thr Thr Thr Pro Val Arg Val
            180                 185                 190

Val Phe Thr Pro Arg Ala Trp Thr Leu Gly Val Tyr Phe Gly Leu Ile
        195                 200                 205

Asn Gly Gly Tyr Ala Ser Leu Ile Ala Trp Leu Pro Ala Phe Tyr Ile
    210                 215                 220
```

```
Glu Ile Gly Ala Ser Ala Gln Tyr Ser Gly Ser Leu Leu Ala Leu Met
225                 230                 235                 240

Thr Leu Gly Gln Ala Ala Gly Ala Leu Leu Met Pro Ala Met Ala Arg
                245                 250                 255

His Gln Asp Arg Arg Lys Leu Leu Met Leu Ala Leu Val Leu Gln Leu
            260                 265                 270

Val Gly Phe Cys Gly Phe Ile Trp Leu Pro Met Gln Leu Pro Val Leu
        275                 280                 285

Trp Ala Met Val Cys Gly Leu Gly Leu Gly Gly Ala Phe Pro Leu Cys
    290                 295                 300

Leu Leu Leu Ala Leu Asp His Ser Val Gln Pro Ala Ile Ala Gly Lys
305                 310                 315                 320

Leu Val Ala Phe Met Gln Gly Ile Gly Phe Ile Ile Ala Gly Leu Ala
                325                 330                 335

Pro Trp Phe Ser Gly Val Leu Arg Ser Ile Ser Gly Asn Tyr Leu Met
                340                 345                 350

Asp Trp Ala Phe His Ala Leu Cys Val Val Gly Leu Met Ile Ile Thr
                355                 360                 365

Leu Arg Phe Ala Pro Val Arg Phe Pro Gln Leu Trp Val Lys Glu Ala
    370                 375                 380

<210> SEQ ID NO 39
<211> LENGTH: 219
<212> TYPE: PRT
<213> ORGANISM: Escherichia coli

<400> SEQUENCE: 39

Met Asp Leu Ile Tyr Phe Leu Ile Asp Phe Ile Leu His Ile Asp Val
1               5                   10                  15

His Leu Ala Glu Leu Val Ala Glu Tyr Gly Val Trp Val Tyr Ala Ile
                20                  25                  30

Leu Phe Leu Ile Leu Phe Cys Glu Thr Gly Leu Val Val Thr Pro Phe
            35                  40                  45

Leu Pro Gly Asp Ser Leu Leu Phe Val Ala Gly Ala Leu Ala Ser Leu
50                  55                  60

Glu Thr Asn Asp Leu Asn Val His Met Met Val Val Leu Met Leu Ile
65                  70                  75                  80

Ala Ala Ile Val Gly Asp Ala Val Asn Tyr Thr Ile Gly Arg Leu Phe
                85                  90                  95

Gly Glu Lys Leu Phe Ser Asn Pro Asn Ser Lys Ile Phe Arg Arg Ser
            100                 105                 110

Tyr Leu Asp Lys Thr His Gln Phe Tyr Glu Lys His Gly Gly Lys Thr
        115                 120                 125

Ile Ile Leu Ala Arg Phe Val Pro Ile Val Arg Thr Phe Ala Pro Phe
130                 135                 140

Val Ala Gly Met Gly His Met Ser Tyr Arg His Phe Ala Ala Tyr Asn
145                 150                 155                 160

Val Ile Gly Ala Leu Leu Trp Val Leu Leu Phe Thr Tyr Ala Gly Tyr
                165                 170                 175

Phe Phe Gly Thr Ile Pro Met Val Gln Asp Asn Leu Lys Leu Leu Ile
            180                 185                 190

Val Gly Ile Ile Val Ser Ile Leu Pro Gly Val Ile Glu Ile Ile
        195                 200                 205

Arg His Lys Arg Ala Ala Ala Arg Ala Ala Lys
```

<210> SEQ ID NO 40
<211> LENGTH: 299
<212> TYPE: PRT
<213> ORGANISM: Escherichia coli

<400> SEQUENCE: 40

Met Ser Arg Lys Asp Gly Val Leu Ala Leu Val Val Val Trp
1               5                   10                  15

Gly Leu Asn Phe Val Ile Lys Val Gly Leu His Asn Met Pro Pro
                20                  25                  30

Leu Met Leu Ala Gly Leu Arg Phe Met Leu Val Ala Phe Pro Ala Ile
                35                  40                  45

Phe Phe Val Ala Arg Pro Lys Val Pro Leu Asn Leu Leu Gly Tyr
        50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                    85                  90                  95

Ala Phe Phe Thr Ile Met Leu Gly Ala Phe Thr Phe Gly Glu Arg Leu
                100                 105                 110

His Gly Lys Gln Leu Ala Gly Ile Ala Leu Ala Ile Phe Gly Val Leu
                115                 120                 125

Val Leu Ile Glu Asp Ser Leu Asn Gly Gln His Val Ala Met Leu Gly
    130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
                180                 185                 190

Ser Leu Ile Leu Asp Gly Ser Ala Thr Met Ile His Ser Leu Val Thr
            195                 200                 205

Ile Asp Met Thr Thr Ile Leu Ser Leu Met Tyr Leu Ala Phe Val Ala
    210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Leu Val Pro Val Val Gly Leu
                245                 250                 255

Ala Ser Ala Ala Leu Leu Leu Asp Glu Arg Leu Thr Gly Leu Gln Phe
                260                 265                 270

Leu Gly Ala Val Leu Ile Met Thr Gly Leu Tyr Ile Asn Val Phe Gly
            275                 280                 285

Leu Arg Trp Arg Lys Ala Val Lys Val Gly Ser
    290                 295

<210> SEQ ID NO 41
<211> LENGTH: 195
<212> TYPE: PRT
<213> ORGANISM: Escherichia coli

<400> SEQUENCE: 41

Met Thr Pro Thr Leu Leu Ser Ala Phe Trp Thr Tyr Thr Leu Ile Thr
1               5                   10                  15

Ala Met Thr Pro Gly Pro Asn Asn Ile Leu Ala Leu Ser Ser Ala Thr

```
            20                  25                  30
Ser His Gly Phe Arg Gln Ser Thr Arg Val Leu Ala Gly Met Ser Leu
        35                  40                  45

Gly Phe Leu Ile Val Met Leu Leu Cys Ala Gly Ile Ser Phe Ser Leu
    50                  55                  60

Ala Val Ile Asp Pro Ala Val His Leu Leu Ser Trp Ala Gly Ala
65                  70                  75                  80

Ala Tyr Ile Val Trp Leu Ala Trp Lys Ile Ala Thr Ser Pro Thr Lys
                85                  90                  95

Glu Asp Gly Leu Gln Ala Lys Pro Ile Ser Phe Trp Ala Ser Phe Ala
            100                 105                 110

Leu Gln Phe Val Asn Val Lys Ile Ile Leu Tyr Gly Val Thr Ala Leu
        115                 120                 125

Ser Thr Phe Val Leu Pro Gln Thr Gln Ala Leu Ser Trp Val Val Gly
    130                 135                 140

Val Ser Val Leu Leu Ala Met Ile Gly Thr Phe Gly Asn Val Cys Trp
145                 150                 155                 160

Ala Leu Ala Gly His Leu Phe Gln Arg Leu Phe Arg Gln Tyr Gly Arg
                165                 170                 175

Gln Leu Asn Ile Val Leu Ala Leu Leu Val Tyr Cys Ala Val Arg
            180                 185                 190

Ile Phe Tyr
        195

<210> SEQ ID NO 42
<211> LENGTH: 512
<212> TYPE: PRT
<213> ORGANISM: Escherichia coli

<400> SEQUENCE: 42

Met Gln Gln Gln Lys Pro Leu Glu Gly Ala Gln Leu Val Ile Met Thr
1               5                   10                  15

Ile Ala Leu Ser Leu Ala Thr Phe Met Gln Val Leu Asp Ser Thr Ile
            20                  25                  30

Ala Asn Val Ala Ile Pro Thr Ile Ala Gly Asn Leu Gly Ser Ser Leu
        35                  40                  45

Ser Gln Gly Thr Trp Val Ile Thr Ser Phe Gly Val Ala Asn Ala Ile
    50                  55                  60

Ser Ile Pro Leu Thr Gly Trp Leu Ala Lys Arg Val Gly Glu Val Lys
65                  70                  75                  80

Leu Phe Leu Trp Ser Thr Ile Ala Phe Ala Ile Ala Ser Trp Ala Cys
                85                  90                  95

Gly Val Ser Ser Leu Asn Met Leu Ile Phe Phe Arg Val Ile Gln
            100                 105                 110

Gly Ile Val Ala Gly Pro Leu Ile Pro Leu Ser Gln Ser Leu Leu Leu
        115                 120                 125

Asn Asn Tyr Pro Pro Ala Lys Arg Ser Ile Ala Leu Ala Leu Trp Ser
    130                 135                 140

Met Thr Val Ile Val Ala Pro Ile Cys Gly Pro Ile Leu Gly Gly Tyr
145                 150                 155                 160

Ile Ser Asp Asn Tyr His Trp Gly Trp Ile Phe Phe Ile Asn Val Pro
                165                 170                 175

Ile Gly Val Ala Val Val Leu Met Thr Leu Gln Thr Leu Arg Gly Arg
            180                 185                 190
```

-continued

```
Glu Thr Arg Thr Glu Arg Arg Ile Asp Ala Val Gly Leu Ala Leu
                195                 200                 205

Leu Val Ile Gly Ile Gly Ser Leu Gln Ile Met Leu Asp Arg Gly Lys
    210                 215                 220

Glu Leu Asp Trp Phe Ser Ser Gln Ile Ile Ile Leu Thr Val Val
225                 230                 235                 240

Ala Val Val Ala Ile Cys Phe Leu Ile Val Trp Glu Leu Thr Asp Asp
                245                 250                 255

Asn Pro Ile Val Asp Leu Ser Leu Phe Lys Ser Arg Asn Phe Thr Ile
                260                 265                 270

Gly Cys Leu Cys Ile Ser Leu Ala Tyr Met Leu Tyr Phe Gly Ala Ile
            275                 280                 285

Val Leu Leu Pro Gln Leu Leu Gln Glu Val Tyr Gly Tyr Thr Ala Thr
    290                 295                 300

Trp Ala Gly Leu Ala Ser Ala Pro Val Gly Ile Ile Pro Val Ile Leu
305                 310                 315                 320

Ser Pro Ile Ile Gly Arg Phe Ala His Lys Leu Asp Met Arg Arg Leu
                325                 330                 335

Val Thr Phe Ser Phe Ile Met Tyr Ala Val Cys Phe Tyr Trp Arg Ala
                340                 345                 350

Tyr Thr Phe Glu Pro Gly Met Asp Phe Gly Ala Ser Ala Trp Pro Gln
            355                 360                 365

Phe Ile Gln Gly Phe Ala Val Ala Cys Phe Phe Met Pro Leu Thr Thr
    370                 375                 380

Ile Thr Leu Ser Gly Leu Pro Pro Glu Arg Leu Ala Ala Ala Ser Ser
385                 390                 395                 400

Leu Ser Asn Phe Thr Arg Thr Leu Ala Gly Ser Ile Gly Thr Ser Ile
                405                 410                 415

Thr Thr Thr Met Trp Thr Asn Arg Glu Ser Met His His Ala Gln Leu
                420                 425                 430

Thr Glu Ser Val Asn Pro Phe Asn Pro Asn Ala Gln Ala Met Tyr Ser
            435                 440                 445

Gln Leu Glu Gly Leu Gly Met Thr Gln Gln Ala Ser Gly Trp Ile
    450                 455                 460

Ala Gln Gln Ile Thr Asn Gln Gly Leu Ile Ile Ser Ala Asn Glu Ile
465                 470                 475                 480

Phe Trp Met Ser Ala Gly Ile Phe Leu Val Leu Gly Leu Val Trp
                485                 490                 495

Phe Ala Lys Pro Pro Phe Gly Ala Gly Gly Gly Gly Ala His
            500                 505                 510

<210> SEQ ID NO 43
<211> LENGTH: 394
<212> TYPE: PRT
<213> ORGANISM: Escherichia coli

<400> SEQUENCE: 43

Met Lys Arg Gln Arg Asn Val Asn Leu Leu Leu Met Leu Val Leu Leu
1               5                   10                  15

Val Ala Val Gly Gln Met Ala Gln Thr Ile Tyr Ile Pro Ala Ile Ala
                20                  25                  30

Asp Met Ala Arg Asp Leu Asn Val Arg Glu Gly Ala Val Gln Ser Val
            35                  40                  45

Met Gly Ala Tyr Leu Leu Thr Tyr Gly Val Ser Gln Leu Phe Tyr Gly
    50                  55                  60
```

```
Pro Ile Ser Asp Arg Val Gly Arg Arg Pro Val Ile Leu Val Gly Met
 65                  70                  75                  80

Ser Ile Phe Met Leu Ala Thr Leu Val Ala Val Thr Thr Ser Ser Leu
                 85                  90                  95

Thr Val Leu Ile Ala Ala Ser Ala Met Gln Gly Met Gly Thr Gly Val
            100                 105                 110

Gly Gly Val Met Ala Arg Thr Leu Pro Arg Asp Leu Tyr Glu Arg Thr
        115                 120                 125

Gln Leu Arg His Ala Asn Ser Leu Leu Asn Met Gly Ile Leu Val Ser
130                 135                 140

Pro Leu Leu Ala Pro Leu Ile Gly Gly Leu Leu Asp Thr Met Trp Asn
145                 150                 155                 160

Trp Arg Ala Cys Tyr Leu Phe Leu Leu Val Leu Cys Ala Gly Val Thr
                165                 170                 175

Phe Ser Met Ala Arg Trp Met Pro Glu Thr Arg Pro Val Asp Ala Pro
            180                 185                 190

Arg Thr Arg Leu Leu Thr Ser Tyr Lys Thr Leu Phe Gly Asn Ser Gly
        195                 200                 205

Phe Asn Cys Tyr Leu Leu Met Leu Ile Gly Gly Leu Ala Gly Ile Ala
210                 215                 220

Ala Phe Glu Ala Cys Ser Gly Val Leu Met Gly Ala Val Leu Gly Leu
225                 230                 235                 240

Ser Ser Met Thr Val Ser Ile Leu Phe Ile Leu Pro Ile Pro Ala Ala
                245                 250                 255

Phe Phe Gly Ala Trp Phe Ala Gly Arg Pro Asn Lys Arg Phe Ser Thr
            260                 265                 270

Leu Met Trp Gln Ser Val Ile Cys Cys Leu Leu Ala Gly Leu Leu Met
        275                 280                 285

Trp Ile Pro Asp Trp Phe Gly Val Met Asn Val Trp Thr Leu Leu Val
290                 295                 300

Pro Ala Ala Leu Phe Phe Gly Ala Gly Met Leu Phe Pro Leu Ala
305                 310                 315                 320

Thr Ser Gly Ala Met Glu Pro Phe Pro Phe Leu Ala Gly Thr Ala Gly
                325                 330                 335

Ala Leu Val Gly Gly Leu Gln Asn Ile Gly Ser Gly Val Leu Ala Ser
            340                 345                 350

Leu Ser Ala Met Leu Pro Gln Thr Gly Gln Gly Ser Leu Gly Leu Leu
        355                 360                 365

Met Thr Leu Met Gly Leu Leu Ile Val Leu Cys Trp Leu Pro Leu Ala
370                 375                 380

Thr Arg Met Ser His Gln Gly Gln Pro Val
385                 390

<210> SEQ ID NO 44
<211> LENGTH: 512
<212> TYPE: PRT
<213> ORGANISM: Escherichia coli

<400> SEQUENCE: 44

Met Ala Ile Thr Lys Ser Thr Pro Ala Pro Leu Thr Gly Gly Thr Leu
  1               5                  10                  15

Trp Cys Val Thr Ile Ala Leu Ser Leu Ala Thr Phe Met Gln Met Leu
             20                  25                  30

Asp Ser Thr Ile Ser Asn Val Ala Ile Pro Thr Ile Ser Gly Phe Leu
```

```
                35                  40                  45
Gly Ala Ser Thr Asp Glu Gly Thr Trp Val Ile Thr Ser Phe Gly Val
 50                  55                  60
Ala Asn Ala Ile Ala Ile Pro Val Thr Gly Arg Leu Ala Gln Arg Ile
 65                  70                  75                  80
Gly Glu Leu Arg Leu Phe Leu Leu Ser Val Thr Phe Phe Ser Leu Ser
                 85                  90                  95
Ser Leu Met Cys Ser Leu Ser Thr Asn Leu Asp Val Leu Ile Phe Phe
                100                 105                 110
Arg Val Val Gln Gly Leu Met Ala Gly Pro Leu Ile Pro Leu Ser Gln
                115                 120                 125
Ser Leu Leu Leu Arg Asn Tyr Pro Pro Glu Lys Arg Thr Phe Ala Leu
130                 135                 140
Ala Leu Trp Ser Met Thr Val Ile Ile Ala Pro Ile Cys Gly Pro Ile
145                 150                 155                 160
Leu Gly Gly Tyr Ile Cys Asp Asn Phe Ser Trp Gly Trp Ile Phe Leu
                165                 170                 175
Ile Asn Val Pro Met Gly Ile Ile Val Leu Thr Leu Cys Leu Thr Leu
                180                 185                 190
Leu Lys Gly Arg Glu Thr Glu Thr Ser Pro Val Lys Met Asn Leu Pro
                195                 200                 205
Gly Leu Thr Leu Leu Val Leu Gly Val Gly Leu Gln Ile Met Leu
                210                 215                 220
Asp Lys Gly Arg Asp Leu Asp Trp Phe Asn Ser Ser Thr Ile Ile Ile
225                 230                 235                 240
Leu Thr Val Val Ser Val Ile Ser Leu Ile Ser Leu Val Ile Trp Glu
                245                 250                 255
Ser Thr Ser Glu Asn Pro Ile Leu Asp Leu Ser Leu Phe Lys Ser Arg
                260                 265                 270
Asn Phe Thr Ile Gly Ile Val Ser Ile Thr Cys Ala Tyr Leu Phe Tyr
                275                 280                 285
Ser Gly Ala Ile Val Leu Met Pro Gln Leu Leu Gln Glu Thr Met Gly
                290                 295                 300
Tyr Asn Ala Ile Trp Ala Gly Leu Ala Tyr Ala Pro Ile Gly Ile Met
305                 310                 315                 320
Pro Leu Leu Ile Ser Pro Leu Ile Gly Arg Tyr Gly Asn Lys Ile Asp
                325                 330                 335
Met Arg Leu Leu Val Thr Phe Ser Phe Leu Met Tyr Ala Val Cys Tyr
                340                 345                 350
Tyr Trp Arg Ser Val Thr Phe Met Pro Thr Ile Asp Phe Thr Gly Ile
                355                 360                 365
Ile Leu Pro Gln Phe Phe Gln Gly Phe Ala Val Ala Cys Phe Phe Leu
                370                 375                 380
Pro Leu Thr Thr Ile Ser Phe Ser Gly Leu Pro Asp Asn Lys Phe Ala
385                 390                 395                 400
Asn Ala Ser Ser Met Ser Asn Phe Phe Arg Thr Leu Ser Gly Ser Val
                405                 410                 415
Gly Thr Ser Leu Thr Met Thr Leu Trp Gly Arg Arg Glu Ser Leu His
                420                 425                 430
His Ser Gln Leu Thr Ala Thr Ile Asp Gln Phe Asn Pro Val Phe Asn
                435                 440                 445
Ser Ser Ser Gln Ile Met Asp Lys Tyr Tyr Gly Ser Leu Ser Gly Val
450                 455                 460
```

Leu Asn Glu Ile Asn Asn Glu Ile Thr Gln Gln Ser Leu Ser Ile Ser
465                 470                 475                 480

Ala Asn Glu Ile Phe Arg Met Ala Ala Ala Phe Ile Leu Leu Thr
            485                 490                 495

Val Leu Val Trp Phe Ala Lys Pro Pro Phe Thr Ala Lys Gly Val Gly
            500                 505                 510

<210> SEQ ID NO 45
<211> LENGTH: 512
<212> TYPE: PRT
<213> ORGANISM: Escherichia coli

<400> SEQUENCE: 45

Met Ala Ile Thr Lys Ser Thr Pro Ala Pro Leu Thr Gly Gly Thr Leu
1               5                   10                  15

Trp Cys Val Thr Ile Ala Leu Ser Leu Ala Thr Phe Met Gln Met Leu
                20                  25                  30

Asp Ser Thr Ile Ser Asn Val Ala Ile Pro Thr Ile Ser Gly Phe Leu
            35                  40                  45

Gly Ala Ser Thr Asp Glu Gly Thr Trp Val Ile Thr Ser Phe Gly Val
50                  55                  60

Ala Asn Ala Ile Ala Ile Pro Val Thr Gly Arg Leu Ala Gln Arg Ile
65                  70                  75                  80

Gly Glu Leu Arg Leu Phe Leu Leu Ser Val Thr Phe Phe Ser Leu Ser
                85                  90                  95

Ser Leu Met Cys Ser Leu Ser Thr Asn Leu Asp Val Leu Ile Phe Phe
                100                 105                 110

Arg Val Val Gln Gly Leu Met Ala Gly Pro Leu Ile Pro Leu Ser Gln
            115                 120                 125

Ser Leu Leu Leu Arg Asn Tyr Pro Pro Glu Lys Arg Thr Phe Ala Leu
130                 135                 140

Ala Leu Trp Ser Met Thr Val Ile Ile Ala Pro Ile Cys Gly Pro Ile
145                 150                 155                 160

Leu Gly Gly Tyr Ile Cys Asp Asn Phe Ser Trp Gly Trp Ile Phe Leu
                165                 170                 175

Ile Asn Val Pro Met Gly Ile Ile Val Leu Thr Leu Cys Leu Thr Leu
            180                 185                 190

Leu Lys Gly Arg Glu Thr Glu Thr Ser Pro Val Lys Met Asn Leu Pro
            195                 200                 205

Gly Leu Thr Leu Leu Val Leu Gly Val Gly Leu Gln Ile Met Leu
210                 215                 220

Asp Lys Gly Arg Asp Leu Asp Trp Phe Asn Ser Ser Thr Ile Ile Ile
225                 230                 235                 240

Leu Thr Val Val Ser Val Ile Ser Leu Ile Ser Leu Val Ile Trp Glu
                245                 250                 255

Ser Thr Ser Glu Asn Pro Ile Leu Asp Leu Ser Leu Phe Lys Ser Arg
            260                 265                 270

Asn Phe Thr Ile Gly Ile Val Ser Ile Thr Cys Ala Tyr Leu Phe Tyr
        275                 280                 285

Ser Gly Ala Ile Val Leu Met Pro Gln Leu Leu Gln Glu Thr Met Gly
        290                 295                 300

Tyr Asn Ala Ile Trp Ala Gly Leu Ala Tyr Ala Pro Ile Gly Ile Met
305                 310                 315                 320

Pro Leu Leu Ile Ser Pro Leu Ile Gly Arg Tyr Gly Asn Lys Ile Asp

```
            325                 330                 335
Met Arg Leu Leu Val Thr Phe Ser Phe Leu Met Tyr Ala Val Cys Tyr
            340                 345                 350

Tyr Trp Arg Ser Val Thr Phe Met Pro Thr Ile Asp Phe Thr Gly Ile
            355                 360                 365

Ile Leu Pro Gln Phe Phe Gln Gly Phe Ala Val Ala Cys Phe Phe Leu
            370                 375                 380

Pro Leu Thr Thr Ile Ser Phe Ser Gly Leu Pro Asp Asn Lys Phe Ala
385                 390                 395                 400

Asn Ala Ser Ser Met Ser Asn Phe Phe Arg Thr Leu Ser Gly Ser Val
                    405                 410                 415

Gly Thr Ser Leu Thr Met Thr Leu Trp Gly Arg Arg Glu Ser Leu His
                    420                 425                 430

His Ser Gln Leu Thr Ala Thr Ile Asp Gln Phe Asn Pro Val Phe Asn
                    435                 440                 445

Ser Ser Ser Gln Ile Met Asp Lys Tyr Tyr Gly Ser Leu Ser Gly Val
450                 455                 460

Leu Asn Glu Ile Asn Asn Glu Ile Thr Gln Gln Ser Leu Ser Ile Ser
465                 470                 475                 480

Ala Asn Glu Ile Phe Arg Met Ala Ala Ile Ala Phe Ile Leu Leu Thr
                    485                 490                 495

Val Leu Val Trp Phe Ala Lys Pro Pro Phe Thr Ala Lys Gly Val Gly
                    500                 505                 510

<210> SEQ ID NO 46
<211> LENGTH: 444
<212> TYPE: PRT
<213> ORGANISM: Escherichia coli

<400> SEQUENCE: 46

Met Ile Leu Asp Thr Val Asp Glu Lys Lys Lys Gly Val His Thr Arg
1               5                   10                  15

Tyr Leu Ile Leu Leu Ile Ile Phe Ile Val Thr Ala Val Asn Tyr Ala
                20                  25                  30

Asp Arg Ala Thr Leu Ser Ile Ala Gly Thr Glu Val Ala Lys Glu Leu
            35                  40                  45

Gln Leu Ser Ala Val Ser Met Gly Tyr Ile Phe Ser Ala Phe Gly Trp
        50                  55                  60

Ala Tyr Leu Leu Met Gln Ile Pro Gly Gly Trp Leu Leu Asp Lys Phe
65                  70                  75                  80

Gly Ser Lys Lys Val Tyr Thr Tyr Ser Leu Phe Phe Trp Ser Leu Phe
                85                  90                  95

Thr Phe Leu Gln Gly Phe Val Asp Met Phe Pro Leu Ala Trp Ala Gly
            100                 105                 110

Ile Ser Met Phe Phe Met Arg Phe Met Leu Gly Phe Ser Glu Ala Pro
        115                 120                 125

Ser Phe Pro Ala Asn Ala Arg Ile Val Ala Ala Trp Phe Pro Thr Lys
130                 135                 140

Glu Arg Gly Thr Ala Ser Ala Ile Phe Asn Ser Ala Gln Tyr Phe Ser
145                 150                 155                 160

Leu Ala Leu Phe Ser Pro Leu Leu Gly Trp Leu Thr Phe Ala Trp Gly
                165                 170                 175

Trp Glu His Val Phe Thr Val Met Gly Val Ile Gly Phe Val Leu Thr
            180                 185                 190
```

```
Ala Leu Trp Ile Lys Leu Ile His Asn Pro Thr Asp His Pro Arg Met
            195                 200                 205

Ser Ala Glu Glu Leu Lys Phe Ile Ser Glu Asn Gly Ala Val Val Asp
210                 215                 220

Met Asp His Lys Lys Pro Gly Ser Ala Ala Ser Gly Pro Lys Leu
225                 230                 235                 240

His Tyr Ile Lys Gln Leu Leu Ser Asn Arg Met Met Leu Gly Val Phe
                245                 250                 255

Phe Gly Gln Tyr Phe Ile Asn Thr Ile Thr Trp Phe Phe Leu Thr Trp
            260                 265                 270

Phe Pro Ile Tyr Leu Val Gln Glu Lys Gly Met Ser Ile Leu Lys Val
            275                 280                 285

Gly Leu Val Ala Ser Ile Pro Ala Leu Cys Gly Phe Ala Gly Gly Val
290                 295                 300

Leu Gly Gly Val Phe Ser Asp Tyr Leu Ile Lys Arg Gly Leu Ser Leu
305                 310                 315                 320

Thr Leu Ala Arg Lys Leu Pro Ile Val Leu Gly Met Leu Leu Ala Ser
                325                 330                 335

Thr Ile Ile Leu Cys Asn Tyr Thr Asn Asn Thr Thr Leu Val Val Met
            340                 345                 350

Leu Met Ala Leu Ala Phe Phe Gly Lys Gly Phe Gly Ala Leu Gly Trp
            355                 360                 365

Pro Val Ile Ser Asp Thr Ala Pro Lys Glu Ile Val Gly Leu Cys Gly
            370                 375                 380

Gly Val Phe Asn Val Phe Gly Asn Val Ala Ser Ile Val Thr Pro Leu
385                 390                 395                 400

Val Ile Gly Tyr Leu Val Ser Glu Leu His Ser Phe Asn Ala Ala Leu
                405                 410                 415

Val Phe Val Gly Cys Ser Ala Leu Met Ala Met Val Cys Tyr Leu Phe
            420                 425                 430

Val Val Gly Asp Ile Lys Arg Met Glu Leu Gln Lys
            435                 440

<210> SEQ ID NO 47
<211> LENGTH: 450
<212> TYPE: PRT
<213> ORGANISM: Escherichia coli

<400> SEQUENCE: 47

Met Ser Ser Leu Ser Gln Ala Ala Ser Val Glu Lys Arg Thr Asn
1               5                   10                  15

Ala Arg Tyr Trp Ile Val Val Met Leu Phe Ile Val Thr Ser Phe Asn
                20                  25                  30

Tyr Gly Asp Arg Ala Thr Leu Ser Ile Ala Gly Ser Glu Met Ala Lys
            35                  40                  45

Asp Ile Gly Leu Asp Pro Val Gly Met Gly Tyr Val Phe Ser Ala Phe
        50                  55                  60

Ser Trp Ala Tyr Val Ile Gly Gln Ile Pro Gly Gly Trp Leu Leu Asp
65                  70                  75                  80

Arg Phe Gly Ser Lys Arg Val Tyr Phe Trp Ser Ile Phe Ile Trp Ser
                85                  90                  95

Met Phe Thr Leu Leu Gln Gly Phe Val Asp Ile Phe Ser Gly Phe Gly
            100                 105                 110

Ile Ile Val Ala Leu Phe Thr Leu Arg Phe Leu Val Gly Leu Ala Glu
        115                 120                 125
```

Ala Pro Ser Phe Pro Gly Asn Ser Arg Ile Val Ala Ala Trp Phe Pro
        130                 135                 140

Ala Gln Glu Arg Gly Thr Ala Val Ser Ile Phe Asn Ser Ala Gln Tyr
145                 150                 155                 160

Phe Ala Thr Val Ile Phe Ala Pro Ile Met Gly Trp Leu Thr His Glu
                165                 170                 175

Val Gly Trp Ser His Val Phe Phe Met Gly Gly Leu Gly Ile Val
            180                 185                 190

Ile Ser Phe Ile Trp Leu Lys Val Ile His Glu Pro Asn Gln His Pro
        195                 200                 205

Gly Val Asn Lys Lys Glu Leu Glu Tyr Ile Ala Ala Gly Gly Ala Leu
    210                 215                 220

Ile Asn Met Asp Gln Gln Asn Thr Lys Val Lys Val Pro Phe Ser Val
225                 230                 235                 240

Lys Trp Gly Gln Ile Lys Gln Leu Leu Gly Ser Arg Met Met Ile Gly
                245                 250                 255

Val Tyr Ile Gly Gln Tyr Cys Ile Asn Ala Leu Thr Tyr Phe Phe Ile
            260                 265                 270

Thr Trp Phe Pro Val Tyr Leu Val Gln Ala Arg Gly Met Ser Ile Leu
        275                 280                 285

Lys Ala Gly Phe Val Ala Ser Val Pro Ala Val Cys Gly Phe Ile Gly
    290                 295                 300

Gly Val Leu Gly Gly Ile Ile Ser Asp Trp Leu Met Arg Arg Thr Gly
305                 310                 315                 320

Ser Leu Asn Ile Ala Arg Lys Thr Pro Ile Val Met Gly Met Leu Leu
                325                 330                 335

Ser Met Val Met Val Phe Cys Asn Tyr Val Asn Val Glu Trp Met Ile
            340                 345                 350

Ile Gly Phe Met Ala Leu Ala Phe Phe Gly Lys Gly Ile Gly Ala Leu
        355                 360                 365

Gly Trp Ala Val Met Ala Asp Thr Ala Pro Lys Glu Ile Ser Gly Leu
    370                 375                 380

Ser Gly Gly Leu Phe Asn Met Phe Gly Asn Ile Ser Gly Ile Val Thr
385                 390                 395                 400

Pro Ile Ala Ile Gly Tyr Ile Val Gly Thr Thr Gly Ser Phe Asn Gly
                405                 410                 415

Ala Leu Ile Tyr Val Gly Val His Ala Leu Ile Ala Val Leu Ser Tyr
            420                 425                 430

Leu Val Leu Val Gly Asp Ile Lys Arg Ile Glu Leu Lys Pro Val Ala
        435                 440                 445

Gly Gln
450

<210> SEQ ID NO 48
<211> LENGTH: 475
<212> TYPE: PRT
<213> ORGANISM: Escherichia coli

<400> SEQUENCE: 48

Met Ser Asp Lys Lys Arg Ser Met Ala Gly Leu Pro Trp Ile Ala
1               5                   10                  15

Ala Met Ala Phe Phe Met Gln Ala Leu Asp Ala Thr Ile Leu Asn Thr
            20                  25                  30

Ala Leu Pro Ala Ile Ala His Ser Leu Asn Arg Ser Pro Leu Ala Met

```
                35                  40                  45
Gln Ser Ala Ile Ile Ser Tyr Thr Leu Thr Val Ala Met Leu Ile Pro
 50                  55                  60

Val Ser Gly Trp Leu Ala Asp Arg Phe Gly Thr Arg Ile Phe Thr
 65                  70                  75                  80

Leu Ala Val Ser Leu Phe Thr Leu Gly Ser Leu Ala Cys Ala Leu Ser
                 85                  90                  95

Asn Ser Leu Pro Gln Leu Val Val Phe Arg Val Ile Gln Gly Ile Gly
                100                 105                 110

Gly Ala Met Met Met Pro Val Ala Arg Leu Ala Leu Leu Arg Ala Tyr
                115                 120                 125

Pro Arg Asn Glu Leu Leu Pro Val Leu Asn Phe Val Ala Met Pro Gly
                130                 135                 140

Leu Val Gly Pro Ile Leu Gly Pro Val Leu Gly Gly Val Leu Val Thr
145                 150                 155                 160

Trp Ala Thr Trp His Trp Ile Phe Leu Ile Asn Ile Pro Ile Gly Ile
                165                 170                 175

Ala Gly Leu Leu Tyr Ala Arg Lys His Met Pro Asn Phe Thr Thr Ala
                180                 185                 190

Arg Arg Arg Phe Asp Ile Thr Gly Phe Leu Leu Phe Gly Leu Ser Leu
                195                 200                 205

Val Leu Phe Ser Ser Gly Ile Glu Leu Phe Gly Glu Lys Ile Val Ala
                210                 215                 220

Ser Trp Ile Ala Leu Thr Val Ile Val Thr Ser Ile Gly Leu Leu Leu
225                 230                 235                 240

Leu Tyr Ile Leu His Ala Arg Arg Thr Pro Asn Pro Leu Ile Ser Leu
                245                 250                 255

Asp Leu Phe Lys Thr Arg Thr Phe Ser Ile Gly Ile Val Gly Asn Ile
                260                 265                 270

Ala Thr Arg Leu Gly Thr Gly Cys Val Pro Phe Leu Met Pro Leu Met
                275                 280                 285

Leu Gln Val Gly Phe Gly Tyr Gln Ala Phe Ile Ala Gly Cys Met Met
                290                 295                 300

Ala Pro Thr Ala Leu Gly Ser Ile Ile Ala Lys Ser Met Val Thr Gln
305                 310                 315                 320

Val Leu Arg Arg Leu Gly Tyr Arg His Thr Leu Val Gly Ile Thr Val
                325                 330                 335

Ile Ile Gly Leu Met Ile Ala Gln Phe Ser Leu Gln Ser Pro Ala Met
                340                 345                 350

Ala Ile Trp Met Leu Ile Leu Pro Leu Phe Ile Leu Gly Met Ala Met
                355                 360                 365

Ser Thr Gln Phe Thr Ala Met Asn Thr Ile Thr Leu Ala Asp Leu Thr
                370                 375                 380

Asp Asp Asn Ala Ser Ser Gly Asn Ser Val Leu Ala Val Thr Gln Gln
385                 390                 395                 400

Leu Ser Ile Ser Leu Gly Val Ala Val Ser Ala Ala Val Leu Arg Val
                405                 410                 415

Tyr Glu Gly Met Glu Gly Thr Thr Val Glu Gln Phe His Tyr Thr
                420                 425                 430

Phe Ile Thr Met Gly Ile Ile Thr Val Ala Ser Ala Ala Met Phe Met
                435                 440                 445

Leu Leu Lys Thr Thr Asp Gly Asn Asn Leu Ile Lys Arg Gln Arg Lys
450                 455                 460
```

Ser Lys Pro Asn Arg Val Pro Ser Glu Ser Glu
465                 470                475

<210> SEQ ID NO 49
<211> LENGTH: 212
<212> TYPE: PRT
<213> ORGANISM: Escherichia coli

<400> SEQUENCE: 49

Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
            20                  25                  30

Lys Asn Ser Val Ser Ser Gly Met Lys Gly Gly Tyr Leu Ala Ala Cys
        35                  40                  45

Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 50
<211> LENGTH: 593
<212> TYPE: PRT
<213> ORGANISM: Escherichia coli

<400> SEQUENCE: 50

Met Arg Ser Phe Ser Gln Leu Trp Pro Thr Leu Lys Arg Leu Leu Ala
1               5                   10                  15

Tyr Gly Ser Pro Trp Arg Lys Pro Leu Gly Ile Ala Val Leu Met Met
            20                  25                  30

Trp Val Ala Ala Ala Ala Glu Val Ser Gly Pro Leu Leu Ile Ser Tyr
        35                  40                  45

Phe Ile Asp Asn Met Val Ala Lys Asn Asn Leu Pro Leu Lys Val Val
    50                  55                  60

Ala Gly Leu Ala Ala Ala Tyr Val Gly Leu Gln Leu Phe Ala Ala Gly
65                  70                  75                  80

Leu His Tyr Ala Gln Ser Leu Leu Phe Asn Arg Ala Ala Val Gly Val
                85                  90                  95

```
Val Gln Gln Leu Arg Thr Asp Val Met Asp Ala Ala Leu Arg Gln Pro
            100                 105                 110

Leu Ser Glu Phe Asp Thr Gln Pro Val Gly Gln Val Ile Ser Arg Val
            115                 120                 125

Thr Asn Asp Thr Glu Val Ile Arg Asp Leu Tyr Val Thr Val Val Ala
            130                 135                 140

Thr Val Leu Arg Ser Ala Ala Leu Val Gly Ala Met Leu Val Ala Met
145                 150                 155                 160

Phe Ser Leu Asp Trp Arg Met Ala Leu Val Ala Ile Met Ile Phe Pro
                165                 170                 175

Val Val Leu Val Val Met Val Ile Tyr Gln Arg Tyr Ser Thr Pro Ile
                180                 185                 190

Val Arg Arg Val Arg Ala Tyr Leu Ala Asp Ile Asn Asp Gly Phe Asn
                195                 200                 205

Glu Ile Ile Asn Gly Met Ser Val Ile Gln Gln Phe Arg Gln Gln Ala
            210                 215                 220

Arg Phe Gly Glu Arg Met Gly Glu Ala Ser Arg Ser His Tyr Met Ala
225                 230                 235                 240

Arg Met Gln Thr Leu Arg Leu Asp Gly Phe Leu Leu Arg Pro Leu Leu
                245                 250                 255

Ser Leu Phe Ser Ser Leu Ile Leu Cys Gly Leu Leu Met Leu Phe Gly
            260                 265                 270

Phe Ser Ala Ser Gly Thr Ile Glu Val Gly Val Leu Tyr Ala Phe Ile
            275                 280                 285

Ser Tyr Leu Gly Arg Leu Asn Glu Pro Leu Ile Glu Leu Thr Thr Gln
            290                 295                 300

Gln Ala Met Leu Gln Gln Ala Val Val Ala Gly Glu Arg Val Phe Glu
305                 310                 315                 320

Leu Met Asp Gly Pro Arg Gln Gln Tyr Gly Asn Asp Asp Arg Pro Leu
                325                 330                 335

Gln Ser Gly Thr Ile Glu Val Asp Asn Val Ser Phe Ala Tyr Arg Asp
            340                 345                 350

Asp Asn Leu Val Leu Lys Asn Ile Asn Leu Ser Val Pro Ser Arg Asn
            355                 360                 365

Phe Val Ala Leu Val Gly His Thr Gly Ser Gly Lys Ser Thr Leu Ala
            370                 375                 380

Ser Leu Leu Met Gly Tyr Tyr Pro Leu Thr Glu Gly Glu Ile Arg Leu
385                 390                 395                 400

Asp Gly Arg Pro Leu Ser Ser Leu Ser His Ser Ala Leu Arg Gln Gly
                405                 410                 415

Val Ala Met Val Gln Gln Asp Pro Val Val Leu Ala Asp Thr Phe Leu
                420                 425                 430

Ala Asn Val Thr Leu Gly Arg Asp Ile Ser Glu Glu Arg Val Trp Gln
            435                 440                 445

Ala Leu Glu Thr Val Gln Leu Ala Glu Leu Ala Arg Ser Met Ser Asp
            450                 455                 460

Gly Ile Tyr Thr Pro Leu Gly Glu Gln Gly Asn Asn Leu Ser Val Gly
465                 470                 475                 480

Gln Lys Gln Leu Leu Ala Leu Ala Arg Val Leu Val Glu Thr Pro Gln
                485                 490                 495

Ile Leu Ile Leu Asp Glu Ala Thr Ala Ser Ile Asp Ser Gly Thr Glu
            500                 505                 510
```

```
Gln Ala Ile Gln His Ala Leu Ala Val Arg Glu His Thr Thr Leu
            515                 520                 525

Val Val Ile Ala His Arg Leu Ser Thr Ile Val Asp Ala Asp Thr Ile
530                 535                 540

Leu Val Leu His Arg Gly Gln Ala Val Glu Gln Gly Thr His Gln Gln
545                 550                 555                 560

Leu Leu Ala Ala Gln Gly Arg Tyr Trp Gln Met Tyr Gln Leu Gln Leu
                565                 570                 575

Ala Gly Glu Glu Leu Ala Ala Ser Val Arg Glu Glu Ser Leu Ser
            580                 585                 590

Ala

<210> SEQ ID NO 51
<211> LENGTH: 471
<212> TYPE: PRT
<213> ORGANISM: Escherichia coli

<400> SEQUENCE: 51

Met Thr Asp Leu Pro Asp Ser Thr Arg Trp Gln Leu Trp Ile Val Ala
1               5                   10                  15

Phe Gly Phe Phe Met Gln Ser Leu Asp Thr Thr Ile Val Asn Thr Ala
                20                  25                  30

Leu Pro Ser Met Ala Gln Ser Leu Gly Glu Ser Pro Leu His Met His
            35                  40                  45

Met Val Ile Val Ser Tyr Val Leu Thr Val Ala Val Met Leu Pro Ala
        50                  55                  60

Ser Gly Trp Leu Ala Asp Lys Val Gly Val Arg Asn Ile Phe Phe Thr
65                  70                  75                  80

Ala Ile Val Leu Phe Thr Leu Gly Ser Leu Phe Cys Ala Leu Ser Gly
                85                  90                  95

Thr Leu Asn Glu Leu Leu Leu Ala Arg Ala Leu Gln Gly Val Gly Gly
            100                 105                 110

Ala Met Met Val Pro Val Gly Arg Leu Thr Val Met Lys Ile Val Pro
        115                 120                 125

Arg Glu Gln Tyr Met Ala Ala Met Thr Phe Val Thr Leu Pro Gly Gln
130                 135                 140

Val Gly Pro Leu Leu Gly Pro Ala Leu Gly Gly Leu Leu Val Glu Tyr
145                 150                 155                 160

Ala Ser Trp His Trp Ile Phe Leu Ile Asn Ile Pro Val Gly Ile Ile
                165                 170                 175

Gly Ala Ile Ala Thr Leu Leu Leu Met Pro Asn Tyr Thr Met Gln Thr
            180                 185                 190

Arg Arg Phe Asp Leu Ser Gly Phe Leu Leu Leu Ala Val Gly Met Ala
        195                 200                 205

Val Leu Thr Leu Ala Leu Asp Gly Ser Lys Gly Thr Gly Leu Ser Pro
210                 215                 220

Leu Thr Ile Ala Gly Leu Val Ala Val Gly Val Val Ala Leu Val Leu
225                 230                 235                 240

Tyr Leu Leu His Ala Arg Asn Asn Arg Ala Leu Phe Ser Leu Lys
                245                 250                 255

Leu Phe Arg Thr Arg Thr Phe Ser Leu Gly Leu Ala Gly Ser Phe Ala
            260                 265                 270

Gly Arg Ile Gly Ser Gly Met Leu Pro Phe Met Thr Pro Val Phe Leu
        275                 280                 285
```

Gln Ile Gly Leu Gly Phe Ser Pro Phe His Ala Gly Leu Met Met Ile
      290                 295                 300

Pro Met Val Leu Gly Ser Met Gly Met Lys Arg Ile Val Val Gln Val
305                 310                 315                 320

Val Asn Arg Phe Gly Tyr Arg Arg Val Leu Val Ala Thr Thr Leu Gly
                325                 330                 335

Leu Ser Leu Val Thr Leu Leu Phe Met Thr Thr Ala Leu Leu Gly Trp
            340                 345                 350

Tyr Tyr Val Leu Pro Phe Val Leu Phe Leu Gln Gly Met Val Asn Ser
        355                 360                 365

Thr Arg Phe Ser Ser Met Asn Thr Leu Thr Leu Lys Asp Leu Pro Asp
370                 375                 380

Asn Leu Ala Ser Ser Gly Asn Ser Leu Leu Ser Met Ile Met Gln Leu
385                 390                 395                 400

Ser Met Ser Ile Gly Val Thr Ile Ala Gly Leu Leu Leu Gly Leu Phe
                405                 410                 415

Gly Ser Gln His Val Ser Val Asp Ser Gly Thr Thr Gln Thr Val Phe
                420                 425                 430

Met Tyr Thr Trp Leu Ser Met Ala Leu Ile Ile Ala Leu Pro Ala Phe
            435                 440                 445

Ile Phe Ala Arg Val Pro Asn Asp Thr His Gln Asn Val Ala Ile Ser
450                 455                 460

Arg Arg Lys Arg Ser Ala Gln
465                 470

<210> SEQ ID NO 52
<211> LENGTH: 408
<212> TYPE: PRT
<213> ORGANISM: Escherichia coli

<400> SEQUENCE: 52

Met Ser Pro Cys Glu Asn Asp Thr Pro Ile Asn Trp Lys Arg Asn Leu
1               5                   10                  15

Ile Val Ala Trp Leu Gly Cys Phe Leu Thr Gly Ala Ala Phe Ser Leu
            20                  25                  30

Val Met Pro Phe Leu Pro Leu Tyr Val Glu Gln Leu Gly Val Thr Gly
        35                  40                  45

His Ser Ala Leu Asn Met Trp Ser Gly Ile Val Phe Ser Ile Thr Phe
    50                  55                  60

Leu Phe Ser Ala Ile Ala Ser Pro Phe Trp Gly Gly Leu Ala Asp Arg
65                  70                  75                  80

Lys Gly Arg Lys Leu Met Leu Leu Arg Ser Ala Leu Gly Met Gly Ile
                85                  90                  95

Val Met Val Leu Met Gly Leu Ala Gln Asn Ile Trp Gln Phe Leu Ile
            100                 105                 110

Leu Arg Ala Leu Leu Gly Leu Leu Gly Gly Phe Val Pro Asn Ala Asn
        115                 120                 125

Ala Leu Ile Ala Thr Gln Val Pro Arg Asn Lys Ser Gly Trp Ala Leu
    130                 135                 140

Gly Thr Leu Ser Thr Gly Gly Val Ser Gly Ala Leu Leu Gly Pro Met
145                 150                 155                 160

Ala Gly Gly Leu Leu Ala Asp Ser Tyr Gly Leu Arg Pro Val Phe Phe
                165                 170                 175

Ile Thr Ala Ser Val Leu Ile Leu Cys Phe Phe Val Thr Leu Phe Cys
            180                 185                 190

```
Ile Arg Glu Lys Phe Gln Pro Val Ser Lys Glu Met Leu His Met
        195                 200                 205

Arg Glu Val Val Thr Ser Leu Lys Asn Pro Lys Leu Val Leu Ser Leu
210                 215                 220

Phe Val Thr Thr Leu Ile Ile Gln Val Ala Thr Gly Ser Ile Ala Pro
225                 230                 235                 240

Ile Leu Thr Leu Tyr Val Arg Glu Leu Ala Gly Asn Val Ser Asn Val
                245                 250                 255

Ala Phe Ile Ser Gly Met Ile Ala Ser Val Pro Gly Val Ala Ala Leu
                260                 265                 270

Leu Ser Ala Pro Arg Leu Gly Lys Leu Gly Asp Arg Ile Gly Pro Glu
                275                 280                 285

Lys Ile Leu Ile Thr Ala Leu Ile Phe Ser Val Leu Leu Ile Pro
290                 295                 300

Met Ser Tyr Val Gln Thr Pro Leu Gln Leu Gly Ile Leu Arg Phe Leu
305                 310                 315                 320

Leu Gly Ala Ala Asp Gly Ala Leu Leu Pro Ala Val Gln Thr Leu Leu
                325                 330                 335

Val Tyr Asn Ser Ser Asn Gln Ile Ala Gly Arg Ile Phe Ser Tyr Asn
                340                 345                 350

Gln Ser Phe Arg Asp Ile Gly Asn Val Thr Gly Pro Leu Met Gly Ala
                355                 360                 365

Ala Ile Ser Ala Asn Tyr Gly Phe Arg Ala Val Phe Leu Val Thr Ala
                370                 375                 380

Gly Val Val Leu Phe Asn Ala Val Tyr Ser Trp Asn Ser Leu Arg Arg
385                 390                 395                 400

Arg Arg Ile Pro Gln Val Ser Asn
                405

<210> SEQ ID NO 53
<211> LENGTH: 391
<212> TYPE: PRT
<213> ORGANISM: Escherichia coli

<400> SEQUENCE: 53

Met Ser Arg Phe Leu Ile Cys Ser Phe Ala Leu Val Leu Leu Tyr Pro
1               5                   10                  15

Ala Gly Ile Asp Met Tyr Leu Val Gly Leu Pro Arg Ile Ala Ala Asp
                20                  25                  30

Leu Asn Ala Ser Glu Ala Gln Leu His Ile Ala Phe Ser Val Tyr Leu
            35                  40                  45

Ala Gly Met Ala Ala Ala Met Leu Phe Ala Gly Lys Val Ala Asp Arg
        50                  55                  60

Ser Gly Arg Lys Pro Val Ala Ile Pro Gly Ala Ala Leu Phe Ile Ile
65                  70                  75                  80

Ala Ser Val Phe Cys Ser Leu Ala Glu Thr Ser Thr Leu Phe Leu Ala
                85                  90                  95

Gly Arg Phe Leu Gln Gly Leu Gly Ala Gly Cys Cys Tyr Val Val Ala
                100                 105                 110

Phe Ala Ile Leu Arg Asp Thr Leu Asp Asp Arg Arg Ala Lys Val
                115                 120                 125

Leu Ser Leu Leu Asn Gly Ile Thr Cys Ile Ile Pro Val Leu Ala Pro
        130                 135                 140

Val Leu Gly His Leu Ile Met Leu Lys Phe Pro Trp Gln Ser Leu Phe
```

```
                    145                 150                 155                 160
        Trp Ala Met Ala Met Met Gly Ile Ala Val Leu Met Leu Ser Leu Phe
                        165                 170                 175

Ile Leu Lys Glu Thr Arg Pro Ala Ala Pro Ala Ala Ser Asp Lys Pro
                        180                 185                 190

Arg Glu Asn Ser Glu Ser Leu Leu Asn Arg Phe Phe Leu Ser Arg Val
                        195                 200                 205

Val Ile Thr Thr Leu Ser Val Ser Val Ile Leu Thr Phe Val Asn Thr
                        210                 215                 220

Ser Pro Val Leu Leu Met Glu Ile Met Gly Phe Glu Arg Gly Glu Tyr
        225                 230                 235                 240

Ala Thr Ile Met Ala Leu Thr Ala Gly Val Ser Met Thr Val Ser Phe
                        245                 250                 255

Ser Thr Pro Phe Ala Leu Gly Ile Phe Lys Pro Arg Thr Leu Met Ile
                        260                 265                 270

Thr Ser Gln Val Leu Phe Leu Ala Ala Gly Ile Thr Leu Ala Val Ser
                        275                 280                 285

Pro Ser His Ala Val Ser Leu Phe Gly Ile Thr Leu Ile Cys Ala Gly
                        290                 295                 300

Phe Ser Val Gly Phe Gly Val Ala Met Ser Gln Ala Leu Gly Pro Phe
        305                 310                 315                 320

Ser Leu Arg Ala Gly Val Ala Ser Ser Thr Leu Gly Ile Ala Gln Val
                        325                 330                 335

Cys Gly Ser Ser Leu Trp Ile Trp Leu Ala Ala Val Val Gly Ile Gly
                        340                 345                 350

Ala Trp Asn Met Leu Ile Gly Ile Leu Ile Ala Cys Ser Ile Val Ser
                        355                 360                 365

Leu Leu Leu Ile Met Phe Val Ala Pro Gly Arg Pro Val Ala Ala His
                        370                 375                 380

Glu Glu Ile His His His Ala
        385                 390

<210> SEQ ID NO 54
<211> LENGTH: 410
<212> TYPE: PRT
<213> ORGANISM: Escherichia coli

<400> SEQUENCE: 54

Met Pro Arg Phe Phe Thr Arg His Ala Ala Thr Leu Phe Phe Pro Met
1               5                   10                  15

Ala Leu Ile Leu Tyr Asp Phe Ala Ala Tyr Leu Ser Thr Asp Leu Ile
                20                  25                  30

Gln Pro Gly Ile Ile Asn Val Val Arg Asp Phe Asn Ala Asp Val Ser
                35                  40                  45

Leu Ala Pro Ala Val Ser Leu Tyr Leu Ala Gly Gly Met Ala Leu
                50                  55                  60

Gln Trp Leu Leu Gly Pro Leu Ser Asp Arg Ile Gly Arg Arg Pro Val
65                  70                  75                  80

Leu Ile Thr Gly Ala Leu Ile Phe Thr Leu Ala Cys Ala Ala Thr Met
                85                  90                  95

Phe Thr Thr Ser Met Thr Gln Phe Leu Ile Ala Arg Ala Ile Gln Gly
                100                 105                 110

Thr Ser Ile Cys Phe Ile Ala Thr Val Gly Tyr Val Thr Val Gln Glu
                115                 120                 125
```

```
Ala Phe Gly Gln Thr Lys Gly Ile Lys Leu Met Ala Ile Ile Thr Ser
    130                 135                 140

Ile Val Leu Ile Ala Pro Ile Ile Gly Pro Leu Ser Gly Ala Ala Leu
145                 150                 155                 160

Met His Phe Met His Trp Lys Val Leu Phe Ala Ile Ile Ala Val Met
                165                 170                 175

Gly Phe Ile Ser Phe Val Gly Leu Leu Leu Ala Met Pro Glu Thr Val
            180                 185                 190

Lys Arg Gly Ala Val Pro Phe Ser Ala Lys Ser Val Leu Arg Asp Phe
        195                 200                 205

Arg Asn Val Phe Cys Asn Arg Leu Phe Leu Phe Gly Ala Ala Thr Ile
210                 215                 220

Ser Leu Ser Tyr Ile Pro Met Met Ser Trp Val Ala Val Ser Pro Val
225                 230                 235                 240

Ile Leu Ile Asp Ala Gly Ser Leu Thr Thr Ser Gln Phe Ala Trp Thr
                245                 250                 255

Gln Val Pro Val Phe Gly Ala Val Ile Val Ala Asn Ala Ile Val Ala
            260                 265                 270

Arg Phe Val Lys Asp Pro Thr Glu Pro Arg Phe Ile Trp Arg Ala Val
        275                 280                 285

Pro Ile Gln Leu Val Gly Leu Ser Leu Leu Ile Val Gly Asn Leu Leu
290                 295                 300

Ser Pro His Val Trp Leu Trp Ser Val Leu Gly Thr Ser Leu Tyr Ala
305                 310                 315                 320

Phe Gly Ile Gly Leu Ile Phe Pro Thr Leu Phe Arg Phe Thr Leu Phe
                325                 330                 335

Ser Asn Lys Leu Pro Lys Gly Thr Val Ser Ala Ser Leu Asn Met Val
            340                 345                 350

Ile Leu Met Val Met Ser Val Ser Val Glu Ile Gly Arg Trp Leu Trp
        355                 360                 365

Phe Asn Gly Gly Arg Leu Pro Phe His Leu Leu Ala Val Val Ala Gly
370                 375                 380

Val Ile Val Val Phe Thr Leu Ala Gly Leu Leu Asn Arg Val Arg Gln
385                 390                 395                 400

His Gln Ala Ala Glu Leu Val Glu Glu Gln
                405                 410

<210> SEQ ID NO 55
<211> LENGTH: 403
<212> TYPE: PRT
<213> ORGANISM: Escherichia coli

<400> SEQUENCE: 55

Met Ser Thr Arg Thr Pro Ser Ser Ser Ser Arg Leu Met Leu Thr
1               5                   10                  15

Ile Gly Leu Cys Phe Leu Val Ala Leu Met Glu Gly Leu Asp Leu Gln
            20                  25                  30

Ala Ala Gly Ile Ala Ala Gly Gly Ile Ala Gln Ala Phe Ala Leu Asp
        35                  40                  45

Lys Met Gln Met Gly Trp Ile Phe Ser Ala Gly Ile Leu Gly Leu Leu
    50                  55                  60

Pro Gly Ala Leu Val Gly Gly Met Leu Ala Asp Arg Tyr Gly Arg Lys
65                  70                  75                  80

Arg Ile Leu Ile Gly Ser Val Ala Leu Phe Gly Leu Phe Ser Leu Ala
                85                  90                  95
```

```
Thr Ala Ile Ala Trp Asp Phe Pro Ser Leu Val Phe Ala Arg Leu Met
            100                 105                 110
Thr Gly Val Gly Leu Gly Ala Ala Leu Pro Asn Leu Ile Ala Leu Thr
        115                 120                 125
Ser Glu Ala Ala Gly Pro Arg Phe Arg Gly Thr Ala Val Ser Leu Met
    130                 135                 140
Tyr Cys Gly Val Pro Ile Gly Ala Ala Leu Ala Thr Leu Gly Phe
145                 150                 155                 160
Ala Gly Ala Asn Leu Ala Trp Gln Thr Val Phe Trp Val Gly Gly Val
            165                 170                 175
Val Pro Leu Ile Leu Val Pro Leu Leu Met Arg Trp Leu Pro Glu Ser
        180                 185                 190
Ala Val Phe Ala Gly Glu Lys Gln Ser Ala Pro Pro Leu Arg Ala Leu
    195                 200                 205
Phe Ala Pro Glu Thr Ala Thr Ala Thr Leu Leu Leu Trp Leu Cys Tyr
210                 215                 220
Phe Phe Thr Leu Leu Val Val Tyr Met Leu Ile Asn Trp Leu Pro Leu
225                 230                 235                 240
Leu Leu Val Glu Gln Gly Phe Gln Pro Ser Gln Ala Ala Gly Val Met
            245                 250                 255
Phe Ala Leu Gln Met Gly Ala Ala Ser Gly Thr Leu Met Leu Gly Ala
        260                 265                 270
Leu Met Asp Lys Leu Arg Pro Val Thr Met Ser Leu Leu Ile Tyr Ser
    275                 280                 285
Gly Met Leu Ala Ser Leu Leu Ala Leu Gly Thr Val Ser Ser Phe Asn
            290                 295                 300
Gly Met Leu Leu Ala Gly Phe Val Ala Gly Leu Phe Ala Thr Gly Gly
305                 310                 315                 320
Gln Ser Val Leu Tyr Ala Leu Ala Pro Leu Phe Tyr Ser Ser Gln Ile
            325                 330                 335
Arg Ala Thr Gly Val Gly Thr Ala Val Ala Val Gly Arg Leu Gly Ala
        340                 345                 350
Met Ser Gly Pro Leu Leu Ala Gly Lys Met Leu Ala Leu Gly Thr Gly
    355                 360                 365
Thr Val Gly Val Met Ala Ala Ser Ala Pro Gly Ile Leu Val Ala Gly
370                 375                 380
Leu Ala Val Phe Ile Leu Met Ser Arg Arg Ser Arg Ile Gln Pro Cys
385                 390                 395                 400
Ala Asp Ala

<210> SEQ ID NO 56
<211> LENGTH: 295
<212> TYPE: PRT
<213> ORGANISM: Escherichia coli

<400> SEQUENCE: 56

Met Pro Gly Ser Leu Arg Lys Met Pro Val Trp Leu Pro Ile Val Ile
1               5                   10                  15
Leu Leu Val Ala Met Ala Ser Ile Gln Gly Gly Ala Ser Leu Ala Lys
            20                  25                  30
Ser Leu Phe Pro Leu Val Gly Ala Pro Gly Val Thr Ala Leu Arg Leu
        35                  40                  45
Ala Leu Gly Thr Leu Ile Leu Ile Ala Phe Phe Lys Pro Trp Arg Leu
    50                  55                  60
```

```
Arg Phe Ala Lys Glu Gln Arg Leu Pro Leu Leu Phe Tyr Gly Val Ser
 65                  70                  75                  80

Leu Gly Gly Met Asn Tyr Leu Phe Tyr Leu Ser Ile Gln Thr Val Pro
             85                  90                  95

Leu Gly Ile Ala Val Ala Leu Glu Phe Thr Gly Pro Leu Ala Val Ala
            100                 105                 110

Leu Phe Ser Ser Arg Arg Pro Val Asp Phe Val Trp Val Val Leu Ala
            115                 120                 125

Val Leu Gly Leu Trp Phe Leu Pro Leu Gly Gln Asp Val Ser His
130                 135                 140

Val Asp Leu Thr Gly Cys Ala Leu Ala Leu Gly Ala Gly Ala Cys Trp
145                 150                 155                 160

Ala Ile Tyr Ile Leu Ser Gly Gln Arg Ala Gly Ala Glu His Gly Pro
                165                 170                 175

Ala Thr Val Ala Ile Gly Ser Leu Ile Ala Ala Leu Ile Phe Val Pro
            180                 185                 190

Ile Gly Ala Leu Gln Ala Gly Glu Ala Leu Trp His Trp Ser Val Ile
            195                 200                 205

Pro Leu Gly Leu Ala Val Ala Ile Leu Ser Thr Ala Leu Pro Tyr Ser
            210                 215                 220

Leu Glu Met Ile Ala Leu Thr Arg Leu Pro Thr Arg Thr Phe Gly Thr
225                 230                 235                 240

Leu Met Ser Met Glu Pro Ala Leu Ala Ala Val Ser Gly Met Ile Phe
                245                 250                 255

Leu Gly Glu Thr Leu Thr Pro Ile Gln Leu Leu Ala Leu Gly Ala Ile
            260                 265                 270

Ile Ala Ala Ser Met Gly Ser Thr Leu Thr Val Arg Lys Glu Ser Lys
            275                 280                 285

Ile Lys Glu Leu Asp Ile Asn
            290         295

<210> SEQ ID NO 57
<211> LENGTH: 206
<212> TYPE: PRT
<213> ORGANISM: Escherichia coli

<400> SEQUENCE: 57

Met Thr Leu Glu Trp Trp Phe Ala Tyr Leu Leu Thr Ser Ile Ile Leu
  1               5                  10                  15

Ser Leu Ser Pro Gly Ser Gly Ala Ile Asn Thr Met Thr Thr Ser Leu
             20                  25                  30

Asn His Gly Tyr Arg Gly Ala Val Ala Ser Ile Ala Gly Leu Gln Thr
             35                  40                  45

Gly Leu Ala Ile His Ile Val Leu Val Gly Val Gly Leu Gly Thr Leu
 50                  55                  60

Phe Ser Arg Ser Val Ile Ala Phe Glu Val Leu Lys Trp Ala Gly Ala
 65                  70                  75                  80

Ala Tyr Leu Ile Trp Leu Gly Ile Gln Gln Trp Arg Ala Ala Gly Ala
                 85                  90                  95

Ile Asp Leu Lys Ser Leu Ala Ser Thr Gln Ser Arg Arg His Leu Phe
            100                 105                 110

Gln Arg Ala Val Phe Val Asn Leu Thr Asn Pro Lys Ser Ile Val Phe
            115                 120                 125

Leu Ala Ala Leu Phe Pro Gln Phe Ile Met Pro Gln Gln Pro Gln Leu
```

```
            130                 135                 140
Met Gln Tyr Ile Val Leu Gly Val Thr Thr Ile Val Val Asp Ile Ile
145                 150                 155                 160

Val Met Ile Gly Tyr Ala Thr Leu Ala Gln Arg Ile Ala Leu Trp Ile
                165                 170                 175

Lys Gly Pro Lys Gln Met Lys Ala Leu Asn Lys Ile Phe Gly Ser Leu
            180                 185                 190

Phe Met Leu Val Gly Ala Leu Leu Ala Ser Ala Arg His Ala
        195                 200                 205

<210> SEQ ID NO 58
<211> LENGTH: 206
<212> TYPE: PRT
<213> ORGANISM: Escherichia coli

<400> SEQUENCE: 58

Met Leu Met Leu Phe Leu Thr Val Ala Met Val His Ile Val Ala Leu
1               5                   10                  15

Met Ser Pro Gly Pro Asp Phe Phe Val Ser Gln Thr Ala Val Ser
                20                  25                  30

Arg Ser Arg Lys Glu Ala Met Met Gly Val Leu Gly Ile Thr Cys Gly
            35                  40                  45

Val Met Val Trp Ala Gly Ile Ala Leu Leu Gly Leu His Leu Ile Ile
        50                  55                  60

Glu Lys Met Ala Trp Leu His Thr Leu Ile Met Val Gly Gly Gly Leu
65                  70                  75                  80

Tyr Leu Cys Trp Met Gly Tyr Gln Met Leu Arg Gly Ala Leu Lys Lys
                85                  90                  95

Glu Ala Val Ser Ala Pro Ala Pro Gln Val Glu Leu Ala Lys Ser Gly
            100                 105                 110

Arg Ser Phe Leu Lys Gly Leu Leu Thr Asn Leu Ala Asn Pro Lys Ala
        115                 120                 125

Ile Ile Tyr Phe Gly Ser Val Phe Ser Leu Phe Val Gly Asp Asn Val
    130                 135                 140

Gly Thr Thr Ala Arg Trp Gly Ile Phe Ala Leu Ile Ile Val Glu Thr
145                 150                 155                 160

Leu Ala Trp Phe Thr Val Val Ala Ser Leu Phe Ala Leu Pro Gln Met
                165                 170                 175

Arg Arg Gly Tyr Gln Arg Leu Ala Lys Trp Ile Asp Gly Phe Ala Gly
            180                 185                 190

Ala Leu Phe Ala Gly Phe Gly Ile His Leu Ile Ile Ser Arg
        195                 200                 205

<210> SEQ ID NO 59
<211> LENGTH: 223
<212> TYPE: PRT
<213> ORGANISM: Escherichia coli

<400> SEQUENCE: 59

Met Met Gln Leu Val His Leu Phe Met Asp Glu Ile Thr Met Asp Pro
1               5                   10                  15

Leu His Ala Val Tyr Leu Thr Val Gly Leu Phe Val Ile Thr Phe Phe
                20                  25                  30

Asn Pro Gly Ala Asn Leu Phe Val Val Gln Thr Ser Leu Ala Ser
            35                  40                  45

Gly Arg Arg Ala Gly Val Leu Thr Gly Leu Gly Val Ala Leu Gly Asp
```

```
            50                  55                  60
Ala Phe Tyr Ser Gly Leu Gly Leu Phe Gly Leu Ala Thr Leu Ile Thr
 65                  70                  75                  80

Gln Cys Glu Glu Ile Phe Ser Leu Ile Arg Ile Val Gly Gly Ala Tyr
                 85                  90                  95

Leu Leu Trp Phe Ala Trp Cys Ser Met Arg Arg Gln Ser Thr Pro Gln
            100                 105                 110

Met Ser Thr Leu Gln Gln Pro Ile Ser Ala Pro Trp Tyr Val Phe Phe
        115                 120                 125

Arg Arg Gly Leu Ile Thr Asp Leu Ser Asn Pro Gln Thr Val Leu Phe
    130                 135                 140

Phe Ile Ser Ile Phe Ser Val Thr Leu Asn Ala Glu Thr Pro Thr Trp
145                 150                 155                 160

Ala Arg Leu Met Ala Trp Ala Gly Ile Val Leu Ala Ser Ile Ile Trp
                165                 170                 175

Arg Val Phe Leu Ser Gln Ala Phe Ser Leu Pro Ala Val Arg Arg Ala
            180                 185                 190

Tyr Gly Arg Met Gln Arg Val Ala Ser Arg Val Ile Gly Ala Ile Ile
        195                 200                 205

Gly Val Phe Ala Leu Arg Leu Ile Tyr Glu Gly Val Thr Gln Arg
    210                 215                 220

<210> SEQ ID NO 60
<211> LENGTH: 454
<212> TYPE: PRT
<213> ORGANISM: Escherichia coli

<400> SEQUENCE: 60

Met Asn Asp Tyr Lys Met Thr Pro Gly Glu Arg Arg Ala Thr Trp Gly
  1               5                  10                  15

Leu Gly Thr Val Phe Ser Leu Arg Met Leu Gly Met Phe Met Val Leu
                 20                  25                  30

Pro Val Leu Thr Thr Tyr Gly Met Ala Leu Gln Gly Ala Ser Glu Ala
            35                  40                  45

Leu Ile Gly Ile Ala Ile Gly Ile Tyr Gly Leu Thr Gln Ala Val Phe
        50                  55                  60

Gln Ile Pro Phe Gly Leu Leu Ser Asp Arg Ile Gly Arg Lys Pro Leu
 65                  70                  75                  80

Ile Val Gly Gly Leu Ala Val Phe Ala Ala Gly Ser Val Ile Ala Ala
                 85                  90                  95

Leu Ser Asp Ser Ile Trp Gly Ile Ile Leu Gly Arg Ala Leu Gln Gly
            100                 105                 110

Ser Gly Ala Ile Ala Ala Ala Val Met Ala Leu Leu Ser Asp Leu Thr
        115                 120                 125

Arg Glu Gln Asn Arg Thr Lys Ala Met Ala Phe Ile Gly Val Ser Phe
    130                 135                 140

Gly Ile Thr Phe Ala Ile Ala Met Val Leu Gly Pro Ile Ile Thr His
145                 150                 155                 160

Lys Leu Gly Leu His Ala Leu Phe Trp Met Ile Ala Ile Leu Ala Thr
                165                 170                 175

Thr Gly Ile Ala Leu Thr Ile Trp Val Val Pro Asn Ser Ser Thr His
            180                 185                 190

Val Leu Asn Arg Glu Ser Gly Met Val Lys Gly Ser Phe Ser Lys Val
        195                 200                 205
```

```
Leu Ala Glu Pro Arg Leu Leu Lys Leu Asn Phe Gly Ile Met Cys Leu
210                 215                 220

His Ile Leu Leu Met Ser Thr Phe Val Ala Leu Pro Gly Gln Leu Ala
225                 230                 235                 240

Asp Ala Gly Phe Pro Ala Ala Glu His Trp Lys Val Tyr Leu Ala Thr
                245                 250                 255

Met Leu Ile Ala Phe Gly Ser Val Pro Phe Ile Ile Tyr Ala Glu
                260                 265                 270

Val Lys Arg Lys Met Lys Gln Val Phe Val Phe Cys Val Gly Leu Ile
            275                 280                 285

Val Val Ala Glu Ile Val Leu Trp Asn Ala Gln Thr Gln Phe Trp Gln
        290                 295                 300

Leu Val Val Gly Val Gln Leu Phe Phe Val Ala Phe Asn Leu Met Glu
305                 310                 315                 320

Ala Leu Leu Pro Ser Leu Ile Ser Lys Glu Ser Pro Ala Gly Tyr Lys
                325                 330                 335

Gly Thr Ala Met Gly Val Tyr Ser Thr Ser Gln Phe Leu Gly Val Ala
                340                 345                 350

Ile Gly Gly Ser Leu Gly Gly Trp Ile Asn Gly Met Phe Asp Gly Gln
        355                 360                 365

Gly Val Phe Leu Ala Gly Ala Met Leu Ala Ala Val Trp Leu Thr Val
    370                 375                 380

Ala Ser Thr Met Lys Glu Pro Pro Tyr Val Ser Ser Leu Arg Ile Glu
385                 390                 395                 400

Ile Pro Ala Asn Ile Ala Ala Asn Glu Ala Leu Lys Val Arg Leu Leu
                405                 410                 415

Glu Thr Glu Gly Ile Lys Glu Val Leu Ile Ala Glu Glu His Ser
                420                 425                 430

Ala Tyr Val Lys Ile Asp Ser Lys Val Thr Asn Arg Phe Glu Ile Glu
                435                 440                 445

Gln Ala Ile Arg Gln Ala
            450

<210> SEQ ID NO 61
<211> LENGTH: 804
<212> TYPE: PRT
<213> ORGANISM: Escherichia coli

<400> SEQUENCE: 61

Met Ile Ala Arg Trp Phe Trp Arg Glu Trp Arg Ser Pro Ser Leu Leu
1               5                   10                  15

Ile Val Trp Leu Ala Leu Ser Leu Ala Val Ala Cys Val Leu Ala Leu
                20                  25                  30

Gly Asn Ile Ser Asp Arg Met Glu Lys Gly Leu Ser Gln Gln Ser Arg
            35                  40                  45

Glu Phe Met Ala Gly Asp Arg Ala Leu Arg Ser Ser Arg Glu Val Pro
        50                  55                  60

Gln Ala Trp Leu Glu Glu Ala Gln Lys Arg Gly Leu Lys Val Gly Lys
65                  70                  75                  80

Gln Leu Thr Phe Ala Thr Met Thr Phe Ala Gly Asp Thr Pro Gln Leu
                85                  90                  95

Ala Asn Val Lys Ala Val Asp Asp Ile Tyr Pro Met Tyr Gly Asp Leu
                100                 105                 110

Gln Thr Asn Pro Pro Gly Leu Lys Pro Gln Ala Gly Ser Val Leu Leu
            115                 120                 125
```

```
Ala Pro Arg Leu Met Ala Leu Leu Asn Leu Lys Thr Gly Asp Thr Ile
        130                 135                 140

Asp Val Gly Asp Ala Thr Leu Arg Ile Ala Gly Glu Val Ile Gln Glu
145                 150                 155                 160

Pro Asp Ser Gly Phe Asn Pro Phe Gln Met Ala Pro Arg Leu Met Met
                165                 170                 175

Asn Leu Ala Asp Val Asp Lys Thr Gly Ala Val Gln Pro Gly Ser Arg
            180                 185                 190

Val Thr Trp Arg Tyr Lys Phe Gly Gly Asn Glu Asn Gln Leu Asp Gly
        195                 200                 205

Tyr Glu Lys Trp Leu Leu Pro Gln Leu Lys Pro Glu Gln Arg Trp Tyr
    210                 215                 220

Gly Leu Glu Gln Asp Glu Gly Ala Leu Gly Arg Ser Met Glu Arg Ser
225                 230                 235                 240

Gln Gln Phe Leu Leu Leu Ser Ala Leu Leu Thr Leu Leu Leu Ala Val
                245                 250                 255

Ala Ala Val Ala Val Ala Met Asn His Tyr Cys Arg Ser Arg Tyr Asp
            260                 265                 270

Leu Val Ala Ile Leu Lys Thr Leu Gly Ala Gly Arg Ala Gln Leu Arg
        275                 280                 285

Lys Leu Ile Val Gly Gln Trp Leu Met Val Leu Thr Leu Ser Ala Val
    290                 295                 300

Thr Gly Gly Ala Ile Gly Leu Leu Phe Glu Asn Val Leu Met Val Leu
305                 310                 315                 320

Leu Lys Pro Val Leu Pro Ala Ala Leu Pro Ala Ser Leu Trp Pro
                325                 330                 335

Trp Leu Trp Ala Leu Gly Thr Met Thr Val Ile Ser Leu Leu Val Gly
            340                 345                 350

Leu Arg Pro Tyr Arg Leu Leu Leu Ala Thr Gln Pro Leu Arg Val Leu
        355                 360                 365

Arg Asn Asp Val Val Ala Asn Val Trp Pro Leu Lys Phe Tyr Leu Pro
    370                 375                 380

Ile Val Ser Val Val Val Leu Leu Leu Ala Gly Leu Met Gly Gly
385                 390                 395                 400

Ser Met Leu Leu Trp Ala Val Leu Ala Gly Ala Val Val Leu Ala Leu
                405                 410                 415

Leu Cys Gly Val Leu Gly Trp Met Leu Leu Asn Val Leu Arg Arg Met
            420                 425                 430

Thr Leu Lys Ser Leu Pro Leu Arg Leu Ala Val Ser Arg Leu Leu Arg
        435                 440                 445

Gln Pro Trp Ser Thr Leu Ser Gln Leu Ser Ala Phe Ser Leu Ser Phe
    450                 455                 460

Met Leu Leu Ala Leu Leu Val Leu Arg Gly Asp Leu Leu Asp Arg
465                 470                 475                 480

Trp Gln Gln Gln Leu Pro Pro Glu Ser Pro Asn Tyr Phe Leu Ile Asn
                485                 490                 495

Ile Ala Thr Glu Gln Val Ala Pro Leu Lys Ala Phe Leu Ala Glu His
            500                 505                 510

Gln Ile Val Pro Glu Ser Phe Tyr Pro Val Val Arg Ala Arg Leu Thr
        515                 520                 525

Ala Ile Asn Asp Lys Pro Thr Glu Gly Asn Glu Asp Glu Ala Leu Asn
    530                 535                 540
```

Arg Glu Leu Asn Leu Thr Trp Gln Asn Thr Arg Pro Asp His Asn Pro
545                 550                 555                 560

Ile Val Ala Gly Asn Trp Pro Pro Lys Ala Asp Glu Val Ser Met Glu
                565                 570                 575

Glu Gly Leu Ala Lys Arg Leu Asn Val Ala Leu Gly Asp Thr Val Thr
            580                 585                 590

Phe Met Gly Asp Thr Gln Glu Phe Arg Ala Lys Val Thr Ser Leu Arg
        595                 600                 605

Lys Val Asp Trp Glu Ser Leu Arg Pro Asn Phe Tyr Phe Ile Phe Pro
    610                 615                 620

Glu Gly Ala Leu Asp Gly Gln Pro Gln Ser Trp Leu Thr Ser Phe Arg
625                 630                 635                 640

Trp Glu Asn Gly Asn Gly Met Leu Thr Gln Leu Asn Arg Gln Phe Pro
                645                 650                 655

Thr Ile Ser Leu Leu Asp Ile Gly Ala Ile Leu Lys Gln Val Gly Gln
            660                 665                 670

Val Leu Glu Gln Val Ser Arg Ala Leu Glu Val Met Val Leu Val
        675                 680                 685

Thr Ala Cys Gly Met Leu Leu Leu Ala Gln Val Gln Val Gly Met
    690                 695                 700

Arg Gln Arg His Gln Glu Leu Val Val Trp Arg Thr Leu Gly Ala Gly
705                 710                 715                 720

Lys Lys Leu Leu Arg Thr Thr Leu Trp Cys Glu Phe Ala Met Leu Gly
                725                 730                 735

Phe Val Ser Gly Leu Val Ala Ala Ile Gly Ala Glu Thr Ala Leu Ala
            740                 745                 750

Val Leu Gln Ala Lys Val Phe Asp Phe Pro Trp Glu Pro Asp Trp Arg
        755                 760                 765

Leu Trp Ile Val Leu Pro Cys Ser Gly Ala Leu Leu Ser Leu Phe
    770                 775                 780

Gly Gly Trp Leu Gly Ala Arg Leu Val Lys Gly Lys Ala Leu Phe Arg
785                 790                 795                 800

Gln Phe Ala Gly

<210> SEQ ID NO 62
<211> LENGTH: 295
<212> TYPE: PRT
<213> ORGANISM: Escherichia coli

<400> SEQUENCE: 62

Met Pro Gly Ser Leu Arg Lys Met Pro Val Trp Leu Pro Ile Val Ile
1               5                   10                  15

Leu Leu Val Ala Met Ala Ser Ile Gln Gly Gly Ala Ser Leu Ala Lys
            20                  25                  30

Ser Leu Phe Pro Leu Val Gly Ala Pro Gly Val Thr Ala Leu Arg Leu
        35                  40                  45

Ala Leu Gly Thr Leu Ile Leu Ile Ala Phe Phe Lys Pro Trp Arg Leu
    50                  55                  60

Arg Phe Ala Lys Glu Gln Arg Leu Pro Leu Leu Phe Tyr Gly Val Ser
65                  70                  75                  80

Leu Gly Gly Met Asn Tyr Leu Phe Tyr Leu Ser Ile Gln Thr Val Pro
                85                  90                  95

Leu Gly Ile Ala Val Ala Leu Glu Phe Thr Gly Pro Leu Ala Val Ala
            100                 105                 110

```
Leu Phe Ser Arg Arg Pro Val Asp Phe Val Trp Val Leu Ala
            115                 120                 125

Val Leu Gly Leu Trp Phe Leu Pro Leu Gly Gln Asp Val Ser His
    130                 135                 140

Val Asp Leu Thr Gly Cys Ala Leu Ala Leu Gly Ala Gly Ala Cys Trp
145                 150                 155                 160

Ala Ile Tyr Ile Leu Ser Gly Gln Arg Ala Gly Ala Glu His Gly Pro
                165                 170                 175

Ala Thr Val Ala Ile Gly Ser Leu Ile Ala Ala Leu Ile Phe Val Pro
            180                 185                 190

Ile Gly Ala Leu Gln Ala Gly Glu Ala Leu Trp His Trp Ser Val Ile
    195                 200                 205

Pro Leu Gly Leu Ala Val Ala Ile Leu Ser Thr Ala Leu Pro Tyr Ser
    210                 215                 220

Leu Glu Met Ile Ala Leu Thr Arg Leu Pro Thr Arg Thr Phe Gly Thr
225                 230                 235                 240

Leu Met Ser Met Glu Pro Ala Leu Ala Ala Val Ser Gly Met Ile Phe
                245                 250                 255

Leu Gly Glu Thr Leu Thr Pro Ile Gln Leu Leu Ala Leu Gly Ala Ile
            260                 265                 270

Ile Ala Ala Ser Met Gly Ser Thr Leu Thr Val Arg Lys Glu Ser Lys
    275                 280                 285

Ile Lys Glu Leu Asp Ile Asn
    290                 295

<210> SEQ ID NO 63
<211> LENGTH: 402
<212> TYPE: PRT
<213> ORGANISM: Escherichia coli

<400> SEQUENCE: 63

Met Thr Val Asn Ser Ser Arg Asn Ala Leu Lys Arg Arg Thr Trp Ala
1               5                   10                  15

Leu Phe Met Phe Phe Phe Leu Pro Gly Leu Leu Met Ala Ser Trp Ala
                20                  25                  30

Thr Arg Thr Pro Ala Ile Arg Asp Ile Leu Ser Val Ser Ile Ala Glu
            35                  40                  45

Met Gly Gly Val Leu Phe Gly Leu Ser Ile Gly Ser Met Ser Gly Ile
        50                  55                  60

Leu Cys Ser Ala Trp Leu Val Lys Arg Phe Gly Thr Arg Asn Val Ile
65                  70                  75                  80

Leu Val Thr Met Ser Cys Ala Leu Ile Gly Met Met Ile Leu Ser Leu
                85                  90                  95

Ala Leu Trp Leu Thr Ser Pro Leu Leu Phe Ala Val Gly Leu Gly Val
            100                 105                 110

Phe Gly Ala Ser Phe Gly Ser Ala Glu Val Ala Ile Asn Val Glu Gly
        115                 120                 125

Ala Ala Val Glu Arg Glu Met Asn Lys Thr Val Leu Pro Met Met His
    130                 135                 140

Gly Phe Tyr Ser Leu Gly Thr Leu Ala Gly Ala Gly Val Gly Met Ala
145                 150                 155                 160

Leu Thr Ala Phe Gly Val Pro Ala Thr Val His Ile Leu Leu Ala Ala
                165                 170                 175

Leu Val Gly Ile Ala Pro Ile Tyr Ile Ala Ile Gln Ala Ile Pro Asp
            180                 185                 190
```

-continued

```
Gly Thr Gly Lys Asn Ala Ala Asp Gly Thr Gln His Gly Glu Lys Gly
            195                 200                 205

Val Pro Phe Tyr Arg Asp Ile Gln Leu Leu Leu Ile Gly Val Val Val
    210                 215                 220

Leu Ala Met Ala Phe Ala Glu Gly Ser Ala Asn Asp Trp Leu Pro Leu
225                 230                 235                 240

Leu Met Val Asp Gly His Gly Phe Ser Pro Thr Ser Gly Ser Leu Ile
                245                 250                 255

Tyr Ala Gly Phe Thr Leu Gly Met Thr Val Gly Arg Phe Thr Gly Gly
            260                 265                 270

Trp Phe Ile Asp Arg Tyr Ser Arg Val Ala Val Arg Ala Ser Ala
            275                 280                 285

Leu Met Gly Ala Leu Gly Ile Gly Leu Ile Ile Phe Val Asp Ser Ala
    290                 295                 300

Trp Val Ala Gly Val Ser Val Leu Trp Gly Leu Gly Ala Ser Leu
305                 310                 315                 320

Gly Phe Pro Leu Thr Ile Ser Ala Ala Ser Asp Thr Gly Pro Asp Ala
                325                 330                 335

Pro Thr Arg Val Ser Val Val Ala Thr Thr Gly Tyr Leu Ala Phe Leu
            340                 345                 350

Val Gly Pro Pro Leu Leu Gly Tyr Leu Gly Glu His Tyr Gly Leu Arg
    355                 360                 365

Ser Ala Met Leu Val Val Leu Ala Leu Val Ile Leu Ala Ala Ile Val
370                 375                 380

Ala Lys Ala Val Ala Lys Pro Asp Thr Lys Thr Gln Thr Ala Met Glu
385                 390                 395                 400

Asn Ser

<210> SEQ ID NO 64
<211> LENGTH: 230
<212> TYPE: PRT
<213> ORGANISM: Escherichia coli

<400> SEQUENCE: 64

Met Lys Ala Phe Asp Leu His Arg Met Ala Phe Asp Lys Val Pro Phe
1               5                   10                  15

Asp Phe Leu Gly Glu Val Ala Leu Arg Ser Leu Tyr Thr Phe Val Leu
            20                  25                  30

Val Phe Leu Phe Leu Lys Met Thr Gly Arg Arg Gly Val Arg Gln Met
        35                  40                  45

Ser Leu Phe Glu Val Leu Ile Ile Leu Thr Leu Gly Ser Ala Ala Gly
    50                  55                  60

Asp Val Ala Phe Tyr Asp Asp Val Pro Met Val Pro Val Leu Ile Val
65                  70                  75                  80

Phe Ile Thr Leu Ala Leu Leu Tyr Arg Leu Val Met Trp Leu Met Ala
                85                  90                  95

His Ser Glu Lys Leu Glu Asp Leu Leu Glu Gly Lys Pro Val Val Ile
            100                 105                 110

Ile Glu Asp Gly Glu Leu Ala Trp Ser Lys Leu Asn Asn Ser Asn Met
        115                 120                 125

Thr Glu Phe Glu Phe Phe Met Glu Leu Arg Leu Arg Gly Val Glu Gln
    130                 135                 140

Leu Gly Gln Val Arg Leu Ala Ile Leu Glu Thr Asn Gly Gln Ile Ser
145                 150                 155                 160
```

```
Val Tyr Phe Phe Glu Asp Asp Lys Val Lys Pro Gly Leu Leu Ile Leu
                165                 170                 175

Pro Ser Asp Cys Thr Gln Arg Tyr Lys Val Val Pro Glu Ser Ala Asp
            180                 185                 190

Tyr Ala Cys Ile Arg Cys Ser Glu Ile Ile His Met Lys Ala Gly Glu
        195                 200                 205

Lys Gln Leu Cys Pro Arg Cys Ala Asn Pro Glu Trp Thr Lys Ala Ser
    210                 215                 220

Arg Ala Lys Arg Val Thr
225                 230

<210> SEQ ID NO 65
<211> LENGTH: 391
<212> TYPE: PRT
<213> ORGANISM: Escherichia coli

<400> SEQUENCE: 65

Met Arg Leu Phe Ser Ile Pro Pro Thr Leu Leu Ala Gly Phe Leu
1               5                   10                  15

Ala Val Leu Ile Gly Tyr Ala Ser Ser Ala Ala Ile Ile Trp Gln Ala
                20                  25                  30

Ala Ile Val Ala Gly Ala Thr Thr Ala Gln Ile Ser Gly Trp Met Thr
            35                  40                  45

Ala Leu Gly Leu Ala Met Gly Val Ser Thr Leu Thr Leu Thr Leu Trp
        50                  55                  60

Tyr Arg Val Pro Val Leu Thr Ala Trp Ser Thr Pro Gly Ala Ala Leu
65                  70                  75                  80

Leu Val Thr Gly Leu Gln Gly Leu Thr Leu Asn Glu Ala Ile Gly Val
                85                  90                  95

Phe Ile Val Thr Asn Ala Leu Ile Val Leu Cys Gly Ile Thr Gly Leu
                100                 105                 110

Phe Ala Arg Leu Met Arg Ile Ile Pro His Ser Leu Ala Ala Ala Met
            115                 120                 125

Leu Ala Gly Ile Leu Leu Arg Phe Gly Leu Gln Ala Phe Ala Ser Leu
        130                 135                 140

Asp Gly Gln Phe Thr Leu Cys Gly Ser Met Leu Leu Val Trp Leu Ala
145                 150                 155                 160

Thr Lys Ala Val Ala Pro Arg Tyr Ala Val Ile Ala Ala Met Ile Ile
                165                 170                 175

Gly Ile Val Ile Val Ile Ala Gln Gly Asp Val Val Thr Thr Asp Val
            180                 185                 190

Val Phe Lys Pro Val Leu Pro Thr Tyr Ile Thr Pro Asp Phe Ser Phe
        195                 200                 205

Ala His Ser Leu Ser Val Ala Leu Pro Leu Phe Leu Val Thr Met Ala
    210                 215                 220

Ser Gln Asn Ala Pro Gly Ile Ala Ala Met Lys Ala Ala Gly Tyr Ser
225                 230                 235                 240

Ala Pro Val Ser Pro Leu Ile Val Phe Thr Gly Leu Leu Ala Leu Val
                245                 250                 255

Phe Ser Pro Phe Gly Val Tyr Ser Val Gly Ile Ala Ala Ile Thr Ala
            260                 265                 270

Ala Ile Cys Gln Ser Pro Glu Ala His Pro Asp Lys Asp Gln Arg Trp
        275                 280                 285

Leu Ala Ala Ala Val Ala Gly Ile Phe Tyr Leu Leu Ala Gly Leu Phe
```

```
                    290                 295                 300
Gly Ser Ala Ile Thr Gly Met Met Ala Leu Pro Val Ser Trp Ile
305                 310                 315                 320

Gln Met Leu Ala Gly Leu Ala Leu Leu Ser Thr Ile Gly Gly Ser Leu
                    325                 330                 335

Tyr Gln Ala Leu His Asn Glu Arg Glu Arg Asp Ala Ala Val Val Ala
                    340                 345                 350

Phe Leu Val Thr Ala Ser Gly Leu Thr Leu Val Gly Ile Gly Ser Ala
                    355                 360                 365

Phe Trp Gly Leu Ile Ala Gly Gly Val Cys Tyr Val Leu Asn Leu
                    370                 375                 380

Ile Ala Asp Arg Asn Arg Tyr
385                 390
```

<210> SEQ ID NO 66
<211> LENGTH: 293
<212> TYPE: PRT
<213> ORGANISM: Escherichia coli

<400> SEQUENCE: 66

```
Met Thr Arg Gln Lys Ala Thr Leu Ile Gly Leu Ile Ala Ile Val Leu
1               5                   10                  15

Trp Ser Thr Met Val Gly Leu Ile Arg Gly Val Ser Glu Gly Leu Gly
                20                  25                  30

Pro Val Gly Gly Ala Ala Ile Tyr Ser Leu Ser Gly Leu Leu Leu
                35                  40                  45

Ile Phe Thr Val Gly Phe Pro Arg Ile Arg Gln Ile Pro Lys Gly Tyr
    50                  55                  60

Leu Leu Ala Gly Ser Leu Leu Phe Val Ser Tyr Glu Ile Cys Leu Ala
65                  70                  75                  80

Leu Ser Leu Gly Tyr Ala Ala Thr His His Gln Ala Ile Glu Val Gly
                85                  90                  95

Met Val Asn Tyr Leu Trp Pro Ser Leu Thr Ile Leu Phe Ala Ile Leu
                100                 105                 110

Phe Asn Gly Gln Lys Thr Asn Trp Leu Ile Val Pro Gly Leu Leu Leu
                115                 120                 125

Ala Leu Val Gly Val Cys Trp Val Leu Gly Gly Asp Asn Gly Leu His
130                 135                 140

Tyr Asp Glu Ile Ile Asn Asn Ile Thr Thr Ser Pro Leu Ser Tyr Phe
145                 150                 155                 160

Leu Ala Phe Ile Gly Ala Phe Ile Trp Ala Ala Tyr Cys Thr Val Thr
                165                 170                 175

Asn Lys Tyr Ala Arg Gly Phe Asn Gly Ile Thr Val Phe Val Leu Leu
                180                 185                 190

Thr Gly Ala Ser Leu Trp Val Tyr Tyr Phe Leu Thr Pro Gln Pro Glu
                195                 200                 205

Met Ile Phe Ser Thr Pro Val Met Ile Lys Leu Ile Ser Ala Ala Phe
                210                 215                 220

Thr Leu Gly Phe Ala Tyr Ala Ala Trp Asn Val Gly Ile Leu His Gly
225                 230                 235                 240

Asn Val Thr Ile Met Ala Val Gly Ser Tyr Phe Thr Pro Val Leu Ser
                245                 250                 255

Ser Ala Leu Ala Ala Val Leu Leu Ser Ala Pro Leu Ser Phe Ser Phe
                260                 265                 270
```

```
Trp Gln Gly Ala Leu Met Val Cys Gly Gly Ser Leu Leu Cys Trp Leu
            275                 280                 285

Ala Thr Arg Arg Gly
        290
```

<210> SEQ ID NO 67
<211> LENGTH: 299
<212> TYPE: PRT
<213> ORGANISM: Escherichia coli

<400> SEQUENCE: 67

```
Met Ser Arg Lys Asp Gly Val Leu Ala Leu Val Val Val Val Val Trp
1               5                   10                  15

Gly Leu Asn Phe Val Ile Lys Val Gly Leu His Asn Met Pro Pro
            20                  25                  30

Leu Met Leu Ala Gly Leu Arg Phe Met Leu Val Ala Phe Pro Ala Ile
        35                  40                  45

Phe Phe Val Ala Arg Pro Lys Val Pro Leu Asn Leu Leu Leu Gly Tyr
50                  55                  60

Gly Leu Thr Ile Ser Phe Ala Gln Phe Ala Phe Leu Phe Cys Ala Ile
65                  70                  75                  80

Asn Phe Gly Met Pro Ala Gly Leu Ala Ser Leu Val Leu Gln Ala Gln
                85                  90                  95

Ala Phe Phe Thr Ile Met Leu Gly Ala Phe Thr Phe Gly Glu Arg Leu
            100                 105                 110

His Gly Lys Gln Leu Ala Gly Ile Ala Leu Ala Ile Phe Gly Val Leu
        115                 120                 125

Val Leu Ile Glu Asp Ser Leu Asn Gly Gln His Val Ala Met Leu Gly
130                 135                 140

Phe Met Leu Thr Leu Ala Ala Ala Phe Ser Trp Ala Cys Gly Asn Ile
145                 150                 155                 160

Phe Asn Lys Lys Ile Met Ser His Ser Thr Arg Pro Ala Val Met Ser
                165                 170                 175

Leu Val Ile Trp Ser Ala Leu Ile Pro Ile Ile Pro Phe Phe Val Ala
            180                 185                 190

Ser Leu Ile Leu Asp Gly Ser Ala Thr Met Ile His Ser Leu Val Thr
        195                 200                 205

Ile Asp Met Thr Thr Ile Leu Ser Leu Met Tyr Leu Ala Phe Val Ala
210                 215                 220

Thr Ile Val Gly Tyr Gly Ile Trp Gly Thr Leu Leu Gly Arg Tyr Glu
225                 230                 235                 240

Thr Trp Arg Val Ala Pro Leu Ser Leu Leu Val Pro Val Val Gly Leu
                245                 250                 255

Ala Ser Ala Ala Leu Leu Leu Asp Glu Arg Leu Thr Gly Leu Gln Phe
            260                 265                 270

Leu Gly Ala Val Leu Ile Met Thr Gly Leu Tyr Ile Asn Val Phe Gly
        275                 280                 285

Leu Arg Trp Arg Lys Ala Val Lys Val Gly Ser
290                 295
```

<210> SEQ ID NO 68
<211> LENGTH: 109
<212> TYPE: PRT
<213> ORGANISM: Escherichia coli

<400> SEQUENCE: 68

Met Ala Gln Phe Glu Trp Val His Ala Ala Trp Leu Ala Leu Ala Ile
1               5                   10                  15

Val Leu Glu Ile Val Ala Asn Val Phe Leu Lys Phe Ser Asp Gly Phe
            20                  25                  30

Arg Arg Lys Ile Phe Gly Leu Leu Ser Leu Ala Ala Val Leu Ala Ala
                35                  40                  45

Phe Ser Ala Leu Ser Gln Ala Val Lys Gly Ile Asp Leu Ser Val Ala
    50                  55                  60

Tyr Ala Leu Trp Gly Gly Phe Gly Ile Ala Ala Thr Leu Ala Ala Gly
65                  70                  75                  80

Trp Ile Leu Phe Gly Gln Arg Leu Asn Arg Lys Gly Trp Ile Gly Leu
                85                  90                  95

Val Leu Leu Leu Ala Gly Met Ile Met Val Lys Leu Ala
                100                 105

<210> SEQ ID NO 69
<211> LENGTH: 403
<212> TYPE: PRT
<213> ORGANISM: Escherichia coli

<400> SEQUENCE: 69

Met Gln Pro Gly Lys Arg Phe Leu Val Trp Leu Ala Gly Leu Ser Val
1               5                   10                  15

Leu Gly Phe Leu Ala Thr Asp Met Tyr Leu Pro Ala Phe Ala Ala Ile
            20                  25                  30

Gln Ala Asp Leu Gln Thr Pro Ala Ser Ala Val Ser Ala Ser Leu Ser
                35                  40                  45

Leu Phe Leu Ala Gly Phe Ala Ala Gln Leu Leu Trp Gly Pro Leu
    50                  55                  60

Ser Asp Arg Tyr Gly Arg Lys Pro Val Leu Ile Gly Leu Thr Ile
65                  70                  75                  80

Phe Ala Leu Gly Ser Leu Gly Met Leu Trp Val Glu Asn Ala Ala Thr
                85                  90                  95

Leu Leu Val Leu Arg Phe Val Gln Ala Val Gly Val Cys Ala Ala Ala
                100                 105                 110

Val Ile Trp Gln Ala Leu Val Thr Asp Tyr Tyr Pro Ser Gln Lys Val
            115                 120                 125

Asn Arg Ile Phe Ala Ala Ile Met Pro Leu Val Gly Leu Ser Pro Ala
        130                 135                 140

Leu Ala Pro Leu Leu Gly Ser Trp Leu Leu Val His Phe Ser Trp Gln
145                 150                 155                 160

Ala Ile Phe Ala Thr Leu Phe Ala Ile Thr Val Leu Ile Leu Pro
                165                 170                 175

Ile Phe Trp Leu Lys Pro Thr Thr Lys Ala Arg Asn Asn Ser Gln Asp
                180                 185                 190

Gly Leu Thr Phe Thr Asp Leu Leu Arg Ser Lys Thr Tyr Arg Gly Asn
            195                 200                 205

Val Leu Ile Tyr Ala Ala Cys Ser Ala Ser Phe Phe Ala Trp Leu Thr
        210                 215                 220

Gly Ser Pro Phe Ile Leu Ser Glu Met Gly Tyr Ser Pro Ala Val Ile
225                 230                 235                 240

Gly Leu Ser Tyr Val Pro Gln Thr Ile Ala Phe Leu Ile Gly Gly Tyr
                245                 250                 255

Gly Cys Arg Ala Ala Leu Gln Lys Trp Gln Gly Lys Gln Leu Leu Pro
                260                 265                 270

```
Trp Leu Leu Val Leu Phe Ala Val Ser Val Ile Ala Thr Trp Ala Ala
            275                 280                 285

Gly Phe Ile Ser His Val Ser Leu Val Glu Ile Leu Ile Pro Phe Cys
        290                 295                 300

Val Met Ala Ile Ala Asn Gly Ala Ile Tyr Pro Ile Val Ala Gln
305                 310                 315                 320

Ala Leu Arg Pro Phe Pro His Ala Thr Gly Arg Ala Ala Leu Gln
                325                 330                 335

Asn Thr Leu Gln Leu Gly Leu Cys Phe Leu Ala Ser Leu Val Val Ser
            340                 345                 350

Trp Leu Ile Ser Ile Ser Thr Pro Leu Leu Thr Thr Thr Ser Val Met
            355                 360                 365

Leu Ser Thr Val Val Leu Val Ala Leu Gly Tyr Met Met Gln Arg Cys
370                 375                 380

Glu Glu Val Gly Cys Gln Asn His Gly Asn Ala Glu Val Ala His Ser
385                 390                 395                 400

Glu Ser His

<210> SEQ ID NO 70
<211> LENGTH: 389
<212> TYPE: PRT
<213> ORGANISM: Escherichia coli

<400> SEQUENCE: 70

Met Lys Ile Asn Tyr Pro Leu Leu Ala Leu Ala Ile Gly Ala Phe Gly
1               5                   10                  15

Ile Gly Thr Thr Glu Phe Ser Pro Met Gly Leu Leu Pro Val Ile Ala
            20                  25                  30

Arg Gly Val Asp Val Ser Ile Pro Ala Ala Gly Met Leu Ile Ser Ala
        35                  40                  45

Tyr Ala Val Gly Val Met Val Gly Ala Pro Leu Met Thr Leu Leu Leu
    50                  55                  60

Ser His Arg Ala Arg Arg Ser Ala Leu Ile Phe Leu Met Ala Ile Phe
65                  70                  75                  80

Thr Leu Gly Asn Val Leu Ser Ala Ile Ala Pro Asp Tyr Met Thr Leu
                85                  90                  95

Met Leu Ser Arg Ile Leu Thr Ser Leu Asn His Gly Ala Phe Phe Gly
            100                 105                 110

Leu Gly Ser Val Val Ala Ala Ser Val Val Pro Lys His Lys Gln Ala
        115                 120                 125

Ser Ala Val Ala Thr Met Phe Met Gly Leu Thr Leu Ala Asn Ile Gly
    130                 135                 140

Gly Val Pro Ala Ala Thr Trp Leu Gly Glu Thr Ile Gly Trp Arg Met
145                 150                 155                 160

Ser Phe Leu Ala Thr Ala Gly Leu Gly Val Ile Ser Met Val Ser Leu
                165                 170                 175

Phe Phe Ser Leu Pro Lys Gly Gly Ala Gly Ala Arg Pro Glu Val Lys
            180                 185                 190

Lys Glu Leu Ala Val Leu Met Arg Pro Gln Val Leu Ser Ala Leu Leu
        195                 200                 205

Thr Thr Val Leu Gly Ala Gly Ala Met Phe Thr Leu Tyr Thr Tyr Ile
    210                 215                 220

Ser Pro Val Leu Gln Ser Ile Thr His Ala Thr Pro Val Phe Val Thr
225                 230                 235                 240
```

```
Ala Met Leu Val Leu Ile Gly Val Gly Phe Ser Ile Gly Asn Tyr Leu
                245                 250                 255

Gly Gly Lys Leu Ala Asp Arg Ser Val Asn Gly Thr Leu Lys Gly Phe
            260                 265                 270

Leu Leu Leu Leu Met Val Ile Met Leu Ala Ile Pro Phe Leu Ala Arg
            275                 280                 285

Asn Glu Phe Gly Ala Ala Ile Ser Met Val Val Trp Gly Ala Ala Thr
290                 295                 300

Phe Ala Val Val Pro Pro Leu Gln Met Arg Val Met Arg Val Ala Ser
305                 310                 315                 320

Glu Ala Pro Gly Leu Ser Ser Val Asn Ile Gly Ala Phe Asn Leu
                325                 330                 335

Gly Asn Ala Leu Gly Ala Ala Gly Gly Ala Val Ile Ser Ala Gly
            340                 345                 350

Leu Gly Tyr Ser Phe Val Pro Val Met Gly Ala Ile Val Ala Gly Leu
            355                 360                 365

Ala Leu Leu Leu Val Phe Met Ser Ala Arg Lys Gln Pro Glu Thr Val
370                 375                 380

Cys Val Ala Asn Ser
385

<210> SEQ ID NO 71
<211> LENGTH: 421
<212> TYPE: PRT
<213> ORGANISM: Escherichia coli

<400> SEQUENCE: 71

Met Ser Gln Asn Lys Ala Phe Ser Thr Pro Phe Ile Leu Ala Val Leu
1               5                   10                  15

Cys Ile Tyr Phe Ser Tyr Phe Leu His Gly Ile Ser Val Ile Thr Leu
                20                  25                  30

Ala Gln Asn Met Ser Ser Leu Ala Glu Lys Phe Ser Thr Asp Asn Ala
            35                  40                  45

Gly Ile Ala Tyr Leu Ile Ser Gly Ile Gly Leu Gly Arg Leu Ile Ser
    50                  55                  60

Ile Leu Phe Phe Gly Val Ile Ser Asp Lys Phe Gly Arg Arg Ala Val
65                  70                  75                  80

Ile Leu Met Ala Val Ile Met Tyr Leu Leu Phe Phe Gly Ile Pro
                85                  90                  95

Ala Cys Pro Asn Leu Thr Leu Ala Tyr Gly Leu Ala Val Cys Val Gly
                100                 105                 110

Ile Ala Asn Ser Ala Leu Asp Thr Gly Gly Tyr Pro Ala Leu Met Glu
            115                 120                 125

Cys Phe Pro Lys Ala Ser Gly Ser Ala Val Ile Leu Val Lys Ala Met
130                 135                 140

Val Ser Phe Gly Gln Met Phe Tyr Pro Met Leu Val Ser Tyr Met Leu
145                 150                 155                 160

Leu Asn Asn Ile Trp Tyr Gly Tyr Gly Leu Ile Ile Pro Gly Ile Leu
                165                 170                 175

Phe Val Leu Ile Thr Leu Met Leu Leu Lys Ser Lys Phe Pro Ser Gln
            180                 185                 190

Leu Val Asp Ala Ser Val Thr Asn Glu Leu Pro Gln Met Asn Ser Lys
        195                 200                 205

Pro Leu Val Trp Leu Glu Gly Val Ser Ser Val Leu Phe Gly Val Ala
```

```
                210                 215                 220
Ala Phe Ser Thr Phe Tyr Val Ile Val Val Trp Met Pro Lys Tyr Ala
225                 230                 235                 240

Met Ala Phe Ala Gly Met Ser Glu Ala Glu Ala Leu Lys Thr Ile Ser
                245                 250                 255

Tyr Tyr Ser Met Gly Ser Leu Val Cys Val Phe Ile Phe Ala Ala Leu
            260                 265                 270

Leu Lys Lys Met Val Arg Pro Ile Trp Ala Asn Val Phe Asn Ser Ala
        275                 280                 285

Leu Ala Thr Ile Thr Ala Ala Ile Ile Tyr Leu Tyr Pro Ser Pro Leu
    290                 295                 300

Val Cys Asn Ala Gly Ala Phe Val Ile Gly Phe Ser Ala Ala Gly Gly
305                 310                 315                 320

Ile Leu Gln Leu Gly Val Ser Val Met Ser Glu Phe Phe Pro Lys Ser
                325                 330                 335

Lys Ala Lys Val Thr Ser Ile Tyr Met Met Met Gly Gly Leu Ala Asn
            340                 345                 350

Phe Val Ile Pro Leu Ile Thr Gly Tyr Leu Ser Asn Ile Gly Leu Gln
        355                 360                 365

Tyr Ile Ile Val Leu Asp Phe Thr Phe Ala Leu Leu Ala Leu Ile Thr
    370                 375                 380

Ala Ile Ile Val Phe Ile Arg Tyr Tyr Arg Val Phe Ile Ile Pro Glu
385                 390                 395                 400

Asn Asp Val Arg Phe Gly Glu Arg Lys Phe Cys Thr Arg Leu Asn Thr
                405                 410                 415

Ile Lys His Arg Gly
            420

<210> SEQ ID NO 72
<211> LENGTH: 404
<212> TYPE: PRT
<213> ORGANISM: Escherichia coli

<400> SEQUENCE: 72

Met Lys Asn Pro Tyr Phe Pro Thr Ala Leu Gly Leu Tyr Phe Asn Tyr
1               5                   10                  15

Leu Val His Gly Met Gly Val Leu Leu Met Ser Leu Asn Met Ala Ser
            20                  25                  30

Leu Glu Thr Leu Trp Gln Thr Asn Ala Ala Gly Val Ser Ile Val Ile
        35                  40                  45

Ser Ser Leu Gly Ile Gly Arg Leu Ser Val Leu Leu Phe Ala Gly Leu
    50                  55                  60

Leu Ser Asp Arg Phe Gly Arg Arg Pro Phe Ile Met Leu Gly Met Cys
65                  70                  75                  80

Cys Tyr Met Ala Phe Phe Phe Gly Ile Leu Gln Thr Asn Asn Ile Ile
                85                  90                  95

Ile Ala Tyr Val Phe Gly Phe Leu Ala Gly Met Ala Asn Ser Phe Leu
            100                 105                 110

Asp Ala Gly Thr Tyr Pro Ser Leu Met Glu Ala Phe Pro Arg Ser Pro
        115                 120                 125

Gly Thr Ala Asn Ile Leu Ile Lys Ala Phe Val Ser Ser Gly Gln Phe
    130                 135                 140

Leu Leu Pro Leu Ile Ile Ser Leu Leu Val Trp Ala Glu Leu Trp Phe
145                 150                 155                 160
```

```
Gly Trp Ser Phe Met Ile Ala Ala Gly Ile Met Phe Ile Asn Ala Leu
                165                 170                 175

Phe Leu Tyr Arg Cys Thr Phe Pro Pro His Pro Gly Arg Arg Leu Pro
            180                 185                 190

Val Ile Lys Lys Thr Thr Ser Ser Thr Glu His Arg Cys Ser Ile Ile
        195                 200                 205

Asp Leu Ala Ser Tyr Thr Leu Tyr Gly Tyr Ile Ser Met Ala Thr Phe
    210                 215                 220

Tyr Leu Val Ser Gln Trp Leu Ala Gln Tyr Gly Gln Phe Val Ala Gly
225                 230                 235                 240

Met Ser Tyr Thr Met Ser Ile Lys Leu Leu Ser Ile Tyr Thr Val Gly
                245                 250                 255

Ser Leu Leu Cys Val Phe Ile Thr Ala Pro Leu Ile Arg Asn Thr Val
            260                 265                 270

Arg Pro Thr Thr Leu Leu Met Leu Tyr Thr Phe Ile Ser Phe Ile Ala
        275                 280                 285

Leu Phe Thr Val Cys Leu His Pro Thr Phe Tyr Val Val Ile Ile Phe
    290                 295                 300

Ala Phe Val Ile Gly Phe Thr Ser Ala Gly Val Val Gln Ile Gly
305                 310                 315                 320

Leu Thr Leu Met Ala Glu Arg Phe Pro Tyr Ala Lys Gly Lys Ala Thr
                325                 330                 335

Gly Ile Tyr Tyr Ser Ala Gly Ser Ile Ala Thr Phe Thr Ile Pro Leu
            340                 345                 350

Ile Thr Ala His Leu Ser Gln Arg Ser Ile Ala Asp Ile Met Trp Phe
        355                 360                 365

Asp Thr Ala Ile Ala Ala Ile Gly Phe Leu Leu Ala Leu Phe Ile Gly
    370                 375                 380

Leu Arg Ser Arg Lys Lys Thr Arg His His Ser Leu Lys Glu Asn Val
385                 390                 395                 400

Ala Pro Gly Gly

<210> SEQ ID NO 73
<211> LENGTH: 452
<212> TYPE: PRT
<213> ORGANISM: Escherichia coli

<400> SEQUENCE: 73

Met Glu Gln Tyr Asp Gln Ile Gly Ala Arg Leu Asp Arg Leu Pro Leu
1               5                   10                  15

Ala Arg Phe His Tyr Arg Ile Phe Gly Ile Ile Ser Phe Ser Leu Leu
                20                  25                  30

Leu Thr Gly Phe Leu Ser Tyr Ser Gly Asn Val Val Leu Ala Lys Leu
            35                  40                  45

Val Ser Asn Gly Trp Ser Asn Asn Phe Leu Asn Ala Ala Phe Thr Ser
        50                  55                  60

Ala Leu Met Phe Gly Tyr Phe Ile Gly Ser Leu Thr Gly Gly Phe Ile
65                  70                  75                  80

Gly Asp Tyr Phe Gly Arg Arg Arg Ala Phe Arg Ile Asn Leu Leu Ile
                85                  90                  95

Val Gly Ile Ala Ala Thr Gly Ala Ala Phe Val Pro Asp Met Tyr Trp
            100                 105                 110

Leu Ile Phe Phe Arg Phe Leu Met Gly Thr Gly Met Gly Ala Leu Ile
        115                 120                 125
```

```
Met Val Gly Tyr Ala Ser Phe Thr Glu Phe Ile Pro Ala Thr Val Arg
            130                 135                 140

Gly Lys Trp Ser Ala Arg Leu Ser Phe Val Gly Asn Trp Ser Pro Met
145                 150                 155                 160

Leu Ser Ala Ala Ile Gly Val Val Ile Ala Phe Phe Ser Trp Arg
                165                 170                 175

Ile Met Phe Leu Leu Gly Gly Ile Gly Ile Leu Leu Ala Trp Phe Leu
                180                 185                 190

Ser Gly Lys Tyr Phe Ile Glu Ser Pro Arg Trp Leu Ala Gly Lys Gly
            195                 200                 205

Gln Ile Ala Gly Ala Glu Cys Gln Leu Arg Glu Val Glu Gln Gln Ile
210                 215                 220

Glu Arg Glu Lys Ser Ile Arg Leu Pro Pro Leu Thr Ser Tyr Gln Ser
225                 230                 235                 240

Asn Ser Lys Val Lys Val Ile Lys Gly Thr Phe Trp Leu Leu Phe Lys
                245                 250                 255

Gly Glu Met Leu Arg Arg Thr Leu Val Ala Ile Thr Val Leu Ile Ala
            260                 265                 270

Met Asn Ile Ser Leu Tyr Thr Ile Thr Val Trp Ile Pro Thr Ile Phe
        275                 280                 285

Val Asn Ser Gly Ile Asp Val Asp Lys Ser Ile Leu Met Thr Ala Val
        290                 295                 300

Ile Met Ile Gly Ala Pro Val Gly Ile Phe Ile Ala Ala Leu Ile Ile
305                 310                 315                 320

Asp His Phe Pro Arg Arg Leu Phe Gly Ser Thr Leu Leu Ile Ile Ile
                325                 330                 335

Ala Val Leu Gly Tyr Ile Tyr Ser Ile Gln Thr Thr Glu Trp Ala Ile
                340                 345                 350

Leu Ile Tyr Gly Leu Val Met Ile Phe Phe Leu Tyr Met Tyr Val Cys
            355                 360                 365

Phe Ala Ser Ala Val Tyr Ile Pro Glu Leu Trp Pro Thr His Leu Arg
370                 375                 380

Leu Arg Gly Ser Gly Phe Val Asn Ala Val Gly Arg Ile Val Ala Val
385                 390                 395                 400

Phe Thr Pro Tyr Gly Val Ala Ala Leu Leu Thr His Tyr Gly Ser Ile
                405                 410                 415

Thr Val Phe Met Val Leu Gly Val Met Leu Leu Cys Ala Leu Val
                420                 425                 430

Leu Ser Ile Phe Gly Ile Glu Thr Arg Lys Val Ser Leu Glu Glu Ile
            435                 440                 445

Ser Glu Val Asn
    450

<210> SEQ ID NO 74
<211> LENGTH: 252
<212> TYPE: PRT
<213> ORGANISM: Escherichia coli

<400> SEQUENCE: 74

Met Ala Ala Lys Asp Arg Ile Gln Ala Ile Lys Gln Met Val Ala Asn
1               5                   10                  15

Asp Lys Lys Val Thr Val Ser Asn Leu Ser Gly Ile Phe Gln Val Thr
                20                  25                  30

Glu Glu Thr Ile Arg Arg Asp Leu Glu Lys Leu Glu Asp Glu Gly Phe
            35                  40                  45
```

```
Leu Thr Arg Thr Tyr Gly Gly Ala Val Leu Asn Thr Ala Met Leu Thr
    50                  55                  60

Glu Asn Ile His Phe Tyr Lys Arg Ala Ser Ser Phe Tyr Glu Glu Lys
65                  70                  75                  80

Gln Leu Ile Ala Arg Lys Ala Leu Pro Phe Ile Asp Asn Lys Thr Thr
                85                  90                  95

Met Ala Ala Asp Ser Ser Ser Thr Val Met Glu Leu Leu Lys Leu Leu
            100                 105                 110

Gln Asp Arg Ser Gly Leu Thr Leu Leu Thr Asn Ser Ala Glu Ala Ile
        115                 120                 125

His Val Leu Ala Gln Ser Glu Ile Lys Val Val Ser Thr Gly Gly Glu
    130                 135                 140

Leu Asn Lys Asn Thr Leu Ser Leu Gln Gly Arg Ile Thr Lys Glu Ile
145                 150                 155                 160

Ile Arg Arg Tyr His Val Asp Ile Met Val Met Ser Cys Lys Gly Leu
                165                 170                 175

Asp Ile Asn Ser Gly Ala Leu Asp Ser Asn Glu Ala Glu Ala Glu Ile
            180                 185                 190

Lys Lys Thr Met Ile Arg Gln Ala Thr Glu Val Ala Leu Leu Val Asp
        195                 200                 205

His Ser Lys Phe Asp Arg Lys Ala Phe Val Gln Leu Ala Asp Phe Ser
    210                 215                 220

His Ile Asn Tyr Ile Ile Thr Asp Lys Ser Pro Gly Ala Glu Trp Ile
225                 230                 235                 240

Ala Phe Cys Lys Asp Asn Asn Ile Gln Leu Val Trp
                245                 250

<210> SEQ ID NO 75
<211> LENGTH: 278
<212> TYPE: PRT
<213> ORGANISM: Escherichia coli

<400> SEQUENCE: 75

Met Leu Ala Asp Ile Arg Tyr Trp Glu Asn Asp Ala Thr Asn Lys His
1               5                   10                  15

Tyr Ala Ile Ala His Phe Asn Val Trp Asn Ala Glu Met Leu Met Gly
                20                  25                  30

Val Ile Asp Ala Ala Glu Glu Ala Lys Ser Pro Val Ile Ile Ser Phe
            35                  40                  45

Gly Thr Gly Phe Val Gly Asn Thr Ser Phe Glu Asp Phe Ser His Met
        50                  55                  60

Met Val Ser Met Ala Gln Lys Ala Thr Val Pro Val Ile Thr His Trp
65                  70                  75                  80

Asp His Gly Arg Ser Met Glu Ile Ile His Asn Ala Trp Thr His Gly
                85                  90                  95

Met Asn Ser Leu Met Arg Asp Ala Ser Ala Phe Asp Phe Glu Glu Asn
            100                 105                 110

Ile Arg Leu Thr Lys Glu Ala Val Asp Phe Phe His Pro Leu Gly Ile
        115                 120                 125

Pro Val Glu Ala Glu Leu Gly His Val Gly Asn Glu Thr Val Tyr Glu
    130                 135                 140

Glu Ala Leu Ala Gly Tyr His Tyr Thr Asp Pro Asp Gln Ala Ala Glu
145                 150                 155                 160

Phe Val Glu Arg Thr Gly Cys Asp Ser Leu Ala Val Ala Ile Gly Asn
```

```
                165                 170                 175
Gln His Gly Val Tyr Thr Ser Glu Pro Gln Leu Asn Phe Glu Val Val
            180                 185                 190

Lys Arg Val Arg Asp Ala Val Ser Val Pro Leu Val Leu His Gly Ala
        195                 200                 205

Ser Gly Ile Ser Asp Ala Asp Ile Lys Thr Ala Ile Ser Leu Gly Ile
    210                 215                 220

Ala Lys Ile Asn Ile His Thr Glu Leu Cys Gln Ala Ala Met Val Ala
225                 230                 235                 240

Val Lys Glu Asn Gln Asp Gln Pro Phe Leu His Leu Glu Arg Glu Val
            245                 250                 255

Arg Lys Ala Val Lys Glu Arg Ala Leu Glu Lys Ile Lys Leu Phe Gly
        260                 265                 270

Ser Asp Gly Lys Ala Glu
        275

<210> SEQ ID NO 76
<211> LENGTH: 459
<212> TYPE: PRT
<213> ORGANISM: Escherichia coli

<400> SEQUENCE: 76

Met Glu Gln Ile Thr Lys Pro His Cys Gly Ala Arg Leu Asp Arg Leu
1               5                   10                  15

Pro Asp Cys Arg Trp His Ser Ser Met Phe Ala Ile Val Ala Phe Gly
            20                  25                  30

Leu Leu Val Cys Trp Ser Asn Ala Val Gly Gly Leu Ile Leu Ala Gln
        35                  40                  45

Leu Lys Ala Leu Gly Trp Thr Asp Asn Ser Thr Thr Ala Thr Phe Ser
    50                  55                  60

Ala Ile Thr Thr Ala Gly Met Phe Leu Gly Ala Leu Val Gly Gly Ile
65                  70                  75                  80

Ile Gly Asp Lys Thr Gly Arg Arg Asn Ala Phe Ile Leu Tyr Glu Ala
                85                  90                  95

Ile His Ile Ala Ser Met Val Val Gly Ala Phe Ser Pro Asn Met Asp
            100                 105                 110

Phe Leu Ile Ala Cys Arg Phe Val Met Gly Val Gly Leu Gly Ala Leu
        115                 120                 125

Leu Val Thr Leu Phe Ala Gly Phe Thr Glu Tyr Met Pro Gly Arg Asn
    130                 135                 140

Arg Gly Thr Trp Ser Ser Arg Val Ser Phe Ile Gly Asn Trp Ser Tyr
145                 150                 155                 160

Pro Leu Cys Ser Leu Ile Ala Met Gly Leu Thr Pro Leu Ile Ser Ala
                165                 170                 175

Glu Trp Asn Trp Arg Val Gln Leu Leu Ile Pro Ala Ile Leu Ser Leu
            180                 185                 190

Ile Ala Thr Ala Leu Ala Trp Arg Tyr Phe Pro Glu Ser Pro Arg Trp
        195                 200                 205

Leu Glu Ser Arg Gly Arg Tyr Gln Glu Ala Gly Lys Val Met Arg Ser
    210                 215                 220

Ile Glu Glu Gly Val Ile Arg Gln Thr Gly Lys Pro Leu Pro Pro Val
225                 230                 235                 240

Val Ile Ala Asp Asp Gly Lys Ala Pro Gln Ala Val Pro Tyr Ser Ala
                245                 250                 255
```

Leu Leu Thr Gly Val Leu Lys Arg Val Ile Gly Ser Cys Val
            260                 265                 270

Leu Ile Ala Met Asn Val Val Gln Tyr Thr Leu Ile Asn Trp Leu Pro
            275                 280                 285

Thr Ile Phe Met Thr Gln Gly Ile Asn Leu Lys Asp Ser Ile Val Leu
290                 295                 300

Asn Thr Met Ser Met Phe Gly Ala Pro Phe Gly Ile Phe Ile Ala Met
305                 310                 315                 320

Leu Val Met Asp Lys Ile Pro Arg Lys Thr Met Gly Val Gly Leu Leu
                325                 330                 335

Ile Leu Ile Ala Val Leu Gly Tyr Ile Tyr Ser Leu Gln Thr Ser Met
            340                 345                 350

Leu Leu Ile Thr Leu Ile Gly Phe Phe Leu Ile Thr Phe Val Tyr Met
            355                 360                 365

Tyr Val Cys Tyr Ala Ser Ala Val Tyr Val Pro Glu Ile Trp Pro Thr
            370                 375                 380

Glu Ala Lys Leu Arg Gly Ser Gly Leu Ala Asn Ala Val Gly Arg Ile
385                 390                 395                 400

Ser Gly Ile Ala Ala Pro Tyr Ala Val Ala Val Leu Leu Ser Ser Tyr
                405                 410                 415

Gly Val Thr Gly Val Phe Ile Leu Leu Gly Ala Val Ser Ile Ile Val
            420                 425                 430

Ala Ile Ala Ile Ala Thr Ile Gly Ile Glu Thr Lys Gly Val Ser Val
            435                 440                 445

Glu Ser Leu Ser Ile Asp Ala Val Ala Asn Lys
450                 455

<210> SEQ ID NO 77
<211> LENGTH: 393
<212> TYPE: PRT
<213> ORGANISM: Escherichia coli

<400> SEQUENCE: 77

Met Thr Cys Ser Thr Ser Leu Ser Gly Lys Asn Arg Ile Val Leu Ile
1               5                   10                  15

Ala Gly Ile Leu Met Ile Ala Thr Thr Leu Arg Val Thr Phe Thr Gly
            20                  25                  30

Ala Ala Pro Leu Leu Asp Thr Ile Arg Ser Ala Tyr Ser Leu Thr Thr
        35                  40                  45

Ala Gln Thr Gly Leu Leu Thr Thr Leu Pro Leu Leu Ala Phe Ala Leu
    50                  55                  60

Ile Ser Pro Leu Ala Ala Pro Val Ala Arg Arg Phe Gly Met Glu Arg
65                  70                  75                  80

Ser Leu Phe Ala Ala Leu Leu Leu Ile Cys Ala Gly Ile Ala Ile Arg
                85                  90                  95

Ser Leu Pro Ser Pro Tyr Leu Leu Phe Gly Gly Thr Ala Val Ile Gly
            100                 105                 110

Gly Gly Ile Ala Leu Gly Asn Val Leu Leu Pro Gly Leu Ile Lys Arg
            115                 120                 125

Asp Phe Pro His Ser Val Ala Arg Leu Thr Gly Ala Tyr Ser Leu Thr
        130                 135                 140

Met Gly Ala Ala Ala Leu Gly Ser Ala Met Val Val Pro Leu Ala
145                 150                 155                 160

Leu Asn Gly Phe Gly Trp Gln Gly Ala Leu Leu Met Leu Met Cys Phe
                165                 170                 175

```
Pro Leu Leu Ala Leu Phe Leu Trp Leu Pro Gln Trp Arg Ser Gln Gln
                180                 185                 190

His Ala Asn Leu Ser Thr Ser Arg Ala Leu His Thr Arg Gly Ile Trp
            195                 200                 205

Arg Ser Pro Leu Ala Trp Gln Val Thr Leu Phe Leu Gly Ile Asn Ser
210                 215                 220

Leu Val Tyr Tyr Val Ile Ile Gly Trp Leu Pro Ala Ile Leu Ile Ser
225                 230                 235                 240

His Gly Tyr Ser Glu Ala Gln Ala Gly Ser Leu His Gly Leu Leu Gln
                245                 250                 255

Leu Ala Thr Ala Ala Pro Gly Leu Leu Ile Pro Leu Phe Leu His His
            260                 265                 270

Val Lys Asp Gln Arg Gly Ile Ala Ala Phe Val Ala Leu Met Cys Ala
        275                 280                 285

Val Gly Ala Val Gly Leu Cys Phe Met Pro Ala His Ala Ile Thr Trp
    290                 295                 300

Thr Leu Leu Phe Gly Phe Gly Ser Gly Ala Thr Met Ile Leu Gly Leu
305                 310                 315                 320

Thr Phe Ile Gly Leu Arg Ala Ser Ser Ala His Gln Ala Ala Ala Leu
                325                 330                 335

Ser Gly Met Ala Gln Ser Val Gly Tyr Leu Leu Ala Ala Cys Gly Pro
            340                 345                 350

Pro Leu Met Gly Lys Ile His Asp Ala Asn Gly Asn Trp Ser Val Pro
        355                 360                 365

Leu Met Gly Val Ala Ile Leu Ser Leu Leu Met Ala Ile Phe Gly Leu
    370                 375                 380

Cys Ala Gly Arg Asp Lys Glu Ile Arg
385                 390

<210> SEQ ID NO 78
<211> LENGTH: 212
<212> TYPE: PRT
<213> ORGANISM: Escherichia coli

<400> SEQUENCE: 78

Met Phe Ala Glu Tyr Gly Val Leu Asn Tyr Trp Thr Tyr Leu Val Gly
1               5                   10                  15

Ala Ile Phe Ile Val Leu Val Pro Gly Pro Asn Thr Leu Phe Val Leu
                20                  25                  30

Lys Asn Ser Val Ser Ser Gly Met Lys Gly Gly Tyr Leu Ala Ala Cys
            35                  40                  45

Gly Val Phe Ile Gly Asp Ala Val Leu Met Phe Leu Ala Trp Ala Gly
        50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
```

```
145                 150                 155                 160
Glu Leu Val Ser Phe Cys Tyr Leu Ser Phe Leu Ile Ile Ser Gly Ala
                165                 170                 175

Phe Val Thr Gln Tyr Ile Arg Thr Lys Lys Leu Ala Lys Val Gly
            180                 185                 190

Asn Ser Leu Ile Gly Leu Met Phe Val Gly Phe Ala Ala Arg Leu Ala
            195                 200                 205

Thr Leu Gln Ser
        210

<210> SEQ ID NO 79
<211> LENGTH: 427
<212> TYPE: PRT
<213> ORGANISM: Escherichia coli

<400> SEQUENCE: 79

Met Ala Leu Asn Thr Pro Gln Ile Thr Pro Thr Lys Lys Ile Thr Val
1               5                   10                  15

Arg Ala Ile Gly Glu Glu Leu Pro Arg Gly Asp Tyr Gln Arg Cys Pro
            20                  25                  30

Gln Cys Asp Met Leu Phe Ser Leu Pro Glu Ile Asn Ser His Gln Ser
        35                  40                  45

Ala Tyr Cys Pro Arg Cys Gln Ala Lys Ile Arg Asp Gly Arg Asp Trp
    50                  55                  60

Ser Leu Thr Arg Leu Ala Ala Met Ala Phe Thr Met Leu Leu Leu Met
65                  70                  75                  80

Pro Phe Ala Trp Gly Pro Leu Leu His Ile Trp Leu Leu Gly Ile
                85                  90                  95

Arg Ile Asp Ala Asn Val Met Gln Gly Ile Trp Gln Met Thr Lys Gln
            100                 105                 110

Gly Asp Ala Ile Thr Gly Ser Met Val Phe Phe Cys Val Ile Gly Ala
        115                 120                 125

Pro Leu Ile Leu Val Thr Ser Ile Ala Tyr Leu Trp Phe Gly Asn Arg
    130                 135                 140

Leu Gly Met Asn Leu Arg Pro Val Leu Leu Met Leu Glu Arg Leu Lys
145                 150                 155                 160

Glu Trp Val Met Leu Asp Ile Tyr Leu Val Gly Ile Gly Val Ala Ser
                165                 170                 175

Ile Lys Val Gln Asp Tyr Ala His Ile Gln Ala Gly Val Gly Leu Phe
            180                 185                 190

Ser Phe Val Ala Leu Val Ile Leu Thr Thr Val Thr Leu Ser His Leu
        195                 200                 205

Asn Val Glu Glu Leu Trp Glu Arg Phe Tyr Pro Gln Arg Pro Ala Thr
    210                 215                 220

Arg Arg Asp Glu Lys Leu Arg Val Cys Leu Gly Cys His Phe Thr Gly
225                 230                 235                 240

Tyr Pro Asp Gln Arg Gly Arg Cys Pro Arg Cys His Ile Pro Leu Arg
                245                 250                 255

Leu Arg Arg Arg His Ser Leu Gln Lys Cys Trp Ala Ala Leu Leu Ala
            260                 265                 270

Ser Ile Val Leu Leu Leu Pro Ala Asn Leu Leu Pro Ile Ser Ile Ile
        275                 280                 285

Tyr Leu Asn Gly Gly Arg Gln Glu Asp Thr Ile Leu Ser Gly Ile Met
    290                 295                 300
```

-continued

```
Ser Leu Ala Ser Ser Asn Ile Ala Val Ala Gly Ile Val Phe Ile Ala
305                 310                 315                 320

Ser Ile Leu Val Pro Phe Thr Lys Val Ile Val Met Phe Thr Leu Leu
            325                 330                 335

Leu Ser Ile His Phe Lys Cys Gln Gln Gly Leu Arg Thr Arg Ile Leu
            340                 345                 350

Leu Leu Arg Met Val Thr Trp Ile Gly Arg Trp Ser Met Leu Asp Leu
            355                 360                 365

Phe Val Ile Ser Leu Thr Met Ser Leu Ile Asn Arg Asp Gln Ile Leu
370                 375                 380

Ala Phe Thr Met Gly Pro Ala Ala Phe Tyr Phe Gly Ala Ala Val Ile
385                 390                 395                 400

Leu Thr Ile Leu Ala Val Glu Trp Leu Asp Ser Arg Leu Leu Trp Asp
            405                 410                 415

Ala His Glu Ser Gly Asn Ala Arg Phe Asp Asp
            420                 425

<210> SEQ ID NO 80
<211> LENGTH: 306
<212> TYPE: PRT
<213> ORGANISM: Escherichia coli

<400> SEQUENCE: 80

Met Arg Phe Arg Gln Leu Leu Pro Leu Phe Gly Ala Leu Phe Ala Leu
1               5                   10                  15

Tyr Ile Ile Trp Gly Ser Thr Tyr Phe Val Ile Arg Ile Gly Val Glu
            20                  25                  30

Ser Trp Pro Pro Leu Met Met Ala Gly Val Arg Phe Leu Ala Ala Gly
        35                  40                  45

Ile Leu Leu Leu Ala Phe Leu Leu Arg Gly His Lys Leu Pro Pro
    50                  55                  60

Leu Arg Pro Leu Leu Asn Ala Ala Leu Ile Gly Leu Leu Leu Ala
65                  70                  75                  80

Val Gly Asn Gly Met Val Thr Val Ala Glu His Gln Asn Val Pro Ser
                85                  90                  95

Gly Ile Ala Ala Val Val Ala Thr Val Pro Leu Phe Thr Leu Cys
            100                 105                 110

Phe Ser Arg Leu Phe Gly Ile Lys Thr Arg Lys Leu Glu Trp Val Gly
        115                 120                 125

Ile Ala Ile Gly Leu Ala Gly Ile Ile Met Leu Asn Ser Gly Gly Asn
    130                 135                 140

Leu Ser Gly Asn Pro Trp Gly Ala Ile Leu Ile Leu Ile Gly Ser Ile
145                 150                 155                 160

Ser Trp Ala Phe Gly Ser Val Tyr Gly Ser Arg Ile Thr Leu Pro Val
                165                 170                 175

Gly Met Met Ala Gly Ala Ile Glu Met Leu Ala Ala Gly Val Val Leu
            180                 185                 190

Met Ile Ala Ser Met Ile Ala Gly Glu Lys Leu Thr Ala Leu Pro Ser
        195                 200                 205

Leu Ser Gly Phe Leu Ala Val Gly Tyr Leu Ala Leu Phe Gly Ser Ile
    210                 215                 220

Ile Ala Ile Asn Ala Tyr Met Tyr Leu Ile Arg Asn Val Ser Pro Ala
225                 230                 235                 240

Leu Ala Thr Ser Tyr Ala Tyr Val Asn Pro Val Val Ala Val Leu Leu
                245                 250                 255
```

```
Gly Thr Gly Leu Gly Gly Glu Thr Leu Ser Lys Ile Glu Trp Leu Ala
            260                 265                 270

Leu Gly Val Ile Val Phe Ala Val Leu Val Thr Leu Gly Lys Tyr
        275                 280                 285

Leu Phe Pro Ala Lys Pro Val Val Ala Pro Val Ile Gln Asp Ala Ser
    290                 295                 300

Ser Glu
305

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90
<211> LENGTH: 547
```

```
<212> TYPE: PRT
<213> ORGANISM: Escherichia coli

<400> SEQUENCE: 90

Met Leu Arg His Ile Leu Thr Ala Lys Asn Leu Leu Ser Asn Pro Ile
1               5                   10                  15

Phe Lys Phe Pro Asn Cys Leu Pro Phe Leu Ser Thr Val Cys Cys Ile
                20                  25                  30

Cys Arg Gln Phe Val Gly Glu Asn Leu Cys Ser Phe Ala Asp Ser Pro
            35                  40                  45

Ser Leu Phe Glu Met Trp Phe His Phe Leu Gln Leu Arg Ser Ala Leu
        50                  55                  60

Asn Ile Ser Ser Ala Leu Arg Gln Val Val His Gly Thr Arg Trp His
65                  70                  75                  80

Ala Lys Arg Lys Ser Tyr Lys Val Leu Phe Trp Arg Glu Ile Thr Pro
                85                  90                  95

Leu Ala Val Pro Ile Phe Met Glu Asn Ala Cys Val Leu Leu Met Gly
                100                 105                 110

Val Leu Ser Thr Phe Leu Val Ser Trp Leu Gly Lys Asp Ala Met Ala
            115                 120                 125

Gly Val Gly Leu Ala Asp Ser Phe Asn Met Val Ile Met Ala Phe Phe
        130                 135                 140

Ala Ala Ile Asp Leu Gly Thr Thr Val Val Ala Phe Ser Leu Gly
145                 150                 155                 160

Lys Arg Asp Arg Arg Ala Arg Val Ala Thr Arg Gln Ser Leu Val
                165                 170                 175

Ile Met Thr Leu Phe Ala Val Leu Leu Ala Thr Leu Ile His His Phe
            180                 185                 190

Gly Glu Gln Ile Ile Asp Phe Val Ala Gly Asp Ala Thr Thr Glu Val
        195                 200                 205

Lys Ala Leu Ala Leu Thr Tyr Leu Glu Leu Thr Val Leu Ser Tyr Pro
210                 215                 220

Ala Ala Ala Ile Thr Leu Ile Gly Ser Gly Ala Leu Arg Gly Ala Gly
225                 230                 235                 240

Asn Thr Lys Ile Pro Leu Leu Ile Asn Gly Ser Leu Asn Ile Leu Asn
                245                 250                 255

Ile Ile Ile Ser Gly Ile Leu Ile Tyr Gly Leu Phe Ser Trp Pro Gly
            260                 265                 270

Leu Gly Phe Val Gly Ala Gly Leu Gly Leu Thr Ile Ser Arg Tyr Ile
        275                 280                 285

Gly Ala Val Ala Ile Leu Trp Val Leu Ala Ile Gly Phe Asn Pro Ala
290                 295                 300

Leu Arg Ile Ser Leu Lys Ser Tyr Phe Lys Pro Leu Asn Phe Ser Ile
305                 310                 315                 320

Ile Trp Glu Val Met Gly Ile Gly Ile Pro Ala Ser Val Glu Ser Val
                325                 330                 335

Leu Phe Thr Ser Gly Arg Leu Leu Thr Gln Met Phe Val Ala Gly Met
            340                 345                 350

Gly Thr Ser Val Ile Ala Gly Asn Phe Ile Ala Phe Ser Ile Ala Ala
        355                 360                 365

Leu Ile Asn Leu Pro Gly Ser Ala Leu Gly Ser Ala Ser Thr Ile Ile
370                 375                 380

Thr Gly Arg Arg Leu Gly Val Gly Gln Ile Ala Gln Ala Glu Ile Gln
385                 390                 395                 400
```

```
Leu Arg His Val Phe Trp Leu Ser Thr Leu Gly Leu Thr Ala Ile Ala
                405                 410                 415

Trp Leu Thr Ala Pro Phe Ala Gly Val Met Ala Ser Phe Tyr Thr Gln
            420                 425                 430

Asp Pro Gln Val Lys His Val Val Ile Leu Ile Trp Leu Asn Ala
        435                 440                 445

Leu Phe Met Pro Ile Trp Ser Ala Ser Trp Val Leu Pro Ala Gly Phe
450                 455                 460

Lys Gly Ala Arg Asp Ala Arg Tyr Ala Met Trp Val Ser Met Leu Ser
465                 470                 475                 480

Met Trp Gly Cys Arg Val Val Gly Tyr Val Leu Gly Ile Met Leu
                485                 490                 495

Gly Trp Gly Val Val Gly Val Trp Met Gly Met Phe Ala Asp Trp Ala
            500                 505                 510

Val Arg Ala Val Leu Phe Tyr Trp Arg Met Val Thr Gly Arg Trp Leu
            515                 520                 525

Trp Lys Tyr Pro Arg Pro Glu Pro Gln Lys Cys Glu Lys Lys Pro Val
        530                 535                 540

Val Ser Glu
545

<210> SEQ ID NO 91
<211> LENGTH: 527
<212> TYPE: PRT
<213> ORGANISM: Escherichia coli

<400> SEQUENCE: 91

Met Glu Trp Ile Ala Asp Pro Ser Ile Trp Ala Gly Leu Ile Thr Leu
1               5                   10                  15

Ile Val Ile Glu Leu Val Leu Gly Ile Asp Asn Leu Val Phe Ile Ala
                20                  25                  30

Ile Leu Ala Glu Lys Leu Pro Pro Lys Gln Arg Asp Arg Ala Arg Val
            35                  40                  45

Thr Gly Leu Leu Leu Ala Met Leu Met Arg Leu Leu Leu Leu Ala Ser
        50                  55                  60

Ile Ser Trp Leu Val Thr Leu Thr Gln Pro Leu Phe Ser Phe Arg Ser
65                  70                  75                  80

Phe Thr Phe Ser Ala Arg Asp Leu Ile Met Leu Phe Gly Gly Phe Phe
                85                  90                  95

Leu Leu Phe Lys Ala Thr Met Glu Leu Asn Glu Arg Leu Glu Gly Lys
                100                 105                 110

Asp Ser Asn Asn Pro Thr Gln Arg Lys Gly Ala Lys Phe Trp Gly Val
            115                 120                 125

Val Thr Gln Ile Val Leu Asp Ala Ile Phe Ser Leu Asp Ser Val
        130                 135                 140

Ile Thr Ala Val Gly Met Val Asp His Leu Leu Val Met Met Ala Ala
145                 150                 155                 160

Val Val Ile Ala Ile Ser Leu Met Leu Met Ala Ser Lys Pro Leu Thr
                165                 170                 175

Gln Phe Val Asn Ser His Pro Thr Ile Val Ile Leu Cys Leu Ser Phe
            180                 185                 190

Leu Leu Met Ile Gly Phe Ser Leu Val Ala Glu Gly Phe Gly Phe Val
        195                 200                 205

Ile Pro Lys Gly Tyr Leu Tyr Ala Ala Ile Gly Phe Ser Val Met Ile
```

```
            210                 215                 220
Glu Ala Leu Asn Gln Leu Ala Ile Phe Asn Arg Arg Phe Leu Ser
225                 230                 235                 240

Ala Asn Gln Thr Leu Arg Gln Arg Thr Thr Glu Ala Val Met Arg Leu
                245                 250                 255

Leu Ser Gly Gln Lys Glu Asp Ala Glu Leu Asp Ala Glu Thr Ala Ser
                260                 265                 270

Met Leu Val Asp His Gly Asn Gln Gln Ile Phe Asn Pro Gln Glu Arg
            275                 280                 285

Arg Met Ile Glu Arg Val Leu Asn Leu Asn Gln Arg Thr Val Ser Ser
            290                 295                 300

Ile Met Thr Ser Arg His Asp Ile Glu His Ile Asp Leu Asn Ala Pro
305                 310                 315                 320

Glu Glu Glu Ile Arg Gln Leu Leu Glu Arg Asn Gln His Thr Arg Leu
                325                 330                 335

Val Val Thr Asp Gly Asp Ala Glu Asp Leu Leu Gly Val Val His
                340                 345                 350

Val Ile Asp Leu Leu Gln Gln Ser Leu Arg Gly Glu Pro Leu Asn Leu
            355                 360                 365

Arg Val Leu Ile Arg Gln Pro Leu Val Phe Pro Glu Thr Leu Pro Leu
370                 375                 380

Leu Pro Ala Leu Glu Gln Phe Arg Asn Ala Arg Thr His Phe Ala Phe
385                 390                 395                 400

Val Val Asp Glu Phe Gly Ser Val Glu Gly Ile Val Thr Leu Ser Asp
                405                 410                 415

Val Thr Glu Thr Ile Ala Gly Asn Leu Pro Asn Glu Val Glu Glu Ile
                420                 425                 430

Asp Ala Arg His Asp Ile Gln Lys Asn Ala Asp Gly Ser Trp Thr Ala
            435                 440                 445

Asn Gly His Met Pro Leu Glu Asp Leu Val Gln Tyr Val Pro Leu Pro
450                 455                 460

Leu Asp Glu Lys Arg Glu Tyr His Thr Ile Ala Gly Leu Leu Met Glu
465                 470                 475                 480

Tyr Leu Gln Arg Ile Pro Lys Pro Gly Glu Val Gln Val Gly Asp
                485                 490                 495

Tyr Leu Leu Lys Thr Leu Gln Val Glu Ser His Arg Val Gln Lys Val
                500                 505                 510

Gln Ile Ile Pro Leu Arg Lys Asp Gly Glu Met Glu Tyr Glu Val
            515                 520                 525

<210> SEQ ID NO 92
<211> LENGTH: 211
<212> TYPE: PRT
<213> ORGANISM: Escherichia coli

<400> SEQUENCE: 92

Met Phe Ser Tyr Tyr Phe Gln Gly Leu Ala Leu Gly Ala Ala Met Ile
1               5                   10                  15

Leu Pro Leu Gly Pro Gln Asn Ala Phe Val Met Asn Gln Gly Ile Arg
                20                  25                  30

Arg Gln Tyr His Ile Met Ile Ala Leu Leu Cys Ala Ile Ser Asp Leu
            35                  40                  45

Val Leu Ile Cys Ala Gly Ile Phe Gly Gly Ser Ala Leu Leu Met Gln
        50                  55                  60
```

```
Ser Pro Trp Leu Leu Ala Leu Val Thr Trp Gly Val Ala Phe Leu
 65                  70                  75                  80

Leu Trp Tyr Gly Phe Gly Ala Phe Lys Thr Ala Met Ser Ser Asn Ile
                 85                  90                  95

Glu Leu Ala Ser Ala Glu Val Met Lys Gln Gly Arg Trp Lys Ile Ile
            100                 105                 110

Ala Thr Met Leu Ala Val Thr Trp Leu Asn Pro His Val Tyr Leu Asp
            115                 120                 125

Thr Phe Val Val Leu Gly Ser Leu Gly Gly Gln Leu Asp Val Glu Pro
            130                 135                 140

Lys Arg Trp Phe Ala Leu Gly Thr Ile Ser Ala Ser Phe Leu Trp Phe
145                 150                 155                 160

Phe Gly Leu Ala Leu Leu Ala Ala Trp Leu Ala Pro Arg Leu Arg Thr
                165                 170                 175

Ala Lys Ala Gln Arg Ile Ile Asn Leu Val Val Gly Cys Val Met Trp
                180                 185                 190

Phe Ile Ala Leu Gln Leu Ala Arg Asp Gly Ile Ala His Ala Gln Ala
            195                 200                 205

Leu Phe Ser
        210

<210> SEQ ID NO 93
<211> LENGTH: 392
<212> TYPE: PRT
<213> ORGANISM: Escherichia coli

<400> SEQUENCE: 93

Met Thr Ala Val Ser Gln Thr Glu Thr Arg Ser Ser Ala Asn Phe Ser
  1               5                  10                  15

Leu Phe Arg Ile Ala Phe Ala Val Phe Leu Thr Tyr Met Thr Val Gly
                 20                  25                  30

Leu Pro Leu Pro Val Ile Pro Leu Phe Val His His Glu Leu Gly Tyr
             35                  40                  45

Gly Asn Thr Met Val Gly Ile Ala Val Gly Ile Gln Phe Leu Ala Thr
 50                  55                  60

Val Leu Thr Arg Gly Tyr Ala Gly Arg Leu Ala Asp Gln Tyr Gly Ala
 65                  70                  75                  80

Lys Arg Ser Ala Leu Gln Gly Met Leu Ala Cys Gly Leu Ala Gly Gly
                 85                  90                  95

Ala Leu Leu Leu Ala Ala Ile Leu Pro Val Ser Ala Pro Phe Lys Phe
            100                 105                 110

Ala Leu Leu Val Val Gly Arg Leu Ile Leu Gly Phe Gly Glu Ser Gln
            115                 120                 125

Leu Leu Thr Gly Ala Leu Thr Trp Gly Leu Gly Ile Val Gly Pro Lys
            130                 135                 140

His Ser Gly Lys Val Met Ser Trp Asn Gly Met Ala Ile Tyr Gly Ala
145                 150                 155                 160

Leu Ala Val Gly Ala Pro Leu Gly Leu Leu Ile His Ser His Tyr Gly
                165                 170                 175

Phe Ala Ala Leu Ala Ile Thr Thr Met Val Leu Pro Val Leu Ala Trp
            180                 185                 190

Ala Cys Asn Gly Thr Val Arg Lys Val Pro Ala Leu Ala Gly Glu Arg
        195                 200                 205

Pro Ser Leu Trp Ser Val Val Gly Leu Ile Trp Lys Pro Gly Leu Gly
210                 215                 220
```

```
Leu Ala Leu Gln Gly Val Gly Phe Ala Val Ile Gly Thr Phe Val Ser
225                 230                 235                 240

Leu Tyr Phe Ala Ser Lys Gly Trp Ala Met Ala Gly Phe Thr Leu Thr
                245                 250                 255

Ala Phe Gly Gly Ala Phe Val Val Met Arg Val Met Phe Gly Trp Met
            260                 265                 270

Pro Asp Arg Phe Gly Gly Val Lys Val Ala Ile Val Ser Leu Leu Val
        275                 280                 285

Glu Thr Val Gly Leu Leu Leu Trp Gln Ala Pro Gly Ala Trp Val
290                 295                 300

Ala Leu Ala Gly Ala Ala Leu Thr Gly Ala Gly Cys Ser Leu Ile Phe
305                 310                 315                 320

Pro Ala Leu Gly Val Glu Val Val Lys Arg Val Pro Ser Gln Val Arg
                325                 330                 335

Gly Thr Ala Leu Gly Gly Tyr Ala Ala Phe Gln Asp Ile Ala Leu Gly
            340                 345                 350

Val Ser Gly Pro Leu Ala Gly Met Leu Ala Thr Thr Phe Gly Tyr Ser
        355                 360                 365

Ser Val Phe Leu Ala Gly Ala Ile Ser Ala Val Leu Gly Ile Ile Val
    370                 375                 380

Thr Ile Leu Ser Phe Arg Arg Gly
385                 390

<210> SEQ ID NO 94
<211> LENGTH: 195
<212> TYPE: PRT
<213> ORGANISM: Escherichia coli

<400> SEQUENCE: 94

Met Thr Pro Thr Leu Leu Ser Ala Phe Trp Thr Tyr Thr Leu Ile Thr
1               5                   10                  15

Ala Met Thr Pro Gly Pro Asn Asn Ile Leu Ala Leu Ser Ser Ala Thr
                20                  25                  30

Ser His Gly Phe Arg Gln Ser Thr Arg Val Leu Ala Gly Met Ser Leu
            35                  40                  45

Gly Phe Leu Ile Val Met Leu Leu Cys Ala Gly Ile Ser Phe Ser Leu
    50                  55                  60

Ala Val Ile Asp Pro Ala Ala Val His Leu Leu Ser Trp Ala Gly Ala
65                  70                  75                  80

Ala Tyr Ile Val Trp Leu Ala Trp Lys Ile Ala Thr Ser Pro Thr Lys
                85                  90                  95

Glu Asp Gly Leu Gln Ala Lys Pro Ile Ser Phe Trp Ala Ser Phe Ala
            100                 105                 110

Leu Gln Phe Val Asn Val Lys Ile Ile Leu Tyr Gly Val Thr Ala Leu
        115                 120                 125

Ser Thr Phe Val Leu Pro Gln Thr Gln Ala Leu Ser Trp Val Val Gly
    130                 135                 140

Val Ser Val Leu Leu Ala Met Ile Gly Thr Phe Gly Asn Val Cys Trp
145                 150                 155                 160

Ala Leu Ala Gly His Leu Phe Gln Arg Leu Phe Arg Gln Tyr Gly Arg
                165                 170                 175

Gln Leu Asn Ile Val Leu Ala Leu Leu Val Tyr Cys Ala Val Arg
            180                 185                 190

Ile Phe Tyr
```

<210> SEQ ID NO 95
<211> LENGTH: 440
<212> TYPE: PRT
<213> ORGANISM: Escherichia coli

<400> SEQUENCE: 95

```
Met Gln Ala Thr Ala Thr Thr Leu Asp His Glu Gln Glu Tyr Thr Pro
1               5                   10                  15

Ile Asn Ser Arg Asn Lys Val Leu Val Ala Ser Leu Ile Gly Thr Ala
            20                  25                  30

Ile Glu Phe Phe Asp Phe Tyr Ile Tyr Ala Thr Ala Ala Val Ile Val
        35                  40                  45

Phe Pro His Ile Phe Phe Pro Gln Gly Asp Pro Thr Ala Ala Thr Leu
    50                  55                  60

Gln Ser Leu Ala Thr Phe Ala Ile Ala Phe Val Ala Arg Pro Ile Gly
65                  70                  75                  80

Ser Ala Val Phe Gly His Phe Gly Asp Arg Val Gly Arg Lys Ala Thr
                85                  90                  95

Leu Val Ala Ser Leu Leu Thr Met Gly Ile Ser Thr Val Val Ile Gly
            100                 105                 110

Leu Leu Pro Gly Tyr Ala Thr Ile Gly Ile Phe Ala Pro Leu Leu Leu
        115                 120                 125

Ala Leu Ala Arg Phe Gly Gln Gly Leu Gly Leu Gly Gly Glu Trp Gly
    130                 135                 140

Gly Ala Ala Leu Leu Ala Thr Glu Asn Ala Pro Pro Arg Lys Arg Ala
145                 150                 155                 160

Leu Tyr Gly Ser Phe Pro Gln Leu Gly Ala Pro Ile Gly Phe Phe Phe
                165                 170                 175

Ala Asn Gly Thr Phe Leu Leu Leu Ser Trp Leu Leu Thr Asp Glu Gln
            180                 185                 190

Phe Met Ser Trp Gly Trp Arg Val Pro Phe Ile Phe Ser Ala Val Leu
        195                 200                 205

Val Ile Ile Gly Leu Tyr Val Arg Val Ser Leu His Glu Ser Pro Val
    210                 215                 220

Phe Glu Lys Val Ala Lys Ala Lys Lys Gln Val Lys Ile Pro Leu Gly
225                 230                 235                 240

Thr Leu Leu Thr Lys His Val Arg Val Thr Val Leu Gly Thr Phe Ile
                245                 250                 255

Met Leu Ala Thr Tyr Thr Leu Phe Tyr Ile Met Thr Val Tyr Ser Met
            260                 265                 270

Thr Phe Ser Thr Ala Ala Pro Val Gly Leu Gly Leu Pro Arg Asn
        275                 280                 285

Glu Val Leu Trp Met Leu Met Met Ala Val Ile Gly Phe Gly Val Met
    290                 295                 300

Val Pro Val Ala Gly Leu Leu Ala Asp Ala Phe Gly Arg Arg Lys Ser
305                 310                 315                 320

Met Val Ile Ile Thr Thr Leu Ile Ile Leu Phe Ala Leu Phe Ala Phe
                325                 330                 335

Asn Pro Leu Leu Gly Ser Gly Asn Pro Ile Leu Val Phe Ala Phe Leu
            340                 345                 350

Leu Leu Gly Leu Ser Leu Met Gly Leu Thr Phe Gly Pro Met Gly Ala
        355                 360                 365
```

Leu Leu Pro Glu Leu Phe Pro Thr Glu Val Arg Tyr Thr Gly Ala Ser
        370             375             380

Phe Ser Tyr Asn Val Ala Ser Ile Leu Gly Ala Ser Val Ala Pro Tyr
385             390             395             400

Ile Ala Ala Trp Leu Gln Thr Asn Tyr Gly Leu Gly Ala Val Gly Leu
            405             410             415

Tyr Leu Ala Ala Met Ala Gly Leu Thr Leu Ile Ala Leu Leu Leu Thr
            420             425             430

His Glu Thr Arg His Gln Ser Leu
            435             440

<210> SEQ ID NO 96
<211> LENGTH: 553
<212> TYPE: PRT
<213> ORGANISM: Escherichia coli

<400> SEQUENCE: 96

Met Ser Asp Ile Ala Leu Thr Val Ser Ile Leu Ala Leu Val Ala Val
1               5                   10                  15

Val Gly Leu Phe Ile Gly Asn Val Lys Phe Arg Gly Ile Gly Leu Gly
            20                  25                  30

Ile Gly Gly Val Leu Phe Gly Gly Ile Ile Val Gly His Phe Val Ser
        35                  40                  45

Gln Ala Gly Met Thr Leu Ser Ser Asp Met Leu His Val Ile Gln Glu
    50                  55                  60

Phe Gly Leu Ile Leu Phe Val Tyr Thr Ile Gly Ile Gln Val Gly Pro
65                  70                  75                  80

Gly Phe Phe Ala Ser Leu Arg Val Ser Gly Leu Arg Leu Asn Leu Phe
                85                  90                  95

Ala Val Leu Ile Val Ile Gly Gly Leu Val Thr Ala Ile Leu His Lys
                100                 105                 110

Lys Leu Phe Asp Ile Pro Leu Pro Val Val Leu Gly Ile Phe Ser Gly
            115                 120                 125

Ala Val Thr Asn Thr Pro Ala Leu Gly Ala Gly Gln Gln Ile Leu Arg
        130                 135                 140

Asp Leu Gly Thr Pro Met Glu Met Val Asp Gln Met Gly Met Ser Tyr
145                 150                 155                 160

Ala Met Ala Tyr Pro Phe Gly Ile Cys Gly Ile Leu Phe Thr Met Trp
                165                 170                 175

Met Leu Arg Val Ile Phe Arg Val Asn Val Glu Thr Glu Ala Gln Gln
            180                 185                 190

His Glu Ser Ser Arg Thr Asn Gly Gly Ala Leu Ile Lys Thr Ile Asn
        195                 200                 205

Ile Arg Val Glu Asn Pro Asn Leu His Asp Leu Ala Ile Lys Asp Val
    210                 215                 220

Pro Ile Leu Asn Gly Asp Lys Ile Ile Cys Ser Arg Leu Lys Arg Glu
225                 230                 235                 240

Glu Thr Leu Lys Val Pro Ser Pro Asp Thr Ile Ile Gln Leu Gly Asp
                245                 250                 255

Leu Leu His Leu Val Gly Gln Pro Ala Asp Leu His Asn Ala Gln Leu
            260                 265                 270

Val Ile Gly Gln Glu Val Asp Thr Ser Leu Ser Thr Lys Gly Thr Asp
        275                 280                 285

Leu Arg Val Glu Arg Val Val Val Thr Asn Glu Asn Val Leu Gly Lys
    290                 295                 300

```
Arg Ile Arg Asp Leu His Phe Lys Glu Arg Tyr Asp Val Ile Ser
305                 310                 315                 320

Arg Leu Asn Arg Ala Gly Val Glu Leu Val Ala Ser Gly Asp Ile Ser
            325                 330                 335

Leu Gln Phe Gly Asp Ile Leu Asn Leu Val Gly Arg Pro Ser Ala Ile
        340                 345                 350

Asp Ala Val Ala Asn Val Leu Gly Asn Ala Gln Gln Lys Leu Gln Gln
    355                 360                 365

Val Gln Met Leu Pro Val Phe Ile Gly Ile Gly Leu Gly Val Leu Leu
370                 375                 380

Gly Ser Ile Pro Val Phe Val Pro Gly Phe Pro Ala Ala Leu Lys Leu
385                 390                 395                 400

Gly Leu Ala Gly Gly Pro Leu Ile Met Ala Leu Ile Leu Gly Arg Ile
                405                 410                 415

Gly Ser Ile Gly Lys Leu Tyr Trp Phe Met Pro Pro Ser Ala Asn Leu
            420                 425                 430

Ala Leu Arg Glu Leu Gly Ile Val Leu Phe Leu Ser Val Val Gly Leu
        435                 440                 445

Lys Ser Gly Gly Asp Phe Val Asn Thr Leu Val Asn Gly Glu Gly Leu
450                 455                 460

Ser Trp Ile Gly Tyr Gly Ala Leu Ile Thr Ala Val Pro Leu Ile Thr
465                 470                 475                 480

Val Gly Ile Leu Ala Arg Met Leu Ala Lys Met Asn Tyr Leu Thr Met
                485                 490                 495

Cys Gly Met Leu Ala Gly Ser Met Thr Asp Pro Pro Ala Leu Ala Phe
            500                 505                 510

Ala Asn Asn Leu His Pro Thr Ser Gly Ala Ala Leu Ser Tyr Ala
        515                 520                 525

Thr Val Tyr Pro Leu Val Met Phe Leu Arg Ile Ile Thr Pro Gln Leu
530                 535                 540

Leu Ala Val Leu Phe Trp Ser Ile Gly
545                 550

<210> SEQ ID NO 97
<211> LENGTH: 206
<212> TYPE: PRT
<213> ORGANISM: Escherichia coli

<400> SEQUENCE: 97

Met Thr Leu Glu Trp Trp Phe Ala Tyr Leu Leu Thr Ser Ile Ile Leu
1               5                   10                  15

Ser Leu Ser Pro Gly Ser Gly Ala Ile Asn Thr Met Thr Thr Ser Leu
            20                  25                  30

Asn His Gly Tyr Arg Gly Ala Val Ala Ser Ile Ala Gly Leu Gln Thr
        35                  40                  45

Gly Leu Ala Ile His Ile Val Leu Val Gly Val Gly Leu Gly Thr Leu
    50                  55                  60

Phe Ser Arg Ser Val Ile Ala Phe Glu Val Leu Lys Trp Ala Gly Ala
65                  70                  75                  80

Ala Tyr Leu Ile Trp Leu Gly Ile Gln Gln Trp Arg Ala Ala Gly Ala
                85                  90                  95

Ile Asp Leu Lys Ser Leu Ala Ser Thr Gln Ser Arg Arg His Leu Phe
            100                 105                 110

Gln Arg Ala Val Phe Val Asn Leu Thr Asn Pro Lys Ser Ile Val Phe
```

```
              115                 120                 125
Leu Ala Ala Leu Phe Pro Gln Phe Ile Met Pro Gln Gln Pro Gln Leu
        130                 135                 140
Met Gln Tyr Ile Val Leu Gly Val Thr Thr Ile Val Val Asp Ile Ile
145                 150                 155                 160
Val Met Ile Gly Tyr Ala Thr Leu Ala Gln Arg Ile Ala Leu Trp Ile
                165                 170                 175
Lys Gly Pro Lys Gln Met Lys Ala Leu Asn Lys Ile Phe Gly Ser Leu
            180                 185                 190
Phe Met Leu Val Gly Ala Leu Leu Ala Ser Ala Arg His Ala
            195                 200                 205

<210> SEQ ID NO 98
<211> LENGTH: 206
<212> TYPE: PRT
<213> ORGANISM: Escherichia coli

<400> SEQUENCE: 98

Met Leu Met Leu Phe Leu Thr Val Ala Met Val His Ile Val Ala Leu
1               5                   10                  15
Met Ser Pro Gly Pro Asp Phe Phe Val Ser Gln Thr Ala Val Ser
            20                  25                  30
Arg Ser Arg Lys Glu Ala Met Met Gly Val Leu Gly Ile Thr Cys Gly
        35                  40                  45
Val Met Val Trp Ala Gly Ile Ala Leu Leu Gly Leu His Leu Ile Ile
    50                  55                  60
Glu Lys Met Ala Trp Leu His Thr Leu Ile Met Val Gly Gly Gly Leu
65                  70                  75                  80
Tyr Leu Cys Trp Met Gly Tyr Gln Met Leu Arg Gly Ala Leu Lys Lys
                85                  90                  95
Glu Ala Val Ser Ala Pro Ala Pro Gln Val Glu Leu Ala Lys Ser Gly
            100                 105                 110
Arg Ser Phe Leu Lys Gly Leu Leu Thr Asn Leu Ala Asn Pro Lys Ala
        115                 120                 125
Ile Ile Tyr Phe Gly Ser Val Phe Ser Leu Phe Val Gly Asp Asn Val
    130                 135                 140
Gly Thr Thr Ala Arg Trp Gly Ile Phe Ala Leu Ile Ile Val Glu Thr
145                 150                 155                 160
Leu Ala Trp Phe Thr Val Val Ala Ser Leu Phe Ala Leu Pro Gln Met
                165                 170                 175
Arg Arg Gly Tyr Gln Arg Leu Ala Lys Trp Ile Asp Gly Phe Ala Gly
            180                 185                 190
Ala Leu Phe Ala Gly Phe Gly Ile His Leu Ile Ile Ser Arg
        195                 200                 205

<210> SEQ ID NO 99
<211> LENGTH: 301
<212> TYPE: PRT
<213> ORGANISM: Escherichia coli

<400> SEQUENCE: 99

Met Ser Ala Ala Gly Lys Ser Asn Pro Leu Ala Ile Ser Gly Leu Val
1               5                   10                  15
Val Leu Thr Leu Ile Trp Ser Tyr Ser Trp Ile Phe Met Lys Gln Val
            20                  25                  30
Thr Ser Tyr Ile Gly Ala Phe Asp Phe Thr Ala Leu Arg Cys Ile Phe
```

```
            35                  40                  45
Gly Ala Leu Val Leu Phe Ile Val Leu Leu Arg Gly Arg Gly Met
 50                  55                  60

Arg Pro Thr Pro Phe Lys Tyr Thr Leu Ala Ile Ala Leu Leu Gln Thr
 65                  70                  75                  80

Cys Gly Met Val Gly Leu Ala Gln Trp Ala Leu Val Ser Gly Gly Ala
                 85                  90                  95

Gly Lys Val Ala Ile Leu Ser Tyr Thr Met Pro Phe Trp Val Val Ile
                100                 105                 110

Phe Ala Ala Leu Phe Leu Gly Glu Arg Leu Arg Arg Gly Gln Tyr Phe
                115                 120                 125

Ala Ile Leu Ile Ala Ala Phe Gly Leu Phe Leu Val Leu Gln Pro Trp
            130                 135                 140

Gln Leu Asp Phe Ser Ser Met Lys Ser Ala Met Leu Ala Ile Leu Ser
145                 150                 155                 160

Gly Val Ser Trp Gly Ala Ser Ala Ile Val Ala Lys Arg Leu Tyr Ala
                165                 170                 175

Arg His Pro Arg Val Asp Leu Leu Ser Leu Thr Ser Trp Gln Met Leu
                180                 185                 190

Tyr Ala Ala Leu Val Met Ser Val Val Ala Leu Leu Val Pro Gln Arg
                195                 200                 205

Glu Ile Asp Trp Gln Pro Thr Val Phe Trp Ala Leu Ala Tyr Ser Ala
            210                 215                 220

Ile Leu Ala Thr Ala Leu Ala Trp Ser Leu Trp Leu Phe Val Leu Lys
225                 230                 235                 240

Asn Leu Pro Ala Ser Ile Ala Ser Leu Ser Thr Leu Ala Val Pro Val
                245                 250                 255

Cys Gly Val Leu Phe Ser Trp Trp Leu Leu Gly Glu Asn Pro Gly Ala
                260                 265                 270

Val Glu Gly Ser Gly Ile Val Leu Ile Val Leu Ala Leu Ala Leu Val
                275                 280                 285

Ser Arg Lys Lys Lys Glu Ala Val Ser Val Lys Arg Ile
            290                 295                 300

<210> SEQ ID NO 100
<211> LENGTH: 184
<212> TYPE: PRT
<213> ORGANISM: Escherichia coli

<400> SEQUENCE: 100

Met Ala Lys Tyr Asn Glu Lys Glu Leu Ala Asp Thr Ser Lys Phe Leu
 1               5                  10                  15

Ser Phe Val Leu Arg His Lys Pro Glu Ala Ile Gly Ile Val Leu Asp
                20                  25                  30

Arg Glu Gly Trp Ala Asp Ile Asp Lys Leu Ile Leu Cys Ala Gln Lys
            35                  40                  45

Ala Gly Lys Arg Leu Thr Arg Ala Leu Leu Asp Thr Val Val Ala Thr
 50                  55                  60

Ser Asp Lys Lys Arg Phe Ser Tyr Ser Ser Asp Gly Arg Cys Ile Arg
 65                  70                  75                  80

Ala Val Gln Gly His Ser Thr Ser Gln Val Ala Ile Ser Phe Ala Glu
                85                  90                  95

Lys Thr Pro Pro Gln Phe Leu Tyr His Gly Thr Ala Ser Arg Phe Leu
                100                 105                 110
```

Asp Glu Ile Lys Lys Gln Gly Leu Ile Ala Gly Arg His Tyr Val
            115                 120                 125

His Leu Ser Ala Asp Glu Ala Thr Ala Arg Lys Val Gly Ala Arg His
    130                 135                 140

Gly Ser Pro Val Ile Leu Thr Val Lys Ala Gln Glu Met Ala Lys Arg
145                 150                 155                 160

Gly Leu Pro Phe Trp Gln Ala Glu Asn Gly Val Trp Leu Thr Ser Thr
                165                 170                 175

Val Ala Val Glu Phe Leu Glu Trp
            180

<210> SEQ ID NO 101
<211> LENGTH: 392
<212> TYPE: PRT
<213> ORGANISM: Escherichia coli

<400> SEQUENCE: 101

Met Pro Ser Ser Thr His Pro Val Glu Arg Phe Ser Phe Ser Thr Ala
1               5                   10                  15

Leu Phe Gly Met Leu Val Leu Thr Leu Gly Met Gly Leu Gly Arg Phe
            20                  25                  30

Leu Tyr Thr Pro Met Leu Pro Val Met Met Ala Glu Gly Ser Phe Ser
        35                  40                  45

Phe Ser Gln Leu Ser Trp Ile Ala Ser Gly Asn Tyr Ala Gly Tyr Leu
    50                  55                  60

Ala Gly Ser Leu Leu Phe Ser Phe Gly Ala Phe His Gln Pro Ser Arg
65                  70                  75                  80

Leu Arg Pro Phe Leu Leu Ala Ser Ala Leu Ala Ser Gly Leu Leu Ile
                85                  90                  95

Leu Ala Met Ala Trp Leu Pro Pro Phe Ile Leu Val Leu Leu Ile Arg
            100                 105                 110

Val Leu Ala Gly Val Ala Ser Ala Gly Met Leu Ile Phe Gly Ser Thr
        115                 120                 125

Leu Ile Met Gln His Thr Arg His Pro Phe Val Leu Ala Ala Leu Phe
    130                 135                 140

Ser Gly Val Gly Ile Gly Ile Ala Leu Gly Asn Glu Tyr Val Leu Ala
145                 150                 155                 160

Gly Leu His Phe Asp Leu Ser Ser Gln Thr Leu Trp Gln Gly Ala Gly
                165                 170                 175

Ala Leu Ser Gly Met Met Leu Ile Ala Leu Thr Leu Leu Met Pro Ser
            180                 185                 190

Lys Lys His Ala Ile Thr Pro Met Pro Leu Ala Lys Thr Glu Gln Gln
        195                 200                 205

Ile Met Ser Trp Trp Leu Leu Ala Ile Leu Tyr Gly Leu Ala Gly Phe
    210                 215                 220

Gly Tyr Ile Ile Val Ala Thr Tyr Leu Pro Leu Met Ala Lys Asp Ala
225                 230                 235                 240

Gly Ser Pro Leu Leu Thr Ala His Leu Trp Thr Leu Val Gly Leu Ser
                245                 250                 255

Ile Val Pro Gly Cys Phe Gly Trp Leu Trp Ala Ala Lys Arg Trp Gly
            260                 265                 270

Ala Leu Pro Cys Leu Thr Ala Asn Leu Leu Val Gln Ala Ile Cys Val
        275                 280                 285

Leu Leu Thr Leu Ala Ser Asp Ser Pro Leu Leu Ile Ile Ser Ser
    290                 295                 300

```
Leu Gly Phe Gly Gly Thr Phe Met Gly Thr Thr Ser Leu Val Met Thr
305                 310                 315                 320

Ile Ala Arg Gln Leu Ser Val Pro Gly Asn Leu Asn Leu Leu Gly Phe
                325                 330                 335

Val Thr Leu Ile Tyr Gly Ile Gly Gln Ile Leu Gly Pro Ala Leu Thr
                340                 345                 350

Ser Met Leu Ser Asn Gly Thr Ser Ala Leu Ala Ser Ala Thr Leu Cys
            355                 360                 365

Gly Ala Ala Ala Leu Phe Ile Ala Ala Leu Ile Ser Thr Val Gln Leu
370                 375                 380

Phe Lys Leu Gln Val Val Thr Ser
385                 390

<210> SEQ ID NO 102
<211> LENGTH: 410
<212> TYPE: PRT
<213> ORGANISM: Escherichia coli

<400> SEQUENCE: 102

Met Pro Arg Phe Phe Thr Arg His Ala Ala Thr Leu Phe Phe Pro Met
1               5                   10                  15

Ala Leu Ile Leu Tyr Asp Phe Ala Ala Tyr Leu Ser Thr Asp Leu Ile
                20                  25                  30

Gln Pro Gly Ile Ile Asn Val Arg Asp Phe Asn Ala Asp Val Ser
                35                  40                  45

Leu Ala Pro Ala Val Ser Leu Tyr Leu Ala Gly Gly Met Ala Leu
    50                  55                  60

Gln Trp Leu Leu Gly Pro Leu Ser Asp Arg Ile Gly Arg Arg Pro Val
65                  70                  75                  80

Leu Ile Thr Gly Ala Leu Ile Phe Thr Leu Ala Cys Ala Ala Thr Met
                85                  90                  95

Phe Thr Thr Ser Met Thr Gln Phe Leu Ile Ala Arg Ala Ile Gln Gly
                100                 105                 110

Thr Ser Ile Cys Phe Ile Ala Thr Val Gly Tyr Val Thr Val Gln Glu
                115                 120                 125

Ala Phe Gly Gln Thr Lys Gly Ile Lys Leu Met Ala Ile Ile Thr Ser
                130                 135                 140

Ile Val Leu Ile Ala Pro Ile Ile Gly Pro Leu Ser Gly Ala Ala Leu
145                 150                 155                 160

Met His Phe Met His Trp Lys Val Leu Phe Ala Ile Ile Ala Val Met
                165                 170                 175

Gly Phe Ile Ser Phe Val Gly Leu Leu Leu Ala Met Pro Glu Thr Val
                180                 185                 190

Lys Arg Gly Ala Val Pro Phe Ser Ala Lys Ser Val Leu Arg Asp Phe
                195                 200                 205

Arg Asn Val Phe Cys Asn Arg Leu Phe Leu Phe Gly Ala Ala Thr Ile
                210                 215                 220

Ser Leu Ser Tyr Ile Pro Met Met Ser Trp Val Ala Val Ser Pro Val
225                 230                 235                 240

Ile Leu Ile Asp Ala Gly Ser Leu Thr Thr Ser Gln Phe Ala Trp Thr
                245                 250                 255

Gln Val Pro Val Phe Gly Ala Val Ile Val Ala Asn Ala Ile Val Ala
                260                 265                 270

Arg Phe Val Lys Asp Pro Thr Glu Pro Arg Phe Ile Trp Arg Ala Val
```

```
            275                 280                 285
Pro Ile Gln Leu Val Gly Leu Ser Leu Leu Ile Val Gly Asn Leu Leu
    290                 295                 300

Ser Pro His Val Trp Leu Trp Ser Val Leu Gly Thr Ser Leu Tyr Ala
305                 310                 315                 320

Phe Gly Ile Gly Leu Ile Phe Pro Thr Leu Phe Arg Phe Thr Leu Phe
                325                 330                 335

Ser Asn Lys Leu Pro Lys Gly Thr Val Ser Ala Ser Leu Asn Met Val
            340                 345                 350

Ile Leu Met Val Met Ser Val Ser Val Glu Ile Gly Arg Trp Leu Trp
                355                 360                 365

Phe Asn Gly Gly Arg Leu Pro Phe His Leu Leu Ala Val Val Ala Gly
370                 375                 380

Val Ile Val Val Phe Thr Leu Ala Gly Leu Leu Asn Arg Val Arg Gln
385                 390                 395                 400

His Gln Ala Ala Glu Leu Val Glu Glu Gln
                405                 410

<210> SEQ ID NO 103
<211> LENGTH: 222
<212> TYPE: PRT
<213> ORGANISM: Escherichia coli

<400> SEQUENCE: 103

Met Arg Glu Gln Ile Lys Gln Asp Ile Asp Leu Ile Glu Ile Leu Phe
1               5                   10                  15

Tyr Leu Lys Lys Lys Ile Arg Val Ile Leu Phe Ile Met Ala Ile Cys
            20                  25                  30

Met Ala Met Val Leu Leu Phe Leu Tyr Ile Asn Lys Asp Asn Ile Lys
        35                  40                  45

Val Ile Tyr Ser Leu Lys Ile Asn Gln Thr Thr Pro Gly Ile Leu Val
    50                  55                  60

Ser Cys Asp Ser Asn Asn Asn Phe Ala Cys Gln Thr Thr Met Thr Glu
65                  70                  75                  80

Asp Val Ile Gln Arg Ile Thr Thr Phe Phe His Thr Ser Pro Asp Val
                85                  90                  95

Lys Asn Arg Glu Ile Arg Leu Glu Trp Ser Gly Asp Lys Arg Ala Leu
            100                 105                 110

Pro Thr Ala Glu Glu Ile Ser Arg Val Gln Ala Ser Ile Ile Lys
        115                 120                 125

Trp Tyr Ala Ser Glu Tyr His Asn Gly Arg Gln Val Leu Asp Glu Ile
    130                 135                 140

Gln Thr Pro Ser Ala Ile Asn Ser Glu Leu Tyr Thr Lys Met Ile Tyr
145                 150                 155                 160

Leu Thr Arg Asn Trp Ser Leu Tyr Pro Asn Gly Asp Gly Cys Val Thr
                165                 170                 175

Ile Ser Ser Pro Glu Ile Lys Asn Lys Tyr Pro Ala Ala Ile Cys Leu
            180                 185                 190

Ala Leu Gly Phe Phe Leu Ser Ile Val Ile Ser Val Met Phe Cys Leu
        195                 200                 205

Val Lys Lys Met Val Asp Glu Tyr Gln Gln Asn Ser Gly Gln
    210                 215                 220

<210> SEQ ID NO 104
<211> LENGTH: 288
```

```
<212> TYPE: PRT
<213> ORGANISM: Escherichia coli

<400> SEQUENCE: 104

Met Gln Arg Leu Glu Gln Arg Ser Pro Asp Ala Ile Leu Leu Leu Phe
1               5                   10                  15

Leu Ile Ala Gln Thr Val Asp Ile Thr Met Pro Val Phe Ala Leu Leu
            20                  25                  30

Ala Leu Val Ala Tyr Ser Val Ser Leu Ala Leu Ile Val Pro Gly Leu
        35                  40                  45

Leu Gln Lys Asn Gly Gly Trp Arg Arg Met Ala Ile Ile Ser Ala Val
    50                  55                  60

Ile Ala Leu Val Cys His Ala Ile Ala Leu Glu Ala Arg Ile Leu Pro
65                  70                  75                  80

Asp Gly Asp Ser Gly Gln Asn Leu Ser Leu Leu Asn Val Gly Ser Leu
                85                  90                  95

Val Ser Leu Met Ile Cys Thr Val Met Thr Ile Val Ala Ser Arg Asn
            100                 105                 110

Arg Gly Trp Leu Leu Leu Pro Ile Val Tyr Ala Phe Ala Leu Ile Asn
        115                 120                 125

Leu Ala Leu Ala Thr Phe Met Pro Asn Glu Tyr Ile Thr His Leu Glu
    130                 135                 140

Ala Thr Pro Gly Met Leu Val His Ile Gly Leu Ser Leu Phe Ser Tyr
145                 150                 155                 160

Ala Thr Leu Ile Ile Ala Ala Leu Tyr Ala Leu Gln Leu Ala Trp Ile
                165                 170                 175

Asp Tyr Gln Leu Lys Asn Lys Lys Leu Ala Phe Asn Gln Glu Met Pro
            180                 185                 190

Pro Leu Met Ser Ile Glu Arg Lys Met Phe His Ile Thr Gln Ile Gly
        195                 200                 205

Val Val Leu Leu Thr Leu Thr Leu Cys Thr Gly Leu Phe Tyr Met His
    210                 215                 220

Asn Leu Phe Ser Met Glu Asn Ile Asp Lys Ala Val Leu Ser Ile Val
225                 230                 235                 240

Ala Trp Phe Val Tyr Ile Val Leu Leu Trp Gly His Tyr His Glu Gly
                245                 250                 255

Trp Arg Gly Arg Arg Val Val Trp Phe Asn Val Ala Gly Ala Val Ile
            260                 265                 270

Leu Thr Leu Ala Tyr Phe Gly Ser Arg Ile Val Gln Gln Leu Ile Ser
        275                 280                 285

<210> SEQ ID NO 105
<211> LENGTH: 324
<212> TYPE: PRT
<213> ORGANISM: Escherichia coli

<400> SEQUENCE: 105

Met Pro Val Met Ile Ser Gly Val Leu Tyr Ala Leu Leu Ala Gly Leu
1               5                   10                  15

Met Trp Gly Leu Ile Phe Val Gly Pro Leu Ile Val Pro Glu Tyr Pro
            20                  25                  30

Ala Met Leu Gln Ser Met Gly Arg Tyr Leu Ala Leu Gly Leu Ile Ala
        35                  40                  45

Leu Pro Ile Ala Trp Leu Gly Arg Val Arg Leu Arg Gln Leu Ala Arg
    50                  55                  60
```

Arg Asp Trp Leu Thr Ala Leu Met Leu Thr Met Met Gly Asn Leu Ile
65                  70                  75                  80

Tyr Tyr Phe Cys Leu Ala Ser Ala Ile Gln Arg Thr Gly Ala Pro Val
                85                  90                  95

Ser Thr Met Ile Ile Gly Thr Leu Pro Val Val Ile Pro Val Phe Ala
            100                 105                 110

Asn Leu Leu Tyr Ser Gln Arg Asp Gly Lys Leu Ala Trp Gly Lys Leu
            115                 120                 125

Ala Pro Ala Leu Ile Cys Ile Gly Ile Gly Leu Ala Cys Val Asn Ile
130                 135                 140

Ala Glu Leu Asn His Gly Leu Pro Asp Phe Asp Trp Ala Arg Tyr Thr
145                 150                 155                 160

Ser Gly Ile Val Leu Ala Leu Ser Val Val Cys Trp Ala Trp Tyr
                165                 170                 175

Ala Leu Arg Asn Ala Arg Trp Leu Arg Glu Asn Pro Asp Lys His Pro
            180                 185                 190

Met Met Trp Ala Thr Ala Gln Ala Leu Val Thr Leu Pro Val Ser Leu
            195                 200                 205

Ile Gly Tyr Leu Val Ala Cys Tyr Trp Leu Asn Thr Gln Thr Pro Asp
210                 215                 220

Phe Ser Leu Pro Phe Gly Pro Arg Pro Leu Val Phe Ile Ser Leu Met
225                 230                 235                 240

Val Ala Ile Ala Val Leu Cys Ser Trp Val Gly Ala Leu Cys Trp Asn
                245                 250                 255

Val Ala Ser Gln Leu Leu Pro Thr Val Ile Leu Gly Pro Leu Ile Val
            260                 265                 270

Phe Glu Thr Leu Ala Gly Leu Leu Tyr Thr Phe Leu Leu Arg Gln Gln
            275                 280                 285

Met Pro Pro Leu Met Thr Leu Ser Gly Ile Ala Leu Leu Val Ile Gly
            290                 295                 300

Val Val Ile Ala Val Arg Ala Lys Pro Glu Lys Pro Leu Thr Glu Ser
305                 310                 315                 320

Val Ser Glu Ser

<210> SEQ ID NO 106
<211> LENGTH: 447
<212> TYPE: PRT
<213> ORGANISM: Escherichia coli

<400> SEQUENCE: 106

Met Leu Asn Ser Ile Leu Val Ile Leu Cys Leu Ile Ala Val Ser Ala
1               5                   10                  15

Phe Phe Ser Met Ser Glu Ile Ser Leu Ala Ala Ser Arg Lys Ile Lys
            20                  25                  30

Leu Lys Leu Leu Ala Asp Glu Gly Asn Ile Asn Ala Gln Arg Val Leu
        35                  40                  45

Asn Met Gln Glu Asn Pro Gly Met Phe Phe Thr Val Val Gln Ile Gly
        50                  55                  60

Leu Asn Ala Val Ala Ile Leu Gly Gly Ile Val Gly Asp Ala Ala Phe
65                  70                  75                  80

Ser Pro Ala Phe His Ser Leu Phe Ser Arg Tyr Met Ser Ala Glu Leu
                85                  90                  95

Ser Glu Gln Leu Ser Phe Ile Leu Ser Phe Ser Leu Val Thr Gly Met
            100                 105                 110

Phe Ile Leu Phe Ala Asp Leu Thr Pro Lys Arg Ile Gly Met Ile Ala
            115                 120                 125

Pro Glu Ala Val Ala Leu Arg Ile Ile Asn Pro Met Arg Phe Cys Leu
        130                 135                 140

Tyr Val Cys Thr Pro Leu Val Trp Phe Asn Gly Leu Ala Asn Ile
145                 150                 155                 160

Ile Phe Arg Ile Phe Lys Leu Pro Met Val Arg Lys Asp Asp Ile Thr
                165                 170                 175

Ser Asp Asp Ile Tyr Ala Val Val Glu Ala Gly Ala Leu Ala Gly Val
            180                 185                 190

Leu Arg Lys Gln Glu His Glu Leu Ile Glu Asn Val Phe Glu Leu Glu
        195                 200                 205

Ser Arg Thr Val Pro Ser Ser Met Thr Pro Arg Glu Asn Val Ile Trp
    210                 215                 220

Phe Asp Leu His Glu Asp Glu Gln Ser Leu Lys Asn Lys Val Ala Glu
225                 230                 235                 240

His Pro His Ser Lys Phe Leu Val Cys Asn Glu Asp Ile Asp His Ile
                245                 250                 255

Ile Gly Tyr Val Asp Ser Lys Asp Leu Leu Asn Arg Val Leu Ala Asn
            260                 265                 270

Gln Ser Leu Ala Leu Asn Ser Gly Val Gln Ile Arg Asn Thr Leu Ile
        275                 280                 285

Val Pro Asp Thr Leu Thr Leu Ser Glu Ala Leu Glu Ser Phe Lys Thr
    290                 295                 300

Ala Gly Glu Asp Phe Ala Val Ile Met Asn Glu Tyr Ala Leu Val Val
305                 310                 315                 320

Gly Ile Ile Thr Leu Asn Asp Val Met Thr Thr Leu Met Gly Asp Leu
                325                 330                 335

Val Gly Gln Gly Leu Glu Glu Gln Ile Val Ala Arg Asp Glu Asn Ser
            340                 345                 350

Trp Leu Ile Asp Gly Gly Thr Pro Ile Asp Asp Val Met Arg Val Leu
        355                 360                 365

Asp Ile Asp Glu Phe Pro Gln Ser Gly Asn Tyr Glu Thr Ile Gly Gly
    370                 375                 380

Phe Met Met Phe Met Leu Arg Lys Ile Pro Lys Arg Thr Asp Ser Val
385                 390                 395                 400

Lys Phe Ala Gly Tyr Lys Phe Glu Val Val Asp Ile Asp Asn Tyr Arg
                405                 410                 415

Ile Asp Gln Leu Leu Val Thr Arg Ile Asp Ser Lys Ala Thr Ala Leu
            420                 425                 430

Ser Pro Lys Leu Pro Asp Ala Lys Asp Lys Glu Glu Ser Val Ala
        435                 440                 445

<210> SEQ ID NO 107
<211> LENGTH: 1219
<212> TYPE: PRT
<213> ORGANISM: Chloroflexus aggregans

<400> SEQUENCE: 107

Met Ser Val Thr Gly Arg Leu Ala Gly Lys Ile Ala Leu Ile Thr Gly
1               5                   10                  15

Gly Ala Gly Asn Ile Gly Ser Glu Met Thr Arg Arg Phe Leu Ala Glu
            20                  25                  30

Gly Ala Thr Val Ile Ile Ser Gly Arg Asn Ser Ala Lys Leu Ala Ala
        35                  40                  45

```
Leu Ala Glu Arg Leu Arg Ser Glu Ala Gly Val Pro Ala Lys Arg Ile
     50                  55                  60

Asp Leu Glu Val Met Asp Gly Ser Asp Pro Ala Ala Val Arg Ala Gly
 65                  70                  75                  80

Val Ala Ala Ile Ile Gly Arg His Gly His Ile Asp Ile Leu Val Asn
                 85                  90                  95

Asn Ala Gly Ser Thr Gly Ala Gln Arg Arg Leu Ala Glu Ile Pro Leu
                100                 105                 110

Asn Glu Thr Asp Arg Asp Leu Asp Asp Glu Ala Leu Ser Thr Ser
                115                 120                 125

Val Ala Asn Leu Leu Gly Met Ala Trp His Leu Met Arg Ile Leu Ser
    130                 135                 140

Pro His Met Pro Pro Gly Ser Ala Ile Ile Asn Ile Ser Thr Ile Phe
145                 150                 155                 160

Ser Arg Ala Glu Tyr Tyr Gly Arg Ile Pro Tyr Val Pro Lys Ala
                165                 170                 175

Ala Leu Asn Thr Leu Thr Gln Ile Ala Ala Arg Glu Leu Gly Ile Arg
                180                 185                 190

Gly Ile Arg Val Asn Thr Ile Phe Pro Gly Pro Ile Glu Ser Glu Arg
            195                 200                 205

Ile Gln Thr Val Phe Gln Arg Met Asp Gln Leu Lys Gly Arg Pro Glu
        210                 215                 220

Gly Asp Thr Ala Ser Gln Phe Leu Ala Thr Met Arg Leu Tyr Arg Ala
225                 230                 235                 240

Asn Asp Gln Gly Gln Leu Glu Arg Arg Phe Pro Thr Ile Cys Asp Val
                245                 250                 255

Ala Asp Ala Ala Val Phe Leu Ala Ser Asp Glu Ala Ala Ala Leu Thr
            260                 265                 270

Gly Glu Thr Ile Glu Val Thr His Gly Met Glu Leu Pro Thr Ser Ser
        275                 280                 285

Glu Thr Ser Leu Leu Ala Arg Thr Asp Leu Arg Thr Ile Asp Ala Asn
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Glu Ala Ala Leu Ala Gln Phe Glu Gln Ala Ile Gly Glu
                340                 345                 350

Ser Arg Arg Leu Ala Gly Glu Ser Phe Ile Pro Pro Ile Ala Leu Pro
            355                 360                 365

Ile Asp Leu Arg Asn Pro Ser Thr Ile Asp Ala Leu Phe Asp Trp Ala
        370                 375                 380

Gly Glu Asn Thr Gly Gly Ile His Ala Ala Val Ile Leu Pro Ala Ser
385                 390                 395                 400

Gly Arg Glu Pro Ala Thr Gln Val Ile Asp Ile Asp Ala His Val
                405                 410                 415

Gln Ala Phe Leu Asn Asp Glu Ile Val Gly Ser Ile Ile Ala Ser
                420                 425                 430

Arg Leu Ala Arg Tyr Trp Gln Ala Gln Arg Ile Ala Pro Gly Ala Arg
            435                 440                 445

Ala Arg Glu Pro Arg Val Ile Phe Leu Ser Asn Gly Ala Ser Thr Ala
    450                 455                 460
```

```
Gly Asn Pro Tyr Gly Arg Ile Gln Ser Ala Ala Ile Glu Gln Leu Ile
465                 470                 475                 480

Arg Val Trp Arg His Glu Ala Ala Leu Asp Tyr Glu Arg Ala Thr Ala
            485                 490                 495

Ala Gly Glu Arg Val Leu Pro Ala Val Trp Ala Ser Gln Ile Val Arg
        500                 505                 510

Phe Ala Asn Arg Ser Leu Glu Gly Leu Glu Phe Ala Cys Ala Trp Thr
    515                 520                 525

Ala Gln Leu Leu His Ser Gln Arg Arg Ile Asn Glu Ile Thr Leu Thr
530                 535                 540

Ile Pro Ala Asp Ile Ser Ala Thr Thr Gly Ala Arg Ser Ala Ser Val
545                 550                 555                 560

Gly Trp Ala Glu Ser Leu Ile Gly Leu His Leu Gly Lys Val Ala Leu
            565                 570                 575

Ile Thr Gly Gly Ser Ala Gly Ile Gly Gln Ile Gly Arg Leu Leu
        580                 585                 590

Ala Leu Ser Gly Ala Arg Val Met Leu Ala Ala Arg Asp Pro His Lys
    595                 600                 605

Leu Glu Gln Ile Gln Ala Thr Ile Arg Ala Glu Leu Ala Glu Val Gly
610                 615                 620

Tyr Thr Asp Val Glu Glu Arg Val Gln Ile Ala Pro Gly Cys Asp Val
625                 630                 635                 640

Ser Ser Glu Glu Gln Leu Val Asp Leu Val Glu Arg Thr Leu Ala Ala
            645                 650                 655

Phe Gly Thr Val Asp Tyr Leu Ile Asn Asn Ala Gly Ile Ala Gly Val
    660                 665                 670

Glu Glu Met Val Ile Asp Met Pro Val Glu Gly Trp Arg Asn Thr Leu
            675                 680                 685

Tyr Ala Asn Leu Ile Ser Asn Tyr Ser Leu Met Arg Lys Leu Ala Pro
    690                 695                 700

Leu Met Lys Lys Gln Gly Ser Gly Tyr Val Leu Asn Val Ser Ser Tyr
705                 710                 715                 720

Phe Gly Gly Glu Lys Asp Ala Ala Ile Pro Tyr Pro Asn Arg Ala Asp
            725                 730                 735

Tyr Ala Val Ser Lys Ala Gly Gln Arg Ala Met Ala Glu Val Phe Ala
        740                 745                 750

Arg Phe Leu Gly Pro Glu Ile Gln Ile Asn Ala Ile Ala Pro Gly Pro
    755                 760                 765

Val Glu Gly Asp Arg Leu Arg Gly Thr Gly Glu Arg Pro Gly Leu Phe
770                 775                 780

Ala Arg Arg Ala Arg Leu Ile Leu Glu Asn Lys Arg Leu Asn Glu Leu
785                 790                 795                 800

His Ala Ala Leu Ile Thr Ala Ala Arg Thr Asp Asn Arg Pro Met Arg
            805                 810                 815

Glu Leu Val Glu Leu Leu Pro Asn Asp Val Ala Ala Leu Ala Gln
        820                 825                 830

His Pro Ala Ala Pro Asp Val Leu Arg Thr Leu Ala Lys Arg Phe Gln
    835                 840                 845

Ser Glu Gly Asp Pro Ala Ala Ser Ser Ser Phe Leu Leu Asn Arg
850                 855                 860

Ser Ile Ala Ala Lys Leu Leu Ala Arg Leu Ile Asn Gly Gly Tyr Asp
865                 870                 875                 880

Leu Pro Ala Asp Ile Phe Ala Asn Leu Ala Val Pro Pro Asp Pro Phe
```

```
                885                 890                 895
Phe Thr Arg Ala Gln Ile Asp Arg Glu Ala Arg Lys Val Arg Asp Gly
                900                 905                 910
Ile Met Gly Met Leu Tyr Leu Gln Arg Met Pro Thr Glu Phe Asp Val
                915                 920                 925
Ala Met Ala Thr Val Tyr Tyr Leu Ala Asp Arg Asn Val Ser Gly Glu
                930                 935                 940
Thr Phe His Pro Ser Gly Gly Leu Arg Tyr Glu Arg Thr Pro Thr Gly
945                 950                 955                 960
Gly Glu Leu Phe Gly Leu Pro Ala Pro Glu Arg Leu Ala Glu Leu Val
                965                 970                 975
Gly Ser Thr Val Tyr Leu Ile Gly Glu His Leu Thr Glu His Leu Asn
                980                 985                 990
Leu Leu Ala Arg Ala Tyr Leu Glu Arg Tyr Gly Ala Arg Gln Val Val
                995                1000                1005
Met Ile Val Glu Thr Glu Ala Gly Ala Glu Lys Met Arg His Leu
               1010                1015                1020
Leu His Asp His Val Glu Ala Gly Arg Leu Pro Ile Ile Val Ala
               1025                1030                1035
Gly Asp Gln Ile Glu Ala Ala Ile Asp Gln Ala Ile Ala Asn Tyr
               1040                1045                1050
Gly Arg Pro Gly Pro Val Val Cys Thr Pro Phe Arg Pro Leu Pro
               1055                1060                1065
Ser Ala Pro Leu Val Gly Arg Lys Asp Ser Asp Trp Ser Thr Val
               1070                1075                1080
Leu Ser Glu Ala Glu Phe Ala Glu Leu Cys Glu His Gln Leu Thr
               1085                1090                1095
His His Phe Arg Val Ala Arg Lys Ile Ala Leu Ser Asp Gly Ala
               1100                1105                1110
Ser Leu Ala Leu Val Thr Pro Glu Thr Thr Ala Thr Ser Ser Thr
               1115                1120                1125
Glu Gln Phe Ala Leu Ala Asn Phe Val Lys Thr Thr Leu His Ala
               1130                1135                1140
Phe Thr Ala Thr Ile Gly Val Glu Ser Glu Arg Thr Ala Gln Arg
               1145                1150                1155
Ile Leu Ile Asn Gln Val Asp Leu Thr Arg Arg Ala Arg Ala Glu
               1160                1165                1170
Glu Pro Arg Asp Pro Arg Glu Arg Gln Gln Glu Leu Glu Arg Phe
               1175                1180                1185
Ile Glu Ala Val Leu Leu Val Thr Ala Pro Leu Pro Pro Glu Ala
               1190                1195                1200
Asp Thr Arg Tyr Ala Gly Arg Ile His Arg Gly Arg Ala Ile Thr
               1205                1210                1215
Val

<210> SEQ ID NO 108
<211> LENGTH: 1221
<212> TYPE: PRT
<213> ORGANISM: Oscillochloris trichoides

<400> SEQUENCE: 108

Met Phe Met Thr Arg Leu Asn Asp Lys Ile Ala Leu Ile Thr Gly Gly
1               5                  10                  15

Ala Gly Thr Ile Gly Glu Val Ile Thr Arg Arg Tyr Leu Glu Glu Gly
```

```
                20                  25                  30
Ala Thr Val Val Met Ala Gly Arg Asn Arg Asp Lys Leu Asp Arg Tyr
                35                  40                  45
Arg Glu Arg Leu Ile Thr Glu Phe His Ala Leu Pro Glu Arg Val Met
                50                  55                  60
Val Val Arg Met Asp Gly Ser Ser Asn Ala Glu Val Arg Met Gly Ile
 65                 70                  75                  80
Ala Ala Val Val Ala His Phe Gly Arg Ile Asp Ile Leu Val Asn Asn
                    85                  90                  95
Ala Gly Ser Ala Gly Ala Arg Gln Arg Leu Pro Ala Ile Pro Leu Leu
                100                 105                 110
Arg Ser Glu Leu Gln Ala Asp Glu Thr Glu Thr Leu Ala Asp Ser Ile
                115                 120                 125
Gly Asn Leu Ile Gly Ile Thr Trp Asn Leu Ile Arg Ala Ala Ala Pro
                130                 135                 140
Phe Met Pro Ala Gly Ser Ser Val Ile Asn Ile Ser Thr Ile Phe Ala
145                 150                 155                 160
Arg Thr Asp Tyr Tyr Gly Arg Ile Pro Tyr Val Val Pro Lys Ala Ala
                    165                 170                 175
Leu His Ala Leu Thr Leu Ala Ala Ala Thr Glu Leu Gly Glu Arg Gly
                180                 185                 190
Ile Arg Val Asn Gln Ile Asn Pro Gly Pro Ile Asp Ser Asp Arg Ile
                195                 200                 205
Arg Thr Val Phe Arg Arg Met Asp Glu Leu Lys Gly Val Pro Glu Gln
                210                 215                 220
Ser Thr Ala Asp Gly Phe Phe Gln Met Met Arg Leu Arg Arg Pro Asn
225                 230                 235                 240
Ala Glu Gly Asp Leu Val Lys Gly Phe Pro Lys Thr Leu Asp Val Ala
                    245                 250                 255
Asn Val Ala Val Phe Leu Gly Ser Ala Glu Ser Ala Ala Leu Ser Gly
                260                 265                 270
Glu Thr Leu Asp Val Thr His Gly Met Ala Val Pro Thr Glu Ser Arg
                275                 280                 285
Thr Thr Leu Thr Ser Arg Pro Gly Leu Arg Ala Val Asp Gly Ser Gly
                290                 295                 300
His Thr Thr Leu Ile Cys Val Gly Asp Gln Ile Glu Glu Ala Ala Ala
305                 310                 315                 320
Leu Thr Gly Val Leu Arg Ala Cys Gly Ala Glu Val Val Ile Gly Phe
                    325                 330                 335
Arg Ser Arg Ala Ala Ile Ala Arg Phe Asp His Leu Ile Glu Arg Gly
                340                 345                 350
Arg His Leu Pro Ser Gln Glu His Val Ala Pro Val Leu Leu Tyr Leu
                355                 360                 365
Asn Pro Thr Glu Pro Glu Ser Ile Asp Gln Ala Leu Arg Trp Met Ala
                370                 375                 380
Thr Asn Leu Asp Leu Pro Thr Ser Val Ile Ile Leu Pro Ala Gln Arg
385                 390                 395                 400
Gln Pro Leu Pro Pro Ser Val Val Arg Ala Ser Asp Glu Glu Val Ala
                    405                 410                 415
Tyr Phe Leu Arg Asp Glu Leu Ser Gly Met Ile Val Leu Ala Ser Arg
                420                 425                 430
Leu Ala Arg Phe Trp Gln Gln Ala Thr Leu Ala Pro Gly Asn Ala Pro
                435                 440                 445
```

-continued

```
Ile Gln Pro Arg Val Leu Phe Met Thr Asn Pro Asp Asp Gly Gln Gly
    450                 455                 460

Asn Leu Tyr Ala Glu Ile Leu Arg Ala Gly Val Glu Gln Leu Cys Arg
465                 470                 475                 480

Val Trp Arg His Glu Ser Gln Leu Asp Tyr Thr Arg Leu Ala Gln Met
                485                 490                 495

Asp Ala His Pro Pro His Ile Arg Pro Val Trp Ala Asn Gln Leu Val
                500                 505                 510

Arg Phe Ala Asn Asn Glu Gln Glu Asn Leu Glu Tyr Cys Cys Ala Trp
            515                 520                 525

Val Ala Lys Ile Leu Leu Ser Glu Arg Thr Ile Glu Glu Leu Asn Leu
530                 535                 540

Tyr Leu Pro Arg Gln Ile Gly Ser Thr Thr Gly Ser Arg Gln Pro Ser
545                 550                 555                 560

Phe Gly Trp Ala Glu Asn Leu Ile Gly Leu His Leu Gly Lys Thr Ala
                565                 570                 575

Leu Ile Thr Gly Gly Ser Ala Gly Ile Gly Ser Gln Ile Ala Arg Leu
                580                 585                 590

Leu Ala Leu Ser Gly Ala Arg Val Met Leu Cys Ala Arg Asp Glu Arg
            595                 600                 605

Lys Leu Ile Gln Met Arg Asp Met Ile Ile Ala Glu Leu Thr Glu Val
610                 615                 620

Gly Tyr Asn Gln Val Glu Ser Arg Val Gln Ile Cys Ala Gly Cys Asp
625                 630                 635                 640

Val Gly Glu Glu Glu Gln Leu Glu Ile Ala Val Gln Arg Thr Leu Asp
                645                 650                 655

Leu Phe Gly His Val Asp Tyr Leu Ile Asn Asn Ala Gly Ile Ala Gly
                660                 665                 670

Ala Glu Glu Met Val Leu Asp Leu Pro Leu Glu Ala Trp Gln Arg Thr
            675                 680                 685

Leu Arg Thr Asn Leu Ile Ser Asn Tyr Ser Leu Ile Arg Lys Leu Ala
690                 695                 700

Pro Gln Met Lys Ser Arg Gly Ser Gly Tyr Ile Leu Asn Val Ser Ser
705                 710                 715                 720

Tyr Phe Gly Gly Glu Lys Tyr Ala Ala Ile Pro Tyr Pro Asn Arg Ala
                725                 730                 735

Asp Tyr Ala Val Ser Lys Ala Gly Gln Arg Ala Leu Gly Glu Ala Leu
                740                 745                 750

Ala Arg Leu Leu Gly Pro Glu Val Gln Ile Asn Ala Met Ala Pro Gly
            755                 760                 765

Pro Val Glu Gly Glu Arg Leu Arg Gly Ser Gly Asp Arg Pro Gly Leu
770                 775                 780

Phe Leu Arg Arg Gly Arg Leu Ile Leu Glu Asn Lys Arg Leu Asn Asp
785                 790                 795                 800

Leu His Ala Thr Leu Ile Ala Ala Glu Arg Glu Thr Gln Val Gly Met
                805                 810                 815

Arg Asp Leu Leu Ala Arg Leu His Asn Asp Val Cys Ala Leu Ile
            820                 825                 830

Asp Asp Pro Ala Ala Pro Thr His Leu Arg Ala Leu Ala Glu Arg Ile
            835                 840                 845

Trp Glu Gln Ser Asp Pro Asn Ser Tyr Ala Arg Ala Phe Phe Met Asn
850                 855                 860
```

```
Ala Asn Ile Ala Thr Lys Leu Leu Ala Arg Leu Phe Asn Ala Asp Gln
865                 870                 875                 880

Ile Asp Ala Gln Thr Phe His Thr Ser Gln Pro Asn Leu Pro Pro Glu
                885                 890                 895

Pro Phe Phe Ala Arg Thr Gln Ile Asp Arg Glu Ala Arg Arg Val Arg
            900                 905                 910

Asp Gly Val Met Ser Met Leu Tyr Leu Gln Arg Met Pro Thr Glu Phe
        915                 920                 925

Asp Val Ala Leu Ala Thr Val Tyr Tyr Leu Asn Asp Arg Ser Val Ser
930                 935                 940

Gly Glu Thr Phe His Pro Ser Gly Leu Arg His Glu Arg Thr Pro
945                 950                 955                 960

Thr Gly Ala Glu Leu Tyr Gly Ser Pro Ala Pro Gln Arg Leu Ala Ser
                965                 970                 975

Leu Ala Gly Ser Thr Val Tyr Leu Ile Gly Glu Ser Met Ala Ala His
            980                 985                 990

Leu Glu Ala Leu Ala Arg Ala Tyr Ile Glu Arg Tyr Ala Ala Thr Arg
        995                 1000                1005

Val Val Leu Ile Cys Ala Thr Pro Ala Gly Val Glu Arg Phe Ser
    1010                1015                1020

His His Leu Ala Asp His Leu Ala Ser Gly Ala Leu Ala Ile Leu
    1025                1030                1035

Ser Ala Glu Glu Gly Ile Glu Ala Ala Leu Ser Glu Ala Leu Arg
    1040                1045                1050

Arg Phe Gly Pro Pro Gly Pro Val Val Ser Thr Pro Phe Gln Pro
    1055                1060                1065

Leu Pro Ser Gln Pro Leu Ile Gly Arg Asn Asp Ser Asp Trp Ser
    1070                1075                1080

Thr Val Leu Asp Val Ala Gly Phe Ser Ala Met Cys Glu Gln Gln
    1085                1090                1095

Leu Thr His His Phe Arg Val Thr Arg Lys Leu Ser Leu Val Ala
    1100                1105                1110

Gly Val Ser Leu Val Leu Val Thr Pro Glu Thr Asp Ser His Ser
    1115                1120                1125

Ser Thr Glu Gln Phe Ala Leu Ala Asn Phe Val Lys Thr Thr Leu
    1130                1135                1140

His Ala Phe Thr Ala Thr Val Gly Val Glu Cys Glu Arg Thr Ala
    1145                1150                1155

His Arg Ile Leu Val Asn Gln Val Asp Leu Gly Arg Gln Ala Arg
    1160                1165                1170

Ala Glu Glu Pro Arg Ser Pro Ala Glu Gln Ala Gln Glu Met Glu
    1175                1180                1185

Arg Phe Ile Asp Ala Ile Met Leu Thr Thr Ala Pro Ile Pro Ala
    1190                1195                1200

Glu Glu Asp Asn Arg Tyr Thr Gly Arg Ile Tyr Arg Gly Arg Ala
    1205                1210                1215

Ile Thr Val
    1220

<210> SEQ ID NO 109
<211> LENGTH: 1220
<212> TYPE: PRT
<213> ORGANISM: Chloroflexus aurantiacus

<400> SEQUENCE: 109
```

```
Met Ser Gly Thr Gly Arg Leu Ala Gly Lys Ile Ala Leu Ile Thr Gly
 1               5                  10                  15
Gly Ala Gly Asn Ile Gly Ser Glu Leu Thr Arg Arg Phe Leu Ala Glu
                 20                  25                  30
Gly Ala Thr Val Ile Ile Ser Gly Arg Asn Arg Ala Lys Leu Thr Ala
             35                  40                  45
Leu Ala Glu Arg Met Gln Ala Glu Ala Gly Val Pro Ala Lys Arg Ile
 50                  55                  60
Asp Leu Glu Val Met Asp Gly Ser Asp Pro Val Ala Val Arg Ala Gly
 65                  70                  75                  80
Ile Glu Ala Ile Val Ala Arg His Gly Gln Ile Asp Ile Leu Val Asn
                 85                  90                  95
Asn Ala Gly Ser Ala Gly Ala Gln Arg Arg Leu Ala Glu Ile Pro Leu
                 100                 105                 110
Thr Glu Ala Glu Leu Gly Pro Gly Ala Glu Glu Thr Leu His Ala Ser
             115                 120                 125
Ile Ala Asn Leu Leu Gly Met Gly Trp His Leu Met Arg Ile Ala Ala
 130                 135                 140
Pro His Met Pro Val Gly Ser Ala Val Ile Asn Val Ser Thr Ile Phe
145                 150                 155                 160
Ser Arg Ala Glu Tyr Tyr Gly Arg Ile Pro Tyr Val Thr Pro Lys Ala
                 165                 170                 175
Ala Leu Asn Ala Leu Ser Gln Leu Ala Ala Arg Glu Leu Gly Ala Arg
             180                 185                 190
Gly Ile Arg Val Asn Thr Ile Phe Pro Gly Pro Ile Glu Ser Asp Arg
                 195                 200                 205
Ile Arg Thr Val Phe Gln Arg Met Asp Gln Leu Lys Gly Arg Pro Glu
 210                 215                 220
Gly Asp Thr Ala His His Phe Leu Asn Thr Met Arg Leu Cys Arg Ala
225                 230                 235                 240
Asn Asp Gln Gly Ala Leu Glu Arg Arg Phe Pro Ser Val Gly Asp Val
                 245                 250                 255
Ala Asp Ala Ala Val Phe Leu Ala Ser Ala Glu Ser Ala Ala Leu Ser
             260                 265                 270
Gly Glu Thr Ile Glu Val Thr His Gly Met Glu Leu Pro Ala Cys Ser
             275                 280                 285
Glu Thr Ser Leu Leu Ala Arg Thr Asp Leu Arg Thr Ile Asp Ala Ser
 290                 295                 300
Gly Arg Thr Thr Leu Ile Cys Ala Gly Asp Gln Ile Glu Glu Val Met
305                 310                 315                 320
Ala Leu Thr Gly Met Leu Arg Thr Cys Gly Ser Glu Val Ile Ile Gly
                 325                 330                 335
Phe Arg Ser Ala Ala Ala Leu Ala Gln Phe Glu Gln Ala Val Asn Glu
                 340                 345                 350
Ser Arg Arg Leu Ala Gly Ala Asp Phe Thr Pro Pro Ile Ala Leu Pro
             355                 360                 365
Leu Asp Pro Arg Asp Pro Ala Thr Ile Asp Ala Val Phe Asp Trp Gly
 370                 375                 380
Ala Gly Glu Asn Thr Gly Gly Ile His Ala Ala Val Ile Leu Pro Ala
385                 390                 395                 400
Thr Ser His Glu Pro Ala Pro Cys Val Ile Glu Val Asp Asp Glu Arg
                 405                 410                 415
```

```
Val Leu Asn Phe Leu Ala Asp Glu Ile Thr Gly Thr Ile Val Ile Ala
                420                 425                 430

Ser Arg Leu Ala Arg Tyr Trp Gln Ser Gln Arg Leu Thr Pro Gly Ala
            435                 440                 445

Arg Ala Arg Gly Pro Arg Val Ile Phe Leu Ser Asn Gly Ala Asp Gln
        450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
        530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
        675                 680                 685

Leu Phe Ala Asn Leu Ile Ser Asn Tyr Ser Leu Met Arg Lys Leu Ala
        690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
        770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                805                 810                 815

His Glu Leu Val Glu Leu Leu Leu Pro Asn Asp Val Ala Ala Leu Glu
            820                 825                 830

Gln Asn Pro Ala Ala Pro Thr Ala Leu Arg Glu Leu Ala Arg Arg Phe
```

835                 840                 845
Arg Ser Glu Gly Asp Pro Ala Ala Ser Ser Ser Ala Leu Leu Asn
    850                 855                 860
Arg Ser Ile Ala Ala Lys Leu Leu Ala Arg Leu His Asn Gly Gly Tyr
865                 870                 875                 880
Val Leu Pro Ala Asp Ile Phe Ala Asn Leu Pro Asn Pro Pro Asp Pro
                885                 890                 895
Phe Phe Thr Arg Ala Gln Ile Asp Arg Glu Ala Arg Lys Val Arg Asp
            900                 905                 910
Gly Ile Met Gly Met Leu Tyr Leu Gln Arg Met Pro Thr Glu Phe Asp
            915                 920                 925
Val Ala Met Ala Thr Val Tyr Tyr Leu Ala Asp Arg Asn Val Ser Gly
930                 935                 940
Glu Thr Phe His Pro Ser Gly Leu Arg Tyr Glu Arg Thr Pro Thr
945                 950                 955                 960
Gly Gly Glu Leu Phe Gly Leu Pro Ser Pro Glu Arg Leu Ala Glu Leu
                965                 970                 975
Val Gly Ser Thr Val Tyr Leu Ile Gly Glu His Leu Thr Glu His Leu
            980                 985                 990
Asn Leu Leu Ala Arg Ala Tyr Leu Glu Arg Tyr Gly Ala Arg Gln Val
                995                1000                1005
Val Met Ile Val Glu Thr Glu Thr Gly Ala Glu Thr Met Arg Arg
    1010                1015                1020
Leu Leu His Asp His Val Glu Ala Gly Arg Leu Met Thr Ile Val
    1025                1030                1035
Ala Gly Asp Gln Ile Glu Ala Ala Ile Asp Gln Ala Ile Thr Arg
    1040                1045                1050
Tyr Gly Arg Pro Gly Pro Val Val Cys Thr Pro Phe Arg Pro Leu
    1055                1060                1065
Pro Thr Val Pro Leu Val Gly Arg Lys Asp Ser Asp Trp Ser Thr
    1070                1075                1080
Val Leu Ser Glu Ala Glu Phe Ala Glu Leu Cys Glu His Gln Leu
    1085                1090                1095
Thr His His Phe Arg Val Ala Arg Lys Ile Ala Leu Ser Asp Gly
    1100                1105                1110
Ala Ser Leu Ala Leu Val Thr Pro Glu Thr Thr Ala Thr Ser Thr
    1115                1120                1125
Thr Glu Gln Phe Ala Leu Ala Asn Phe Ile Lys Thr Thr Leu His
    1130                1135                1140
Ala Phe Thr Ala Thr Ile Gly Val Glu Ser Glu Arg Thr Ala Gln
    1145                1150                1155
Arg Ile Leu Ile Asn Gln Val Asp Leu Thr Arg Arg Ala Arg Ala
    1160                1165                1170
Glu Glu Pro Arg Asp Pro His Glu Arg Gln Gln Glu Leu Glu Arg
    1175                1180                1185
Phe Ile Glu Ala Val Leu Leu Val Thr Ala Pro Leu Pro Pro Glu
    1190                1195                1200
Ala Asp Thr Arg Tyr Ala Gly Arg Ile His Arg Gly Arg Ala Ile
    1205                1210                1215
Thr Val
    1220

<210> SEQ ID NO 110

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcgtagtaaa ggaggtaaca tatg                                         24

<210> SEQ ID NO 111
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
caatttattt aaggaggact cttaagatg                                    29

<210> SEQ ID NO 112
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gaaatttcat accacaggcg aaggaggaaa aaccatg                           37

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ggaagaacaa ggggtgtaca tg                                           22

<210> SEQ ID NO 114
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggaagaatta aggggggacaa gggggaataa tg                               32

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcgtagtagc cgggtgataa ggagccgtaa catg                              34

<210> SEQ ID NO 116
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
gcgtagtagc tgatataaaa ggaggtaacg gatg                                   34

<210> SEQ ID NO 117
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caatttattt ttgttcaccc aaggagtatt gctaatg                                37

<210> SEQ ID NO 118
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caatttattt accgaaataa aaggagggat gcgaatg                                37

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcttcccaca acactggcgg actccatcat g                                      31

<210> SEQ ID NO 120
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Leu Ser Gly Gly Gly Gly Ser Gly Gly Gly Gly Ser Gly Gly Gly Gly
1               5                   10                  15

Ser Gly Gly Gly Gly Ser Ala Ala Ala
            20                  25
```

ACETYL-COA CARBOXYLASES

CLAIM OF PRIORITY

This application is a Continuation of and claims the benefit of priority to U.S. patent application Ser. No. 15/269,382 filed on Sep. 19, 2016 which is a Continuation of and claims the benefit of priority to U.S. patent application Ser. No. 14/215,379 filed on Mar. 17, 2014, which claims the benefit of priority to U.S. Provisional Application No. 61/852,387, filed on Mar. 15, 2013, the benefit of priority of each of which is claimed hereby, and each of which are incorporated by reference herein in its entirety.

BACKGROUND OF THE INVENTION

There is a need for alternative production methods of industrial chemicals used for various consumer products and fuels that are currently made from petroleum. One alternative method is the use of engineered microorganisms to produce industrial chemicals. Currently, in the field of bioproduced chemicals there is a need to improve microbial enzyme performance, enhanced production rate in order to reach the goal of becoming an at-cost replacement basis for petro-based chemicals.

A common challenge faced in field of bio-produced chemicals in microorganisms is that any one modification to a host cell may require coordination with other modifications in order to successfully enhance chemical bioproduction.

The current invention provides methods, systems of fermentation, genetically modified microorganisms, modified enhanced enzymes for chemical production, all of which may be used in various combinations to increase chemical production of a desired chemical product.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

The present invention relates to genetically modified organisms capable of producing an industrial chemical product of interest, wherein the genetic modification includes introduction of nucleic acid sequences coding for polynucleotides encoding one or more of the following: (1) an acetyl-CoA carboxylase gene with one or more of its subunits fused together in the genetic structure of the organism; (2) an acetyl-CoA carboxylase gene having a predefined stoichiometric ratio of each of the four ACCase subunits relative to one another; (3) a monofunctional malonyl-CoA reductase gene capable of catalyzing the conversion of malonyl-CoA to malonate semialdehyde and one or more genes encoding one or more of the following enzymes: ydfG, mmsB, NDSD, rutE, and nemA; (4) a monofunctional malonyl-CoA reductase gene capable of catalyzing the conversion of malonyl-CoA to malonate semialdehyde and one or more genes encoding one or more enzymes capable of converting malonate semialdehyde keto form to 3-HP, and one or more genes encoding one or more enzymes capable of converting either the malonate semialdehyde enol form or the malonate semialdehyde hydrated form to 3-HP; (5) a monofunctional malonyl-CoA reductase enzyme fused to a dehydrogenase enzyme that is either: (a) primarily not NADPH-dependent, (b) primarily NADH-dependent, (c) primarily flavin-dependent, (d) less susceptible to 3-HP inhibition at high concentration, and/or (e) catalyzes a reaction pathway to 3-HP that is substantially irreversible; (6) a monofunctional malonyl-CoA reductase enzyme fused to one or more malonate semialdehyde dehydrogenase enzymes; (7) a malonyl-CoA reductase gene that is mutated to enhance its activity at lower temperatures; (8) salt-tolerant enzymes; (9) a gene that facilitates the exportation of a chemical product of interest or the export of an inhibitory chemical from within the cell to the extracellular media; and/or (10) a gene that facilitates the importation from the extracellular media to within the cell of a reactant, precursor, and/or metabolite used in the organism's production pathway for producing a chemical product of interest.

The present invention further relates to methods of producing a chemical product using the genetically modified organisms of the invention. The present invention further includes products made from these methods. In accordance with certain embodiments that product is acetyl-CoA, malonyl-CoA, malonate semialdehyde, 3-hydroxypropionic acid (3-HP), acrylic acid, 1,3 propanediol, malonic acid, ethyl 3-HP, propiolactone, acrylonitrile, acrylamide, methyl acrylate, a polymer including super absorbent polymers and polyacrylic acid, or a consumer product.

The present invention further relates to a method of producing a chemical product from a renewable carbon source through a bioproduction process that comprises a controlled multi-phase production process wherein the initiation and/or completion of one or more phases of the production process is controlled by genetic modifications to the organism producing the chemical product and/or is controlled by changes made to the cell environment. In accordance with this aspect of the invention, the bioproduction process may include two or more of the following phases: (1) growth phase; (2) induction phase; and (3) production phase. The present invention further includes products made from these methods.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 Shows various embodiments of the genetic modules used for optimizing expression in host cells.

Figure 1:
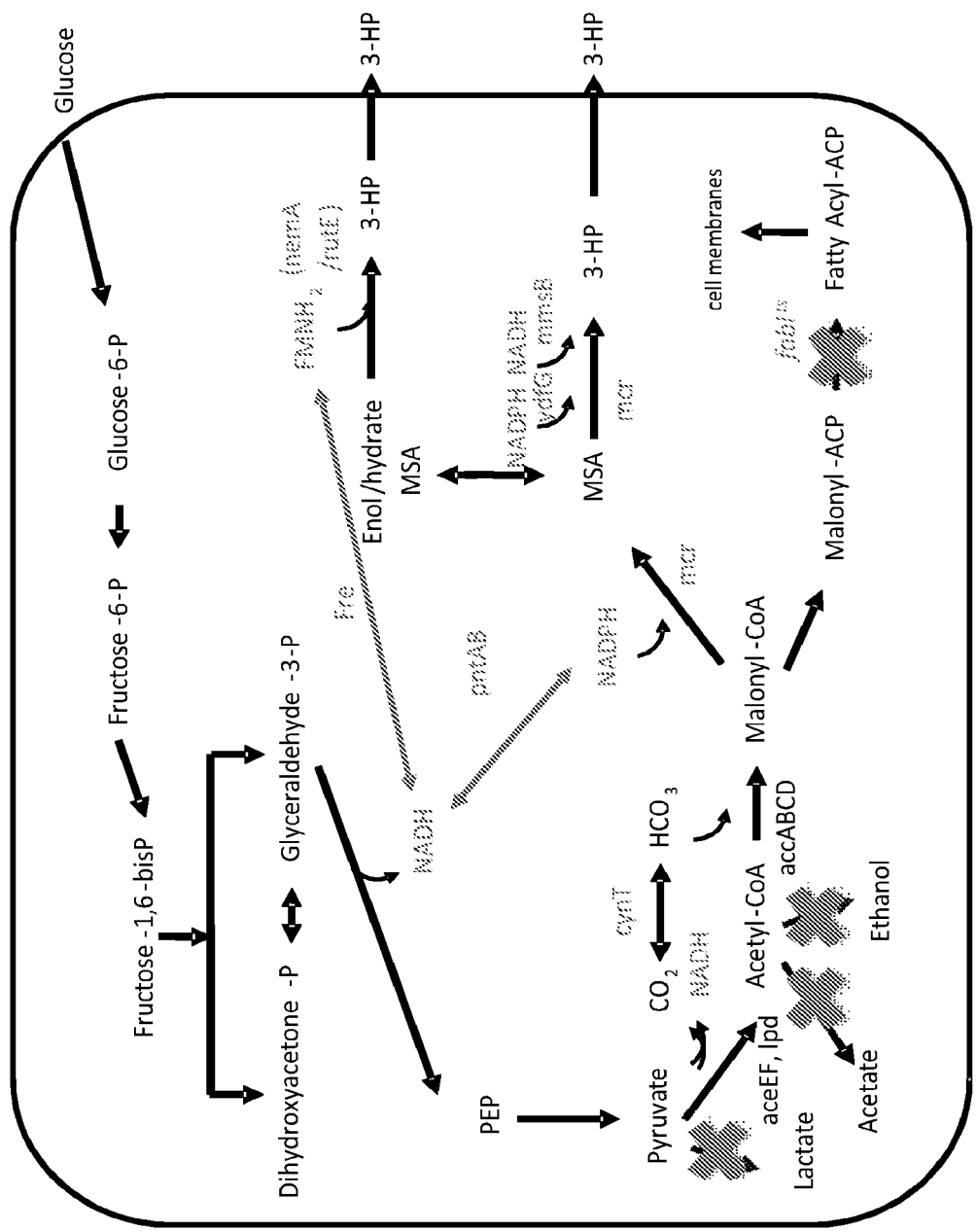
FIG. 1 Depicts some embodiments of the metabolic pathways to produce 3-hydroxypropionic acid.

Table 1 Lists the accession numbers for genes encoding ACCase subunits from *Halomonas elongate*.

Table 2 Depicts some embodiments of the RBS sequences used to enhance expression of *H. elongate* ACCase subunits.

Table 3 Shows the improvement in 3-HP production by RBS-optimized expression of *H. elongata* ACCase subunits.

Table 4 Shows some embodiments of the ACCase subunit fusions that increase and ACCase enzyme complex activity.

Table 5 Shows some of the genetic modifications of a host cell for increase chemical production.

DETAILED DESCRIPTION OF THE INVENTION

Definitions

The term "homology" refers to the optimal alignment of sequences (either nucleotides or amino acids), which may be conducted by computerized implementations of algorithms. "Homology", with regard to polynucleotides, for example, may be determined by analysis with BLASTN version 2.0 using the default parameters. "Homology", with respect to polypeptides (i.e., amino acids), may be determined using a program, such as BLASTP version 2.2.2 with the default parameters, which aligns the polypeptide or fragments (and can also align nucleotide fragments) being compared and determines the extent of amino acid identity or similarity between them. It will be appreciated that amino acid "homology" includes conservative substitutions, i.e. those that substitute a given amino acid in a polypeptide by another amino acid of similar characteristics. Typically seen as conservative substitutions are the following replacements: replacements of an aliphatic amino acid such as Ala, Val, Leu and He with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue. For example, homologs can have at least 99%, 98%, 97%, 96%, 95%, 94%, 93%, 92%, 91%, 90%, 89%, 88%, 87%, 86%, 85%, 84%, 83%, 82%, 81% or 80% overall amino acid or nucleotide identity to the gene or proteins of the invention; or can have 99%, 98%, 97%, 96%, 95%, 94%, 93%, 92%, 91%, 90%, 89%, 88%, 87%, 86%, 85%, 84%, 83%, 82%, 81% or 80% amino acid or nucleotide to the essential protein functional domains of the gene or proteins of the invention; or at least 99%, 98%, 97%, 96%, 95%, 94%, 93%, 92%, 91%, 90%, 89%, 88%, 87%, 86%, 85%, 84%, 83%, 82%, 81% or 80% overall amino acid or nucleotide to the essential binding amino acids within an essential functional domain of the gene or proteins of the invention.

The above descriptions and methods for sequence homology are intended to be exemplary and it is recognized that this concept is well-understood in the art. Further, it is appreciated that nucleic acid sequences may be varied and still provide a functional enzyme, and such variations are within the scope of the present invention. The term "enzyme homolog" can also mean a functional variant.

The term "Functional homolog" means a polypeptide that is determined to possess an enzymatic activity and specificity of an enzyme of interest but which has an amino acid sequence different from such enzyme of interest. A corresponding "homolog nucleic acid sequence" may be constructed that is determined to encode such an identified enzymatic functional variant.

The term "3-HP" means 3-hydroxypropionic acid.

The term "heterologous DNA," "heterologous nucleic acid sequence," and the like as used herein refers to a nucleic acid sequence wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Embodiments of the present invention may result from introduction of an expression vector into a host microorganism, wherein the expression vector contains a nucleic acid sequence coding for an enzyme that is, or is not, normally found in a host microorganism. With reference to the host microorganism's genome prior to the introduction of the heterologous nucleic acid sequence, then, the nucleic acid sequence that codes for the enzyme is heterologous (whether or not the heterologous nucleic acid sequence is introduced into that genome). The term "heterologous" is intended to include the term "exogenous" as the latter term is generally used in the art as well as "endogenous".

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

I. Introduction

The present invention relates to various genetically modified microorganisms, methods for making the same, and use of the same in making industrial products. Any and all of the microorganisms herein may include a combination of genetic alterations as described herein. The present invention contemplates, for example, a genetically modified microorganism having one or more of the following genetic modifications (i) an alteration that affects the stoichiometric ratio, expression or production of one or more ACCase enzyme genes (ii) a recombinant ACCase gene having at least 80% sequence homology to an ACCase gene from a salt tolerant organism (iii) a genetic alteration in one or more non-ACCase genes (iv) one or more genetic alterations that encodes for one or more exporters capable of exporting 3-HP out of a cell (v) new hybrid molecules or co-expressed of a mono-functional malonyl-CoA reductase enzyme with various 3-HP dehydrogenase proteins that: (a) exhibit less inhibition by high 3-HP concentrations (b) that is less reversible or irreversible (c) enzymes that utilized NADH (d) enzymes that utilized flavin (vi) one or more genetic alterations that can be used to switch the carbon in the standard metabolic pathways of the cells to a pathway engineered to produce a chemical. More details about each of the above modifications and how the modification are used together to increase chemical production in a host cell is described below.

The present invention also relates to methods of fermentation. The genetically modified microorganisms are cultured under conditions that optimized a host cell for increase chemical production. The bio-production process may include two or more of the following phases of fermentation: (1) growth phase where the culture organism replicates itself and the carbon intermediate product is built up; (2) the induction phase, where the expression of key enzymes critical to the chemical production is induced and the enzymes accumulate within the organism to carry out the engineered pathway reactions required to further produce the chemical product (3) production phase is where the organism expresses proteins that provide for continuously production the desired chemical product. The above phases are further controlled by (1) addition and amount of the initiating reactant added to the reaction vessel (2) key enzymes engineered into the organism using promoters that are sensitive to (e.g., activated by) the depletion of the initiating reactant. Addition details about the fermentation process of the invention are disclosed below.

II. Acetyl-CoA Carboxylase
Malonyl-CoA Flux

One of the steps in the biosynthesis of 3-HP involves the reaction catalyzed by acetyl-CoA carboxylase (ACCase) enzyme. ACCase is a primary control point in the 3-HP pathway shown in FIG. 1 (previously described in) for the converting acetyl-CoA to malonyl-CoA and hence to malonate semialdehyde and 3-HP. The present invention contemplates the use of genetic modifications that increase activity of ACCase complex enzymes to thereby increase 3-HP production in a host cell.

Fused Subunits

The acetyl-CoA carboxylase complex (ACCase) is a multi-subunit protein. Prokaryotes and plants have multi-subunit ACCs composed of several polypeptides encoded by distinct genes. However, humans and most other eukaryotes, such as yeast, have evolved an ACC with CT and BC catalytic domains and biotin carboxyl carrier domains on a single polypeptide. The biotin carboxylase (BC) activity, biotin carboxyl carrier protein (BCCP), and carboxyl transferase (CT) activity are each contained on a different subunit. In *E. coli* the ACCase complex is derived from multi polypeptide transcribed by distinct, separable protein components known as accA, accB, accC, and accD.

Acetyl-CoA carboxylase is a biotin-dependent enzyme that catalyzes the irreversible carboxylation of acetyl-CoA to produce malonyl-CoA through its two catalytic activities, biotin carboxylase (BC) and carboxyltransferase (CT). The first reaction is carried out by BC and involves the ATP-dependent carboxylation of biotin with bicarbonate. The carboxyl group is transferred from biotin to acetyl-CoA to form malonyl-CoA in the second reaction, which is catalyzed by CT. The main function of ACCase complex in the cell is to provide the malonyl-CoA substrate for the biosynthesis of fatty acids.

The conversion of acetyl-CoA to malonyl-CoA is an important step in the bioconversion of a renewable carbon source (such as, for example, sugar or natural gas) to a useful industrial chemical (such as, for example, 3-hydroxypropionic acid (3-HP)). In certain organisms, such as *E. coli* or yeast, the native ACCase expression from the chromosome alone is insufficient to enable the organism to produce chemicals such as 3-HP at a rate to support a commercial scale operation. Overexpression of the ACCase complex has been shown to provide some advantage [U.S. Ser. No. 12/891,760 U.S. Ser. No. 12/891,790 U.S. Ser. No. 13/055,138].

Applicants have discovered that the introduction of an acetyl-CoA carboxylase gene with one or more of its subunits fused is beneficial to the production of a chemical product in a host cell. In certain aspects of the invention, fusion is the two gene products produced from a single polypeptide controlled by a single promoter, will further enhance an organism's bioproduction of an industrial chemical. In certain aspects of the invention, fusion is the two gene products produced by at least one promoter, will further enhance an organism's bioproduction of an industrial chemical. In certain aspects of the invention, fusion is the two gene products produced from a single polypeptide controlled by at least one inducible promoter, will further enhance an organism's bioproduction of an industrial chemical. Keeping components of the ACCase complex fused together in the genetic structure of an organism can be advantageous because it enhances the stability of the non-native ACCase genetic modification and it facilitates equimolar expression of the fused acc subunits.

In particular, the subunit-fused ACCase may be an accA-accB, accA-accC, accA-accD, accB-accC, accB-accD, accC-accD, accA-accB-accC, accA-accB-accD, accA-accC-accD, accB-accC-accD or accA-accB-accC-accD fused subunit that have having at least 80% sequence homology to *E. coli* accA, accB, accC and accD or is a functional homolog thereof. In addition, the organism may include any combination of these fused subunits, or any combination of these fused subunits together with one or more of the four non-fused subunits. When such combinations are used, the subunits (fused and non-fused) may be expressed on the same plasmid or on different plasmids or on the chromosome of the organism.

In accordance with a preferred embodiment, an accA-accD fused subunit is introduced into an organism either alone or in combination with the accB-accC fused subunit, the accB gene, and/or the accC gene. In accordance with a preferred embodiment, the organism is a bacteria, and preferably *E. coli* or *Cupriavidus necator.*

Composition Stoichiometry

Composition stoichiometry is the quantitative relationships among elements that comprise a compound. A stoichiometric ratio of a reagent is the optimum amount or ratio where, assuming that the reaction proceeds to completion. Although stoichiometric terms are traditionally reserved for chemical compounds, theses theoretical consideration of stoichiometry are relevant when considering the optimal function of heterologous multi-subunit protein in a host cell.

In accordance with another aspect of the invention, the stoichiometric ratio of each of the four ACCase subunits relative to one another is important, and each such ratio can be between 0 and about 10, and preferably between about 0.5 to about 2 or about 7 to about 9. In accordance with a preferred embodiment the ratios for the protein subunits are accA:accB:accC:accD are 1:2:1:1. In accordance with a preferred embodiment, an organism is genetically modified to include an accA-accD fused subunit, an accB non-fused subunit, and an accC non-fused subunit, with the molar ratios of the accDA fusion:accB:accC being about 1:2:1, which is close to the optimum for enzymatic activity.

In certain embodiments where an organism is engineered to make 3-HP, in order to get optimal function in a host cell of a heterologous ACCase enzyme complex it is important to engineer the stoichiometry of these subunits in such a way that provides maximal production of 3-HP such that the subunit can make a more stable enzyme complex when overexpressed in the cell.

In certain aspects the invention provides for the controlled expression of the natural accA, accB, accC, and accD subunits of *E. coli* or having at least 80% sequence homology to *E. coli* accA, accB, accC and accD. In certain aspects the invention provides for the inducible expression of the natural accA, accB, accC, and accD subunits of *E. coli* or having at least 80% sequence homology to *E. coli* accA, accB, accC, and accD. In certain aspects the invention provides for the low, medium, high and/or inducible expression of the natural accA, accB, accC, and accD subunits of *E. coli* or having at least 80% sequence homology to *E. coli* accA, accB, accC and accD.

In certain aspects the invention provides for the expression of the natural accC and accD subunits of *E. coli* or having at least 80% sequence homology to *E. coli* accA, accB, accC and accD in low, medium, high or inducible expression. In certain aspects the invention provides for the expression of the natural accB and accA subunits of *E. coli* or having at least 80% sequence homology to *E. coli* accA, accB, accC, and accD in low, medium, high or inducible expression. In certain aspects the invention provides for the expression of the natural accC and accD subunits with the accA subunit of *E. coli* or having at least 80% sequence homology to *E. coli* accA, accB, accC, and accD in low, medium, high or inducible expression. In certain aspects the invention provides for the expression of the natural accC and accD subunits with the accB subunit of *E. coli* or having at least 80% sequence homology to *E. coli* accA, accB, accC, and accD in low, medium, high or inducible expression.

In certain aspects the invention provides for the expression of a fusion of two, three, or all of the four ACCase subunits in one polypeptide in low, medium, high or inducible expression. Such fusion may include any of the following combinations of the ACCase subunits: accA-accB, accA-accC, accA-accD, accB-accC, accB-accD, accC-accD, accA-accB-accC, accA-accB-accD, accA-accC-accD, accB-accC-accD, and accA-accB-accC-accD have having at least 80% sequence homology to *E. coli* accA, accB, accC and accD or is a functional homolog thereof.

In certain aspects the invention provides for ACC complex in the stoichiometry of these subunits of the accCB and accDA in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression. In certain aspects the invention provides for ACC complex in the stoichiometry of these subunits of the accDA and accCB in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression.

In certain aspects the invention provides for the stoichiometry of the accD-A subunits in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression. In certain aspects the invention provides for the stoichiometry of the accC-B subunits in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression. In certain aspects the invention provides for the stoichiometry of the accC-A subunits in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression. In certain aspects the invention provides for the stoichiometry of the accC-B subunits in a 1:1, 1:2, 1:3, 1:4, 1:5, 1:6, 1:7, 1:8, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:4, 4:5, 4:6, 4:7, 4:8, 5:1, 5:3, 5:4, 5:5, 5:6, 5:7, 5:8, 6:1, 6:3, 6:4, 6:5, 6:6, 6:7, 6:8, 7:1, 7:3, 7:4, 7:5, 7:6, 7:7, 7:8, 8:1, 8:3, 8:4, 8:5, 8:6, 8:7, or 8:8 in low, medium, high or inducible expression.

III. Conversion of Malonyl-CoA to Malonate Semialdehyde

One of the steps in the biosynthesis of 3-HP involves the conversion of malonyl-CoA (MCA) to malonate semialdehyde (MSA) and the conversion of malonate semialdehyde (MSA) to 3-HP (WO2011/038364). In accordance with another aspect of the present invention, the present invention contemplates the use of novel enzymes and/or combinations of enzymes to catalyze the reaction in a microorganism from MCA to MSA, which results in enhanced cellular bioproduction of 3-HP in the host cell.

In certain aspects the invention provides novel enzyme compositions or co-expression of a combinations of enzyme compositions to catalyze the conversion of malonyl-CoA to 3-HP. A general overview of the enzymes and the relevant reaction pathways methods are shown in FIG. 1.

In accordance with this aspect of the invention, malonyl-CoA is converted to malonate semialdehyde by a malonyl-CoA reductase and malonate semialdehyde is converted to 3-HP through either or both of two alternative pathways.

In accordance with one aspect of the invention, malonyl-CoA is converted to malonate semialdehyde by a monofunctional malonyl-CoA reductase that catalyzes the malonyl-CoA conversion, but does not catalyze the malonate semialdehyde conversion.

In one embodiment, the microorganism herein comprise a genetic modification that include the monofunctional malonyl-CoA reductase may be derived from *Sulfolobus tokodaii* (stMCR) (SEQ ID NO.. 15 nucleic acid, SEQ ID NO. 16 protein sequence) or a functional homolog of stMCR or a homolog with at least 80% identity.

In some embodiments, the microorganism herein comprise a genetic modification that include the bi-functional malonyl-CoA reductase comprised of two protein fragments with one fragment having malonyl-CoA reductase activity and the other fragment having malonate semialdehyde dehydrogenase activity may be derived from *Chloroflexus aurantiacus* (caMCR).

MCR-Dehydrogenase Enzymes for Conversion of 3-HP Ions

Figure 2:
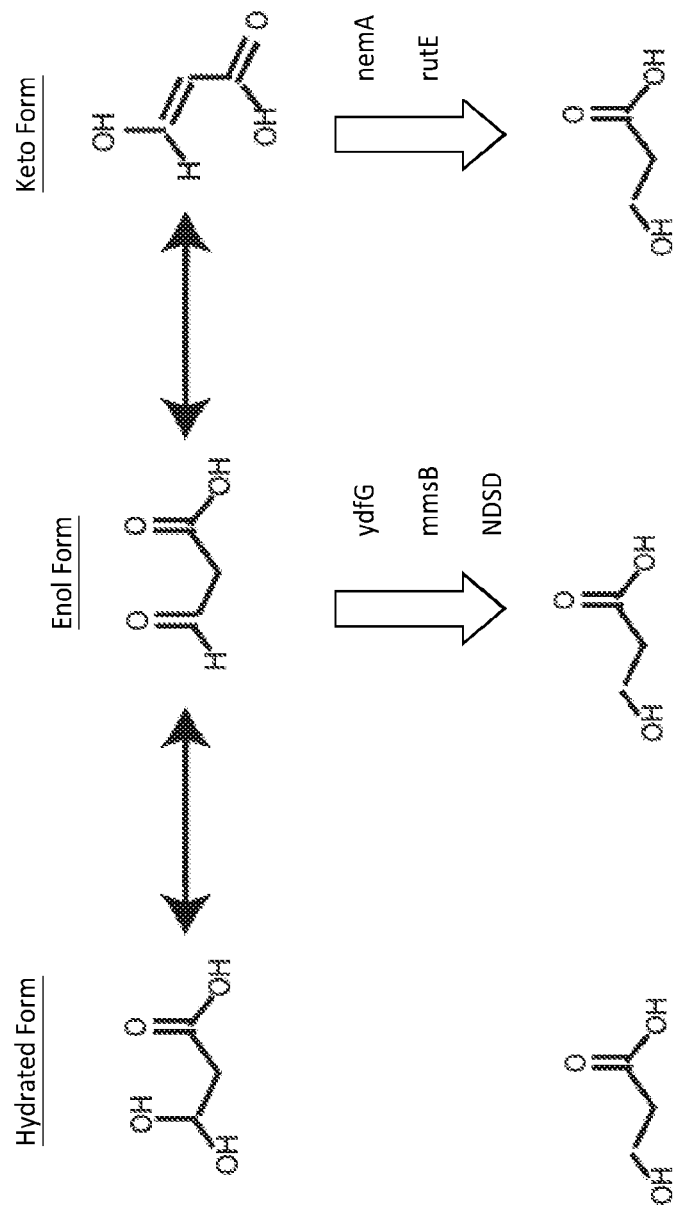
FIG. 2 Depicts some embodiments of the of various equilibrium states in the malonate semialdehyde to 3-HP reaction in a cell environment.

Following the conversion of the malonyl-CoA to malonate semialdehyde, the malonate semialdehyde is converted to 3-HP through either or both of two alternative pathways. Malonate semialdehyde may exist in at least three states; the keto form, the enol form, and hydrate form, as shown in FIG. 2. Malonate semialdehyde in the enol form, which will stabilize this form when compared to other aldehydes where the enol form is highly unfavored in the equilibrium among the three forms.

The malonate semialdehyde keto form is converted to 3-HP utilizing a 3-hydroxy acid dehydrogenase enzyme (ydfG SEQ ID NO. 21 nucleic acid, SEQ ID NO. 22 protein), a 3-hydroxyisobutyrate dehydrogenase enzyme (*Pseudomonas aeruginosa* mmsB, SEQ ID No 23 nucleic acid, SEQ ID NO. 24 protein), and/or NAD+-dependent serine dehydrogenase (*Pseudomonas* NDSD, SEQ ID NO. 25 nucleic acid, SEQ ID NO. 26 protein). In accordance with a preferred embodiment, *Pseudomonas* mmsB, *Pseudomonas* NDSD, and *E. coli* ydfG are used. The gene, ydfG from *E. coli* is largely NADPH dependent, whereas mmsB and NDSD from *Pseudomonas* can utilize either NADPH or NADH.

The malonate semialdehyde enol form is converted to 3-HP utilizing an N-ethylmaleimide reductase (nemA, SEQ ID NO. 17 nucleic acid, SEQ ID NO. 18 protein), and/or a malonic semialdehyde reductase (rutE, SEQ ID NO.19 nucleic acid, SEQ ID NO. 20 protein) from *E. coli*. These enzymes does not directly utilize NADPH or NADH. Instead, these enzymes utilize a flavin mononucleotide that is cycled between oxidized and reduced states by NADPH or NADH. The enol pathway also has advantages over the keto pathway in that equilibrium between the malonate semialdehyde enol form and 3-HP significantly favors 3-HP, making the reaction much less reversible, and essentially irreversible.

The malonate semialdehyde hydrated form may also be converted to 3-HP by either the 3-HP dehydrogenase or malonate semialdehyde reductase enzymes, although the hydrated form is more likely to be converted to the enol form as the equilibrium continuously readjusts.

In one embodiment, the microorganism herein comprise a genetic modification that include (i.e., microorganism) includes a polynucleotide encoding: (1) a monofunctional malonyl-CoA reductase gene capable of catalyzing the conversion of malonyl-CoA to malonate semialdehyde; and (2) one or more genes encoding one or more of the following enzymes: ydfG, mmsB, NDSD, rutE, and nemA or a functional homolog or a homolog with at least 80% identity.

In accordance with another aspect of the invention, there is provided an organism that is genetically modified to make 3-HP, wherein the genetic modification includes a polynucleotide encoding: (1) a monofunctional malonyl-CoA reductase gene capable of catalyzing the conversion of malonyl-CoA to malonate semialdehyde; (2) one or more genes encoding one or more enzymes capable of converting malonate semialdehyde keto form to 3-HP; and (3) one or more genes encoding one or more enzymes capable of converting either the malonate semialdehyde enol form or the malonate semialdehyde hydrated form to 3-HP.

In certain aspects the invention provides monofunctional malonyl-CoA reductase enzyme fused to a dehydrogenase enzyme that is either: (1) primarily not NADPH-dependent; (2) primarily NADH-dependent; (3) primarily flavin-dependent; (4) less susceptible to 3-HP inhibition at high concentration; and/or (5) catalyzes a reaction pathway to 3-HP that is substantially irreversible.

In certain aspects the invention also provides monofunctional malonyl-CoA reductase enzyme fused to a dehydrogenase enzyme that is NADPH-dependent.

Suitable 3-HP dehydrogenase enzymes that are largely NADH-dependent that can be used with the claimed invention include, but are not limited to, mmsB or NDSD. Suitable malonate reductase enzymes that are flavin-dependent include, but are not limited to, rutE and nemA. Suitable 3-HP dehydrogenase enzymes that are less susceptible 3-HP inhibition at high concentration that can be used with the claimed invention include, but are not limited to, ydfG and NDSD. Suitable 3-HP dehydrogenase or malonate semialdehyde dehydrogenase enzymes that catalyze a reaction pathway to 3-HP that is substantially irreversible are rutE and nemA.

In certain aspects the invention provides monofunctional malonyl-CoA reductase enzyme fused to one or more dehydrogenase enzymes. Malonate semialdehyde, which is the intermediate product in the conversion of malonyl-CoA to 3-HP can be very reactive. Therefore, it is advantageous to have a reaction pathway wherein the residence time of malonate semialdehyde within the cell is minimized, and its conversion to 3-HP occurs quickly. By fusing the malonyl-CoA reductase with the malonate semialdehyde dehydrogenase to create a multi-domain protein (e.g., two domain protein) and having the MCR and dehydrogenase domains adjacent in the sequence, when the the malonate semialdehyde is quickly is quickly converted to 3-HP.

In certain aspects the invention provides first monofunctional malonyl-CoA reductase enzyme fused to a first dehydrogenase enzyme of one type and second monofunctional malonyl-CoA reductase enzyme fused to a dehydrogenase enzyme of a different type than the first dehydrogenase enzyme. Suitable different dehydrogenase enzymes include, but are not limited to, enzymes that function on the different forms of malonate semialdehyde.

In certain aspects the invention provides for microorganisms comprising a genetic modification that include but are not limited to the malonyl-CoA reductase from *S. tokadaii* is fused to ydfG, mmsB, NDSD, rutE, or nemA (or some combination thereof). The fused enzyme may include any of the following configurations: mcr-ydfG, mcr-mmsB, mcr-NDSD, mcr-rutE, mcr-nemA, mcr-ydfG-mmsB, mcr-ydfG-NDSD, mcr-ydfG-rutE, mcr-ydfG-nemA, mcr-mmsB-ydfG, mcr-mmsB-NDSD, mcr-mmsB-rutE, mcr-mmsB-nemA, mcr-NDSD-ydfG, mcr-NDSD-mmsB, mcr-NDSD-rutE, mcr-NDSD-nemA, mcr-rutE-ydfG, mcr-rutE-mmsB, mcr-rutE-NDSD, mcr-rutE-nemA, mcr-nemA-ydfG, mcr-nemA-mmsB, mcr-nemA-NDSD, or mcr-nemA-rutE or functional homolog or homolog with 80% sequence identity thereof.

In certain aspects the invention provides for microorganisms comprising a genetic modification that include but are not limited to the malonyl-CoA reductase from *C. aggregans* is fused to ydfG, mmsB, NDSD, rutE, or nemA (or some combination thereof). The fused enzyme may include any of the following configurations: mcr-ydfG, mcr-mmsB, mcr-NDSD, mcr-rutE, mcr-nemA, mcr-ydfG-mmsB, mcr-ydfG-NDSD, mcr-ydfG-rutE, mcr-ydfG-nemA, mcr-mmsB-ydfG, mcr-mmsB-NDSD, mcr-mmsB-rutE, mcr-mmsB-nemA, mcr-NDSD-ydfG, mcr-NDSD-mmsB, mcr-NDSD-rutE, mcr-NDSD-nemA, mcr-rutE-ydfG, mcr-rutE-mmsB, mcr-rutE-NDSD, mcr-rutE-nemA, mcr-nemA-ydfG, mcr-nemA-mmsB, mcr-nemA-NDSD, or mcr-nemA-rutE or functional homolog or homolog with 80% sequence identity thereof.

In certain aspects the invention provides for microorganisms comprising a genetic modification that include but are not limited to the malonyl-CoA reductase from *O. trichoides* is fused to ydfG, mmsB, NDSD, rutE, or nemA (or some combination thereof). The fused enzyme may include but are not limited to any of the following configurations: mcr-ydfG, mcr-mmsB, mcr-NDSD, mcr-rutE, mcr-nemA, mcr-ydfG-mmsB, mcr-ydfG-NDSD, mcr-ydfG-rutE, mcr-ydfG-nemA, mcr-mmsB-ydfG, mcr-mmsB-NDSD, mcr-mmsB-rutE, mcr-mmsB-nemA, mcr-NDSD-ydfG, mcr-NDSD-mmsB, mcr-NDSD-rutE, mcr-NDSD-nemA, mcr-rutEydfG, mcr-rutE-mmsB, mcr-rutE-NDSD, mcr-rutE-nemA, mcr-nemA-ydfG, mcr-nemA-mmsB, mcr-nemA-NDSD, or mcr-nemA-rutE or functional homolog or homolog with 80% sequence identity thereof.

Enhanced Mutated Monofunctional MCR for Bioproduction

In certain aspects the invention provides for microorganisms comprising a genetic modification that include mutated form of stMCR that has enhanced activity at about 20° C. to about 44° C., about 30° C. to about 37° C., or about 32° C. to about 38° C. Such mutate forms may be designed based on the crystal structure now available for stMCR [Demmer et al., J. Biol. Chem. 288:6363-6370, 2013].

It is also contemplated the carboxylase domains of the malonyl-CoA reductase derived from *Chloroflexus aggregans, Oscillochloris trichoides* can be enhanced by mutations in the carboxylase binding domain to provide increased 3-HP production over the natural occurring enzyme.

The carboxylase activity of the malonyl-CoA reductase derived from *Chloroflexus aurantiacus* can be enhanced activity. In certain aspects the invention provides for mutated form of it carboxylase domain to provide increased 3-HP production over the natural occurring enzyme.

In certain aspects the invention provides for microorganisms comprising a genetic modification that include carboxylase domains of the malonyl-CoA reductase derived from *C. aggregans* is fused to ydfG, mmsB, NDSD, rutE, or nemA (or some combination thereof). It is contemplated that the any of the enhanced MCR by mutation, as provide above, may be fused in any of the following configurations including but not limited to mcr-ydfG, mcr-mmsB, mcr-NDSD, mcr-rutE, mcr-nemA, mcr-ydfG-mmsB, mcr-ydfG-NDSD, mcr-ydfG-rutE, mcr-ydfG-nemA, mcr-mmsB-ydfG, mcr-mmsB-NDSD, mcr-mmsB-rutE, mcr-mmsB-nemA, mcr-NDSD-ydfG, mcr-NDSD-mmsB, mcr-NDSD-rutE, mcr-NDSD-nemA, mcr-rutE-ydfG, mcr-rutE-mmsB, mcr-rutE-NDSD, mcr-rutE-nemA, mcr-nemA-ydfG, mcr-nemA-mmsB, mcr-nemA-NDSD, or mcr-nemA-rutE or functional homolog or homolog with 80% sequence identity thereof.

IV. Salt-Tolerant Enzymes

The growth of engineered microorganism for enhanced production of a chemical product, such as *E. coli* is severely inhibited by high salt concentrations accumulated when the chemical product is produced at high rate within the organism.

Dose-dependent studies with increasing amounts of NaCl and Na-3-HP show that salt has inhibitory effects on ACCase activity which is essential to fatty acid biosynthesis of membranes required for growth and propagation and for the production of 3-HP (see EXAMPLE 1). Thus, the use of salt-tolerant enzymes in 3-HP production should increase 3-HP production in a host cell.

A. Enzymes from Halophilic Organisms

Halophiles are characterized as organisms with a great affinity for salt. In some instances a halophilic organism is one that requires at least 0.05M, 0.1M, 0.2M, 0.3M or 0.4M concentrations of salt (NaCl) for growth. Halophiles live in hypersaline environments that are generally defined occurring to their salt concentration of their habitats. Halophilic organisms that are defined as "Slight salt affinity" have optimal growth at 2-5% NaCl, moderate halophiles have optimal growth at 5-20% NaCl and extreme halophiles have optimal growth at 20-30% NaCl.

Depending on the conditions of that the genetically engineered microorganism is under one might use homologous enzymes of the invention specifically, for example, from a moderate halophiles or an extreme halophiles depending on the engineered cell's environment.

In certain aspects the invention provides for microorganisms comprising a genetic modification that includes enzymes of the invention provided herein from slight halophiles organisms. In certain aspects the invention provides for microorganisms comprising a genetic modification that includes enzymes of the invention provided herein from moderate halophiles organisms. In certain aspects the invention provides for microorganisms comprising a genetic modification that includes homologous enzymes of the invention provided herein from extreme halophiles organisms.

Homology with genes provided by the invention may be determined by analysis with BLASTN version 2.0 provided through the NCBI website. Homology with proteins provided by the invention may be determined by analysis with BLASTP version 2.2.2 provided through the NCBI website. This program with aligns the disclosed fragments being compared and determines the extent of identity or similarity between them.

To date there are many sequenced halophilic organisms which can be used with the claimed invention. Examples of some sequenced halophilic organisms include but are not limited to *Chromohalobacter salexigens, Flexistipes sinusarabici* strain (MAS10T), *Halobacterium* sp. NRC-1, *Haloarcula marismortui, Natronomonas pharaonis, Haloquadratum walsbyi, Haloferax volcanii, Halorubrum lacusprofundi, Halobacterium* sp. R-1, *Halomicrobium mukohataei, Halorhabdus utahensis, Halogeometricum borinquense, Haloterrigena turkmenica, Natronobacterium gregoryi* SP2, *Halalkalicoccus jeotgali, Natrialba magadii, Haloarcula hispanica, Halopiger xanaduensis, Halophilic archaeon* DL31, *Haloferax mediterranei, Halovivax ruber, Natronococcus gregoryi*, and *Natronococcus occultus*.

Examples of suitable moderate halophilic organisms in which homologous enzymes of the invention can be derived from include but are not limited to eukaryotes such as crustaceans (e.g. *Artemia salina*), insects (e.g. *Ephydra hians*), certain plants from the genera *Salicornia* spp, algae (e.g. *Dunaliella viridis*), fungi, and protozoa (e.g. *Fabrea salina*), phototrophic organisms, such as planktonic and microbial mat-formers cyanobacteria as well as other anaerobic red and green sulphur bacteria from the genera *Ectothiorhodospira* spp.) and non-sulphur bacteria from the genera *Chromatium* spp.; gram-negative anaerobic bacteria, for example from the genera *Haloanaerobacter* spp. some of which are methanogenic, for example from the genera *Methanohalophilus* spp. and either aerobic or facultative such as species from the genera *Halomonas, Chromohalobacter, Salinovibrio, Pseudomonas*, for example (e.g. *Halomonase elongate*); gram-positive bacteria from genera such as *Halobacillus, Bacillus, Marinococcus*, etc. as well as some actinomycetes, for example, *Actinopolyspora halophila*.

Genomic and Proteomic Hallmarks of Halophilic Organisms

Comparative genomic and proteomic studies of halophiles and non-halophiles reveal some common trends in the genomes and proteomes of halophiles. At the protein level, halophilic organisms are characterized by low hydrophobicity, over-representation of acidic residues, especially Asp, under-representation of Cys, lower propensities for helix formation and higher propensities for coil structure.

At the DNA level, halophilic organisms are characterized by the dinucleotide abundance profiles of halophilic genomes bear some common characteristics, which are quite distinct from those of non-halophiles, and hence may be regarded as specific genomic signatures for salt-adaptation. The synonymous codon usage in halophiles also exhibits similar patterns regardless of their long-term evolutionary history.

In certain aspects the invention provides for microorganisms comprising a genetic modification that the proteins provided by the invention that are modified for salt tolerance such that they has low hydrophobicity, over-representation of acidic residues, especially Asp, under-representation of Cys, lower propensities for helix formation and higher propensities for coil structure.

Suitable salt-tolerant enzymes can include enzymes from salt-tolerant organisms. Salt-tolerant organisms (such as, for example, halophiles) include any living organism that are adapted to living in conditions of high salinity. Suitable salt-tolerant enzymes can include enzymes from salt-tolerant organism that are homologs of the following enzymes: Sucrose-6-phosphate hydrolase (cscA from *E. coli*), glucose-6-phosphate isomerase (pgi from *E. coli*), fructokinase (cscK from *E. coli*), fructose-1,6-bisphosphatase (yggF from *E. coli*), fructose 1,6-bisphosphatase (ybhA from *E. coli*), fructose 1,6-bisphosphatase II (glpX from *E. coli*), fructose-1,6-bisphosphatase monomer (fbp from *E. coli*), 6-phosphofructokinase-1 monomer (pfkA from *E. coli*), 6-phosphofructokinase-2 monomer (pfkB from *E. coli*), fructose bisphosphate aldolase monomer (fbaB from *E. coli*), fructose bisphosphate aldolase monomer (fbaA from *E. coli*), triose phosphate isomerase monomer (tpiA), glyceraldehyde 3-phosphate dehydrogenase-A monomer (gapA from *E. coli*), phosphoglycerate kinase (pgk), 2,3-bisphosphoglycerate-independent phosphoglycerate mutase (gpmM from *E. coli*), 2,3-bisphosphoglycerate-dependent or tdcE (from *E. coli*), phosphoglycerate mutase (gpmA), enolase (eno from *E. coli*), phosphoenolpyruvate carboxylase (ppc from *E. coli*), malate dehydrogenase (mdh), fumarase A (fum from *E. coli*), fumarase B (fumB), fumarase C (fumC from *E. coli*), phosphoenolpyruvate synthetase (ppsA from *E. coli*), pyruvate kinase I monomer (pykF from *E. coli*), pyruvate kinase II monomer (pykA from *E. coli*), fumarate reductase (frdABCD from *E. coli*), lipoamide dehydrogenase (lpd from *E. coli*), pyruvate dehydrogenase (aceE from *E. coli*), pyruvate dehydrogenase (aceF from *E. coli*), pyruvate formate-lyase (pflB from *E. coli*), acetyl-CoA carboxylase (accABCD from *E. coli*), malonyl CoA reductase (mcr), 3HP dehydrogenase (mmsB, NDSD, or ydfG), malonate semialdehyde reductase (nemA, rutE from *E. coli*), or a combination thereof.

Suitable salt-tolerant enzyme homologs that can be used with the claimed invention can have at least 99%, 98%, 97%, 96%, 95%, 94%, 93%, 92%, 91%, 90%, 89%, 88%, 87%, 86%, 85%, 84%, 83%, 82%, 81% or 80%, overall amino acid or nucleotide identity to the above enzymes. Suitable salt-tolerant enzyme homologs that can be used with the claimed invention can have at least 99%, 98%, 97%, 96%, 95%, 94%, 93%, 92%, 91%, 90% 89%, 88%, 87%, 86%, 85%, 84%, 83%, 82%, 81% or 80%, amino acid or nucleotide to the essential protein function domains of the enzymes above. Suitable salt-tolerant enzyme homologs that can be used with the claimed invention can have at least 99%, 98%, 97%, 96%, 95%, 94%, 93%, 92%, 91%, 90%, 89%, 88%, 87%, 86%, 85%, 84%, 83%, 82%, 81% or 80% overall amino acid or nucleotide to the essential binding amino acids within an essential protein function domain of the enzymes above.

In accordance with a preferred embodiment of the invention, suitable salt-tolerant enzyme homologs are enzymes from one of the following organisms: *Halomonas elongata, Salinibacter rubur,* or *Halobacterium* species (Archaea).

In accordance with a preferred embodiment of the present invention, there is provided a non-salt-tolerant organism that is genetically modified to make 3-HP, wherein the genetic modification includes a polynucleotide encoding an acetyl-CoA carboxylase from a salt-tolerant organism. In accordance with a preferred embodiment, the acetyl-CoA carboxylase subunits accA, accB, accC and accD is from *Halomonas elongata*.

V. Chemical Transporter

In accordance with another aspect of the present invention, any of the microorganisms herein may be genetically modified to introduce a nucleic acid sequence coding for a polypeptide that: (1) facilitates the exportation of the chemical of interest or the export of an inhibitory chemical from within the cell to the extracellular media; and/or (2) facilitates the importation from the extracellular media to within the cell of a reactant, precursor, and/or metabolite used in the organism's production pathway for producing the chemical of interest.

3-HP Exporter

In accordance with a preferred embodiment, this invention relates to the bioproduction of 3-HP using a genetically modified *E. coli* organism. Thus, the present invention contemplates of a host cell genetically modified to express or increase expression of an exporter that can function to transfer 3HP from the cellular environment extracellularly.

Bacterial cells, such as *E. coli*, have at least five different types of exporters: the major facilitator superfamily (MFS); the ATP-binding cassette superfamily (ABC); the small multidrug resistance family (SMR); the resistance-nodulation-cell division superfamily (RND); and the multi antimicrobial extrusion protein family (MATE). In addition, amino acid exporters, which are common to almost all host cells, are likely to export 3-HP. Additionally, solvent tolerance transporters, for example bromoacetate, butanol, isobutanol and the alike may be used to export 3-HP.

In certain aspects the invention provides a host cell with a recombinant exporter wherein the exporter is an MFS exporter, ABC exporter, SMR exporter, RND exporter, MATE exporter, amino acid exporter, solvent tolerance transporter or a combination thereof.

Suitable exporters that can be used with the s herein invention include but are not limited to acrD, bcr, cusA, dedA, eamA, eamB, eamH, emaA, emaB, emrB, emrD, emrKY, emrY, garP, gudP, hsrA, leuE, mdlB, mdtD, mdtG, mdtL, mdtM, mhpT, rhtA, rhtB, rhtC, thtB, yahN, yajR, ybbP, ybiF, ybjJ, ycaP, ydcO, yddG, ydeD, ydgE, yddG, ydhC, ydhP, ydiN, ydiM, ydjE, ydjl, ydjK, yeaS, yedA, yeeO, yegH, yggA, yfcJ, yfiK, yhjE, yidE, yigK, yigJ, yijE, yjil, yjiJ, yjiO, ykgH, ypjD, ytfF, ytfL or functional homolog or homolog with 80% sequence identity thereof. Other potential transporter proteins may be identified using topology analysis as illustrated in [Daley et al., Science 308: 1321-1323, 2005].

In certain aspects the invention provides the exporter to be improved for binding to 3-HP. In certain aspects the invention provides the exporters named to be further enhance by genetic modification of the predicted cytoplasmic domain to increase 3-HP binding. In certain aspects the invention provides the exporter to be improved for binding to 3-HP. In certain aspects the invention provides the exporters named to be further enhance by genetic modification of the predicted transmembrane binding domain to increase 3-HP binding or incorporation into the host cell membrane.

Suitable exporter homologs that can be used with the claimed invention can have at least 99%, 98%, 97%, 96%, 95%, 94%, 93%, 92%, 91%, 90%, 89%, 88%, 87%, 86%, 85%, 84%, 83%, 82%, 81% or 80% overall amino acid or nucleotide identity to the above exporters. Suitable exporter homologs that can be used with the claimed invention can have 99%, 98%, 97%, 96%, 95%, 94%, 93%, 92%, 91%, 90%, 89%, 88%, 87%, 86%, 85%, 84%, 83%, 82%, 81% or 80% amino acid or nucleotide to the essential protein function domains of the exporters above. Suitable exporter homologs that can be used with the claimed invention can have at least 99%, 98%, 97%, 96%, 95%, 94%, 93%, 92%, 91%, 90%, 89%, 88%, 87%, 86%, 85%, 84%, 83%, 82%, 81% or 80% overall amino acid or nucleotide to the essential binding amino acids within an essential exporter domain of the enzymes above.

In certain aspects the invention provides for at least of the exporters provided herein to be expressed in a host cell to increase the chemical production of 3-HP in a host cell. In certain aspects the invention provides for at least of the exporters provided herein to be expressed in a host cell and with a genetic modification of tig to increase the chemical production of 3-HP in a host cell.

In certain aspects the invention provides for one exporter to be further modified by on one more genetic modulates so that the expression level and timing of expression of the exporter can be controlled in the host cell. In certain aspects the invention provides for one exporter to be further modified by an inducible promoter, RBS, high, multicopy plasmid or combination thereof, as provide herein, in order to control its expression in the host cell.

In certain aspects the invention provides exporters provide herein to be expressed in a host cell in equal ratio. In certain aspects the invention provides exporters provide herein to be expressed in a host cell in equal 1:2 ratio. In certain aspects the invention provides exporters provide herein to be expressed in a host cell in equal 1:3 ratio. In certain aspects the invention provides exporters provide herein to be expressed in a host cell in equal 1:4 ratio. In certain aspects the invention provides exporters provide herein to be expressed in a host cell in equal 2:3 ratio.

In certain aspects the invention provides for the exporter to maintain the host cell at pH 7.0-7.4 during the continuous production phase. In certain aspects the invention provides for the exporter and the means for importing a base inside the cell in order to maintain the host cell at pH 7.0-7.4 during the continuous production phase. In certain aspects the invention provides for the exporter maintain the host cell at pH 3.0 to pH 4.0, pH 4.0 to pH 5.0, pH 5.0 to pH 6.0, pH 6.0 to pH 7.0, pH 7.0 to pH 8.0, pH 8.0 to pH 9.0, or pH 9.0 to pH 10.0 pH 7.0-7.3 during the continuous production phase. In certain aspects the invention provides for the exporter and the means for importing a base inside the cell in order to maintain the host cell at pH 3.0 to pH 4.0, pH 4.0 to pH 5.0, pH 5.0 to pH 6.0, pH 6.0 to pH 7.0, pH 7.0 to pH 8.0, pH 8.0 to pH 9.0, or pH 9.0 to pH 10.0 pH 7.0-7.3 during the continuous production phase.

In accordance with this aspect of the present invention, addition modifications to the host cell may be made to further enhance the transporter's function. In particular, deletion of the tig gene from the genome of the host cell may enhance expression and total activity of integral membrane proteins such as exporters and importers.

Bicarbonate Importer

Figure 3:
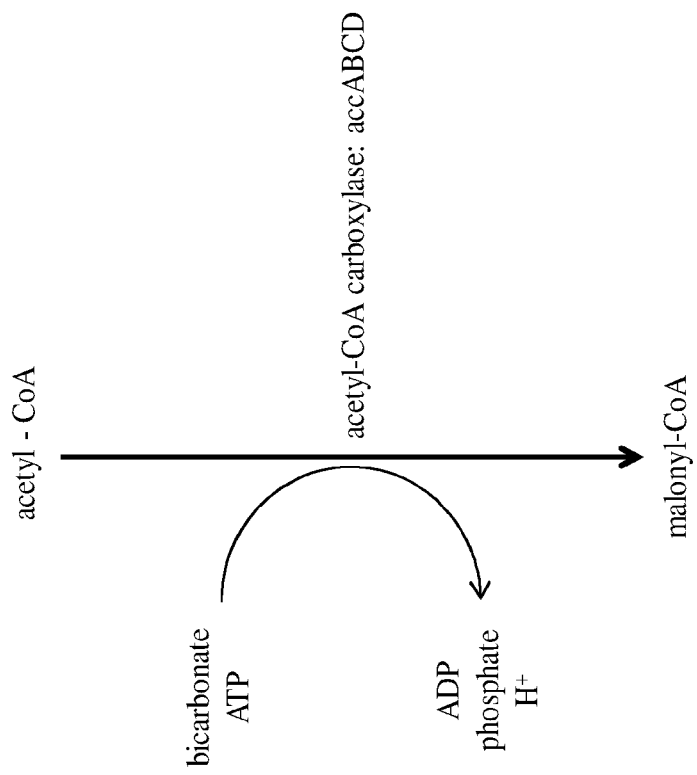
FIG. 3 Depicts some embodiments of the reaction catalyzed by acetyl-CoA carboxylase (ACCase)

One of the key steps in the conversion of biomass to 3-HP is the conversion of acetyl-CoA to malonyl-CoA, which is illustrated in FIG. 3.

As shown in FIG. 3, this reaction is catalyzed by the acetyl-CoA carboxylase, and bicarbonate is a reactant needed to drive the reaction. One of the primary sources of bicarbonate to drive this reaction is carbon dioxide within the cell. Carbon dioxide is readily diffusible through a cell's membrane, and a natural equilibrium will be reached between the intracellular and extracellular carbon dioxide. As a cell produces carbon dioxide it migrates through the cell, and since it is not very soluble in the media, it will bubble out of the system and more intracellular carbon dioxide will migrate out of the cell to maintain the equilibrium. This process impedes the production of 3-HP since bicarbonate (which is in equilibrium with the dissolved carbon dioxide in the form of carbonic acid) is needed to drive the acetyl-CoA→malonyl-CoA reaction, and the intracellular carbon dioxide is the primary source for intracellular bicarbonate.

In accordance with one aspect of the present invention, an organism is provided that includes a heterologous gene encoded therein that acts as a carbon dioxide importer (i.e., it enhances the importation of carbon dioxide into the cell or inhibits the exportation of carbon dioxide from the cell), which results in increased intracellular carbon dioxide. Use of $CO_2$ an importer mitigates against the natural outflow of carbon dioxide.

In accordance with this aspect of the invention, there is provided an organism that is genetically modified, wherein the genetic modification includes a polynucleotide encoding a gene capable of importing extracellular carbon dioxide from the media to within the cell membrane or inhibiting the exportation of intracellular carbon dioxide from within the cell membrane to the media. In accordance with a preferred embodiment of the present invention, a microorganism is genetically modified to encode one or more of the following heterologous genes: bicA from *Synechococcus* species, ychM gene product of *E. coli*, yidE gene product of *E. coli*, any of the bicarbonate transporters as described in [Felce and Saier, J. Mol. Microbiol. Biotechnol. 8: 169-176, 2004 or any amino acid sequences homologous thereof (e.g., at least 80%, 85%, 90%, 95%, or 99% homologous to the amino acids sequences of the CO2 importer/exporters described herein].

Bioproduction Methods

In some applications of the invention the host cell is genetically modified for increased malonyl-CoA flux by at least one heterologous ACCase complex, such as Table 4 to further increase chemical bio-production in host cell. In some applications of the invention the host cell is genetically modified with heterologous salt tolerant enzymes, such as Table 5 to increase chemical bio-production in a host cell. In some applications of the invention the host cell is genetically modified with heterologous 3-HP exporters to further increase chemical bio-production in a host cell.

In some applications of the invention the host cell is genetically modified by at least one heterologous gene and/or salt tolerant heterologous gene of FIG. 1 or Table 5 and at least one 3-HP exporter provided herein to further increase chemical bioproduction in a host cell.

In some applications of the invention the host cell is genetically modified with a heterologous gene for increased malonyl-CoA flux, 3-HP export, at least one heterologous and/or salt tolerant heterologous gene, as provided herein, to increase chemical bio-production in a host cell. In some applications of the invention the host cell is genetically modified for increased malonyl-CoA flux, 3-HP export, at least one heterologous gene and/or salt tolerant heterologous gene and the host cell is genetically modified by at least one gene, as provided herein to increase chemical bioproduction in a host cell.

When utilizing certain organisms to create certain products, it may be advantageous to control each phase discretely. For example, depending on the pathway involved, reactions, reactants, intermediates and byproducts created during cell growth can inhibit enzyme induction and/or the organism's ability to produce the desired chemical product. Similarly, reactions, reactants, intermediates and byproducts created as part of the production pathway can impact cell growth, and even the increased concentration of the chemical product as it is produced can impede cell replication. Table. 5

VI. Multi-Phase Fermentation

In accordance with another aspect of the present invention, there is provided a method of producing a chemical product from a carbon source through a bioproduction process that comprises a controlled multi-phase production process. The multi-phase production process includes an initiation and/or completion of one or more phases of the production process is controlled by genetic modifications to the organism producing the chemical product and/or is controlled by changes made to the cell environment.

In accordance with this aspect of the invention, the bioproduction process may include two or more of the following phases: (1) growth phase; (2) induction phase; and (3) production phase. During the growth phase, the organism replicates itself and the biocatalyst needed to produce the chemical product is built up. During the induction phase, expression of key enzymes critical to the production of the chemical is induced and the enzymes accumulate within the biocatalyst to carry out the reactions required to produce the product. During the production phase organism produces the desired chemical product.

The initiation and/or completion of the growth, induction and/or production phases are controlled. In accordance with the present invention, the growth phase is dependent on the presence of a critical external reactant that will initiate growth. The initiation and completion of the growth phase is controlled by the addition and amount of the initiating reactant added to the reaction vessel.

In accordance with certain preferred embodiments of the present invention, the chemical product is 3-HP and the production organism is $E.\ coli$ or yeast. The critical external reactant may be phosphate, which is needed for replication of $E.\ coli$ cells. In accordance with a preferred embodiment, the growth phase is initiated by the addition of phosphate to a reaction vessel (together with a carbon source such as sugar and the $E.\ coli$ cells), and the duration of the growth phase is controlled by the amount of phosphate added to the system.

The induction phase is controlled by genetic modifications to the producing organism. The key enzymes triggered during this phase are engineered into the organism using promoters that are sensitive to (e.g., activated by) the depletion of the initiating reactant. As a result, once the initiating reactant is depleted, the growth phase ends, the key enzymes are activated and the induction phase begins.

In accordance with a preferred embodiment, the induction phase is controlled by key genes that encode for enzymes in the biosynthetic pathway for the product into the production organism using promoters that are activated by phosphate depletion. In one embodiment where the chemical product is 3-HP and the production organism is $E.\ coli$, the key genetic modifications may include one or more of the following: mcr, mmsB, ydfG, rutE, nemA and NDSD; genes that encode individual or fused subunits of ACCase, such as accA, accB, accC, accD, accDA fusion, and accCB fusion, and the promoters may include one or more of the promoters that direct expression of the following $E.\ coli$ genes: amn, tktB, xasA, yibD, ytfK, pstS, phoH, phnC, or other phosphate-regulated genes as described in [Baek and Lee, FEMS Microbiol Lett 264: 104-109, 2006]. In accordance with this embodiment, once the phosphate is depleted, expression of the key enzymes is activated by their promoters and the induction phase begins.

The production phase may also be controlled by genetic modifications. For example, the organism can be engineered to included mutated forms of enzymes critical to the initiation of production of the chemical product. These initiation enzymes may facilitate initiation of production either by: (1) becoming active and serving a key function in the production pathway; and/or (2) becoming inactive and thereby turning off a branch pathway or other competitive pathway that prevents or limits the production pathway leading to the chemical product. In accordance with a preferred embodiment, initiation enzymes are mutated to form temperature sensitive variants of the enzymes that are either activated by or deactivated at certain temperatures. As a result, the production phase is initiated by changing the changing the temperature within the reaction vessel.

In one embodiment, the production phase is controlled by genetically modifying the microorganism with a heterologous nucleotide sequence encoding i one or more of the following temperature sensitive enzymes: $fabI^{ts}$ (SEQ ID NO. 27), $fabB^{ts}$ (SEQ ID NO.28) and $fabD^{ts}$ (SEQ ID NO. 29). These enzymes are deactivated or shut-off at the desired temperature for production of the chemical product. These enzymes play a key role shuttling carbon atoms into the fatty acid synthesis pathway. Although fatty acid synthesis pathway is critical during the growth phase, it inhibits production of the chemical product. Once the reaction vessel temperature is changed, the temperature sensitive enzymes are deactivated and the fatty acid synthesis pathway shuts down thereby allowing the production pathway of the chemical product to ramp up.

In accordance with the present invention, the growth phase can last be between 10 to 40 hours, or about 15 to about 35 hours, or about 20 to about 30 hours. The induction phase may be for about 1 to about 6 hours, about 1 to about 5 hours, or about 2 to about 4 hours. The production phase may be greater than 5, 10, 15, 20, 25, 30, 35, 40, 45, 50, 55, 60, 65, 70, 75, 80, 85, 90, 95 or 100 hours depending on the amount of chemical product that is desired.

In accordance with the present invention, the growth phase and induction phase are conducted at a temperature of about 25° C. to about 35° C., about 28° C. to about 32° C., or about 30° C. The production phase is conducted at a temperature of about 35° C. to about 45° C., about 35° C. to about 40° C., or about 36° C. to about 38° C. Preferably, the production phase temperature is higher than the induction phase temperature, and the increase in temperature that initiates the production phase occurs over a period of about 1 to about 5 hours, about 1 to about 3 hours, about 2 hours, or about 1 hour.

In accordance with the present invention, there is provided a method of producing a chemical product from a renewable carbon source through a bioproduction process comprising:
 (1) constructing a genetically modified organism capable of converting said renewable carbon source to said chemical product, wherein said genetically modified organism requires inorganic phosphate for growth and comprises: (a) at least one heterologous gene whose expression is regulated by a promoter sensitive to inorganic phosphate levels within a culture system, wherein said gene provides a critical function in converting said carbon source to said chemical product and is not required for the genetically modified organism to replicate; and (b) a gene encoding a temperature-sensitive enzyme;

(2) forming a culture system comprising said carbon source in an aqueous medium and said genetically modified microorganism;

(3) maintaining the culture system under conditions that allow the genetically modified microorganism to replicate comprising maintaining a sufficient level of inorganic phosphate within said culture system;

(4) allowing the inorganic phosphate to deplete thereby triggering the expression of the gene regulated by a promoter sensitive to inorganic phosphate levels; and (5) changing the temperature of the culture system thereby activating or deactivating said temperature-sensitive enzyme and initiating the production of said chemical product.

In accordance with the present invention, there is provided a method of producing 3-hydropropionic acid (3-HP) from a renewable carbon source, comprising:

(1) constructing a genetically modified organism capable of converting said renewable carbon source to 3-HP, wherein said genetically modified organism requires inorganic phosphate for growth and comprises: (a) at least one heterologous gene whose expression is regulated by a promoter sensitive to inorganic phosphate levels within a culture system, wherein said gene is selected from the group consisting of mcr, mmsB, ydfG, rutE, nemA, NDSD, accA, accB, accC, accD, accDA fusion, and accCB fusion; and (b) a gene encoding a temperature-sensitive enzyme selected from the group consisting of fabI, fabB and fabD;

(2) forming a culture system comprising said carbon source in an aqueous medium, phosphate and said genetically modified microorganism, and thereby initiating a growth phase during which the genetically modified microorganism replicates;

(3) maintaining a sufficient level of inorganic phosphate within said culture system until the desired level of cell growth is achieved;

(4) allowing the inorganic phosphate to deplete thereby initiating an induction phase which begins the expression of said gene regulated by a promoter sensitive to inorganic phosphate levels; and (5) changing the temperature of the culture system thereby activating or deactivating said temperature-sensitive enzyme and initiating a growth phase during which said genetically modified microorganism produces 3-HP.

Fermentation Conditions

Depending on the host cell fermentation may be performed under aerobic, microaerobic, or anaerobic conditions, with or without agitation. The operation of culture systems to achieve aerobic, microaerobic and anaerobic conditions are well known to those of ordinary skill in the art.

Suitable pH ranges for fermentation depend on the multiple factors such as the host cell. In some applications of the invention fermentation can occur between various pH ranges for example, pH 3.0 to pH 4.0, pH 4.0 to pH 5.0, pH 5.0 to pH 6.0, pH 6.0 to pH 7.0, pH 7.0 to pH 8.0, pH 8.0 to pH 9.0, or pH 9.0 to pH 10.0. However, the actual pH conditions for a particular application are not meant to be limited by these ranges and can be between the expressed pH ranges if it provides more optimal production of the fermentation process, such as increased 3-HP production.

VII. Genes and Proteins for the Bioproduction of Chemicals

An overview of the engineered pathways provided by the invention in a host cell is shown in FIG. 1. Various combinations of the pathways shown can be carried out by various combinations of genetic modifications to key enzymes either in the intrinsic pathways or supplied through the transformation of a heterologous gene.

In some applications of the genetically modified microorganism of the invention may comprise a single genetic modification, or one or more genetic modifications. Various types of genetic modifications that can be used with the invention are disclosed herein.

In some embodiments the genetic modified organism of the invention can comprise a genetic modification to the following gene/proteins or a homolog with at least 80% identity to or a functional homolog of: bifunctional malonyl-CoA reductase (MCR from *Chloroflexus aurantiacus*), monofunctional malonyl-CoA reductase (caMCR from *Chloroflexus aurantiacus*), malonyl-CoA reductase (stMCR from *Sulfolobus tokodaii*.), Enzyme: malonyl-CoA reductase (cgMCR from *Chloroflexus aggregans*), Enzyme: malonyl-CoA reductase (otMCR from *Oscillochloris trichoides*), Polypeptide: host restriction; endonuclease R (hsdR from *E. coli*), lactose metabolism (lac from *E. coli*), L-rhamnulose kinase (rhaB from *E. coli*), rhamnulose-1-phosphate aldolase (rhaD from *E. coli*), Enzyme: β-galactosidase (lacZ from *E. coli*), L-ribulose 5-phosphate 4-epimerase (araD from *E. coli*), L-ribulokinase (araB from *E. coli*), Enzyme: D-lactate dehydrogenase-fermentative (ldhA from *E. coli*), enzyme: pyruvate formate-lyase (pflB from *E. coli*), Enzyme: phosphate acetyltransferase/phosphate propionyltransferase (pta from *E. coli*), Enzyme: pyruvate oxidase (poxB from *E. coli*), Enzyme: methylglyoxal synthase (mgsA from *E. coli*), enzyme: Acetate kinase (ackA from *E. coli*), enzymes: phosphotransacetylase-acetate kinase (pta-ack from *E. coli*), Enzyme: enoyl-[acyl-carrier-protein] reductase (fabI from *E. coli*), Protein: zeocin binding protein (zeoR from *Streptoalloteichus hindustanus*), Enzyme: carboxytransferase moiety of acetyl-CoA carboxylase (accAD from *E. coli*), Enzyme: triose phosphate isomerase (tpiA from *E. coli*), Enzyme: biotoin carboxylase moiety of acetyl-CoA carboxylase (accBC from *E. coli*), Enzyme: transhydrogenase (pntAB from *E. coli*), Polypeptide: Lad DNA-binding transcriptional repressor (lacI from *E. coli*), Enzyme: β-ketoacyl-ACP synthases I (fabB from *E. coli*), Enzyme: β-ketoacyl-ACP synthases II (fabF from *E. coli*), Enzyme: malonyl-CoA-ACP transacylase (fabD from *E. coli*), Enzyme: pantothenate kinase (coaA from *E. coli*), Enzyme: pyruvate dehydrogenase complex (aceEF from *E. coli*), Enzyme: 3-hydroxyisobutyrate/3-HP dehydrogenase (mmsB from *Pseudomonas aeruginosa*), Enzyme: lipoamide dehydrogenase (lpd from *E. coli*), Enzyme: γ-glutamyl-γ-aminobutyraldehyde dehydrogenase (puuC from *E. coli*), Enzyme: malate synthase A (aceB from *E. coli*), Enzyme: isocitrate lyase (aceA from *E. coli*), Enzyme: isocitrate dehydrogenase phosphatase/kinase (aceK from *E. coli*), Enzyme: 3-hydroxy acid dehydrogenase (ydfG from *E. coli*), Enzyme: acetyl CoA carboxylase (accADBC from *E. coli*), Polypeptide: predicted transcriptional regulator (yieP from *E. coli*), Blastocyin resistance gene (BSD from *Schizosaccharomyces pombe*), Enzyme: pyridine nucleotide transhydrogenase (udha from *E. coli*), Protein: Cra DNA-binding transcriptional dual regulator (fruR from *E. coli*), (SCB from *E. coli*), enzyme: aldehyde dehydrogenase B (aldB from *E. coli*), Enzyme: carbonic anhydrase (cynT from *E. coli*), Enzyme: cyanase (cynS from *E. coli*), DNA gyrase toxin-antitoxin system (ccdAB from *E. coli*), Enzyme: phosphoglycerate mutase (pgi from *E. coli*), ArcA transcriptional dual regulator or Aerobic respiration control (arcA from *E. coli*), Enzyme: 6-phosphofructokinase (pfk from *E. coli*), Enzyme: glyceraldehyde 3-phosphate dehydrogenase-A complex (gapA from *E. coli*), aldehyde dehydrogenase A (alda from *E. coli*), Enzyme: glutamate dehydrogenase (gdhA from *E. coli*), Enzyme: NADH-dependent serine dehydrogenase (NDSD from *Pseudomonas aeruginosa*), Protein: threonine/homoserine efflux transporter (rhtA from *E. coli*), Enzyme: glyceraldehyde 3-phosphate dehydrogenase (gapN from *E. coli*), Phosphotransferase system (pts from *E. coli*), Enzyme: 6-phosphofructokinase II (pfkB from *E. coli*), Enzyme: methylmalonate-semialdehyde dehydrogenase (mmsA from *Pseudomonas aeruginosa*), Oxaloacetate:beta-alanine aminotransferase (OAT-1 from *Bacillus cereus*), Enzyme: aspartate 1-decarboxylase (panD from *E. coli*), Gene that confers resistance to valine (ValR from *E. coli*), Enzyme: glucokinase (glk from *E. coli*), Polypeptide: 30 S ribosomal sununit protein S12 (rpsL from *E. coli*), Polypeptide: CynR DNA-binding transcriptional repressor (cynR from *E. coli*), Transporter: galactose:H+ symporter (galP from *E. coli*), aspartate aminotransferase (aspC from *E. coli*), Enzyme: alpha-ketoglutarate reductase (serA from *E. coli*), Enzyme: 6-phosphofructokinase I (pfkA from *E. coli*), Enzyme: phosphoenolpyruvate carboxylase (ppc from *E. coli*), Enzyme: succinate-semialdehyde dehydrogenase (NADP+) (gabD from *E. coli*), Enzyme: pyruvate kinase (pyk from *E. coli*), Enzyme: oxaloacetate 4-decarboxylase (OAD from *Leuconostoc mesenteroides*), Enzyme: trigger factor; a molecular chaperone involved in cell division (tig from *E. coli*), Transcription Unit (ptsHIcrr from *E. coli*), Enzyme: acetyl-CoA acetaldehyde dehydrogenase/alcohol dehydrogenase (adhE from *E. coli*), Enzyme: fattyacyl thioesterase I (tesA from *E. coli*), Enzyme: guanosine 3'-diphosphate 5'-triphosphate 3'-diphosphatase (spoT from *E. coli*), combination of genes encoding accABCD subunits (from *E. coli* and *Halomonas elongata*), pol (from *E. coli*), Enzyme: GDP pyrophosphokinase/GTP pyrophosphokinase (relA from *E. coli*), [Enzyme Name] (me from *E. coli*), Enzyme: citrate synthase (gltA from *E. coli*), Polypeptide: DNA gyrase, subunit A (gyrA from *E. coli*), Enzyme: multifunctional 2-keto-3-deoxygluconate 6-phosphate aldolase and 2-keto-4-hydroxyglutarate aldolase and oxaloacetate decarboxylase (eda from *E. coli*), thiamin biosynthesis (thi from *E. coli*), Polypeptide: acetolactate synthase II (ilvG from *E. coli*), acetyl CoA carboxylase (accDACB from *E. coli*), Citrate synthase (ArCS from *Arthrobacter aurescens*), Acetyl-CoA carboxylase from *Corynebacter glutamicum* (CgACC from *Corynebacter glutamicum*), Polypeptide: ferrichrome/phage/antibiotic outer membrane porin FhuA (fhuA from *E. coli*), Transporter: phosphate:H+ symporter PitA (pitA from *E. coli*), Transporter: uracil:H+ symporter (uraA from *E. coli*), Enzyme: uracil phosphoribosyltransferase (upp from *E. coli*), Enzyme: acylphosphatase (yccX from *E. coli*), acetyl-CoA synthetase (acsA from *E. coli*), Polypeptide: restriction of methylated adenine (mrr from *E. coli*), Protein: TrpR transcriptional repressor (trpR from *E. coli*), Enzymes: glutamate 5-semialdehyde dehydrogenase/gamma-glutamyl kinase (proAB from *E. coli*), methylcytosine restriction system (mcrBC from *E. coli*), Protein: citrate lyase, citrate-ACP transferase component (citF from *E. coli*), Enzyme: thioesterase II (tesB from *E. coli*), Enzyme: DNA-specific endonuclease I (endA from *E. coli*), Enzyme: phosphate acetyltransferase (eutD from *E. coli*), Enzyme: propionate kinase (tdcD from *E. coli*), tRNA: tRNA glnV (supE from *E. coli*), Enzyme: DNA-binding, ATP-dependent protease La (lon from *E. coli*), Polypeptide: DNA strand exchange and recombination protein with protease and nuclease activity (recA from *E. coli*), Transcription Unit: restriction endonulease component of EcoKI restriction-modification system (hsdRMS from *E. coli*), Enzyme: restriction of DNA at 5-methylcytosine residues (mcrA from *E. coli*) araD (from *E. coli*), araB (from *E. coli*), rhaD (from *E. coli*), rhaB (from *E. coli*), ack (from *E. coli*), fruR (from *E. coli*), gapA (from *E. coli*), lad (from *E. coli*), lacZ (from *E. coli*), ldhA (from *E. coli*), mgsA (from *E. coli*), pfkA (from *E. coli*), pflB (from *E. coli*), pgi (from *E. coli*), poxB (from *E. coli*), pta-ack (from *E. coli*), ptsH (from *E. coli*), glut1 (from *E. coli*) and/or ack (from *E. coli*) or any combination thereof.

The use of genetic modifications in genetic elements, genes, proteins or the use of compounds, such as siRNA technology, anti-sense technology, and small molecule inhibitors supplied to the host cell that modulate the expression of gene and proteins provided by the present invention are also contemplated.

In some embodiments the genetic modified organism of the invention uses genetic elements such as siRNA ect, genes, proteins or compounds supplied to the host cell to modulate one or more of the following: bifunctional malonyl-CoA reductase (MCR from *Chloroflexus aurantiacus*), monofunctional malonyl-CoA reductase (caMCR from *Chloroflexus aurantiacus*), malonyl-CoA reductase (stMCR from *Sulfolobus tokodaii*.), Enzyme: malonyl-CoA reductase (cgMCR from *Chloroflexus aggregans*), Enzyme: malonyl-CoA reductase (otMCR from *Oscillochloris trichoides*), Polypeptide: host restriction; endonuclease R (hsdR from *E. coli*), lactose metabolism (lac from *E. coli*), L-rhamnulose kinase (rhaB from *E. coli*), rhamnulose-1-phosphate aldolase (rhaD from *E. coli*), Enzyme: β-galactosidase (lacZ from *E. coli*), L-ribulose 5-phosphate 4-epimerase (araD from *E. coli*), L-ribulokinase (araB from *E. coli*), Enzyme: D-lactate dehydrogenase-fermentative (ldhA from *E. coli*), enzyme: pyruvate formate-lyase (pflB from *E. coli*), Enzyme: phosphate acetyltransferase/phosphate propionyltransferase (pta from *E. coli*), Enzyme: pyruvate oxidase (poxB from *E. coli*), Enzyme: methylglyoxal synthase (mgsA from *E. coli*), enzyme: Acetate kinase (ackA from *E. coli*), enzymes: phosphotransacetylase-acetate kinase (pta-ack from *E. coli*), Enzyme: enoyl-[acyl-carrier-protein] reductase (fabI from *E. coli*), Protein: zeocin binding protein (zeoR from *Streptoalloteichus hindustanus*), Enzyme: carboxytransferase moiety of acetyl-CoA carboxylase (accAD from *E. coli*), Enzyme: triose phosphate isomerase (tpiA from *E. coli*), Enzyme: biotoin carboxylase moiety of acetyl-CoA carboxylase (accBC from *E. coli*), Enzyme: transhydrogenase (pntAB from *E. coli*), Polypeptide: Lad DNA-binding transcriptional repressor (lacI from *E. coli*), Enzyme: β-ketoacyl-ACP synthases I (fabB from *E. coli*), Enzyme: β-ketoacyl-ACP synthases II (fabF from *E. coli*), Enzyme: malonyl-CoA-ACP transacylase (fabD from *E. coli*), Enzyme: pantothenate kinase (coaA from *E. coli*), Enzyme: pyruvate dehydrogenase complex (aceEF from *E. coli*), Enzyme: 3-hydroxyisobutyrate/3-HP dehydrogenase (mmsB from *Pseudomonas aeruginosa*), Enzyme: lipoamide dehydrogenase (lpd from *E. coli*), Enzyme: γ-glutamyl-γ-aminobutyraldehyde dehydrogenase (puuC from *E. coli*), Enzyme: malate synthase A (aceB from *E. coli*), Enzyme: isocitrate lyase (aceA from *E. coli*), Enzyme: isocitrate dehydrogenase phosphatase/kinase (aceK from *E. coli*), Enzyme: 3-hydroxy acid dehydrogenase (ydfG from *E. coli*), Enzyme: acetyl CoA carboxylase (accADBC from *E. coli*), Polypeptide: predicted transcriptional regulator (yieP from *E. coli*), Blastocyin resistance gene (BSD from *Schizosaccharomyces pombe*), Enzyme: pyridine nucleotide transhydrogenase (udha from *E. coli*), Protein: Cra DNA-binding transcriptional dual regulator (fruR from *E. coli*), (SCB from *E. coli*), enzyme: aldehyde dehydrogenase B (aldB from *E. coli*), Enzyme: carbonic anhydrase (cynT from *E. coli*), Enzyme: cyanase (cynS from *E. coli*), DNA gyrase toxin-antitoxin system (ccdAB from *E. coli*), Enzyme: phosphoglycerate mutase (pgi from *E. coli*), ArcA transcriptional dual regulator or Aerobic respiration control (arcA from *E. coli*), Enzyme: 6-phosphofructokinase (pfk from *E. coli*), Enzyme: glyceraldehyde 3-phosphate dehydrogenase-A complex (gapA from *E. coli*), aldehyde dehydrogenase A (alda from *E. coli*), Enzyme: glutamate dehydrogenase (gdhA from *E. coli*), Enzyme: NADH-dependent serine dehydrogenase (NDSD from *Pseudomonas aeruginosa*), Protein: threonine/homoserine efflux transporter (rhtA from *E. coli*), Enzyme: glyceraldehyde 3-phosphate dehydrogenase (gapN from *E. coli*), Phosphotransferase system (pts from *E. coli*), Enzyme: 6-phosphofructokinase II (pfkB from *E. coli*), Enzyme: methylmalonate-semialdehyde dehydrogenase (mmsA from *Pseudomonas aeruginosa*), Oxaloacetate:beta-alanine aminotransferase (OAT-1 from *Bacillus cereus*), Enzyme: aspartate 1-decarboxylase (panD from *E. coli*), Gene that confers resistance to valine (ValR from *E. coli*), Enzyme: glucokinase (glk from *E. coli*), Polypeptide: 30 S ribosomal sununit protein S12 (rpsL from *E. coli*), Polypeptide: CynR DNA-binding transcriptional repressor (cynR from *E. coli*), Transporter: galactose:H+ symporter (galP from *E. coli*), aspartate aminotransferase (aspC from *E. coli*), Enzyme: alpha-ketoglutarate reductase (serA from *E. coli*), Enzyme: 6-phosphofructokinase I (pfkA from *E. coli*), Enzyme: phosphoenolpyruvate carboxylase (ppc from *E. coli*), Enzyme: succinate-semialdehyde dehydrogenase (NADP+) (gabD from *E. coli*), Enzyme: pyruvate kinase (pyk from *E. coli*), Enzyme: oxaloacetate 4-decarboxylase (OAD from *Leuconostoc mesenteroides*), Enzyme: trigger factor; a molecular chaperone involved in cell division (tig from *E. coli*), Transcription Unit (ptsHIcrr from *E. coli*), Enzyme: acetyl-CoA acetaldehyde dehydrogenase/alcohol dehydrogenase (adhE from *E. coli*), Enzyme: fattyacyl thioesterase I (tesA from *E. coli*), Enzyme: guanosine 3'-diphosphate 5'-triphosphate 3'-diphosphatase (spoT from *E. coli*), combination of genes encoding accABCD subunits (from *E. coli* and *Halomonas elongata*), pol (from *E. coli*), Enzyme: GDP pyrophosphokinase/GTP pyrophosphokinase (relA from *E. coli*), [Enzyme Name] (me from *E. coli*), Enzyme: citrate synthase (gltA from *E. coli*), Polypeptide: DNA gyrase, subunit A (gyrA from *E. coli*), Enzyme: multifunctional 2-keto-3-deoxygluconate 6-phosphate aldolase and 2-keto-4-hydroxyglutarate aldolase and oxaloacetate decarboxylase (eda from *E. coli*), thiamin biosynthesis (thi from *E. coli*), Polypeptide: acetolactate synthase II (ilvG from *E. coli*), acetyl CoA carboxylase (accDACB from *E. coli*), Citrate synthase (ArCS from *Arthrobacter aurescens*), Acetyl-CoA carboxylase from *Corynebacter glutamicum* (CgACC from *Corynebacter glutamicum*), Polypeptide: ferrichrome/phage/antibiotic outer membrane porin FhuA (fhuA from *E. coli*), Transporter: phosphate:H+ symporter PitA (pitA from *E. coli*), Transporter: uracil:H+ symporter (uraA from *E. coli*), Enzyme: uracil phosphoribosyltransferase (upp from *E. coli*), Enzyme: acylphosphatase (yccX from *E. coli*), acetyl-CoA synthetase (acsA from *E. coli*), Polypeptide: restriction of methylated adenine (mrr from *E. coli*), Protein: TrpR transcriptional repressor (trpR from *E. coli*), Enzymes: glutamate 5-semialdehyde dehydrogenase/gamma-glutamyl kinase (proAB from *E. coli*), methylcytosine restriction system (mcrBC from *E. coli*), Protein: citrate lyase, citrate-ACP transferase component (citF from *E. coli*), Enzyme: thioesterase II (tesB from *E. coli*), Enzyme: DNA-specific endonuclease I (endA from *E. coli*), Enzyme: phosphate acetyltransferase (eutD from *E. coli*), Enzyme: propionate kinase (tdcD from *E. coli*), tRNA: tRNA glnV (supE from *E. coli*), Enzyme: DNA-binding, ATP-dependent protease La (lon from *E. coli*), Polypeptide: DNA strand exchange and recombination protein with protease and nuclease activity (recA from *E. coli*), Transcription Unit: restriction endonulease component of EcoKI restriction-modification system (hsdRMS from *E. coli*), Enzyme: restriction of DNA at 5-methylcytosine residues (mcrA from *E. coli*). In some embodiment the genetic modifications listed above are modified further with the genetic modules provided herein.

In some embodiment the genetic modification of the genes, proteins and enzymes of the invention can be for the method of bioproduction of various chemicals which can be used to make various consumer products described herein.

In some embodiment the genetic modification of the genes, proteins and enzymes of the invention can be for the bioproduction of 1,4-butanediol (1,4-BDO) (U.S. Pub. No. 20110190513). In some embodiment the genetic modification of the genes, proteins and enzymes of the invention can be for the bioproduction of butanol (U.S. application Ser. No. 13/057,359). In some embodiment the genetic modification of the genes, proteins and enzymes of the invention can be for the bioproduction of isobutanol (U.S. application Ser. No. 13/057,359)

In some embodiment the genetic modification of the genes, proteins and enzymes of the invention can be for the bioproduction of 3-HP such and its aldehyde metabolites (U.S. application Ser. No. 13/062,917).

In some embodiment the genetic modification of the genes, proteins and enzymes of the invention can be for the bioproduction of polyketide chemical products (U.S. application Ser. No. 13/575,581).

In some embodiment the genetic modification of the genes, proteins and enzymes of the invention can be for the bioproduction of fatty acid methyl esters (U.S. Pub. No. 20110124063). In some embodiment the genetic modification of the genes, proteins and enzymes of the invention can be for the bioproduction of C4-C18 fatty acids (U.S. App No. 61/682,127).

Genetic Modifications

Various methods to achieve such genetic modification in a host strain are well known to one skilled in the art. Example of genetic modification that can be used by the claimed invention include, but are not limited to, increasing expression of an endogenous genetic element; increasing expression of an exogenous genetic element; decreasing functionality of a repressor gene; increasing functionality of a repressor gene; increasing functionality of a activator gene; decreasing functionality of a activator gene; introducing a genetic change or element integrated in the host genome, introducing a heterologous genetic element permanently, by integration into the genome or transiently by transformation with plasmid; increasing copy number of a nucleic acid sequence encoding a polypeptide catalyzing an enzymatic conversion step; mutating a genetic element to provide a mutated protein to increase specific enzymatic activity; mutating a genetic element to provide a mutated protein to decrease specific enzymatic activity; over-expressing of gene; reduced the expression of a gene; knocking out or deleting a gene; altering or modifying feedback inhibition; providing an enzyme variant comprising one or more of an impaired binding sites or active sites; increasing functionality of a siRNA, decreasing functionality of a siRNA, increasing functionality of a antisense molecule, decreasing functionality of a antisense molecule, addition of genetic modules such as RBS, '3 UTR elements to increase mRNA stability or translation; deletion of genetic modules such as RBS, '3 UTR elements to decrease mRNA stability or translation; addition or modification of genetic modules such as '5 UTR elements to increase transcription; deletion or modification of genetic modules such as '5 UTR and elements to increase transcription. In addition other genetic modules, provide herein, such a multicopy plasmids and various promoters can be used to further modify of the genetic modifications provide herein. Additionally, as known to those of ordinarily skill in the art compounds such as siRNA technology, anti-sense technology, and small molecule in inhibitors can be used to alter gene expression in the same manner as a genetic modification.

Screening methods, such as SCALE in combination with random mutagenesis may be practiced to provide genetic modifications that provide a benefit to increased production of 3-HP in a host cell. Examples of random mutagenesis can include insertions, deletions and substitutions of one or more nucleic acids in a nucleic acid of interest. In various embodiments a genetic modification results in improved enzymatic specific activity and/or turnover number of an enzyme. Without being limited, changes may be measured by one or more of the following: KM; Kcat, Kavidity, gene expression level, protein expression level, level of a product known to be produced by the enzyme, 3-HP tolerance, or by 3-HP production or by other means.

Host Cells

In some applications of the invention the host cell can be a gram-negative bacterium. In some applications of the invention the host cell can be from the genera *Zymomonas, Escherichia, Pseudomonas, Alcaligenes*, or *Klebsiella*. In some applications of the invention the host cell can be *Escherichia coli, Cupriavidus necator, Oligotropha carboxidovorans*, or *Pseudomonas putida*. In some applications of the invention the host cell is one or more an *E. coli* strains.

In some applications of the invention the host cell can be a gram-positive bacterium. In some applications of the invention the host cell can be from the genera *Clostridium, Salmonella, Rhodococcus, Bacillus, Lactobacillus, Enterococcus, Paenibacillus, Arthrobacter, Corynebacterium*, or *Brevibacterium*. In some applications of the invention the host cell is *Bacillus licheniformis, Paenibacillus macerans, Rhodococcus erythropolis, Lactobacillus plantarum, Enterococcus faecium, Enterococcus gallinarium, Enterococcus faecalis*, or *Bacillus subtilis*. In some applications of the invention the host cell is *B. subtilis* strain.

In some applications of the invention the host cell is yeast. In some applications of the invention the host cell can be from the genera *Pichia, Candida, Hansenula* or *Saccharomyces*. In some applications of the invention the host cell is *Saccharomyces cerevisiae*. In some applications of the invention the host cell is *Saccharomyces pombe.*

In some applications of the invention the host cell is an alga. In some applications of the invention the host cell is a *halophile*. In some applications of the invention the host cell is an alga. In some applications of the invention the host cell is a chemolithotrophic bacterium.

In some applications of the invention the host cell is comprised of multiple host cell types. In some applications of the invention the host cell is comprised of one host cell type. In some applications of the invention the host cell is comprised of one more species or strain of a host cell type.

Downstream Consumer Products Chemicals

3-HP purified according to the methods provided in this disclosure may be converted to various other products having industrial uses including, but not limited to, acrylamide, acrylic acid, esters of acrylic acid, 1,3-propanediol, and other chemicals, collectively referred to as "downstream chemical products" or "downstream products." In some instances the conversion is associated with the separation and/or purification steps. These downstream chemical products are useful for producing a variety of consumer products which are described in more detail below. The methods of the present invention include steps to produce downstream products of 3-HP.

As a C3 building block, 3-HP offers much potential in a variety of chemical conversions to commercially important intermediates, industrial end products, and consumer products. For example, 3-HP may be converted to acrylic acid, acrylates (e.g., acrylic acid salts and esters), 1,3-propanediol, malonic acid, ethyl-3-hydroxypropionate, ethyl ethoxy propionate, propiolactone, acrylamide, or acrylonitrile.

Additionally, 3-HP may be oligomerized or polymerized to form poly(3-hydroxypropionate) homopolymers, or co-polymerized with one or more other monomers to form various co-polymers. Because 3-HP has a single stereoisomer, polymerization of 3-HP is not complicated by the stereo-specificity of monomers during chain growth. This is in contrast to (S)-2-hydroxypropanoic acid (also known as lactic acid), which has two (D, L) stereoisomers that should be considered during its polymerizations.

As will be further described, 3-HP can be converted into derivatives starting (i) substantially as the protonated form of 3-hydroxypropionic acid; (ii) substantially as the deprotonated form, 3-hydroxypropionate; or (iii) as mixtures of the protonated and deprotonated forms. Generally, the fraction of 3-HP present as the acid versus the salt will depend on the pH, the presence of other ionic species in solution, temperature (which changes the equilibrium constant relating the acid and salt forms), and, to some extent, pressure. Many chemical conversions may be carried out from either of the 3-HP forms, and overall process economics will typically dictate the form of 3-HP for downstream conversion.

Acrylic acid obtained from 3-HP purified by the methods described in this disclosure may be further converted to various polymers. For example, the free-radical polymerization of acrylic acid takes place by polymerization methods known to the skilled worker and can be carried out, for example, in an emulsion or suspension in aqueous solution or another solvent. Initiators, such as but not limited to organic peroxides, are often added to aid in the polymerization. Among the classes of organic peroxides that may be used as initiators are diacyls, peroxydicarbonates, monoperoxycarbonates, peroxyketals, peroxyesters, dialkyls, and hydroperoxides. Another class of initiators is azo initiators, which may be used for acrylate polymerization as well as co-polymerization with other monomers. U.S. Pat. Nos. 5,470,928; 5,510,307; 6,709,919; and 7,678,869 teach various approaches to polymerization using a number of initiators, including organic peroxides, azo compounds, and other chemical types, and are incorporated by reference for such teachings as applicable to the polymers described herein.

Accordingly, it is further possible for co-monomers, such as crosslinkers, to be present during the polymerization. The free-radical polymerization of the acrylic acid obtained from dehydration of 3-HP, as produced herein, in at least partly neutralized form and in the presence of crosslinkers is practiced in certain embodiments. This polymerization may result in hydrogels which can then be comminuted, ground and, where appropriate, surface-modified, by known techniques.

An important commercial use of polyacrylic acid is for superabsorbent polymers. This specification hereby incorporates by reference Modern Superabsorbent Polymer Technology, Buchholz and Graham (Editors), Wiley-VCH, 1997, in its entirety for its teachings regarding superabsorbent polymers components, manufacture, properties and uses. Superabsorbent polymers are primarily used as absorbents for water and aqueous solutions for diapers, adult incontinence products, feminine hygiene products, and similar consumer products. In such consumer products, superabsorbent materials can replace traditional absorbent materials such as cloth, cotton, paper wadding, and cellulose fiber. Superabsorbent polymers absorb, and retain under a slight mechanical pressure, up to 25 times or more their weight in liquid. The swollen gel holds the liquid in a solid, rubbery state and prevents the liquid from leaking. Superabsorbent polymer particles can be surface-modified to produce a shell structure with the shell being more highly cross-linked than the rest of the particle. This technique improves the balance of absorption, absorption under load, and resistance to gel-blocking. It is recognized that superabsorbent polymers have uses in fields other than consumer products, including agriculture, horticulture, and medicine.

Superabsorbent polymers are prepared from acrylic acid (such as acrylic acid derived from 3-HP provided herein) and a crosslinker, by solution or suspension polymerization. Exemplary methods include those provided in U.S. Pat. Nos. 5,145,906; 5,350,799; 5,342,899; 4,857,610; 4,985,518; 4,708,997; 5,180,798; 4,666,983; 4,734,478; and 5,331,059, each incorporated by reference for their teachings relating to superabsorbent polymers.

Among consumer products, a diaper, a feminine hygiene product, and an adult incontinence product are made with superabsorbent polymer that itself is made substantially from acrylic acid converted from 3-HP made in accordance with the present invention.

Diapers and other personal hygiene products may be produced that incorporate superabsorbent polymers made from acrylic acid made from 3-HP which is produced and purified by the teachings of the present application. The following provides general guidance for making a diaper that incorporates such superabsorbent polymer. The superabsorbent polymer first is molded into an absorbent pad that may be vacuum formed, and in which other materials, such as a fibrous material (e.g., wood pulp) are added. The absorbent pad then is assembled with sheet(s) of fabric, generally a nonwoven fabric (e.g., made from one or more of nylon, polyester, polyethylene, and polypropylene plastics) to form diapers.

More particularly, in one non-limiting process, multiple pressurized nozzles, located above a conveyer belt, spray superabsorbent polymer particles (e.g., about 400 micron size or larger), fibrous material, and/or a combination of these onto the conveyer belt at designated spaces/intervals. The conveyor belt is perforated and under vacuum from below, so that the sprayed on materials are pulled toward the belt surface to form a flat pad. In various embodiments, fibrous material is applied first on the belt, followed by a mixture of fibrous material and the superabsorbent polymer particles, followed by fibrous material, so that the superabsorbent polymer is concentrated in the middle of the pad. A leveling roller may be used toward the end of the belt path to yield pads of uniform thickness. Each pad thereafter may be further processed, such as to cut it to a proper shape for the diaper, or the pad may be in the form of a long roll sufficient for multiple diapers. Thereafter, the pad is sandwiched between a top sheet and a bottom sheet of fabric (one generally being liquid pervious, the other liquid impervious), for example on a conveyor belt, and these are attached together, for example by gluing, heating or ultrasonic welding, and cut into diaper-sized units (if not previously so cut). Additional features may be provided, such as elastic components, strips of tape, etc., for fit and ease of wearing by a person.

The ratio of the fibrous material to polymer particles is known to affect performance characteristics. In some cases, this ratio is between 75:25 and 90:10 (see e.g., U.S. Pat. No. 4,685,915, incorporated by reference for its teachings of diaper manufacture). Other disposable absorbent articles may be constructed in a similar fashion, such as absorbent articles for adult incontinence, feminine hygiene (sanitary napkins), tampons, etc. (see, for example, U.S. Pat. Nos. 5,009,653; 5,558,656; and 5,827,255 incorporated by reference for their teachings of sanitary napkin manufacture).

Low molecular weight polyacrylic acid has uses for water treatment, and as a flocculant and thickener for various applications including cosmetics and pharmaceutical preparations. For these applications, the polymer may be uncrosslinked or lightly cross-linked, depending on the specific application. The molecular weights are typically from about 200 to about 1,000,000 g/mol. Preparation of these low molecular weight polyacrylic acid polymers is described in U.S. Pat. Nos. 3,904,685; 4,301,266; 2,798,053; and 5,093,472, each of which is incorporated by reference for its teachings relating to methods to produce these polymers.

Acrylic acid may be co-polymerized with one or more other monomers selected from acrylamide, 2-acrylamido-2-methylpropanesulfonic acid, N,N-dimethylacrylamide, N-isopropylacrylamide, methacrylic acid, and methacrylamide, to name a few. The relative reactivities of the monomers affect the microstructure and thus the physical properties of the polymer. Co-monomers may be derived from 3-HP, or otherwise provided, to produce co-polymers. Ullmann's Encyclopedia of Industrial Chemistry, Polyacrylamides and Poly(Acrylic Acids), WileyVCH Verlag GmbH, Wienham (2005), is incorporated by reference herein for its teachings of polymer and co-polymer processing.

Acrylic acid can in principle be copolymerized with almost any free-radically polymerizable monomers including styrene, butadiene, acrylonitrile, acrylic esters, maleic acid, maleic anhydride, vinyl chloride, acrylamide, itaconic acid, and so on. End-use applications typically dictate the co-polymer composition, which influences properties. Acrylic acid also may have a number of optional substitutions and, after such substitutions, may be used as a monomer for polymerization, or co-polymerization reactions. As a general rule, acrylic acid (or one of its co-polymerization monomers) may be substituted by any substituent that does not interfere with the polymerization process, such as alkyl, alkoxy, aryl, heteroaryl, benzyl, vinyl, allyl, hydroxy, epoxy, amide, ethers, esters, ketones, maleimides, succinimides, sulfoxides, glycidyl and silyl (see e.g., U.S. Pat. No. 7,678,869, incorporated by reference above, for further discussion). The following paragraphs provide a few non-limiting examples of copolymerization applications.

Paints that comprise polymers and copolymers of acrylic acid and its esters are in wide use as industrial and consumer products. Aspects of the technology for making such paints can be found in e.g., U.S. Pat. Nos. 3,687,885 and 3,891,591, incorporated by reference for their teachings of such paint manufacture. Generally, acrylic acid and its esters may form homopolymers or copolymers among themselves or with other monomers, such as amides, methacrylates, acrylonitrile, vinyl, styrene and butadiene. A desired mixture of homopolymers and/or copolymers, referred to in the paint industry as "vehicle" (or "binder") are added to an aqueous solution and agitated sufficiently to form an aqueous dispersion that includes sub-micrometer sized polymer particles. The paint cures by coalescence of these vehicle particles as the water and any other solvent evaporate. Other additives to the aqueous dispersion may include pigment, filler (e.g., calcium carbonate, aluminum silicate), solvent (e.g., acetone, benzol, alcohols, etc., although these are not found in certain no VOC paints), thickener, and additional additives depending on the conditions, applications, intended surfaces, etc. In many paints, the weight percent of the vehicle portion may range from about nine to about 26 percent, but for other paints the weight percent may vary beyond this range.

Acrylic-based polymers are used for many coatings in addition to paints. For example, for paper coating latexes, acrylic acid is used from 0.1-5.0%, along with styrene and butadiene, to enhance binding to the paper and modify rheology, freeze-thaw stability and shear stability. In this context, U.S. Pat. Nos. 3,875,101 and 3,872,037 are incorporated by reference for their teachings regarding such latexes. Acrylate-based polymers also are used in many inks, particularly UV curable printing inks. For water treatment, acrylamide and/or hydroxy ethyl acrylate are commonly co-polymerized with acrylic acid to produce low molecular-weight linear polymers. In this context, U.S. Pat. Nos. 4,431,547 and 4,029,577 are incorporated by reference for their teachings of such polymers. Co-polymers of acrylic acid with maleic acid or itaconic acid are also produced for water-treatment applications, as described in U.S. Pat. No. 5,135,677, incorporated by reference for that teaching. Sodium acrylate (the sodium salt of glacial acrylic acid) can be co-polymerized with acrylamide (which may be derived from acrylic acid via amidation chemistry) to make an anionic co-polymer that is used as a flocculant in water treatment.

For thickening agents, a variety of co-monomers can be used, such as those described in U.S. Pat. Nos. 4,268,641 and 3,915,921, incorporated by reference for their description of these co-monomers. U.S. Pat. No. 5,135,677 describes a number of co-monomers that can be used with acrylic acid to produce water-soluble polymers, and is incorporated by reference for such description.

In some cases, conversion to downstream products may be made enzymatically. For example, 3-HP may be converted to 3-HP-CoA, which then may be converted into polymerized 3-HP with an enzyme having polyhydroxy acid synthase activity (EC 2.3.1.-). Also, 1,3-propanediol can be made using polypeptides having oxidoreductase activity or reductase activity (e.g., enzymes in the EC 1.1.1.- class of enzymes). Alternatively, when creating 1,3-propanediol from 3-HP, a combination of (1) a polypeptide having aldehyde dehydrogenase activity (e.g., an enzyme from the 1.1.1.34 class) and (2) a polypeptide having alcohol dehydrogenase activity (e.g., an enzyme from the 1.1.1.32 class) can be used. Polypeptides having lipase activity may be used to form esters. Enzymatic reactions such as these may be conducted in vitro, such as using cell-free extracts, or in vivo.

Thus, various embodiments described in this disclosure, such as methods of making a chemical, include conversion steps to any downstream products of microbially produced 3-HP, including but not limited to those chemicals described herein, in the incorporated references, and known in the art. For example, in some cases, 3-HP is produced and converted to polymerized-3-HP (poly-3-HP) or acrylic acid. In some cases, 3-HP or acrylic acid can be used to produce polyacrylic acid (polymerized acrylic acid, in various forms), methyl acrylate, acrylamide, acrylonitrile, propiolactone, ethyl 3-HP, malonic acid, 1,3-propanediol, ethyl acrylate, n-butyl acrylate, hydroxypropyl acrylate, hydroxyethyl acrylate, isobutyl acrylate, 2-ethylhexyl acrylate, and acrylic acid or an acrylic acid ester to which an alkyl or aryl addition may be made, and/or to which halogens, aromatic amines or amides, and aromatic hydrocarbons may be added.

a) Reactions that form downstream compounds such as acrylates or acrylamides can be conducted in conjunction with use of suitable stabilizing agents or inhibiting agents reducing the likelihood of polymer formation. See, for example, U.S. Publication No. 2007/0219390, incorporated by reference in its entirety. Stabilizing agents and/or inhibiting agents include, but are not limited to, e.g., phenolic compounds (e.g., dimethoxyphenol (DMP) or alkylated phenolic compounds such as di-tert-butyl phenol), quinones (e.g., t-butyl hydroquinone or the monomethyl ether of hydroquinone (MEHQ)), and/or metallic copper or copper salts (e.g., copper sulfate, copper chloride, or copper acetate). Inhibitors and/or stabilizers can be used individually or in combinations as will be known by those of skill in the art.

In some cases, the one or more downstream compounds are recovered at a molar yield of up to about 100 percent, or a molar yield in the range from about 70 percent to about 90 percent, or a molar yield in the range from about 80 percent to about 100 percent, or a molar yield in the range from about 90 percent to about 100 percent. Such yields may be the result of single-pass (batch or continuous) or iterative separation and purification steps in a particular process.

The methods described in this disclosure can also be used to produce downstream compounds derived from 3-HP, such as but not limited to, polymerized-3-HP (poly-3-HP), acrylic acid, polyacrylic acid (polymerized acrylic acid, in various forms), copolymers of acrylic acid and acrylic esters, acrylamide, acrylonitrile, propiolactone, ethyl 3-HP, malonic acid, and 1,3-propanediol. Also, among esters that are formed are methyl acrylate, ethyl acrylate, n-butyl acrylate, hydroxypropyl acrylate, hydroxyethyl acrylate, isobutyl acrylate, and 2-ethylhexyl acrylate. These and/or other acrylic acid and/or other acrylate esters may be combined, including with other compounds, to form various known acrylic acid-based polymers. Numerous approaches may be employed for such downstream conversions, generally falling into enzymatic, catalytic (chemical conversion process using a catalyst), thermal, and combinations thereof (including some wherein a desired pressure is applied to accelerate a reaction). For example, without being limiting, acrylic acid may be made from 3-HP via a dehydration reaction, methyl acrylate may be made from 3-HP via dehydration and esterification, the latter to add a methyl group (such as using methanol), acrylamide may be made from 3-HP via dehydration and amidation reactions, acrylonitrile may be made via a dehydration reaction and forming a nitrile moiety, propiolactone may be made from 3-HP via a ring-forming internal esterification reaction, ethyl-3-HP may be made from 3-HP via esterification with ethanol, malonic acid may be made from 3-HP via an oxidation reaction, and 1,3-propanediol may be made from 3-HP via a reduction reaction. Additionally, it is appreciated that various derivatives of the derivatives of 3-HP and acrylic acid may be made, such as the various known polymers of acrylic acid and its derivatives. Production of such polymers is considered within the scope of the present invention. Copolymers containing acrylic acid and/or esters have been widely used in the pharmaceutical formulation to achieve extended or sustained release of active ingredients, for example as coating material. Downstream compounds may also be converted to consumer products such as diapers, carpet, paint, and adhesives.

Another important product, acrylamide, has been used in a number of industrial applications. Acrylamide may be produced from 3-HP, for example, without being limiting, via an esterification-amidation-dehydration sequence. Refluxing an alcohol solution of 3-HP in the presence of an acid or Lewis acid catalyst described herein would lead to a 3-HP ester. Treatment of the 3-HP ester with either an ammonia gas or an ammonium ion could yield 3-HP amide. Finally, dehydration of the 3-HP amide with dehydration reagents described elsewhere in this disclosure could produce acrylamide. The steps mentioned herein may be rearranged to produce the same final product acrylamide. Polymerization of acrylamide can be achieved, for example, and without being limiting, by radical polymerization. Polyacrylamide polymers have been widely used as additives for treating municipal drinking water and waste water. In addition, they have found applications in gel electrophoresis, oil-drilling, papermaking, ore processing, and the manufacture of permanent press fabrics.

VIII. Expression Systems General Concepts

The following general concepts are applicable to embodiments of the invention described above.

Multicopy Plasmids

The researcher is faced with a myriad of genetic module options when designing a plasmid for expression of a heterologous protein in a host cell. How to optimize an expression plasmid system often depends on the downstream use of the expressed protein.

Different cloning vectors or plasmids are maintained at different copy numbers, dependent on the replicon of the plasmid. Most general cloning plasmids can carry a DNA insert up to around 15 kb in size.

Multicopy plasmids can be used for the expression of recombinant genes in *Escherichia coli*. Examples of include multicopy plasmids include high-copy, medium-copy and low-copy plasmids (see FIG. 8). The high copy number is generally desired for maximum gene expression. However, the metabolic burden effects can result from multiple plasmid copies could prove to be detrimental for maximum productivity in certain metabolic engineering applications by adding significant metabolic burden to the system.

The low-copy plasmids for example, pBR322 is based on the original ColE1 replicon and thus has a copy number of 15-20. The pACYC series of plasmids are based on the p15A replicon, which has a copy number of 18-22, whereas pSC101 has even a lower copy number around 5, and BACs are maintained at one copy per cell. Such low copy plasmids may be useful in metabolic engineering applications, particularly when one or more of the substrates used in the recombinant pathway are required for normal cellular metabolism and can be toxic to the cell at high levels.

However, the used of high-copy plasmids may be useful in enhanced cellular metabolism contexts. The mutant ColE1 replicon, as found in the pUC series of plasmids produces a copy number of 500-700 as a result of a point mutation within the RNAII regulatory molecule.

There are transcription and translation vectors. Transcription vectors are utilized when the DNA to be cloned has an ATG start codon and a prokaryotic ribosome-binding site. Translation vectors contain an efficient ribosome-binding site and, therefore, it is not necessary for the target DNA to contain one. This is particularly useful in cases where the initial portion of the gene may be cleaved in an effort to improve solubility. Another consideration when choosing a transcription or translation vector is the source of the DNA to be expressed. Prokaryotic genes usually have a ribosome-binding site that is compatible with the host *E. coli* translation machinery, whereas eukaryotic genes do not. Normal prokaryotic gene expression may be enhanced by use of an engineered promoter and ribosome-binding site.

Promoters

A promoter is a region of DNA that initiates transcription of a particular gene. In bacteria, transcription is initiated by the promoter being recognized by RNA polymerase and an associated sigma factor, which are often brought to the promoter site by an activator protein's binding to its own DNA binding site located by the promoter.

Promoter selection is an important factor when designing an expression plasmid system. A promoter is located upstream of the ribosome-binding site. Owing to the fact that many heterologous protein products are toxic to the cell, the promoter can be regulated so that the heterologous protein is expressed at the appropriate amount and time to reduced the burden on the cell host.

Historically, the most commonly used promoters have been the lactose (lac) and tryptophan (trp) promoters. These two promoters were combined to create the hybrid promoters tac and trc that are also commonly used. Other common promoters are the phage lambda promoters, the phage T7 promoter (T7), and the alkaline phosphatase promoter (phoA).

Promoters can be constitutive and inducible. Constitutive promoter is active in all circumstances in the cell, while regulated or inducible promoter become active in response to specific stimuli. In addition the strength of the promoter can also differ. A strong promoter has a high frequency of transcription and generates the heterologous protein as 10-30% of the total cellular protein production (for examples see FIG. 8). Chemically-inducible promoters that can be used in various aspects of the invention include but are not limited to promoters whose transcriptional activity is regulated by the presence or absence of alcohol, tetracycline, steroids, metal and other compounds. Physically-inducible promoters that can be used in various aspects of the invention include but are not limited to including promoters whose transcriptional activity is regulated by the presence or absence of light and low or high temperatures.

In order to be an inducible promoter, the promoter should be initially be completely repressed to transcription and then transcription induced with the addition of an inducer to allow expression at the time that expression is desired in the host cell. Alternatively, an inducible promoter may be responsive to the lack of a substance, such as inorganic phosphate, such that the absence of inorganic phosphate will allow expression at the time that expression is desired in the host cell (for examples see FIG. 8).

Ribosome Binding Sites

A Ribosome Binding Sites (RBS) is an RNA sequence upstream of the start codon that affects the rate at which a particular gene or open reading frame (ORF) is translated. One can tailor an RBS site to a particular gene. Ribosome Binding Sites (RBSs) are typically short sequences, often less than 20 base pairs. Various aspects of RBS design are known to affect the rate at which the gene is translated in the cell. The RBS module can influences the translation rate of a gene largely by two known mechanisms. First, the rate at which ribosomes are recruited to the mRNA and initiate translation is dependent on the sequence of the RBS. Secondly, the sequence of the RBS can also affect the stability of the mRNA in the cell, which in turn affects the number of proteins. Through the use of genetic expression modules the expression of desired genes, such as genes encoding enzymes in the biosynthetic pathway for 3-HP, can be tailored activity either at the transcriptional and translational level.

One can access the registry RBS collection as a starting point for designing an RBS <<http://partsregistry.org/Ribosome_Binding_Sites/Catalog>>. The Registry has collections of RBSs that are recommended for general protein expression in *E. coli* and other prokaryotic hosts. In addition, each family of RBSs has multiple members covering a range of translation initiation rates. There are also several consensus RBS sequence for *E. coli* have been described. However, it is important to keep in mind the known RBS functions and mechanisms in a larger context. For example, in certain contexts the RBS can interact with upstream sequences, such as sequence that comprise the promoter or an upstream ORF. In other contexts, the RBS may interact with downstream sequences, for example the ribosome enzyme binds jointly to the RBS and start codon at about the same time. These potential interactions should be considered in the overall RBS sequence design. The degree of secondary structure near the RBS can affect the translation initiation rate. This fact can be used to produce regulated translation initiation rates.

The Shine-Dalgarno portion of the RBS is critical to the strength of the RBS. The Shine-Dalgarno is found at the end of the 16s rRNA and is the portion that binds with the mRNA and includes the sequence 5'-ACCUCC-3'. RBSs will commonly include a portion of the Shine-Dalgarno sequence. One of the ribosomal proteins, 51, is known to bind to adenine bases upstream from the Shine-Dalgarno sequence. As a result, the RBS can be made stronger by adding more adenines in the sequence upstream of the RBS.

When considering the design of the spacing between the RBS and the start codon, it is important to think of the aligned spacing rather than just the absolute spacing. While the Shine-Dalgarno portion of the RBS is critical to the strength of the RBS, the sequence upstream of the Shine-Dalgarno sequence is also important. Note that the promoter may add some bases onto the start of the mRNA that may affect the strength of the RBS by affecting S1 binding.

Computer programs that design RBS sequence to match protein coding sequences, desired upstream sequences including regulatory mRNA sequences, and account of secondary structure are known [Salis, Mirsky, and Voight, Nature Biotechnology 27: 946-950, 2009] and were used to optimize RBSs for the ACCase subunit genes as described in (see EXAMPLE 3).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Salt Inhibition Studies in *E. coli*

Figure 4:
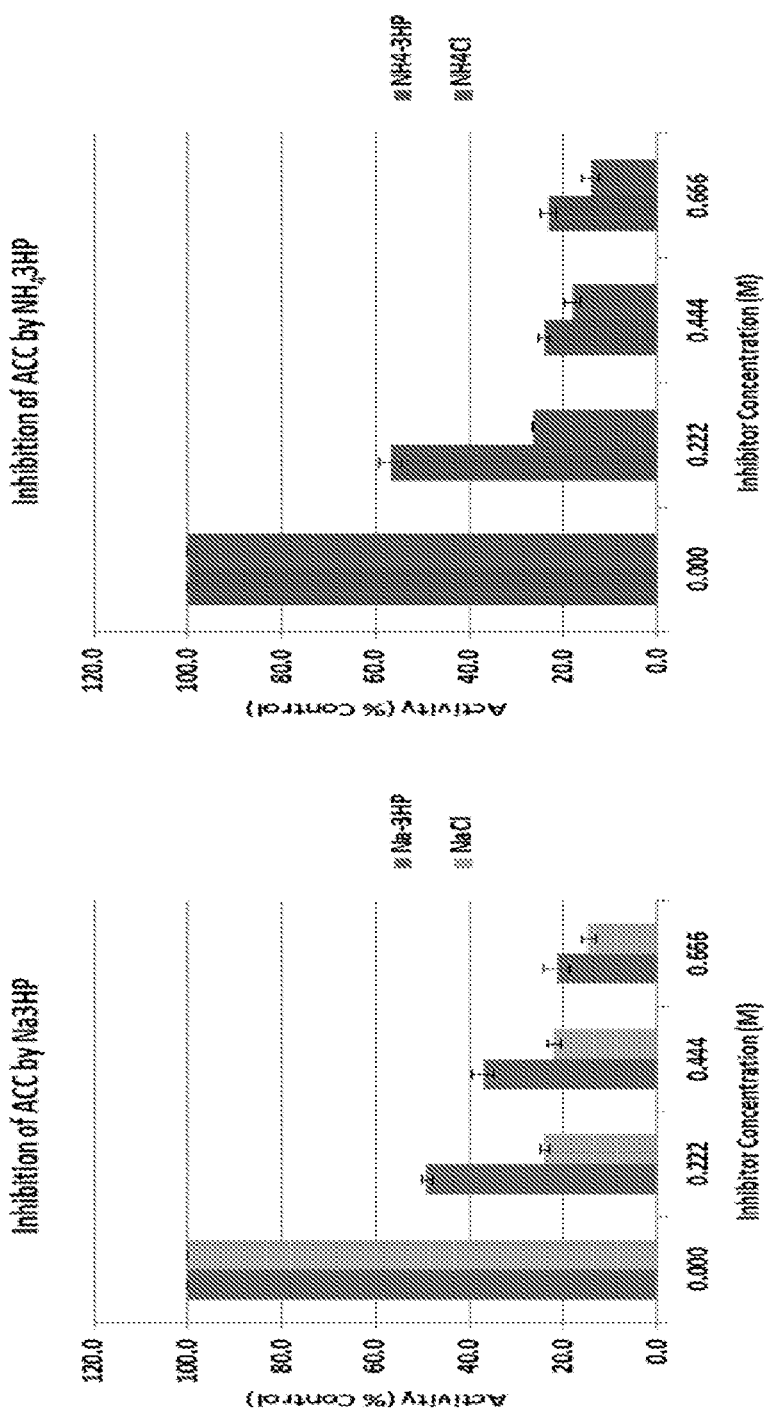
FIG. 4 Shows the inhibition of ACCase enzyme activity by high salt concentration.

The activity of ACCase complex, a critical enzyme in the conversion of acetyl-CoA to malonyl-CoA, the immediate precursor for 3-HP, is severely inhibited by salt. Dose-dependent effects on ACCase activity was observed in the presence of NaCl, $NH_4Cl$, Na-3-HP, or $NH_4$-3-HP such that salt levels near 0.44M resulted in decreasing the activity of the ACCase enzyme by approximately 80%, while salts of 3-HP levels near 0.66M decreased the activity of the ACCase enzyme by approximately 80% relative to control (FIG. 4). Levels of greater than 0.66M (60 g/L) are expected to be present for commercially viable commercial production of 3-HP.

Example 2: ACCase from Halophilic Organism

Halophilic organisms, such as *Halomonas elongata*, are found in environments with high salt concentrations and, in general, have a salt internal concentration >2.5-3M. It is hypothesized that enzymes derived from any salt-tolerant species should be more resistant to enzyme inhibition by salts, such as 3-HP. Further, these enzymes that have greater salt tolerance should in turn have extended production under high salt conditions than enzymes with lower salt tolerance.

Accordingly, the genes encoding the accA, accB, accC, accD of *H. elongata* described in Table 1 were synthesized for expression in *E. coli* using codons optimized for this organism and supplied individually on pUC57 plasmids without promoters. Synthetic operons comprising the subunits were assembled using the Gibson assembly method.

TABLE 1

Accession numbers for genes encoding ACCase subunits from *Halomonas elongata*

| Gene | Accession number | SEQ ID NO. |
| --- | --- | --- |
| accA | YP_003898857.1 | SEQ ID NO. 1, 2 |
| accB | YP_003897250.1 | SEQ ID NO. 3, 4 |
| accC | YP_003897249.1 | SEQ ID NO. 5, 6 |
| accD | YP_003897309.1 | SEQ ID NO. 7, 8 |

Each gene was amplified by PCRs with Pfu Ultra II HS using the manufacturer's instructions, and the PCR products were purified using the Zymo PCR Cleanup kit. Concentrations of products were measured using the Nanodrop spectophotometer. The Gibson Assembly kit (NEB) was used to construct plasmids expressing the ACCase subunit genes as directed by the manufacturer. The effect of $NH_4$-3-HP and $NH_4Cl$ on *H. elongata* ACCase was tested and compared to the *E. coli* ACCase. As shown in FIG. 4, whereas the *E. coli* ACCase is significantly inhibited by the salts, the ACCase from the halophile is less affected by either $NH_4$-3-HP or by $NH_4Cl$. This result indicated that use of the *H. elongata* ACCase in 3-HP production strains would in beneficial in relieving 3-HP inhibition of the conversion of acetyl-CoA to malonyl-CoA, a critical step in the pathway.

Example 3: RBS-Optimized Genes

Enzyme expression is regulated at transcriptional and translational levels in prokaryotes. Ribosome Binding Sites (RBS) are 15 nucleotide segments which are known to control the level of protein expression in microorganisms. To enhance *H. elongata* ACCase expression various customized RBS were constructed and optimized for *E. coli* translation expression. Table 2 shows the RBS sequences used to increase expression of the individual subunits.

individual genes accA, accB, accC, and accD may result in strains with even higher ACCase expression and activity.

TABLE 3

Improvement in 3-HP production by RBS-optimized expression of *H. elongata* ACCase subunits.

| *H. elongata* ACCase expression plasmid | 3HP (g/l · OD) |
|---|---|
| Parent 2-4 | 0.06 |
| B2 | 0.81 |

TABLE 2

RBS sequences used to enhance expression of *H. elongate* ACCase subunits.

| *H. elongata* ACC expression plasmid | Modified RBS sequences preceeding ATG (underlined) | | | |
|---|---|---|---|---|
| | He_accD | He_accA | He_accC | He_accB |
| Parent 2-4 | 5'-GCGTAGTAAAGGAGGTAACATATG | 5'-CAATTTATTTAAGGAGGACTCTTAAGATG | 5'-GAAATTTCATACCACAGGCGAAGGAGGAAAAACCATG | 5'-GGAAGAACAAGGGGTGTACATG |
| B2 | Same as 2-4 | Same as 2-4 | Same as 2-4 | 5'-ggaagaattaagggggacaaggggaataATG |
| 13A | 5'-gcgtagtagccgggtgataaggagccgtaacATG | Same as 2-4 | Same as 2-4 | |
| 14C | 5'-gcgtagtagctgatataaaaggaggtaacggATG | Same as 2-4 | Same as 2-4 | Same as 2-4 |
| 15C | Same as 2-4 | 5'-caatttattttttgttcacccaaggagtattgctaATG | Same as 2-4 | Same as 2-4 |
| 17C | Same as 2-4 | 5'-caatttatttaccgaaataaaaggagggatgcgaATG | Same as 2-4 | Same as 2-4 |
| 35C | 5'-gcgtagtagccgggtgataaggagccgtaacATG | 5'-caatttattttttgttcacccaaggagtattgctaATG | Same as 2-4 | Same as 2-4 |
| 36C | 5'-gcgtagtagccgggtgataaggagccgtaacATG | 5'-caatttatttaccgaaataaaaggagggatgcgaATG | Same as 2-4 | Same as 2-4 |
| 36C-8 | 5'-gcgtagtagccgggtgataaggagccgtaacATG | 5'-caatttatttaccgaaataaaaggagggatgcgaATG | Same as 2-4 | 5'-ggaagaattaagggggacaaggggaataATG |
| 72B | 5'-gcgtagtagccgggtgataaggagccgtaacATG | 5'-caatttatttaccgaaataaaaggagggatgcgaATG | 5'-TCTTCCCACAACACTGGCGGACTCCATCATG | 5'-GAAATTTCATACCACAGGCGAAGGAGGAAAAACCATG |
| 105F | 5'-gcgtagtagccgggtgataaggagccgtacATG | 5'-caatttattttttgttcacccaaggagtattgctaATG | 5'-TCTTCCCACAACACTGGCGGACTCCATCATG | 5'-GAAATTTCATACCACAGGCGAAGGAGGAAAAACCATG |

The expression performance of the RBS-optimized *H. elongata* ACCases was evaluated by 3-HP production in a 96-well format, each in triplicate wells, and the averaged results shown in Table 3. Specific 3HP production is shown as g/L per $OD_{600}$. As may be seen in Table 3, enhancing the efficiency of the RBS in strains B2, 35C, and 72 B clearly resulted in increased malonyl-CoA production leading to increased 3-HP production. It is evident from these results that combinations of enhanced RBS's before each of the

TABLE 3-continued

Improvement in 3-HP production by RBS-optimized expression of *H. elongata* ACCase subunits.

| *H. elongata* ACCase expression plasmid | 3HP (g/l · OD) |
|---|---|
| 13A | 0.01 |

TABLE 3-continued

Improvement in 3-HP production by RBS-optimized expression of *H. elongata* ACCase subunits.

| *H. elongata* ACCase expression plasmid | 3HP (g/l · OD) |
|---|---|
| 14C | 0.54 |
| 15C | 0.14 |
| 17C | 0.08 |
| 35C | 0.68 |
| 36C | 0.31 |
| 36C-8 | 0.31 |
| 72B | 0.57 |
| 105F | 0.19 |

Example 4: Coordinated Expression by Subunit Fusions

In nature ACCase subunit genes from prokaryotes such as *E. coli* and *H. elongata* have been shown to have a quaternary structure: $accA_2:accD_2:accB_4:accC_2$. However, the intrinsic levels of the ACCase subunit genes are too low for optimal production. Therefore, for optimal production it is ideal to have overexpression to be coordinated in a similar manner.

Expression of the genes encoding each ACCase subunit is regulated at transcriptional and translational levels. Coordinated overexpression of the ACCase subunit genes, accA, accB, accC, accD should give better ACCase activity. Examples of fusions of accC-B proteins exist in bacteria. It is hypothesized that coordinated overexpression may be achieved by fusion of subunit genes should ensures equimolar expression of the subunit genes at the optimal time.

Figure 5:
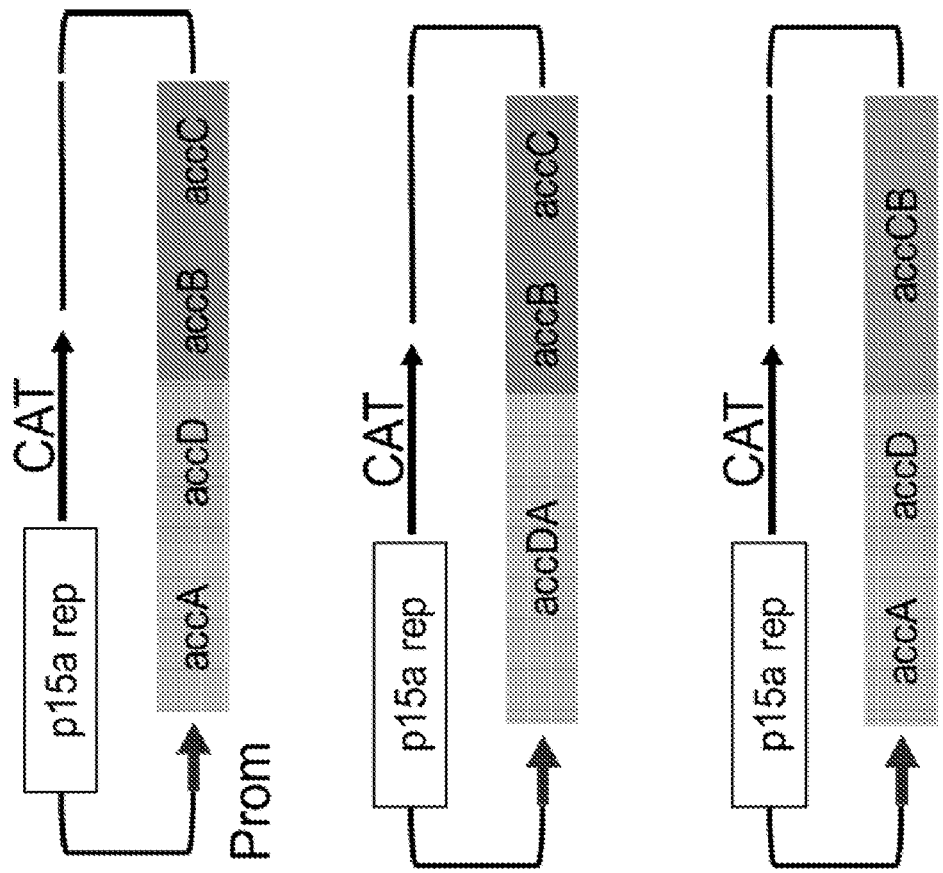
FIG. 5 Depicts some embodiments of the fusion ACCase subunit gene constructs overexpressed in *E. coli*. CAT=chloramphenicol resistance marker; p15a rep=replication origin; red arrow=promoter.

The following ACCase subunit gene fusion were constructed and the constructs overexpressed in *E. coli*: (A) Control ABCD, (B) fusion of accC-B (SEQ ID NO. s 9, 10) subunit genes as seen in bacteria, (C) fusion of accD-A subunit genes using a flexible 15-amino acid linker (Linker sequence LSGGGGSGGGGSGGGGSGGGGSAAA; SEQ ID NO. s 11, 12) as depicted in FIG. 5.

Figure 6:
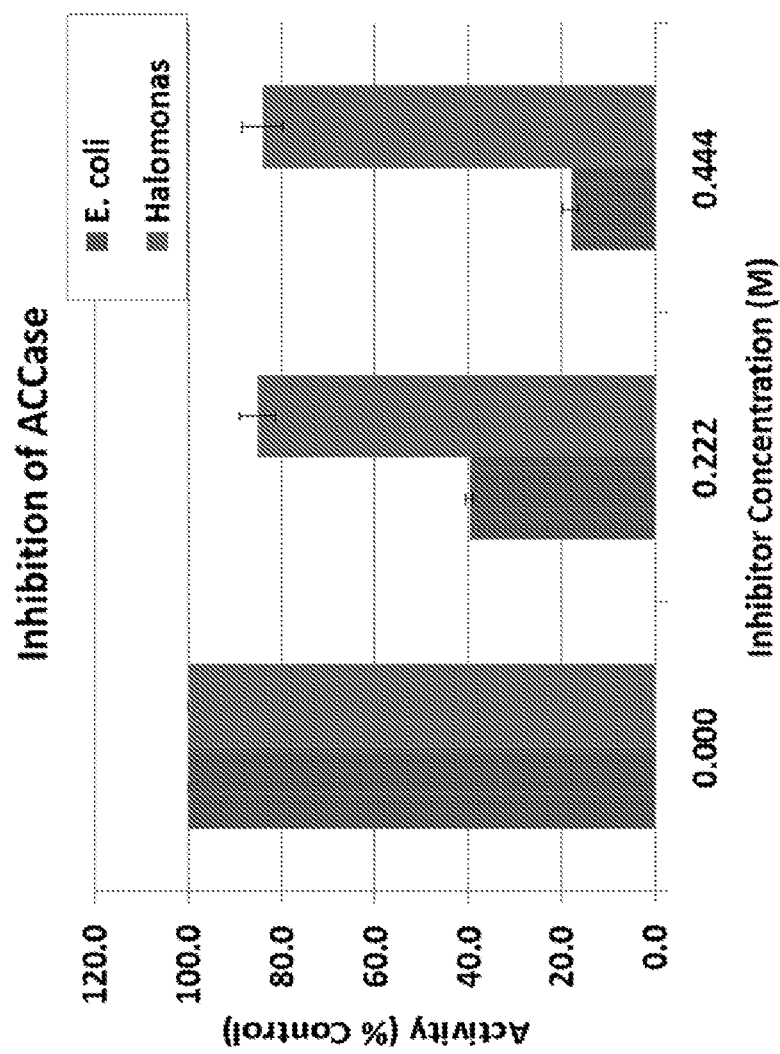
FIG. 6 Show improved production of 3-HP in fermentors by genetically modified organism with DA fusion ACCase.

The performance of the ACC fusions were tested for their ACCase activity and for various 3-HP production metrics in Table 4. ACCase activity was determined in cell lysates using an assay for malonyl-CoA production as described in [Kroeger, Zarzycki, and Fuchs, Analytical Biochem. 411: 100-105, 2011]. Production of 3-HP was determined in cells co-transformed with a plasmid bearing the genes encoding the malonyl-CoA reductase from *S. tokadaii* and *E. coli* ydfG providing a 3-HP dehydrogenase to complete the metabolic pathway from malonyl-CoA to 3HP. These results show that the strain with the fused accDA genes had higher average specific productivity of 3-HP compared to the parental strain in which the overexpressed ACCase is not fused. FIG. 6 shows that the benefit of the accDA fusion were also manifested in 3-HP production in fermentors with environmental controls of nutrient feed, pH, aeration, and temperature.

Table 4:

TABLE 4

Table 4: ACC Fusions and ACCase activity

| Strain designation | Plasmid | Avg specific prodn rate (g/gDCW · h) at TS + 6 | Avg specific prodn rate (g/gDCW · hr) at TS + 20 | ACCase specific activity at TS + 6 (U/mg) |
|---|---|---|---|---|
| BX3_783 | Parent (unfused ACCase) | 0.160 | 0.146 | 0.057 |
| BX3_829 | No ACC | 0.069 | 0.062 | 0.000 |
| BX3_837 | EC ACC DA fusion | 0.209 | 0.201 | 0.054 |

Example 5: 3-HP Exporter

Figure 7:
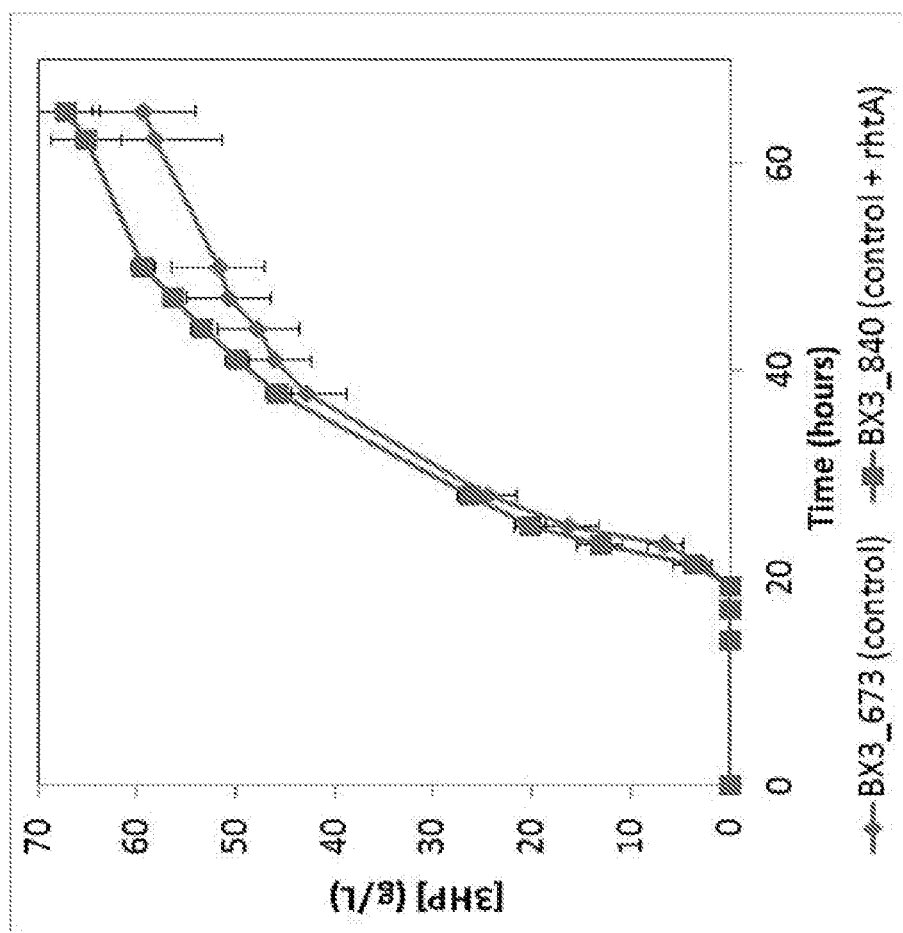
FIG. 7 Shows improved production of 3-HP in fermentors by genetically modified organism with overexpression of rhtA exporter.
Figure 9:
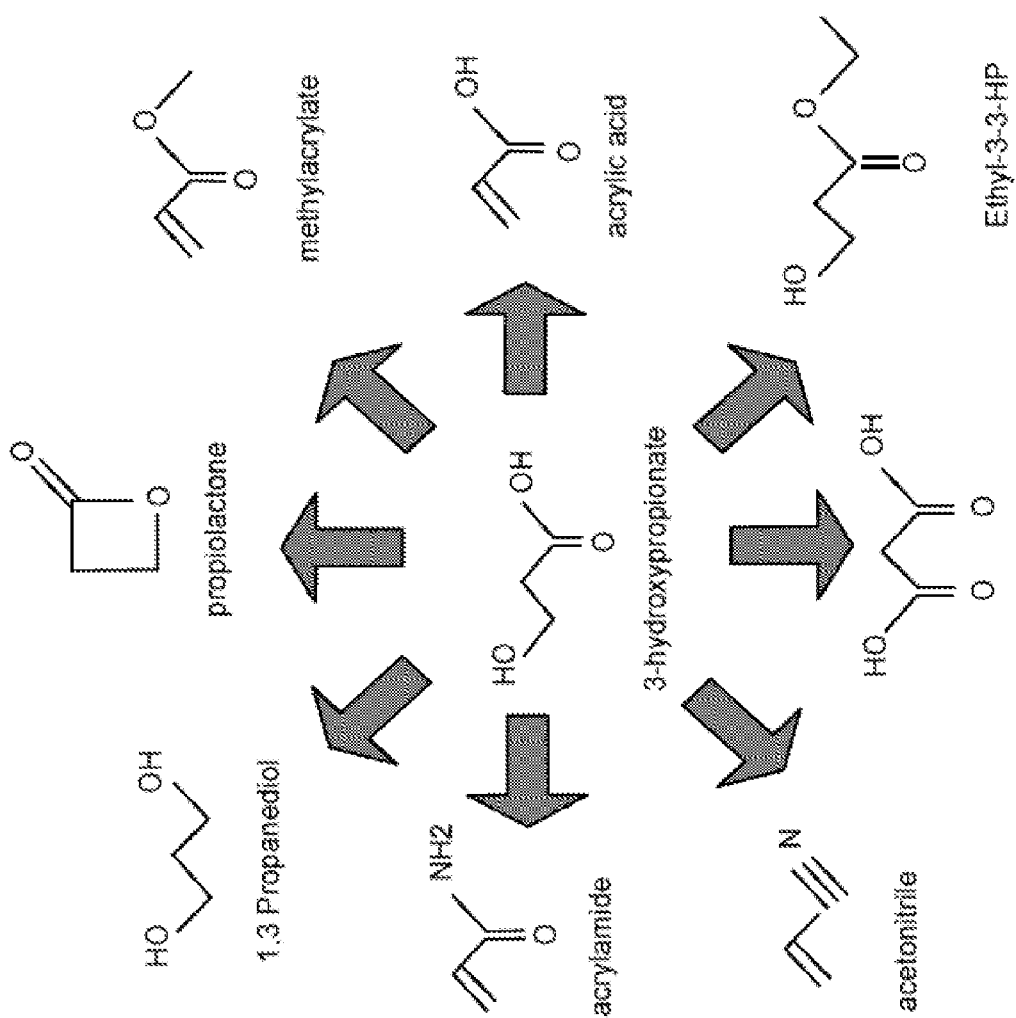
FIG. 9 Shows various chemical products that can made from various embodiments of the invention.

Growth inhibition has been demonstrated for *E. coli* strains grown in the presence of 3-HP at levels as low as 20 g/L. To produce high titers of 3-HP the production host is required to balance production with overcoming inhibition. A known chemical exporter from *E. coli* that has been previously characterized for homoserine transport, rhtA, was evaluated for increased production of 3-HP. A mutant version of the exporter, rhtA(P2S) (SEQ ID NO. 30 nucleic acid, SEQ ID NO. 31 protein) was synthesized behind the PtpiA promoter and inserted into the pTRC-PyibD-MCR plasmid behind a terminator using the Gibson Assembly kit (NEB) according to manufacturer's instructions. The effects of overexpression of rhtA were evaluated in 1 L fermentation compared to the control plasmid without rhtA. As shown in FIG. 7, overexpression of rhtA resulted in a significant improvement in 3HP titer compared to the control production strain. Construction of plasmids expressing another putative transporter, ydcO (SEQ ID NO. 32 nucleic acid, SEQ ID NO. 33 protein) is carried out in the same manner.

Example 6 Bicarbonate Importer (Prophetic)

Increased import of bicarbonate to increase availability of bicarbonate for the ACCase reaction will increase production of malonyl-CoA and hence products derived metabolically from malonyl-CoA, such as 3-HP. The gene encoding the bicA bicarbonate transporter (SEQ ID NO. 13) of *Synechococcus* sp. was synthesized using codons optimized for expression in *E. coli* (SEQ ID NO. 14) and expressed using the *E. coli* tal promoter in a strain cotransformed with plasmids encoding ACCase and MCR functions. Production of 3-HP by this strain is compared to that achieved by a control strain without overexpressed bicA.

What is claimed is:

1. A genetically modified microorganism comprising: a heterologous gene encoding a malonyl-CoA reductase: and a heterologous gene encoding an acetyl-CoA carboxylase (ACCase) polypeptide fusion wherein the polypeptide fusion comprises at least two subunits of an ACCase enzyme selected from the group consisting of accA-accB, accA-accC, accA-accD, accB-accC, accB-accD, accC-accD, accA-accB-accC, accA-accB-accD, accA-accC-accD, accB-accC-accD and accA-accB-accC-accD.

2. The genetically modified microorganism of claim 1, wherein the malonyl-CoA reductase is a monofunctional malonyl-CoA reductase.

3. The genetically modified microorganism of claim 1, wherein the malonyl-CoA reductase has at least 80% sequence identity to SEQ ID NO: 16.

4. The genetically modified microorganism of claim 1, further comprising a heterologous gene encoding a succinate-semialdehyde dehydrogenase.

5. The genetically modified microorganism of claim 2, wherein the succinate-semialdehyde dehydrogenase is gabD from *E. coli*.

6. The genetically modified microorganism of claim 1, further comprising a heterologous gene encoding a pyruvate kinase.

7. The genetically modified microorganism of claim 6, wherein the pyruvate kinase is pyk from *E. coli*.

8. A method of producing a chemical product comprising:
a heterologous gene encoding a malonyl-CoA reductase; and
culturing a genetically modified microorganism comprising a heterologous gene encoding an acetyl-CoA carboxylase (ACCase) polypeptide fusion wherein the polypeptide fusion comprises at least two subunits of an ACCase enzyme selected from the group consisting of accA-accB, accA-accC, accA-accD, accB-accC, accB-accD, accC-accD, accA-accB-accC, accA-accB-accD, accA-accC-accD, accB-accC-accD and accA-accB-accC-accD,
wherein the chemical product comprises acetyl-CoA, malonyl-CoA, malonate semialdehyde, or malonic acid.

9. The method of claim 8, wherein the malonyl-CoA reductase is a monofunctional malonyl-CoA reductase.

10. The method of claim 8, wherein the malonyl-CoA reductase has at least 80% sequence identity to SEQ ID NO: 16.

11. The method of claim 8, wherein the genetically modified microorganism further comprises a heterologous gene encoding a succinate-semialdehyde dehydrogenase.

12. The method of claim 11, wherein the succinate-semialdehyde dehydrogenase is gabD from *E. coli*.

13. The method of claim 8, wherein the genetically modified microorganism further comprises a heterologous gene encoding a pyruvate kinase.

14. The method of claim 13, wherein the pyruvate kinase is pyk from *E. coli*.

* * * * *